United States Patent [19]
Bauer et al.

[11] Patent Number: 6,051,217
[45] Date of Patent: *Apr. 18, 2000

[54] THERAPEUTIC USES OF INTERLEUKIN-3 (IL-3) MULTIPLE MUTATION POLYPEPTIDES

[75] Inventors: S. Christopher Bauer, New Haven; Mark Allen Abrams; Sarah Ruth Braford-Goldberg, both of St. Louis; Maire Helena Caparon, Chesterfield; Alan Michael Easton, Maryland Heights; Barbara Kure Klein, St. Louis; John P. McKearn, Glencoe, all of Mo.; Peter O. Olins, Lafayette, Colo.; Kumnan Paik, Wilmette, Ill.; John W. Thomas, Town & Country, Mo.

[73] Assignee: G. D. Searle & Co., Chicago, Ill.

[*] Notice: This patent is subject to a terminal disclaimer.

[21] Appl. No.: 08/470,081

[22] Filed: Jun. 6, 1995

Related U.S. Application Data

[60] Division of application No. 08/411,795, filed as application No. PCT/US93/11197, Nov. 22, 1993, Pat. No. 5,604,116, which is a continuation-in-part of application No. 07/981,044, Nov. 24, 1992, abandoned.

[51] Int. Cl.$^7$ .......................... A61K 38/20; C12N 15/24; C07K 14/54
[52] U.S. Cl. ........................................ 424/85.2; 435/69.52
[58] Field of Search .......................... 424/85.2; 435/69.52

[56] References Cited

U.S. PATENT DOCUMENTS

| | | |
|---|---|---|
| 4,877,729 | 10/1989 | Clark et al. . |
| 4,959,455 | 9/1990 | Clark et al. . |
| 5,032,395 | 7/1991 | Clark et al. . |
| 5,166,322 | 11/1992 | Shaw et al. . |
| 5,516,512 | 5/1996 | Dorssers et al. . |
| 5,604,116 | 2/1997 | Bauer et al. . |

FOREIGN PATENT DOCUMENTS

| | | |
|---|---|---|
| 275598 | 7/1988 | European Pat. Off. . |
| 413383 | 2/1991 | European Pat. Off. . |
| 3/236400 | 10/1991 | Japan . |
| 4/63595 | 2/1992 | Japan . |
| 2210883 | 6/1989 | United Kingdom . |
| 88/00598 | 1/1988 | WIPO . |
| 88/04691 | 6/1988 | WIPO . |
| 88/05469 | 7/1988 | WIPO . |
| 88/06161 | 8/1988 | WIPO . |
| 90/01039 | 2/1990 | WIPO . |
| 90/10705 | 9/1990 | WIPO . |
| 90/12874 | 11/1990 | WIPO . |
| 91/00350 | 1/1991 | WIPO . |
| 91/02754 | 3/1991 | WIPO . |
| 91/07988 | 6/1991 | WIPO . |
| 92/06116 | 4/1992 | WIPO . |
| 93/07171-A1 | 4/1993 | WIPO . |

OTHER PUBLICATIONS

Yang et al, in *Cell* 47:3 (1986).
Dorsers et al, *Gene* 55:115 (1987).
Phillips et al, *Gene*, 84, 501 (1989).
Clark–Lewis et al, *Science* 231:134 (1986).
Clark–Lewis et al, *Proc.Nat.Acad.Sci.USA* 85:7897 (1988).
Lokker et al, *J.Biol.Chem.*, 266(16):10624 (1991).
Clark–Lewis et al, Immune Regulation by Characterized Polypeptides, Alan R. Liss, Inc. (1987) p. 323–334.
Ihle et al, *J.Immunol.* 126:2184 (1981).
Fung et al, *Nature*, 307, 233 (1984).
Yokota et al, *Proc.Nat.Acad.Sci.USA* 81:1070 (1984).
Dorssers et al, *J.Biol.Chem* 266(31):21310 (1991).
Koshansky et al, *J.Clin.Invest*, 90:1879 (1992).
Lopez et al, *Proc.Natl.Acad.Sci.USA* 89:11842–11846 (1992).
Lokker et al, The EMBO JOUR. 10:2125–2131 (1991).

*Primary Examiner*—David L. Fitzgerald
*Attorney, Agent, or Firm*—Dennis Bennett

[57] ABSTRACT

The present invention relates to recombinant human interleukin-3 (hIL-3) variant or mutant proteins (muteins). These hIL-3 muteins contain amino acid substitutions and may also have amino acid deletions at both the N- and C-termini. The invention also relates to pharmaceutical compositions containing the hIL-3 muteins and methods for using them. Additionally, the present invention relates to recombinant expression vectors comprising nucleotide sequences encoding the hIL-3 muteins, related microbial expression systems, and processes for making the hIL-3 muteins using the microbial expression systems. Included in the present invention are deletion mutants of hIL-3 in which from 1 to 14 amino acids have been deleted from the N-terminus, and from 1 to 15 amino acids (a.a.119 to 133) have been deleted from the C-terminus, and which also contain amino acid substitutions in the polypeptide. These hIL-3 multiple mutation polypeptides may have biological activities similar to or better than hIL-3 and, in some cases, may also have an improved side effect profile.

132 Claims, 25 Drawing Sheets

```
      1                    5                         10
ATG GCT CCA ATG ACT CAG ACT ACT TCT CTT AAG ACT TCT
Met Ala Pro Met Thr Gln Thr Thr Ser Leu Lys Thr Ser 15                    20                   25
TGG GTT AAC TGC TCT AAC ATG ATC GAT GAA ATT ATA ACA
Trp Val Asn Cys Ser Asn Met Ile Asp Glu Ile Ile Thr 30                    35
CAC TTA AAG CAG CCA CCT TTG CCT TTG CTG GAC TTC AAC
His Leu Lys Gln Pro Pro Leu Pro Leu Leu Asp Phe Asn 40                    45                  50
AAC CTC AAT GGG GAA GAC CAA GAC ATT CTG ATG GAA AAT
Asn Leu Asn Gly Glu Asp Gln Asp Ile Leu Met Glu Asn 55                    60
AAC CTT CGA AGG CCA AAC CTG GAG GCA TTC AAC AGG GCT
Asn Leu Arg Arg Pro Asn Leu Glu Ala Phe Asn Arg Ala 65                          70                    75
GTC AAG AGT TTA CAG AAT GCA TCA GCA ATT GAG AGC ATT
Val Lys Ser Leu Gln Asn Ala Ser Ala Ile Glu Ser Ile 80                    85                  90
CTT AAA AAT CTC CTG CCA TGT CTG CCC CTG GCC ACG GCC
Leu Lys Asn Leu Leu Pro Cys Leu Pro Leu Ala Thr Ala 95                   100
GCA CCC ACG CGA CAT CCA ATC CAT ATC AAG GAC GGT GAC
Ala Pro Thr Arg His Pro Ile His Ile Lys Asp Gly Asp 105                   110                   115
TGG AAT GAA TTC CGT CGT AAA CTG ACC TTC TAT CTG AAA
Trp Asn Glu Phe Arg Arg Lys Leu Thr Phe Tyr Leu Lys 120                   125
ACC TTG GAG AAC GCG CAG GCT CAA CAG ACC ACT CTG TCG
Thr Leu Glu Asn Ala Gln Ala Gln Gln Thr Thr Leu Ser

130
CTA GCG ATC TTT TAA TAA   [SEQ ID NO:144]
Leu Ala Ile Phe END END   [SEQ ID NO:128]
```

FIG. 1

```
         ClaI
aa20      ATCGATGAAATCATCACCCACCTGAAGCAGCCACCGCTGCCGCTGGACTTCAACAAC
       1  ------+---------+---------+---------+---------+---------+  60
          IleAspGluIleIleThrHisLeuLysGlnProProLeuProLeuAspPheAsnAsn
                                                                    EcoRV    XhoI

CTCAATGGTGAAGACCAAGATATCCTGATGGAAATAACCTTCGTCGTCCAAACCTCGAG
       61 ------+---------+---------+---------+---------+---------+  120
          LeuAsnGlyGluAspGlnAspIleLeuMetGluAsnLeuArgArgProAsnLeuGlu
                                                         PstI NsiI

GCATTCAACCGTGCTGTCAAGTCTCTGCAGAATGCAT  [SEQ ID NO:145]  aa70
       121 ------+---------+---------+---------   157
          AlaPheAsnArgAlaValLysSerLeuGlnAsnAla  [SEQ ID NO:146]
```

FIG. 2: ClaI to NsiI Replacement Fragment

FIG. 2

```
              N
              c
              o                                              H
              I                                              p
                                                             a
                                                             I
        CCATGGCTCCAATGACTCAGACTACTTCTCTTAAGACTTCTTGGGTTAACTGCTCTAACA
    1   ---------+---------+---------+---------+---------+---------+  60
        GGTACCGAGGTTACTGAGTCTGATGAAGAGAATTCTGAAGAACCCAATTGACGAGATTGT

MetAlaProMetThrGlnThrThrSerLeuLysThrSerTrpValAsnCysSerAsnMet
                    C
                    l
                    a
                    I
        TGATCGATGAAATTATAACACACTTAAAGCAGCCACCTTTGCCTTTGCTGGACTTCAACA
    61  ---------+---------+---------+---------+---------+---------+  120
        ACTAGCTACTTTAATATTGTGTGAATTTCGTCGGTGGAAACGGAAACGACCTGAAGTTGT

IleAspGluIleIleThrHisLeuLysGlnProProLeuProLeuLeuAspPheAsnAsn

ACCTCAATGGGGAAGACCAAGACATTCTGATGGAAAATAACCTTCGAAGGCCAAACCTGG
    121 ---------+---------+---------+---------+---------+---------+  180
        TGGAGTTACCCCTTCTGGTTCTGTAAGACTACCTTTTATTGGAAGCTTCCGGTTTGGACC

LeuAsnGlyGluAspGlnAspIleLeuMetGluAsnAsnLeuArgArgProAsnLeuGlu
                                                   N
                                                   s
                                                   i
                                                   I
        AGGCATTCAACAGGGCTGTCAAGAGTTTACAGAATGCATCAGCAATTGAGAGCATTCTTA
    181 ---------+---------+---------+---------+---------+---------+- 240
        TCCGTAAGTTGTCCCGACAGTTCTCAAATGTCTTACGTAGTCGTTAACTCTCGTAAGAAT

AlaPheAsnArgAlaValLysSerLeuGlnAsnAlaSerAlaIleGluSerIleLeuLys

AAAATCTCCTGCCATGTCTGCCCCTGGCCACGGCCGCACCCACGCGACATCCAATCCATA
    241 ---------+---------+---------+---------+---------+---------+  300
        TTTTAGAGGACGGTACAGACGGGGACCGGTGCCGGCGTGGGTGCGCTGTAGGTTAGGTAT

AsnLeuLeuProCysLeuProLeuAlaThrAlaAlaProThrArgHisProIleHisIle
```

FIG. 3A

```
                                         E
                                         c
                                         o
                                         R
                                         I
      TCAAGGACGGTGACTGGAATGAATTCCGTCGTAAACTGACCTTCTATCTGAAAACCTTGG
301   ---------+---------+---------+---------+---------+---------+  360
      AGTTCCTGCCACTGACCTTACTTAAGGCAGCATTTGACTGGAAGATAGACTTTTGGAACC

LysAspGlyAspTrpAsnGluPheArgArgLysLeuThrPheTyrLeuLysThrLeuGlu

H
                                                            i
                                                            n
                                  N                         d
                                  h                         I
                                  e                         I
                                  I
      AGAACGCGCAGGCTCAACAGACCACTCTGTCGCTAGCGATCTTTTAATAAGCTT
361   ---------+---------+---------+---------+---------+---+  414
      TCTTGCGCGTCCGAGTTGTCTGGTGAGACAGCGATCGCTAGAAAATTATTCGAA

AsnAlaGlnAlaGlnGlnThrThrLeuSerLeuAlaIlePheEndEnd
```

FIG. 3B

```
    ATGATGATTACTCTGCGCAAACTTCCTCTGGCGGTTGCCGTCGCAGCGGGCGTAATGTCT
 1  ------------+------------+------------+------------+------------+------------+ 60
    TACTACTAATGAGACGCGTTTGAAGGAGACCGCCAACGGCAGCGTCGCCCGCATTACAGA

MetMetIleThrLeuArgLysLeuProLeuAlaValAlaValAlaAlaGlyValMetSer
              N
              c
              o
              I
    GCTCAGGCCATGGCTAACTGC        [SEQ ID NO: 149]
 61 ------------+------------+- 81
    CGAGTCCGGTACCGATTGACG        [SEQ ID NO: 150]

AlaGlnAlaMetAlaAsnCys        [SEQ ID NO: 14]
                      ↑
``` lamB Signal Peptide

FIG. 8

THERAPEUTIC USES OF INTERLEUKIN-3 (IL-3) MULTIPLE MUTATION POLYPEPTIDES

This a divisional of U.S. Ser. No. 08/411,795, now U.S. Pat. No. 5,604,116, which was filed as international application PCT/US93/11197 on Nov. 22, 1993, which entered the U.S. national stage under 35 U.S.C. § 371 on Apr. 6, 1995; and PCT/US93/11197 in turn is a Continuation in Part of U.S. Ser. No. 07/981,044; filed Nov. 24, 1992 which is now abandoned. The noted applications ate incorporated herein by reference.

FIELD OF THE INVENTION

The present invention relates to mutants or variants of human interleukin-3 (hIL-3) which contain multiple amino acid substitutions and which may have portions of the native hIL-3 molecule deleted. These hIL-3 multiple mutation polypeptides retain one or more activities of native hIL-3 and may also show improved hematopoietic cell-stimulating activity and/or an improved activity profile which may include reduction of undesirable biological activities associated with native hIL-3.

BACKGROUND OF THE INVENTION

Colony stimulating factors (CSFs) which stimulate the differentiation and/or proliferation of bone marrow cells have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, mega-karyocyte and pure and mixed erythroid colonies.

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 12:2184 (1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 30:233 (1984) and Yokota, et al., PROC. NATL. ACAD. SCI. USA 82:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 5:115 (1987), found a clone from a human cDNA library which hybridized with mIL-3. This hybridization was the result of the high degree of homology between the 3' noncoding regions of mIL-3 and hIL-3. This CDNA coded for an hIL-3 ($Pro^8$) sequence.

U.S. Pat. No. 4,877,729 and U.S. Pat. No. 4,959,454 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogues synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140} \rightarrow Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA B:7897 (1988)).

International Patent Application (PCT) WO 88/00598 discloses gibbon- and human-like IL-3. The hIL-3 contains a $Ser^8 \rightarrow Pro8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1 \rightarrow Asp^1$, $Trp13 \rightarrow Arg^{13}$ (pGB/IL-302) and $Ala^1 \rightarrow Asp^1$, $Met^3 \rightarrow Thr^3$ (pGB/IL-304) and one triple mutant $Ala^1 \rightarrow Asp^1$, $Leu^9 \rightarrow Pro^9$, $Trp^{13} \rightarrow Arg^{13}$ (pGB/IL-303).

WO 88/05469 describes how deglycosylation mutants can be obtained and suggests mutants of $Arg^{54}Arg^{55}$ and $ArglO^8ArglO^9LysllO$ might avoid proteolysis upon expression in *Saccharomyces cerevisiae* by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are $Met^2 \rightarrow Ile^2$ and $Ile^{131} \rightarrow Leu^{131}$. It is not disclosed whether the contemplated neutralities were obtained for these two mutations.

WO 91/00350 discloses nonglycosylated hIL-3 analog proteins, for example, hIL-3 ($Pro^8 Asp^{15} Asp^{70}$), $Met^3$ rhuI-3 ($Pro^8 Asp^{15} Asp^{70}$); $Thr^4$ rhuL-3 ($Pro^8 Asp^{15} Asp^{70}$) and $Thr^6$ rhuIL-3 ($Pro^8 Asp^{15} Asp^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at $Met^3$, $Thr^4$, or $Thr^6$.

WO 91/12874 discloses cysteine added variants (CAVs) of IL-3 which have at least one Cys residue substituted for a naturally occurring amino acid residue.

SUMMARY OF THE INVENTION

The present invention relates to recombinant human interleukin-3 (hIL-3) variant or mutant proteins (muteins). These hIL-3 muteins contain amino acid substitutions and may also have amino acid deletions at either/or both the N- and C-termini. Preferably, these mutant polypeptides of the present invention contain four or more amino acids which differ from the amino acids found at the corresponding positions in the native hIL-3 polypeptide. The invention also relates to pharmaceutical compositions containing the hIL-3 muteins, DNA coding for the muteins, and methods for using the muteins. Additionally, the present invention relates to recombinant expression vectors comprising nucleotide sequences encoding the hIL-3 muteins, related microbial expression systems, and processes for making the hIL-3 muteins using the microbial expression systems.

The present invention includes mutants of hIL-3 in which from 1 to 14 amino acids have been deleted from the N-terminus and/or from 1 to 15 amino acids have been deleted from the C-terminus, and in which multiple amino acid substitutions have been made. Preferred muteins of the present invention are those in which amino acids 1 to 14 have been deleted from the N-terminus, amino acids 126 to 133 have been deleted from the C-terminus, and which also contain from about four to about twenty-six amino acid substitutions in the polypeptide sequence. These hIL-3 multiple mutation polypeptides may have biological activities similar to or better than hIL-3 and, in some cases, may also have an improved side effect profile, i.e., some muteins may have a better therapeutic index than native hIL-3. The present invention also provides muteins which may function as IL-3 antagonists or as discrete antigenic fragments for the production of antibodies useful in immunoassay and immunotherapy protocols. In addition to the use of the hIL-3 multiple mutation polypeptides of the present invention in vivo, it is envisioned that in vitro uses would include the ability to stimulate bone marrow and blood cell activation and growth before infusion into patients.

Antagonists of hIL-3 would be particularly useful in blocking the growth of certain cancer cells like AML, CML and certain types of B lymphoid cancers. Other conditions where antagonists would be useful include those in which certain blood cells are produced at abnormally high numbers or are being activated by endogenous ligands. Antagonists would effectively compete for ligands, presumably naturally occurring hemopoietins including and not limited to IL-3, GM-CSF and IL-5, which might trigger or augment the growth of cancer cells by virtue of their ability to bind to the IL-3 receptor complex while intrinsic activation properties of the ligand are diminished. IL-3, GM-CSF and/or IL-5 also play a role in certain asthmatic responses. An antagonist of the IL-3 receptor may have the utility in this disease by blocking receptor-mediated activation and recruitment of inflammatory cells.

BRIEF DESCRIPTION OF THE DRAWINGS

FIG. 1 is the human IL-3 gene for E. coli expression (pMON5873), encoding the polypeptide sequence of natural (wild type) human IL-3 [SEQ ID NO:128], plus an initiator methionine, as expressed in E. coli, with the amino acids numbered from the N-terminus of the natural hIL-3.

FIG. 2: ClaI to NsiI Replacement Fragment. FIG. 2 shows the nucleotide sequence of the replacement fragment used between the ClaI and NsiI sites of the hIL-3 gene. The codon choice used in the fragment corresponds to that found in highly expressed E. coli genes (Gouy and Gautier, 1982). Three new unique restriction sites, EcoRV, XhoI and PstI were introduced for the purpose of inserting synthetic gene fragments. The portion of the coding sequence shown encodes hIL-3 amino acids 20–70.

FIGS. 3A–3B show the nucleotide and amino acid sequence of the gene in pMON5873 with the sequence extending from NcoI through HindIII. The codon choices used to encode amino acids 1–14 and 107–133 correspond to that found in highly expressed E. coli genes.

FIG. 8 shows the DNA sequence and resulting amino acid sequence of the LamB signal peptide.

DETAILED DESCRIPTION OF THE INVENTION

Figure 4:
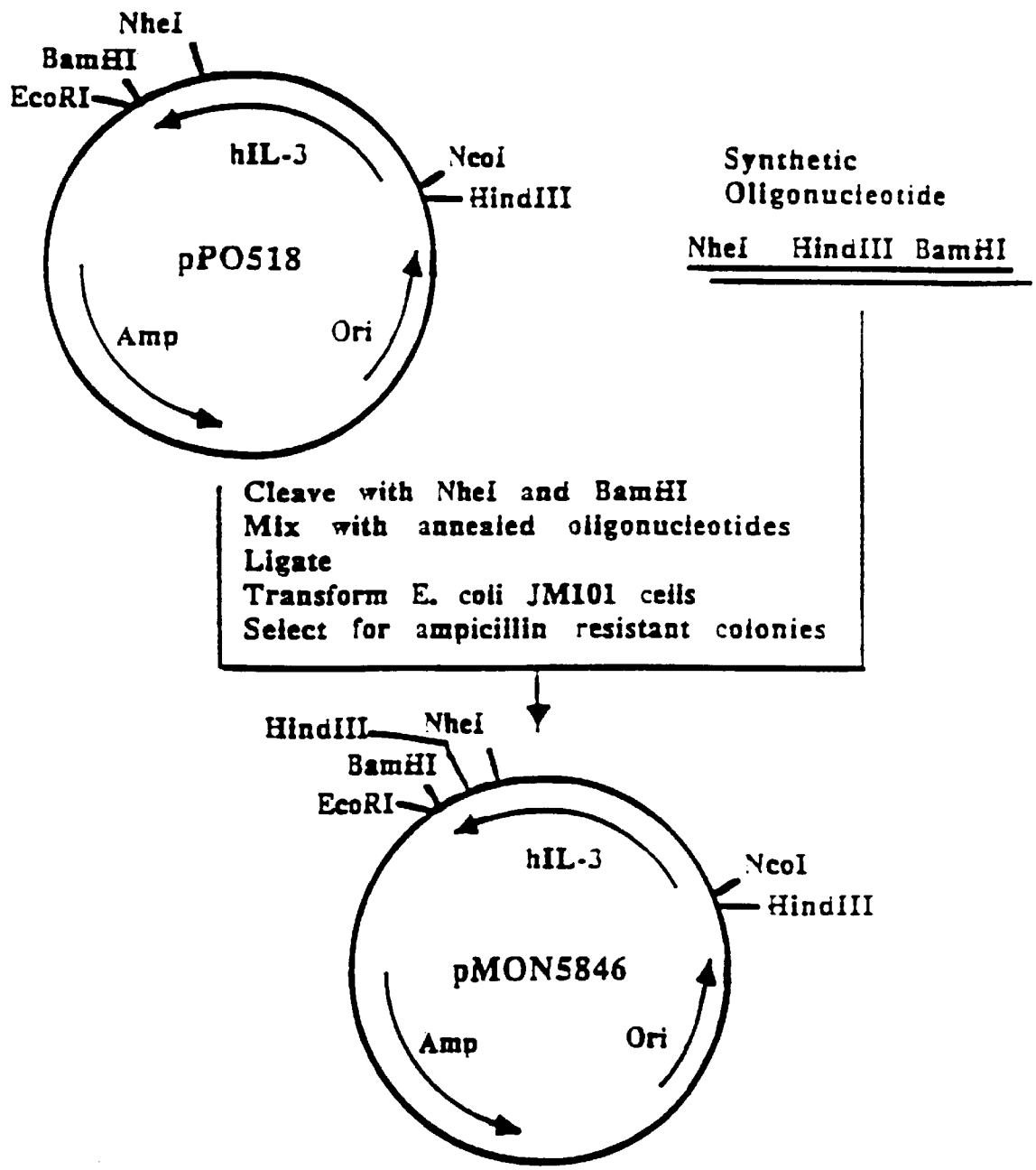
FIG. 4 shows the construction of the plasmid vector pMON5846 which encodes [Met-(1–133) hIL-3 ($Arg^{129}$)].

The present invention relates to muteins of human interleukin-3 (hIL-3) in which amino acid substitutions have been made at four or more positions in amino acid sequence of the polypeptide and to muteins which have substantially the same structure and substantially the same biological activity. Preferred muteins of the present invention are (15–125)hIL-3 deletion mutants which have deletions of amino acids 1 to 14 at the N-terminus and 126 to 133 at the C-terminus and which also have four or more amino acid substitutions in the polypeptide and muteins having substantially the same structure and substantially the same biological activity. Among the preferred muteins are those having twenty-six amino acid substitutions. As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

The present invention also includes the DNA sequences which code for the mutant polypeptides, DNA sequences which are substantially similar and perform substantially the same function, and DNA sequences which differ from the DNAs encoding the muteins of the invention only due to the degeneracy of the genetic code.

Included in the present invention are novel mutant human interleukin-3 polypeptides comprising a polypeptide having the amino acid sequence of native human interleukin-3 wherein amino acids 126 to 133 have been deleted from the C-terminus of the native human interleukin-3 polypeptide and amino acids 1 to 14 have been deleted from the N-terminus of the native human interleukin-3 polypeptide and, in addition, polypeptides also have four or more amino acid substitutions in the polypeptide sequence.

Also included in the present invention are the DNA sequences coding for the muteins of the present invention; the oligonucleotide intermediates used to construct the mutant DNAS; and the polypeptides coded for by these oligonucleotides. These polypeptides may be useful as antagonists or as antigenic fragments for the production of antibodies useful in immunoassay and immunotherapy protocols.

The mutant hIL-3 polypeptides of the present invention may also have methionine, alanine, or methionine-alanine residues inserted at the N-terminus.

The present invention includes human interleukin-3 mutant polypeptide Formula I:

```
Ala Pro Met Thr Gln Thr Thr Ser Leu Lys Thr Ser Trp Val Asn   [SEQ ID NO:15]
 1           5                  10                  15

Cys Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa
             50                  55                  60

Xaa Xaa Xaa Xaa Xaa Xaa Xaa Xaa Xaa Xaa Xaa Xaa Xaa Xaa Xaa
             65                  70                  75

Xaa Xaa Xaa Xaa Xaa Xaa Xaa Xaa Xaa Xaa Xaa Xaa Xaa Xaa Xaa
             80                  85                  90

Xaa Xaa Xaa Xaa Xaa Xaa Xaa Xaa Xaa Xaa Xaa Xaa Xaa Xaa Xaa
             95                 100                 105

Xaa Phe Xaa Xaa Xaa Xaa Xaa Xaa Xaa Xaa Xaa Xaa Xaa Xaa Xaa
            110                 115                 120

Xaa Xaa Xaa Gln Gln Thr Thr Leu Ser Leu Ala Ile Phe
            125                 130
``` wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Leu, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;

Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Serf Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Serf Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133) human interleukin-3.

Included in the present invention are human interleukin-3 mutant polypeptide of the Formula II:

```
Ala Pro Met Thr Gln Thr Thr Ser Leu Lys Thr Ser Trp Val Asn  [SEQ ID NO:16]
 1            5                    10                      15

Cys Xaa Xaa Xaa Xaa Glu Xaa Xaa Xaa Xaa Leu Xaa Xaa Xaa
            20                  25                      30

Xaa Xaa Xaa Xaa Xaa Xaa Xaa Xaa Xaa Leu Xaa Xaa Glu Xaa Xaa
                35                      40                      45

Xaa Xaa Leu Xaa Xaa Xaa Xaa Xaa Xaa Xaa Xaa Leu Xaa Xaa
                50                      55                  60

Xaa Xaa Xaa Xaa Xaa Xaa Xaa Xaa Xaa Xaa Xaa Xaa Xaa
                65                      70                  75

Xaa Xaa Leu Xaa Xaa Xaa Xaa Xaa Cys Xaa Pro Xaa Xaa Xaa Xaa
                80                      85                      90

Xaa Xaa Xaa Arg Xaa Xaa Xaa Xaa Xaa Xaa Xaa Asp Xaa Xaa
                95                      100                     105

Xaa Phe Xaa Xaa Lys Leu Xaa Phe Xaa Xaa Xaa Xaa Leu Xaa Xaa
                110                     115                     120

Xaa Xaa Xaa Gln Gln Thr Thr Leu Ser Leu Ala Ile Phe
                125                     130
``` wherein
Xaa at position 17 is Ser, Gly, Asp, Met, or Gln;
Xaa at position 18 is Asn, His, Leu, Ile, Phe, Arg, or Gln;
Xaa at position 19 is Met, Phe, Ile, Arg, or Ala;
Xaa at position 20 is Ile or Pro;
Xaa at position 21 is Asp or Glu;
Xaa at position 23 is Ile, Val, Ala, Leu, or Gly;
Xaa at position 24 is Ile, Val, Phe, or Leu;
Xaa at position 25 is Thr, His, Gly, Gln, Arg, Pro, or Ala;
Xaa at position 26 is His, Phe, Gly, Arg, or Ala;
Xaa at position 28 is Lys, Leu, Gln, Gly, Pro, or Val;
Xaa at position 29 is Gln, Asn, Leu, Arg, or Val;
Xaa at position 30 is Pro, His, Thr, Gly, or Gln;
Xaa at position 31 is Pro, Asp, Gly, Ala, Arg, Leu, or Gln;
Xaa at position 32 is Leu, Arg, Gln, Asn, Gly, Ala, or Glu;
Xaa at position 33 is Pro, Leu, Gln, Ala, or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 36 is Asp or Leu;
Xaa at position 37 is Phe, Ser, Pro, Trp, or Ile;
Xaa at position 38 is Asn or Ala;
Xaa at position 41 is Asn, Cys, Arg, His, Met, or Pro;
Xaa at position 42 is Gly, Asp, Ser, Cys, Ala, Asn, Ile, Leu, Met, Tyr, Val or Arg;
Xaa at position 44 is Asp or Glu;
Xaa at position 45 is Gln, Val, Met, Leu, Thr, Lys, Ala, Asn, Glu, Ser, or Trp;
Xaa at position 46 is Asp, Phe, Ser, Thr, Cys, Ala, Asn, Gln, Glu, His, Ile, Lys, Tyr, Val or Gly;
Xaa at position 47 is Ile, Val, or His;
Xaa at position 49 is Met, Asn, or Asp;
Xaa at position 50 is Glu, Thr, Ala, Asn, Ser or Asp;
Xaa at position 51 is Asn, Arg, Met, Pro, Ser, Thr, or His;
Xaa at position 52 is Asn or Gly;
Xaa at position 53 is Leu, Met, or Phe;
Xaa at position 54 is Arg, Ala, or Ser;
Xaa at position 55 is Arg, Thr, Val, Leu, or Gly;
Xaa at position 56 is Pro, Gly, Cys, Ser, Gln, Ala, Arg, Asn, Glu, His, Leu, Thr, Val or Lys;

Xaa at position 59 is Glu, Tyr, His, Leu, or Arg;
Xaa at position 60 is Ala, Ser, Asn, or Thr;
Xaa at position 61 is Phe or Ser;
Xaa at position 62 is Asn, Val, Pro, Thr, or Ile;
Xaa at position 63 is Arg, Tyr, Lys, Ser, His, or Val;
Xaa at position 64 is Ala or Asn;
Xaa at position 65 is Val, Thr, Leu, or Ser;
Xaa at position 66 is Lys, Ile, Arg, Val, Asn, Glu, or Ser;
Xaa at position 67 is Ser, Phe, Val, Gly, Asn, Ile, or His;
Xaa at position 68 is Leu, Val, Ile, Phe, or His;
Xaa at position 69 is Gln, Ala, Pro, Thr, Glu, Arg, or Gly;
Xaa at position 70 is Asn or Pro;
Xaa at position 71 is Ala, Met, Pro, Arg, Glu, Thr, or Gln;
Xaa at position 72 is Ser, Glu, Met, Ala, His, Asn, Arg, or Asp;
Xaa at position 73 is Ala, Glu, Asp, Leu, Ser, Gly, Thr, Arg, or Pro;
Xaa at position 74 is Ile or Met;
Xaa at position 75 is Glu, Gly, Asp, Ser, or Gln;
Xaa at position 76 is Ser, Val, Ala, Asn, Glu, Pro, Gly, or Asp;
Xaa at position 77 is Ile, Ser, or Leu;
Xaa at position 79 is Lys, Thr, Gly, Asn, Met, Arg, Ile, Gly, or Asp;
Xaa at position 80 is Asn, Val, Gly, Thr, Leu, Glu, or Arg;
Xaa at position 81 is Leu, or Val;
Xaa at position 82 is Leu, Gln, Trp, Arg, Asp, Ala, Asn, Glu, His, Met, Phe, Ser, Thr, Tyr or Val;
Xaa at position 83 is Pro, Ala, Thr, Trp, or Met;
Xaa at position 85 is Leu or Val;
Xaa at position 87 is Leu or Ser;
Xaa at position 88 is Ala, Arg, or Trp;
Xaa at position 89 is Thr, Asp, Glu, His, Asn, or Ser;
Xaa at position 90 is Ala, Asp, or Met;
Xaa at position 91 is Ala, Pro, Ser, Thr, Phe, Leu, or Asp;
Xaa at position 92 is Pro or Ser;
Xaa at position 93 is Thr, Asp, Ser, Pro, Ala, Leu, or Arg;
Xaa at position 95 is His, Pro, Arg, Val, Leu, Gly, Asn, Ile, Phe, Ser or Thr;
Xaa at position 96 is Pro or Tyr;
Xaa at position 97 is Ile, Val, or Ala;
Xaa at position 98 is His, Ile, Asn, Leu, Asp, Ala, Thr, Leu, Arg, Gln, Glu, lys, Met, Ser, Tyr, Val or Pro;

Xaa at position 99 is Ile, Leu, Val, or Phe;
Xaa at position 100 is Lys, Leu, His, Arg, Ile, Gln, Pro, or Ser;
Xaa at position 101 is Asp, Pro, Met, Lys, His, Thr, Val, Asn, Ile, Leu or Tyr;
Xaa at position 102 is Gly, Glu, Lys, or Ser;
Xaa at position 104 is Trp, Val, Tyr, Met, or Leu;
Xaa at position 105 is Asn, Pro, Ala, Phe, Ser, Trp, Gln, Tyr, Leu, Lys, Ile, Asp, or His;
Xaa at position 106 is Glu, Ser, Ala, or Gly;
Xaa at position 108 is Arg, Ala, Gln, Ser or Lys;
Xaa at position 109 is Arg, Thr, Glu, Leu, Ser, or Gly;
Xaa at position 112 is Thr, Val, Gln, Glu, His, or Ser;
Xaa at position 114 is Tyr or Trp;
Xaa at position 115 is Leu or Ala;
Xaa at position 116 is Lys, Thr, Met, Val, Trp, Ser, Leu, Ala, Asn, Gln, His, Met, Phe, Tyr or Ile;
Xaa at position 117 is Thr, Ser, or Asn;
Xaa at position 119 is Glu, Ser, Pro, Leu, Thr, or Tyr;
Xaa at position 120 is Asn, Pro, Leu, His, Val, or Gln;
Xaa at position 121 is Ala, Serf Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133) human interleukin-3.

Included in the present invention are human interleukin-3 mutant polypeptide of the Formula III:

Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg or Lys;
Xaa at position 64 is Ala or Asn;
Xaa at position 65 is Val or Thr;
Xaa at position 66 is Lys or Arg;
Xaa at position 67 is Ser. Phe, or His;
Xaa at position 68 is Leu, Ile, Phe, or His;
Xaa at position 69 is Gln, Ala, Pro, Thr, Glu, Arg, or Gly;

```
Ala Pro Met Thr Gln Thr Thr Ser Leu Lys Thr Ser Trp Val Asn [SEQ ID NO:17]
 1               5                  10                  15

Cys Xaa Xaa Xaa Ile Xaa Glu Xaa Xaa Xaa Xaa Leu Lys Xaa Xaa
                20                  25                  30

Xaa Xaa Xaa Xaa Xaa Asp Xaa Xaa Asn Leu Asn Xaa Glu Xaa Xaa
                35                  40                  45

Xaa Ile Leu Met Xaa Xaa Asn Leu Xaa Xaa Xaa Asn Leu Glu Xaa
                50                  55                  60

Phe Xaa Xaa Xaa Xaa Xaa Xaa Xaa Xaa Asn Xaa Xaa Xaa Ile Glu
                65                  70                  75

Xaa Xaa Leu Xaa Xaa Leu Xaa Xaa Cys Xaa Pro Xaa Xaa Thr Ala
                80                  85                  90

Xaa Pro Xaa Arg Xaa Xaa Xaa Xaa Xaa Xaa Xaa Gly Asp Xaa Xaa
                95                 100                 105

Xaa Phe Xaa Xaa Lys Leu Xaa Phe Xaa Xaa Xaa Xaa Leu Glu Xaa
               110                 115                 120

Xaa Xaa Xaa Gln Gln Thr Thr Leu Ser Leu Ala Ile Phe
               125                 130
``` wherein

Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;

Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, Gly, or Asp;

Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Arg, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp, Pro, Met, Lys, His, Thr, Pro, Asn, Ile, Leu or Tyr;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys, Thr, Val, Trp, Ser, Ala, His, Met, Phe, Tyr or Ile;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 35 of the amino acids designated by Xaa are different from the corresponding amino acids of native (1–133)human interleukin-3.

Included in the present invention are human interleukin-3 mutant polypeptide of the Formula IV:

```
Ala Pro Met Thr Gln Thr Thr Ser Leu Lys Thr Ser Trp Val Asn  [SEQ ID NO:18]
 1           5               10                  15
Cys Xaa Xaa Met Ile Asp Glu Xaa Ile Xaa Xaa Leu Lys Xaa Xaa
             20              25                  30
Pro Xaa Pro Xaa Xaa Asp Phe Xaa Asn Leu Asn Xaa Glu Asp Xaa
             35              40                  45
Xaa Ile Leu Met Xaa Xaa Asn Leu Arg Xaa Xaa Asn Leu Glu Ala
             50              55                  60
Phe Xaa Arg Xaa Xaa Lys Xaa Xaa Xaa Asn Ala Ser Ala Ile Glu
             65              70                  75
Xaa Xaa Leu Xaa Xaa Leu Xaa Pro Cys Leu Pro Xaa Xaa Thr Ala
             80              85                  90
Xaa Pro Xaa Arg Xaa Pro Ile Xaa Xaa Xaa Xaa Gly Asp Trp Xaa
             95             100                 105
Glu Phe Xaa Xaa Lys Leu Xaa Phe Tyr Leu Xaa Xaa Leu Glu Xaa
            110             115                 120
Xaa Xaa Xaa Gln Gln Thr Thr Leu Ser Leu Ala Ile Phe
            125             130
``` wherein
Xaa at position 17 is Ser, Gly, Asp, or Gln;
Xaa at position 18 is Asn, His, or Ile;
Xaa at position 23 is Ile, Ala, Leu, or Gly;
Xaa at position 25 is Thr, His, or Gln;
Xaa at position 26 is His or Ala;
Xaa at position 29 is Gln or Asn;
Xaa at position 30 is Pro or Gly;
Xaa at position 32 is Leu, Arg, Asn, or Ala;
Xaa at position 34 is Leu, Val, Ser, Ala, Arg, Gln, Glu, Ile, Phe, Thr, or Met;
Xaa at position 35 is Leu, Ala, Asn, or Pro;
Xaa at position 38 is Asn or Ala;
Xaa at position 42 is Gly, Asp, Ser, Ala, Asn, Ile, Leu, Met, Tyr or Arg;
Xaa at position 45 is Gln, Val, Met, Leu, Ala, Asn, Glu, or Lys;
Xaa at position 46 is Asp, Phe, Ser, Gln, Glu, His, Val or Thr;
Xaa at position 50 is Glu Asn, Ser or Asp;
Xaa at position 51 is Asn, Arg, Pro, Thr, or His;
Xaa at position 55 is Arg, Leu, or Gly;
Xaa at position 56 is Pro, Gly, Ser, Ala, Asn, Val, Leu or Gln;
Xaa at position 62 is Asn, Pro, or Thr;
Xaa at position 64 is Ala or Asn;
Xaa at position 65 is Val or Thr;
Xaa at position 67 is Ser or Phe;
Xaa at position 68 is Leu or Phe;
Xaa at position 69 is Gln, Ala, Glu, or Arg;
Xaa at position 76 is Ser, Val, Asn, Pro, or Gly;
Xaa at position 77 is Ile or Leu;
Xaa at position 79 is Lys, Asn, Met, Arg, Ile, or Gly;
Xaa at position 80 is Asn, Gly, Glu, or Arg;
Xaa at position 82 is Leu, Gln, Trp, Arg, Asp, Asn, Glu, His, Met, Phe, Ser, Thr, Tyr or Val;
Xaa at position 87 is Leu or Ser;
Xaa at position 88 is Ala or Trp;

Xaa at position 91 is Ala or Pro;
Xaa at position 93 is Thr, Asp, or Ala;
Xaa at position 95 is His, Pro, Arg, Val, Gly, Asn, Ser or Thr;
Xaa at position 98 is His, Ile, Asn, Ala, Thr, Gln, Glu, Lys, Met, Ser, Tyr, Val or Leu;
Xaa at position 99 is Ile or Leu;
Xaa at position 100 is Lys or Arg;
Xaa at position 101 is Asp, Pro, Met, Lys, Thr, His, Pro, Asn, Ile, Leu or Tyr;
Xaa at position 105 is Asn, Pro, Ser, Ile or Asp;
Xaa at position 108 is Arg, Ala, or Ser;
Xaa at position 109 is Arg, Thr, Glu, Leu, or Ser;
Xaa at position 112 is Thr or Gln;
Xaa at position 116 is Lys, Val, Trp, Ala, His, Phe, Tyr or Ile;
Xaa at position 117 is Thr or Ser;
Xaa at position 120 is Asn, Pro, Leu, His, Val, or Gln;
Xaa at position 121 is Ala, Ser, Ile, Pro, or Asp;
Xaa at position 122 is Gln, Met, Trp, Phe, Pro, His, Ile, or Tyr;
Xaa at position 123 is Ala, Met, Glu, Ser, or Leu;
and which can additionally have Met- preceding the amino acid in position 1; and wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133)human interleukin-3.

Included in the present invention are (15–125)human interleukin-3 mutant polypeptides of the Formula V:

Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;

```
Asn Cys Xaa Xaa Xaa Xaa Xaa Xaa Xaa Xaa Xaa Xaa Xaa Xaa Xaa  [SEQ ID NO:19]
 1       5              10                      15

Xaa Xaa Xaa Xaa Xaa Xaa Xaa Xaa Xaa Asn Xaa Xaa Xaa Xaa Xaa
                20                      25                      30

Xaa Xaa Xaa Xaa Xaa Xaa Xaa Xaa Xaa Xaa Xaa Xaa Xaa Xaa Xaa
                35                      40                      45

Xaa Xaa Xaa Xaa Xaa Xaa Xaa Xaa Xaa Xaa Xaa Xaa Xaa Xaa Xaa
                50                      55                      60

Xaa Xaa Xaa Xaa Xaa Xaa Xaa Xaa Xaa Xaa Xaa Xaa Xaa Xaa Xaa
                65                      70                      75

Xaa Xaa Xaa Xaa Xaa Xaa Xaa Xaa Xaa Xaa Xaa Xaa Xaa Xaa Xaa
                80                      85                      90

Xaa Xaa Phe Xaa Xaa Xaa Xaa Xaa Xaa Xaa Xaa Xaa Xaa Xaa Xaa
                95                      100                     105

Xaa Xaa Xaa Xaa Gln Gln
                110
``` wherein
Xaa at position 3 is Ser. Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Leu, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;

Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, Met, or;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;

Xaa at position 48 is Asn, His, Val, Arg, Pro, Thr, Asp, or Ile;
Xaa at position 49 is Arg, Tyr, Trp, Lys, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;

Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Arg, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
and which can additionally have Met- or Met-Ala- preceding the amino acid in position 1; and wherein from 4 to 44 of the amino acids designated by Xaa are different from the corresponding native amino acids of (1–133) human interleukin-3; or a polypeptide having substantially the same structure and substantially the same biological activity.

Included in the present invention are (15–125)human interleukin-3 mutant polypeptides of the Formula VI:

```
Asn Cys Xaa Xaa Xaa Xaa Xaa Glu Xaa Xaa Xaa Xaa Leu Xaa Xaa [SEQ ID NO:20]
 1           5                   10                  15

Xaa Xaa Xaa Xaa Xaa Xaa Xaa Xaa Xaa Asn Leu Xaa Xaa Glu Xaa
                 20                  25                  30

Xaa Xaa Xaa Leu Xaa Xaa Xaa Xaa Xaa Xaa Xaa Asn Leu Xaa
                 35                  40                  45

Xaa Xaa Xaa Xaa Xaa Xaa Xaa Xaa Xaa Xaa Xaa Xaa Xaa Xaa Xaa
                 50                  55                  60

Xaa Xaa Xaa Leu Xaa Xaa Xaa Xaa Xaa Cys Xaa Pro Xaa Xaa Xaa
                 65                  70                  75
```

```
-continued

Xaa Xaa Xaa Xaa Arg Xaa Xaa Xaa Xaa Xaa Xaa Xaa Xaa Asp Xaa
                80                  85                      90

Xaa Xaa Phe Xaa Xaa Lys Leu Xaa Phe Xaa Xaa Xaa Xaa Leu Xaa
                95                  100                     105

Xaa Xaa Xaa Xaa Gln Gln
                110
``` wherein

Xaa at position 3 is Ser, Gly, Asp, Met, or Gln;
Xaa at position 4 is Asn, His, Leu, Ile, Phe, Arg, or Gln;
Xaa at position 5 is Met, Phe, Ile, Arg, or Ala;
Xaa at position 6 is lie or Pro;
Xaa at position 7 is Asp, or Glu;
Xaa at position 9 is Ile, Val, Ala, Leu, or Gly;
Xaa at position 10 is Ile, Val, Phe, or Leu;
Xaa at position 11 is Thr, His, Gly, Gln, Arg, Pro, or Ala;
Xaa at position 12 is His, Phe, Gly, Arg, or Ala;
Xaa at position 14 is Lys, Leu, Gln, Gly, Pro, or Val;
Xaa at position 15 is Gln, Asn, Leu, Arg, or Val;
Xaa at position 16 is Pro, His, Thr, Gly, or Gln:
Xaa at position 17 is Pro, Asp, Gly, Ala, Arg, Leu, or Gln;
Xaa at position 18 is Leu, Arg, Gln, Asn, Gly, Ala, or Glu;
Xaa at position 19 is Pro, Leu, Gln, Ala, or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 22 is Asp or Leu;
Xaa at position 23 is Phe, Ser, Pro, Trp, or Ile;
Xaa at position 24 is Asn or Ala;
Xaa at position 27 is Asn, Cys, Arg, His, Met, or Pro;
Xaa at position 28 is Gly, Asp, Ser, Cys, Ala, Asn, Ile, Leu, Met, Tyr, or Arg;
Xaa at position 30 is Asp, or Glu;
Xaa at position 31 is Gln, Val, Met, Leu, Thr, Lys, Ala, Asn Glu, Ser or Trp;
Xaa at position 32 is Asp, Phe, Ser, Thr, Cys, Ala, Asn, Gln, Glu, His, Ile, Lys, Tyr, Val or Gly;
Xaa at position 33 is Ile, Val, or His;
Xaa at position 35 is Met, Asn, or Asp;
Xaa at position 36 is Glu, Thr, Ala, Asn, Ser or Asp;
Xaa at position 37 is Asn, Arg, Met, Pro, Ser, Thr, or His;
Xaa at position 38 is Asn or Gly;
Xaa at position 39 is Leu, Met, or Phe;
Xaa at position 40 is Arg, Ala or Ser;
Xaa at position 41 is Arg, Thr, Val, Leu, or Gly;
Xaa at position 42 is Pro, Gly, Cys, Ser, Gln, Ala, Arg, Asn, Glu, His, Leu, Thr, Val or Lys;
Xaa at position 45 is Glu, Tyr, His, Leu, or Arg;
Xaa at position 46 is Ala, Ser, Asn, or Thr;
Xaa at position 47 is Phe or Ser;
Xaa at position 48.is Asn, Val, Pro, Thr, or Ile;
Xaa at position 49 is Arg, Tyr, Lys, Ser, His, or Val;
Xaa at position 50 is Ala or Asn;
Xaa at position 51 is Val, Thr, Leu, or Ser;
Xaa at position 52 is Lys, Ile, Arg, Val, Asn, Glu, or Ser;
Xaa at position 53 is Ser, Phe, Val, Gly, Asn, Ile, or His;
Xaa at position 54 is Leu, Val, Ile, Phe, or His;
Xaa at position 55 is Gln, Ala, Pro, Thr, Glu, Arg, or Gly;
Xaa at position 56 is Asn or Pro;
Xaa at position 57 is Ala, Met, Pro, Arg, Glu, Thr, or Gln;
Xaa at position 58 is Ser, Glu, Met, Ala, His, Asn, Arg, or Asp;
Xaa at position 59 is Ala, Glu, Asp, Leu, Ser, Gly, Thr, Arg, or Pro;

Xaa at position 60 is Ile or Met;
Xaa at position 61 is Glu, Gly, Asp, Ser, or Gln;
Xaa at position 62 is Ser, Val, Ala, Asn, Glu, Pro, Gly, or Asp;
Xaa at position 63 is Ile, Ser, or Leu;
Xaa at position 65 is Lys, Thr, Gly, Asn, Met, Arg, Ile, or Asp;
Xaa at position 66 is Asn, Val, Gly, Thr, Leu, Glu, or Arg;
Xaa at position 67 is Leu, or Val;
Xaa at position 68 is Leu, Gln, Trp, Arg, Asp, Ala, Asn, Glu, His, Met, Phe, Ser, Thr, Tyr or Val;
Xaa at position 69 is Pro, Ala, Thr, Trp, or Met;
Xaa at position 71 is Leu or Val;
Xaa at position 73 is Leu or Ser;
Xaa at position 74 is Ala, Arg, or Trp;
Xaa at position 75 is Thr, Asp, Glu, His, Asn, or Ser;
Xaa at position 76 is Ala, Asp, or Met;
Xaa at position 77 is Ala, Pro, Ser, Thr, Phe, Leu, or Asp;
Xaa at position 78 is Pro or Ser;
Xaa at position 79 is Thr, Asp, Ser, Pro, Ala, Leu, or Arg;
Xaa at position 81 is His, Pro, Arg, Val, Leu, Gly, Asn, Ile, Phe, Ser or Thr;
Xaa at position 82 is Pro or Tyr;
Xaa at position 83 is Ile, Val, or Ala;
Xaa at position 84 is His, Ile, Asn, Leu, Asp, Ala, Thr, Arg, Gln, Glu, Lys, Met, Ser, Tyr, Val or Pro;
Xaa at position 85 is Ile, Leu, Val, or Phe;
Xaa at position 86 is Lys, Leu, His, Arg, Ile, Gln, Pro or Ser;
Xaa at position 87 is Asp, Pro, Met, Lys, His, Thr, Val, Asn, Ile, Leu or Tyr;
Xaa at position 88 is Gly, Glu, Lys, or Ser;
Xaa at position 90 is Trp, Val, Tyr, Met, or Leu;
Xaa at position 91 is Asn, Pro, Ala, Phe, Ser, Trp, Gln, Tyr, Leu, Lys, Ile, Asp, or His;
Xaa at position 92 is Glu, Ser, Ala, or Gly;
Xaa at position 94 is Arg, Ala, Gln, Ser or Lys;
Xaa at position 95 is Arg, Thr, Glu, Leu, Ser, or Gly;
Xaa at position 98 is Thr, Val, Gln, Glu, His, or Ser;
Xaa at position 100 is Tyr or Trp;
Xaa at position 101 is Leu or Ala;
Xaa at position 102 is Lys, Thr, Met, Val, Trp, Ser, Leu, Ala, Asn, Gln, His, Met, Phe, Tyr or Ile;
Xaa at position 103 is Thr, Ser, or Asn;
Xaa at position 105 is Glu, Ser, Pro, Leu, Thr, or Tyr;
Xaa at position 106 is Asn, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
and which can additionally have Met- or Met-Ala- preceding the amino acid in position 1; and wherein from 4 to 44 of the amino acids designated by Xaa are different from the corresponding amino acids of native (1–133) human interleukin-3; or a polypeptide having substantially the same structure and substantially the same biological activity.

Included in the present invention are (15–125)human interleukin-3 mutant polypeptides of the Formula VII:

```
Asn Cys Xaa Xaa Xaa Ile Xaa Glu Xaa Xaa Xaa Xaa Leu Lys Xaa [SEQ ID NO:21]
 1           5               10                  15

Xaa Xaa Xaa Xaa Xaa Xaa Asp Xaa Xaa Asn Leu Asn Xaa Glu Xaa
            20                  25                  30

Xaa Xaa Ile Leu Met Xaa Xaa Asn Leu Xaa Xaa Xaa Asn Leu Glu
            35                  40                  45

Xaa Phe Xaa Xaa Xaa Xaa Xaa Xaa Xaa Asn Xaa Xaa Xaa Ile
            50                  55                  60

Glu Xaa Xaa Leu Xaa Xaa Leu Xaa Xaa Cys Xa

Included in the present invention are (15–125)human interleukin-3 mutant polypeptides of the Formula VIII:

[SEQ ID NO:22]

```
Asn Cys Xaa Xaa Met Ile Asp Glu Xaa Ile Xaa Xaa Leu Lys Xaa
 1           5                  10                  15

Xaa Pro Xaa Pro Xaa Xaa Asp Phe Xaa Asn Leu Asn Xaa Glu Asp
                 20                  25                  30

Xaa Xaa Ile Leu Met Xaa Xaa Asn Leu Arg Xaa Xaa Asn Leu Glu
                 35                  40                  45

Ala Phe Xaa Arg Xaa Xaa Lys Xaa Xaa Xaa Asn Ala Ser Ala Ile
                 50                  55                  60

Glu Xaa Xaa Leu Xaa Xaa Leu Xaa Pro Cys Leu Pro Xaa Xaa Thr
                 65                  70                  75

Ala Xaa Pro Xaa Arg Xaa Pro Ile Xaa Xaa Xaa Xaa Gly Asp Trp
                 80                  85                  90

Xaa Glu Phe Xaa Xaa Lys Leu Xaa Phe Tyr Leu Xaa Xaa Leu Glu
                 95                 100                 105

Xaa Xaa Xaa Xaa Gln Gln
                110
``` wherein
Xaa at position 3 is Ser. Gly, Asp, or Gln;
Xaa at position 4 is Asn, His, or Ile;
Xaa at position 9 is Ile, Ala, Leu, or Gly;
Xaa at position 11 is Thr, His, or Gln;
Xaa at position 12 is His or Ala;
Xaa at position 15 is Gln or Asn;
Xaa at position 16 is Pro or Gly;
Xaa at position 18 is Leu, Arg, Asn, or Ala;
Xaa at position 20 is Leu, Val, Ser, Ala, Arg, Gln, Glu, Ile, Phe, Thr or Met;
Xaa at position 21 is Leu, Ala, Asn, or Pro;
Xaa at position 24 is Asn or Ala;
Xaa at position 28 is Gly, Asp, Ser, Ala, Asn, Ile, Leu, Met, Tyr or Arg;
Xaa at position 31 is Gln, Val, Met, Leu, Ala, Asn, Glu or Lys;
Xaa at position 32 is Asp, Phe, Ser, Ala, Gln, Glu, His, Val or Thr;
Xaa at position 36 is Glu, Asn, Ser or Asp;
Xaa at position 37 is Asn, Arg, Pro, Thr, or His;
Xaa at position 41 is Arg, Leu, or Gly;
Xaa at position 42 is Pro, Gly, Ser, Ala, Asn, Val, Leu or Gln;
Xaa at position 48 is Asn, Pro, or Thr;
Xaa at position 50 is Ala or Asn;
Xaa at position 51 is Val or Thr;
Xaa at position 53 is Ser or Phe;
Xaa at position 54 is Leu or Phe;
Xaa at position 55 is Gln, Ala, Glu, or Arg;
Xaa at position 62 is Ser, Val, Asn, Pro, or Gly;
Xaa at position 63 is Ile or Leu;
Xaa at position 65 is Lys, Asn, Met, Arg, Ile, or Gly;
Xaa at position 66 is Asn, Gly, Glu, or Arg;
Xaa at position 68 is Leu, Gln, Trp, Arg, Asp, Asn, Glu, His, Met, Phe, Ser, Thr, Tyr or Val;
Xaa at position 73 is Leu or Ser;
Xaa at position 74 is Ala or Trp;
Xaa at position 77 is Ala or Pro;
Xaa at position 79 is Thr, Asp, or Ala;
Xaa at position 81 is His, Pro, Arg, Val, Gly, Asn, Ser or Thr;
Xaa at position 84 is His, Ile, Asn, Ala, Thr, Arg, Gln, Glu, Lys, Met, Ser, Tyr, Val or Leu;
Xaa at position 85 is Ile or Leu;
Xaa at position 86 is Lys or Arg;
Xaa at position 87 is Asp, Pro, Met, Lys, His, Pro, Asn, Ile, Leu or Tyr;
Xaa at position 91 is Asn, Pro, Ser, Ile or Asp;
Xaa at position 94 is Arg, Ala, or Ser;
Xaa at position 95 is Arg, Thr, Glu, Leu, or Ser;
Xaa at position 98 is Thr or Gln;
Xaa at position 102 is Lys, Val, Trp, or Ile;
Xaa at position 103 is Thr, Ala, His, Phe, Tyr or Ser;
Xaa at position 106 is Asn, Pro, Leu, His, Val, or Gln;
Xaa at position 107 is Ala, Ser, Ile, Pro, or Asp;
Xaa at position 108 is Gln, Met, Trp, Phe, Pro, His, Ile, or Tyr;
Xaa at position 109 is Ala, Met, Glu, Ser, or Leu;
and which can additionally have Met- or Met-Ala- preceding the amino acid in position 1; and wherein from 4 to 26 of the amino acids designated by Xaa are different from the corresponding amino acids of native (1–133)human interleukin-3; or a polypeptide having substantially the same structure and substantially the same biological activity.

The present invention includes polypeptides of the formula

[SEQ ID NO:129]

```
        1                   5                  10
(Met)_m-Ala Pro Met Thr Gln Thr Thr Ser Leu Lys Thr 15                  20
Ser Trp Val Asn Cys Ser Xaa Xaa Xaa Asp Glu Xaa Ile 25                  30                  35
Xaa His Leu Lys Xaa Pro Pro Xaa Pro Xaa Leu Asp Xaa 40                  45                  50
Xaa Asn Leu Asn Xaa Glu Asp Xaa Xaa Ile Leu Xaa Xaa 55                  60
Xaa Asn Leu Arg Xaa Xaa Asn Leu Xaa Xaa Phe Xaa Xaa 65                  70                  75
Ala Xaa Lys Xaa Leu Xaa Asn Ala Ser Xaa Ile Glu Xaa 80                  85
Ile Leu Xaa Asn Leu Xaa Pro Cys Xaa Pro Xaa Xaa Thr
```

```
                     -continued
90                       95                     100
Ala Xaa Pro Xaa Arg Xaa Pro Ile Xaa Ile Xaa Xaa Gly 105                     110                 115
Asp Trp Xaa Glu Phe Arg Xaa Lys Leu Xaa Phe Tyr Leu 120                     125
Xaa Xaa Leu Glu Xaa Ala Gln Xaa Gln Gln Thr Thr Leu 130
Ser Leu Ala Ile Phe
``` wherein m is 0 or 1; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; with the proviso that from four to twenty-six of the amino acids designated by Xaa are different from the corresponding amino acids of native human interleukin-3; or a polypeptide having substantially the same structure and substantially the same biological activity.

Preferred polypeptides of the present invention are those of the formula

```
                                         [SEQ ID NO:130]
        1                   5                    10
(Met_m-Ala_n)_p-Asn Cys Ser Xaa Xaa Xaa Asp Glu Xaa Ile 15                      20
Xaa His Leu Lys Xaa Pro Pro Xaa Pro Xaa Leu Asp Xaa 25                      30                  35
Xaa Asn Leu Asn Xaa Glu Asp Xaa Xaa Ile Leu Xaa Xaa 40                      45
Xaa Asn Leu Arg Xaa Xaa Asn Leu Xaa Xaa Phe Xaa Xaa 50                  55                  60
Ala Xaa Lys Xaa Leu Xaa Asn Ala Ser Xaa Ile Glu Xaa 65                      70                  75
Ile Leu Xaa Asn Xaa Xaa Pro Cys Xaa Pro Xaa Xaa Thr 80                      85
Ala Xaa Pro Xaa Arg Xaa Pro Ile Xaa Ile Xaa Xaa Gly 90                      95                 100
Asp Trp Xaa Glu Phe Arg Xaa Lys Leu Xaa Phe Tyr Leu 105                     110
Xaa Xaa Leu Glu Xaa Ala Gln Xaa Gln Gln
``` wherein m is 0 or 1; n is 0 or 1; p is 0 or 1; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser;

Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser;

Xaa at position 67 is Leu, Glu, or Val; Xaa at position 68 is Leu, Glu, Val or Trp; Xaa at position 71 is Leu or Val;

Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; with the proviso that from four to twenty-six of the amino acids designated by Xaa are different from the corresponding amino acids of native (15–125)human interleukin-3; or a polypeptide having substantially the same structure and substantially the same biological activity.

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence", refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. (1990); Ganser, A, et al. (1990); Falk, S., et al. (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Many or all of these biological activities of hIL-3 involve signal transduction and high affinity receptor binding. Mutant polypeptides of the present invention may exhibit useful properties such as having similar or greater biological activity when compared to native hIL-3 or by having improved half-life or decreased adverse side effects, or a combination of these properties. They may also be useful as antagonists. hIL-3 mutant polypeptides which have little or no activity when compared to native hIL-3 may still be useful as antagonists, as antigens for the production of antibodies for use in immunology or immunotherapy, as genetic probes or as intermediates used to construct other useful hIL-3 muteins. Since hIL-3 functions by binding to its receptor(s) and triggering second messages resulting in competent signal transduction, hIL-3 muteins of this invention may be useful in helping to determine which specific amino acid sequences are responsible for these activities.

The novel hIL-3 mutant polypeptides of the present invention will preferably have at least one biological property of human IL-3 or of an IL-3-like growth factor and may have more than one IL-3-like biological property, or an improved property, or a reduction in an undesirable biological property of human IL-3. Some mutant polypeptides of the present invention may also exhibit an improved side effect profile. For example, they may exhibit a decrease in leukotriene release or histamine release when compared to native hIL-3 or (15–125) hIL-3. Such hIL-3 or hIL-3-like biological properties may include one or more of the following biological characteristics and in vivo and in vitro activities.

One such property is the support of the growth and differentiation of progenitor cells committed to erythroid, lymphoid, and myeloid lineages. For example, in a standard human bone marrow assay, an IL-3-like biological property is the stimulation of granulocytic type colonies, megakaryocytic type colonies, monocyte/macrophage type colonies, and erythroid bursts. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Human IL-3 also has some biological activities which may in some cases be undesirable, for example the ability to stimulate leukotriene release and the ability to stimulate increased histamine synthesis in spleen and bone marrow cultures and in vivo.

Biological activity of hIL-3 and hIL-3 mutant proteins of the present invention is determined by DNA synthesis by human acute myelogenous leukemia cells (AML). The factor-dependent cell line AML 193 was adapted for use in testing biological activity.

One object of the present invention is to provide hIL-3 muteins and hIL-3 deletion muteins with four or more amino acid substitutions in the polypeptide sequence which have similar or improved biological activity in relation to native hIL-3 or native (15–125)hIL-3.

The present invention includes mutant polypeptides comprising minimally amino acids residues 15 to 118 of hIL-3 with or without additional amino acid extensions to the N-terminus and/or C-terminus which further contain four or more amino acid substitutions in the amino acid sequence of the polypeptide. It has been found that the (15–125)hIL-3 mutant is more soluble than is hIL-3 when expressed in the cytoplasm of E. coli, and the protein is secreted to the periplasm in E. coli at higher levels compared to native hIL-3.

When expressed in the E. coli cytoplasm, the above-mentioned mutant hIL-3 polypeptides of the present invention may also be constructed with Met-Ala- at the N-terminus so that upon expression the Met is cleaved off leaving Ala at the N-terminus. These mutant hIL-3 polypeptides may also be expressed in E. coli by fusing a signal peptide to the N-terminus. This signal peptide is cleaved from the polypeptide as part of the secretion process. Secretion in E. coli can be used to obtain the correct amino acid at the N-terminus (e.g., $Asn^{15}$ in the (15–125) hIL-3 polypeptide) due to the precise nature of the signal peptidase. This is in contrast to the heterogeneity often observed at the N-terminus of proteins expressed in the cytoplasm in E. coli.

The hIL-3 mutant polypeptides of the present invention may have hIL-3 or hIL-3-like activity. For example, they may possess one or more of the biological activities of native hIL-3 and may be useful in stimulating the production of hematopoietic cells by human or primate progenitor cells. The hIL-3 muteins of the present invention and pharmaceutical compositions containing them may be useful in the treatment of conditions in which hematopoietic cell populations have been reduced or destroyed due to disease or to treatments such as radiation or chemotherapy.

hIL-3 muteins of the present invention may also be useful as antagonists which block the hIL-3 receptor by binding specifically to it and preventing binding of the agonist.

One potential advantage of the (15–125) hIL-3 muteins of the present invention, particularly those which retain activity similar to or better than that of native hIL-3, is that it may be possible to use a smaller amount of the biologically active mutein to produce the desired therapeutic effect. This may make it possible to reduce the number of treatments necessary to produce the desired therapeutic effect. The use of smaller amounts may also reduce the possibility of any potential antigenic effects or other possible undesirable side effects. For example, if a desired therapeutic effect can be achieved with a smaller amount of polypeptide it may be possible to reduce or eliminate side effects associated with the administration of native IL-3 such as the stimulation of leukotriene and/or histamine release. The hIL-3 muteins of the present invention may also be useful in the activation of stem cells or progenitors which have low receptor numbers. Pharmaceutical compositions containing (15–125) hIL-3 muteins of the present invention can be administered parenterally, intravenously, or subcutaneously.

As another aspect of the present invention, there is provided a novel method for producing the novel family of human IL-3 muteins. The method of the present invention involves culturing a suitable cell or cell line, which has been transformed with a vector containing a DNA sequence coding for expression of a novel hIL-3 mutant polypeptide. Suitable cells or cell lines may be bacterial cells. For example, the various strains of E. coli are well-known as host cells in the field of biotechnology. Examples of such strains include E. coli strains JM101 (Yanish-Perron, et al. (1985)] and MON105 [Obukowicz, et al. (1992)]. Various strains of B. subtilis may also be employed in this method. Many strains of yeast cells known to those skilled in the art are also available as host cells for expression of the polypeptides of the present invention.

Also suitable for use in the present invention are mammalian cells, such as Chinese hamster ovary cells (CHO).

General methods for expression of foreign genes in mammalian cells are reviewed in: Kaufman, R. J. (1987) High level production of proteins in mammalian cells, in *Genetic Engineering, Principles and Methods*, Vol. 9, J. K. Setlow, editor, Plenum Press, New York. An expression vector is constructed in which a strong promoter capable of functioning in mammalian cells drives transcription of a eukaryotic secretion signal peptide coding region, which is translationally fused to the coding region for the hIL-3 variant. For example, plasmids such as pcDNA I/Neo, pRc/RSV, and pRc/CMV (obtained from Invitrogen Corp., San Diego, Calif.) can be used. The eukaryotic secretion signal peptide coding region can be from the hIL-3 gene itself or it can be from another secreted mammalian protein (Bayne, M. L. et al. (1987) *Proc. Natl. Acad. Sci. USA* 84, 2638–2642). After construction of the vector containing the hIL-3 variant gene, the vector DNA is transfected into mammalian cells. Such cells can be, for example, the COS7, HeLa, BHK, CHO, or mouse L lines. The cells can be cultured, for example, in DMEM media (JRH Scientific). The hIL-3 variant secreted into the media can be recovered by standard biochemical approaches following transient expression 24–72 hours after transfection of the cells or after establishment of stable cell lines following selection for neomycin resistance. The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al., U.S. Pat. No. 4,419,446. Another suitable mammalian cell line is the monkey COS-1 cell line. A similarly useful mammalian cell line is the CV-1 cell line.

Where desired, insect cells may be utilized as host cells in the method of the present invention. See, e.g. Miller et al, *Genetic Engineering,* 8:277–298 (Plenum Press 1986) and references cited therein. In addition, general methods for expression of foreign genes in insect cells using Baculovirus vectors are described in: Summers, M. D. and Smith, G. E. (1987)—A manual of methods for Baculovirus vectors and insect cell culture procedures, Texas Agricultural Experiment Station Bulletin No. 1555. An expression vector is constructed comprising a Baculovirus transfer vector, in which a strong Baculovirus promoter (such as the polyhedron promoter) drives transcription of a eukaryotic secretion signal peptide coding region, which is translationally fused to the coding region for the hIL-3 variant polypeptide. For example, the plasmid pVL1392 (obtained from Invitrogen Corp., San Diego, Calif.) can be used. After construction of the vector carrying the hIL-3 variant gene, two micrograms of this DNA is cotransfected with one microgram of Baculovirus DNA (see Summers & Smith, 1987) into insect cells, strain SF9. Pure recombinant Baculovirus carrying the hIL-3 variant is used to infect cells cultured, for example, in Excell 401 serum-free medium (JRH Biosciences, Lenexa, Kansas). The hIL-3 variant secreted into the medium can be recovered by standard biochemical approaches.

Another aspect of the present invention provides plasmid DNA vectors for use in the method of expression of these novel hIL-3 muteins. These vectors contain the novel DNA sequences described above which code for the novel polypeptides of the invention. Appropriate vectors which can transform microorganisms capable of expressing the hIL-3 muteins include expression vectors comprising nucleotide sequences coding for the hIL-3 muteins joined to transcriptional and translational regulatory sequences which are selected according to the host cells used.

Vectors incorporating modified sequences as described above are included in the present invention and are useful in the production of the hIL-3 mutant polypeptides. The vector employed in the method also contains selected regulatory sequences in operative association with the DNA coding sequences of the invention and capable of directing the replication and expression thereof in selected host cells.

Additional details may be found in WO 94/12639, which is hereby incorporated by reference in its entirety.

All references, patents or applications cited herein are incorporated by reference in their entirety.

The present invention also includes the construction and expression of (15–125)human interleukin-3 muteins having four or more amino acid substitutions in secretion vectors that optimize accumulation of correctly folded, active polypeptide. While many heterologous proteins have been secreted in *E. coli* there is still a great deal of unpredictability and limited success (Stader and Silhavy 1990). Full-length hIL-3 is such a protein, where attempts to secrete the protein in *E. coli* resulted in low secretion levels. Secretion of the variant (15–125) hIL-3 mutant polypeptides of the present invention as a fusion with a signal peptide such as LamB results in correctly folded protein that can be removed from the periplasm of *E. coli* by osmotic shock fractionation. This property of the variant (15–125) hIL-3 muteins allows for the direct and rapid screening for bioactivity of the secreted material in the crude osmotic shock fraction, which is a significant advantage. Furthermore, it provides a means of using the (15–125)hIL-3 muteins to conduct structure activity relationship (SAR) studies of the hIL-3 molecule. A further advantage of secretion of (15–125) hIL-3 muteins fused to the LamB signal peptide is that the secreted polypeptide has the correct N-terminal amino acid (Asn) due to the precise nature of the cleavage of the signal peptide by signal peptidase, as part of the secretion process.

The (15–125)hIL-3 muteins of the present invention may include hIL-3 polypeptides having Met-, Ala- or Met-Ala-attached to the N-terminus. When the muteins are expressed in the cytoplasm of *E. coli*, polypeptides with and without Met attached to the N-terminus are obtained. The methionine can in some cases be removed by methionine aminopeptidase.

Amino terminal sequences of hIL-3 muteins made in *E. coli* were determined using the method described by Hunkapillar et al., (1983). It was found that hIL-3 proteins made in *E. coli* from genes encoding Met-(15–125)hIL-3 were isolated as Met-(15–125) hIL-3. Proteins produced from genes encoding Met-Ala-(15–125) hIL-3 were produced as Ala-(15–125) hIL-3. The N-termini of proteins made in the cytoplasm of *E. coli* are affected by posttranslational processing by methionine aminopeptidase (Ben-Bassat et al., 1987) and possibly by other peptidases.

One method of creating the preferred hIL-3 (15–125) mutant genes is cassette mutagenesis [Wells, et al. (1985)] in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis [Zoller and Smith (1982, 1983, 1984), Smith (1985), Kunkel (1985), Taylor, et al. (1985), Deng and Nickoloff (1992)] or polymerase chain reaction (PCR) techniques [Saiki, (1985)].

Pairs of complementary synthetic oligonucleotides encoding portions of the amino terminus of the hIL-3 gene can be made and annealed to each other. Such pairs would have protruding ends compatible with ligation to NcoI at one end. The NcoI site would include the codon for the initiator methionine. At the other end of oligonucleotide pairs, the protruding (or blunt) ends would be compatible with a restriction site that occurs within the coding sequence of the hIL-3 gene. The DNA sequence of the oligonucleotide would encode sequence for amino acids of hIL-3 with the exception of those substituted and/or deleted from the sequence.

The NcoI enzyme and the other restriction enzymes chosen should have recognition sites that occur only once in the DNA of the plasmid chosen. Plasmid DNA can be treated with the chosen restriction endonucleases then ligated to the annealed oligonucleotides. The ligated mixtures can be used to transform competent JM101 cells to resistance to an appropriate antibiotic. Single colonies can be picked and the plasmid DNA examined by restriction analysis and/or DNA sequencing to identify plasmids with mutant hIL-3 genes.

One example of a restriction enzyme which cleaves within the coding sequence of the hIL-3 gene is ClaI whose recognition site is at codons 20 and 21. The use of ClaI to cleave the sequence of hIL-3 requires that the plasmid DNA be isolated from an *E. coli* strain that fails to methylate adenines in the DNA at GATC recognition sites. This is because the recognition site for ClaI, ATCGAT, occurs within the sequence GATCGAT which occurs at codons 19, 20 and 21 in the hIL-3 gene. The A in the GATC sequence is methylated in most *E. coli* host cells. This methylation prevents ClaI from cleaving at that particular sequence. An example of a strain that does not methylate adenines is GM48.

Interpretation of activity of single amino acid mutants in IL-3 (15–125)

As illustrated in Tables 6 and 9, there are certain positions in the IL-3 (15–125) molecule which are intolerant of substitutions, in that most or all substitutions at these positions resulted in a considerable decrease in bioactivity. There are two likely classes of such "down-mutations": mutations that affect overall protein structure, and mutations that interfere directly with the interaction between the IL-3 molecule and its receptor. Mutations affecting the three-dimensional structure of the protein will generally lie in the interior of the protein, while mutations affecting receptor binding will generally lie on the surface of the protein. Although the three-dimensional structure of IL-3 is unknown, there are simple algorithms which can aid in the prediction of the structure. One such algorithm is the use of "helical wheels" (Kaiser, E. T. & Kezdy, F. J., Science, 223:249–255 (1984)). In this method, the presence of alpha helical protein structures can be predicted by virtue of their amphipathic nature. Helices in globular proteins commonly have an exposed hydrophilic side and a buried hydrophobic side. As a broad generalization, in globular proteins, hydrophobic residues are present in the interior of the protein, and hydrophilic residues are present on the surface. By displaying the amino acid sequence of a protein on such a "helical wheel" it is possible to derive a model for which amino acids in alpha helices are exposed and which are buried in the core of the protein. Such an analysis of the IL-3 (15–125) molecule predicts that the following helical residues are buried in the core: M19, I20, I23, I24, L27, L58, F61, A64, L68, A71, I74, I77, L78, L81, W104, F107, L111, Y114, L115, L118.

In addition, cysteine residues at positions 16 and 84 are linked by a disulfide bond, which is important for the overall structure or "folding" of the protein. Finally, mutations which result in a major disruption of the protein structure may be expressed at low level in the secretion system used in our study, for a variety of reasons: either because the mis-folded protein is poorly recognized by the secretion machinery of the cell; because mis-folding of the protein results in aggregation, and hence the protein cannot be readily extracted from the cells; or because the mis-folded protein is more susceptible to degradation by cellular proteases. Hence, a block in secretion may indicate which positions in the IL-3 molecule which are important for maintenance of correct protein structure.

In order to retain the activity of a variant of IL-3, it is necessary to retain both the structural integrity of the protein, and retain the specific residues important for receptor contact. Hence it is possible to define specific amino acid residues in IL-3 (15–125) which must be retained in order to preserve biological activity.

Residues predicted to be important for interaction with the receptor: D21, E22, E43, D44, L48, R54, R94, D103, K110, F113.

Residues predicted to be structurally important: C16, L58, F61, A64, I74, L78, L81, C84, P86, P92, P96, F107, L111, L115, L118.

The hIL-3 muteins of the present invention may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with the polypeptides of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs and of infection or hemorrhage. Therapeutic treatment of leukopenia with these hIL-3 mutant polypeptides of the present invention may avoid undesirable side effects caused by treatment with presently available drugs.

The hIL-3 muteins of the present invention may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin and sulfa drugs, phenothiazones, tranquilizers such as meprobamate, and diuretics. The hIL-3 muteins of the present invention may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. The hIL-3 muteins of the present invention may be useful in treating such hematopoietic deficiency.

The treatment of hematopoietic deficiency may include administration of the hIL-3 mutein of a pharmaceutical composition containing the hIL-3 mutein to a patient. The hIL-3 muteins of the present invention may also be useful for the activation and amplification of hematopoietic precursor cells by treating these cells in vitro with the muteins of the present invention prior to injecting the cells into a patient.

Various immunodeficiencies e.g., in T and/or B lymphocytes, or immune disorders, e.g., rheumatoid arthritis, may also be beneficially affected by treatment with the hIL-3 mutant polypeptides of the present invention. Immunodeficiencies may be the result of viral infections e.g. HTLVI, HTLVII, HTLVIII, severe exposure to radiation, cancer therapy or the result of other medical treatment. The hIL-3 mutant polypeptides of the present invention may also be employed, alone or in combination with other hematopoietins, in the treatment of other blood cell deficiencies, including thrombocytopenia (platelet deficiency), or anemia. Other uses for these novel polypeptides are in the treatment of patients recovering from bone marrow transplants in vivo and ex vivo, and in the development of monoclonal and polyclonal antibodies generated by standard methods for diagnostic or therapeutic use.

Other aspects of the present invention are methods and therapeutic compositions for treating the conditions referred to above. Such compositions comprise a therapeutically effective amount of one or more of the hIL-3 muteins of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.2–150 μg/kg of non-glycosylated IL-3 protein per kilogram of body weight. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given mutein vs. the activity of native (reference) IL-3 and it would not be unreasonable to note that dosage regimens may include doses as low as 0.1 microgram and as high as 1 milligram per kilogram of body weight per day. In addition, there may exist specific circumstances where dosages of IL-3 mutein would be adjusted higher or lower than the range of 10–200 micrograms per kilogram of body weight. These include co-administration with other CSF or growth factors; co-administration with chemotherapeutic drugs and/or radiation; the use of glycosylated IL-3 mutein; and various patient-related issues mentioned earlier in this section. As indicated above, the therapeutic method and compositions may also include co-administration with other human factors. A non-exclusive list of other appropriate hematopoietins, CSFs and interleukins for simultaneous or serial co-administration with the polypeptides of the present invention includes GM-CSF, CSF-1, G-CSF, Meg-CSF, M-CSF, erythropoietin (EPO), IL-1, IL-4, IL-2, IL-5, IL-6, IL-7, IL-8, IL-9, IL-10, IL-11, LIF, B-cell growth factor, B-cell differentiation factor and eosinophil differentiation factor, stem cell factor (SCF) also known as steel factor or c-kit ligand, or combinations thereof. The dosage recited above would be adjusted to compensate for such additional components in the therapeutic composition. Progress of the treated patient can be monitored by periodic assessment of the hematological profile, e.g., differential cell count and the like.

Materials and methods for hTL-3 Mutein Expression in *E. coli*

Unless noted otherwise, all specialty chemicals were obtained from Sigma Co., (St. Louis, Mo.). Restriction endonucleases, T4 poly-nucleotides kinase, *E. coli* DNA polymerase I large fragment (Klenow) and T4 DNA ligase were obtained from New England Biolabs (Beverly, Mass.).

*Escherichia coli* strains

Strain JM101: delta (pro lac), supE, thi, F'(traD36, rpoAB, lacI-Q, lacZdeltaM15) (Messing, 1979). This strain can be obtained from the American Type Culture Collection (ATCC), 12301 Parklawn Drive, Rockville, Md. 20852, accession number 33876. MON 105 (W3110 rpoH358) is a derivative of W3110 (Bachmann, 1972) and has been assigned ATCC accession number 55204. Strain GM48: dam-3, dcm-6, gal, ara, lac, thr, leu, tonA, tsx (Marinus, 1973) was used to make plasmid DNA that is not methylated at the sequence GATC.

Genes and plasmids

The gene used for hIL-3 production in *E. coli* was obtained from British Biotechnology Incorporated, Cambridge, England, catalogue number BBG14. This gene is carried on a pUC based plasmid designated pP0518.

The plasmids used for production of hIL-3 in *E. coli* contain genetic elements whose use has been described (Olins et al., 1988; Olins and Rangwala, 1990). The replicon used is that of pBR327 (Covarrubias, et al., 1981) which is maintained at a copy number of about 100 in the cell (Soberon et al., 1980). A gene encoding the beta-lactamase protein is present on the plasmids. This protein confers ampicillin resistance on the cell. This resistance serves as a selectable phenotype for the presence of the plasmid in the cell.

For cytoplasmic expression vectors the transcription promoter was derived from the recA gene of *E. coli* (Sancar et al., 1980). This promoter, designated precA, includes the RNA polymerase binding site and the lexa repressor binding site (the operator). This segment of DNA provides high level transcription that is regulated even when the recA promoter is on a plasmid with the pBR327 origin of replication (Olins et al., 1988) incorporated herein by reference.

In secretion expression plasmids the transcription promoter was derived from the ara B, A, and D genes of *E. coli* (Greenfield et al., 1978). This promoter is designated pAra-BAD and is contained on a 323 base pair Sac.T, BglII restriction fragment. The LamB secretion leader (Wong et al., 1988, Element et al., 1981) was fused to the N-terminus of the hIL-3 gene at the recognition sequence for the enzyme NcoI (5'CCATGG3'). The hIL-3 genes used were engineered to have a HindIII recognition site (5'AAGCTT3') following the coding sequence of the gene.

These hIL-3 variants were expressed as a fusion with the LamB signal peptide shown in FIG. 8, operatively joined to the araBAD promoter (Greenfield, 1978) and the g10-L ribosome binding site (Olins et al. 1988). The processed form was selectively released from the periplasm by osmotic shock as a correctly folded and fully active molecule. Secretion of (15–125) hIL-3 was further optimized by using low inducer (arabinose) concentration and by growth at 30°

C. These conditions resulted in lower accumulation levels of unprocessed LamB signal peptide (15–125) hIL-3 fusion, maximal accumulation levels of processed (15–125) hIL-3 and selective release of (15–125) hIL-3 by osmotic shock fractionation. The use of a tightly regulated promoter such as araBAD from which the transcription level and hence the expression level can be modulated allowed for the optimization of secretion of (15–125) hIL-3.

The ribosome binding site used is that from gene 10 of phage T7 (Olins et al., 1988). This is encoded in a 100 base pair (bp) fragment placed adjacent to precA. In the plasmids used herein, the recognition sequence for the enzyme NcoI (CCATGG) follows the g10-L. It is at this NcoI site that the hIL-3 genes are joined to the plasmid. It is expected that the nucleotide sequence at this junction will be recognized in mRNA as a functional start site for translation (Olins et al., 1988). The hIL-3 genes used were engineered to have a HindIII recognition site (AAGCTT) downstream from the coding sequence of the gene. At this HindIII site is a 514 base pair RsaI fragment containing the origin of replication of the single stranded phage f1 (Dente et al., 1983; Olins, et al., 1990) both incorporated herein by reference. A plasmid containing these elements is pMON2341. Another plasmid containing these elements is pMON5847 which has been deposited at the American Type Culture Collection, 12301 Parklawn Drive, Rockville, Md. 20852 under the accession number ATCC 68912.

Synthesis of Oligonucleotides

Oligonucleotides were synthesized on Nucleotide Synthesizer model 380A or 380B from Applied Biosystems, Inc. (Foster City, Calif.). Oligonucleotides were purified by polyacrylamide gel electrophoresis at concentrations from 12–20% (19:1 crosslinked) in 0.5× Tris borate buffer (0.045 M Tris, 0.045 M boric acid, 1.25 mM EDTA) followed by passage through a Nensorb column obtained from New England Nuclear (Boston, Mass.) using a PREP Automated Sample Processor obtained from DuPont, Co. (Wilmington, Del.).

Quantitation of synthetic oligonucleotides

Synthetic oligonucleotides were resuspended in water and quantitated by reading the absorbance at 260nm on a Beckman DU40 Spectrophotometer (Irvine, California) using a one centimeter by one millimeter quartz cuvette (Maniatis, 1982). The concentration was determined using an extinction coefficient of $1 \times 10^4$ (Voet et al., 1963; Mahler and Cordes, 1966). The oligonucleotides were then diluted to a desired concentration.

Quantitation of synthetic DNA fragments can also be achieved by adding 10 to 100 picomoles of DNA to a solution containing kinase buffer (25 mM Tris pH 8.0, 10 mM $MgCl_2$, 10 mM DTT and 2 mM spermidine). To the reaction mix is added ATP to 20 micromolar, ATP radiolabeled at the gamma phosphate (5000–10,0000 dpm/pmol) and 5 units of T4 polynucleotide kinase. Radiolabelled material is obtained from New England Nuclear (Boston, Mass.). The 10 microliter mixture is incubated at 37° C. for one hour. A 1 microliter aliquot of the mixture was chromatographed on DEAE paper (Whatman) in 0.3 M ammonium bicarbonate. The counts that remained at the origin were used to determine the concentration of the synthetic DNA.

Recombinant DNA methods

Isolation of plasmid DNA from *E. coli* cultures was performed as described (Birnboim and Doly, 1979). Some DNAs were purified by Magic™ columns, available from Promega (Madison, Wis.).

Purified plasmid DNA was treated with restriction endonucleases according to manufacturer's instructions. Analysis of the DNA fragments produced by treatment with restriction enzymes was done by agarose or polyacrylamide gel electrophoresis. Agarose (DNA grade from Fisher, Pittsburgh Pa.) was used at a concentration of 1.0% in a Tris-acetate running buffer (0.04 M Tris-acetate, 0.001M EDTA). Polyacrylamide (BioRad, Richmond Calif.) was used at a concentration of 6% (19:1 crosslinked) in 0.5× Tris-borate buffer (0.045 M Tris, 0.045 M boric acid, 1.25 mM EDTA), hereafter referred to as PAGE.

DNA polymerase I, large fragment, Klenow enzyme was used according to manufacturers instructions to catalyze the addition of mononucleotides from 5' to 3' of DNA fragments which had been treated with restriction enzymes that leave protruding ends. The reactions were incubated at 65° C. for 10 minutes to heat inactivate the Klenow enzyme.

The synthetic oligonucleotides were made without 5' or 3' terminal phosphates. In cases where such oligonucleotides were ligated end to end, the oligonucleotides were treated at a concentration of 10 picomoles per microliter with T4 polynucleotide kinase in the following buffer: 25 mM Tris, pH 8.0, 10 wM $MgCl_2$, 10 mM dithiothreitol, 2 mM spermidine, 1 mM rATP. After incubation for 30 minutes at 37° C., the samples were incubated at 65° C. for five minutes to heat inactivate the kinase.

Synthetic gene assembly

The (15–125) hIL-3 gene was divided into four regions separated by five convenient restriction sites. In each of the four regions synthetic oligonucleotides were designed so that they would anneal in complementary pairs, with protruding single stranded ends, and when the pairs were properly assembled would result in a DNA sequence that encoded a portion of the hIL-3 gene. Amino acid substitutions in the hIL-3 gene were made by designing the oligonucleotides to encode the desired substitutions. The complementary oligonucleotides were annealed at concentration of 1 picomole per microliter in ligation buffer plus 50 mM NaCl. The samples were heated in a 100 ml beaker of boiling water and permitted to cool slowly to room temperature. One picomole of each of the annealed pairs of oligonucleotides were ligated with approximately 0.2 picomoles of plasmid DNA, digested with the appropriate restriction enzymes, in ligation buffer (25 mM Tris pH 8.0, 10 mM MgCl2, 10 mM dithiothreitol, 1 mM ATP, 2mM spermidine) with T4 DNA ligase obtained from New England Biolabs (Beverly, Mass.) in a total volume of 20 μl at room temperature overnight.

DNA fragments were isolated from agarose gels by intercepting the restriction fragments on DEAE membranes from Schleicher and Schuell (Keene, New Hampshire) and eluting the DNA in 10 mM Tris, 1 mM EDTA, 1 M NaCl at 55° C. for 1 hour, according to manufacturer's directions. The solutions containing the DNA fragment were concentrated and desalted by using Centricon 30 concentrators from Amicon (W. R. Grace, Beverly Mass.) according to the manufacturer's directions. Ligations were performed at 15° C. overnight, except as noted, in ligation buffer.

Polymerase Chain Reaction

Polymerase Chain Reaction (hereafter referred to as PCR) techniques (Saiki, 1985) used the reagent kit and thermal cycler from Perkin-Elmer Cetus (Norwalk, Conn.). PCR is based on a thermostable DNA polymerase from *Thermus aquaticus*. The PCR technique is a DNA amplification method that mimics the natural DNA replication process in that the number of DNA molecules doubles after each cycle, in a way similar to in vivo replication. The DNA polymerase mediated extension is in a 5' to 3' direction. The term "primer" as used herein refers to an oligonucleotide sequence that provides an end to which the DNA polymerase can add nucleotides that are complementary to a nucleotide sequence. The latter nucleotide sequence is referred to as the "template", to which the primers are annealed. The amplified PCR product is defined as the region comprised between the 5' ends of the extension primers. Since the primers have defined sequences, the product will have discrete ends, corresponding to the primer sequences. The primer extension reaction was carried out using 20 picomoles (pmoles) of each of the oligonucleotides and 1 picogram of template plasmid DNA for 35 cycles (1 cycle is defined as 94 degrees C. for one minute, 50 degrees C. for two minutes and 72 degrees for three minutes.). The reaction mixture was extracted with an equal volume of phenol/chloroform (50% phenol and 50% chloroform, volume to volume) to remove proteins. The aqueous phase, containing the amplified DNA, and solvent phase were separated by centrifugation for 5 minutes in a microcentrifuge (Model 5414 Eppendorf Inc, Fremont Calif.). To precipitate the amplified DNA the aqueous phase was removed and transferred to a fresh tube to which was added 1/10 volume of 3M NaOAc (pH 5.2) and 2.5 volumes of ethanol (100% stored at minus 20 degrees C.). The solution was mixed and placed on dry ice for 20 minutes. The DNA was pelleted by centrifugation for minutes in a microcentrifuge and the solution was removed from the pellet. The DNA pellet was washed with 70% ethanol, ethanol removed and dried in a speedvac concentrator (Savant, Farmingdale, N.Y.). The pellet was resuspended in 25 microliters of TE (20 mM Tris-HCl pH 7.9, 1 mM EDTA). Alternatively the DNA was precipitated by adding equal volume of 4M $NH_4OAc$ and one volume of isopropanol [Treco et al., (1988)]. The solution was mixed and incubated at room temperature for 10 minutes and centrifuged. These conditions selectively precipitate DNA fragments larger than ~20 bases and were used to remove oligonucleotide primers. One quarter of the reaction was digested with restriction enzymes [Higuchi, (1989)] an on completion heated to 70 degrees C. to inactivate the enzymes.

Recovery of recombinant plasmids from ligation mixes

E. coli JM101 cells were made competent to take up DNA. Typically, 20 to 100 ml of cells were grown in LB medium to a density of approximately 150 Klett units and then collected by centrifugation. The cells were resuspended in one half culture volume of 50 mM $CaCl_2$ and held at 4° C. for one hour. The cells were again collected by centrifugation and resuspended in one tenth culture volume of 50 mM $CaCl_2$. DNA was added to a 150 microliter volume of these cells, and the samples were held at 4° C. for minutes. The samples were shifted to 42° C. for one minute, one milliliter of LB was added, and the samples were shaken at 37° C. for one hour. Cells from these samples were spread on plates containing ampicillin to select for transformants. The plates were incubated overnight at 37° C. Single colonies were picked, grown in LB supplemented with ampicillin overnight at 37° C. with shaking. From these cultures DNA was isolated for restriction analysis.

Culture medium

LB medium (Maniatis et al., 1982) was used for growth of cells for DNA isolation. M9 minimal medium supplemented with 1.0% casamino acids, acid hydrolyzed casein, Difco (Detroit, Mich.) was used for cultures in which recombinant hIL-3 was produced. The ingredients in the M9 medium were as follows: 3 g/liter $KH_2PO_4$, 6 g/l $Na_2HPO_4$, 0.5 g/l NaCl, 1 g/l $NH_4Cl$, 1.2 mM $MgSO_4$, 0.025 mM $CaCl_2$, 0.2% glucose (0.2% glycerol with the AraBAD promoter), 1% casamino acids, 0.1 ml/l trace minerals (per liter 108 g $FeCl_3.6H_2O$, 4.0 g $ZnSO_4.7H_2O$, 7.0 $CoCl_2.2H_2O$, 7.0 g $Na_2MoO_4.2H_2O$, 8.0 g $CuSO_4.5H_2O$, 2.0 g $H_3BO_3$, 5.0 g $MnSO_4.H_2O$, 100 ml concentrated HCl). Bacto agar was used for solid media and ampicillin was added to both liquid and solid LB media at 200 micrograms per milliliter.

DNA sequence analysis

The nucleotide sequencing of plasmid DNA was determined using a Genesis 2000 sequencer obtained from DuPont (Wilmington, Delaware) according to the methods of Prober et al. (1987) and Sanger et al. (1977).Some DNA sequences were performed using Sequenase™ polymerase (U.S. Biochemicals, Cleveland, Ohio) according to manufacturer's directions.

Production of recombinant hIL-3 muteins in E. coli with vectors employing the recA promoter E. coli strains harboring the plasmids of interest were grown at 37° C. in M9 plus casamino acids medium with shaking in a Gyrotory water bath Model G76 from New Brunswick Scientific (Edison, N.J.). Growth was monitored with a Klett Summerson meter (green 54 filter), Klett Mfg. Co. (New York, N.Y.). At a Klett value of approximately 150, an aliquot of the culture (usually one milliliter) was removed for protein analysis. To the remaining culture, nalidixic acid (10 mg/ml) in 0.1 N NaOH was added to a final concentration of 50 µg/ml. The cultures were shaken at 37° C. for three to four hours after addition of nalidixic acid. A high degree of aeration was maintained throughout the bacterial growth in order to achieve maximal production of the desired gene product. The cells were examined under a light microscope for the presence of refractile bodies (RBs). One milliliter aliquots of the culture were removed for analysis of protein content.

Production of recombinant hTL-3 proteins from the pAraBAD promoter in E. coli

E. coli strains harboring the plasmids of interest were grown at 30° C. with shaking in M9 medium plus casamino acids and glycerol. Growth was monitored with a Klett Summerson calorimeter, using a green 54 filter. At a Klett value of about 150, an aliquot of the culture (usually one milliliter) was removed for protein analysis. To the remaining culture, 20% arabinose was added to a final concentration of 0.05%. The cultures were shaken at 30° C. for three to four hours after addition of arabinose. A high degree of aeration was maintained throughout the bacterial growth in order to achieve maximal production of the desired gene product. One milliliter aliquots of the culture were removed for analysis of protein content.

Secretion and osmotic shock

Three hour post induction samples were fractionated by osmotic shock [Neu and Heppel (1965)]. The optical density (Klett value) of the cultures was determined and 1 ml of cells were centrifuged in a Sigma microcentrifuge (West Germany) model 202MK in 1.5 mls snap top microcentrifuge tubes for 5 minutes at 10,000 rpm. The cell pellet was resuspended very gently by pipeting in a room temperature sucrose solution (20% sucrose w/v, 30 mM Tris-Hcl pH7.5, lmM EDTA), using 1 µl/1 Klett unit. Following a 10 minute incubation at room temperature, the cells were centrifuged for 5 minutes at 10,000 rpm. The sucrose fraction was carefully removed from the cell pellet. The cell pellet was then resuspended very gently by pipeting in ice cold distilled water, using 1 µl/1 Klett unit. Following a 10 minute incubation on ice, the cells were centrifuged for 5 minutes at 12,000 rpm. The water fraction was carefully removed. Equal volumes of the sucrose and water fractions were pooled and aliquoted to provide samples for activity screening.

Analysis of protein content of E. coli cultures producing hIL-3 mutant polypeptides Bacterial cells from cultures treated as described above were collected from the medium by centrifugation. Aliquots of these cells were resuspended in SDS loading buffer (4×: 6 g SDS, 10 ml beta-mercaptoethanol, 25 ml upper Tris gel stock (0.5 M Tris HCl pH 6.8, 0.4% SDS) brought to 50 ml with glycerol, 0.2% bromophenol blue was added) at a concentration of one microliter per Klett unit. These samples were incubated at 85° C. for five minutes and vortexed. Five or ten microliter aliquots of these samples were loaded on 15% polyacrylamide gels prepared according to the method of Laemmli (1970). Protein bands were visualized by staining the gels with a solution of acetic acid, methanol and water at 5:1:5 ratio (volume to volume) to which Coomassie blue had been added to a final concentration of 1%. After staining, the gels were washed in the same solution without the Coomassie blue and then washed with a solution of 7% acetic acid, 5% methanol. Gels were dried on a gel drier Model SE1160 obtained from Hoeffer (San Francisco, Calif.). The amount of stained protein was measured using a densitometer obtained from Joyce-Loebl (Gateshead, England). The values obtained were a measure of the amount of the stained hIL-3 protein compared to the total of the stained protein of the bacterial cells.

Western blot analysis of hIL-3 muteins made in E. coli

In some E. coli cultures producing hIL-3, the level of accumulation of the hIL-3 protein is lower than 5% of total bacterial protein. To detect hIL-3 produced at this level, Western blot analysis was used. Proteins from cultures induced with nalidixic acid or arabinose were run on polyacrylamide gels as described above except that volumes of sample loaded were adjusted to produce appropriate signals. After electrophoresis, the proteins were electroblotted to APT paper, Transa-bind, Schleicher and Schuell (Keene, N.H.) according to the method of Renart et al. (1979). Antisera used to probe these blots had been raised in rabbits, using peptides of the sequence of amino acids 20 to 41 and 94 to 118 of hIL-3 as the immunogens. The presence of bound antibody was detected with Staphylococcal protein A radiolabeled with 125j, obtained from New England Nuclear (Boston, Massachusetts).

Fractionation of E. coli cells producing hIL-1 proteins in the cytoplasm

Cells from E. coli cultures harboring plasmids that produce hIL-3 muteins were induced with nalidixic acid. After three hours, the hIL-3 muteins accumulated in refractile bodies. The first step in purification of the hIL-3 muteins was to sonicate cells. Aliquots of the culture were resuspended from cell pellets in sonication buffer: 10 mM Tris, pH 8.0, 1 mM EDTA, 50 mM NaCl and 0.1 mM PMSF. These resuspended cells were subjected to several repeated sonication bursts using the microtip from a Sonicator cell disrupter, Model W-375 obtained from Heat Systems-Ultrasonics Inc. (Farmingdale, N.Y.). The extent of sonication was monitored by examining the homogenates under a light microscope. When nearly all of the cells had been broken, the homogenates were fractionated by centrifugation. The pellets, which contain most of the refractile bodies, are highly enriched for hIL-3 muteins.

Methods-Extraction, Refolding and Purification of Interleukin-3 (IL-3) Muteins Expressed as Refractile Bodies in E. coli.

Extraction of refractile bodies (RB's):

For each gram of RB's (and typically one gram is obtained from a 300 ml E. coli culture), 5 ml of a solution containing 6M guanidine hydrochloride (GnHCl), 50 mM 2-N-cyclohexylaminoethanesulfonic acid (CHES) pH 9.5 and 20 mM dithiothreitol (DTT) was added. The RB's were extracted with a Bio-Homogenizer for 15–30 seconds and gently rocked for 2 hours at 5 degrees centigrade (5° C.) to allow the protein to completely reduce and denature.

Refolding of the IL-3 muteins

The protein solution was transferred to dialysis tubing (1000 molecular weight cut-off) and dialyzed against at least 100 volumes of 4M GnHCl—50 mM CHES pH 8.0. The dialysis was continued overnight at 5° C. while gently stirring. Subsequently dialysis was continued against at least 100 volumes of 2M GnHCl—50 mM CHES pH 8.0 and dialyzed overnight at 5° C. while gently stirring.

Purification of the IL-3 muteins

The protein solution was removed from the dialysis tubing and acidified by the addition of 40% acetonitrile ($CH_3CN$)—0.2% trifluoroacetic acid (TFA) to a final concentration of 20% $CH_3CN$—0.1% TFA. This was centrifuged (16,000× g for 5 minutes) to clarify and the supernatant was loaded onto a Vydac C-18 reversed phase column (10×250 mm) available from Vydac (Hesperia, Calif.) previously equilibrated in 20% $CH_3CN$—0.1% TFA. The column was eluted with a linear gradient (0.2% CH3CN/minute) between 40–50% $CH_3CN$—0.1% TFA at a flow rate of 3 ml/minute while collecting 1.5 ml fractions. The fractions were analyzed by polyacrylamide gel electrophoresis (SDS-PAGE) and the appropriate fractions pooled. The pooled material was dried by lyophilization or in a Speed Vac concentrator. The dry powder was reconstituted with 10 mM ammonium bicarbonate pH 7.5, centrifuged (16,000× g for 5 minutes) to clarify and assayed for protein concentration by the method of Bradford (1976) with bovine serum albumin as the standard. Such protein can be further analyzed by additional techniques such as, SDS-PAGE, electrospray mass spectrometry, reverse phase HPLC, capillary zone electrophoresis, amino acid composition analysis, and ELISA (enzyme-linked immunosorbent assay).

hIL-3 SANDWICH ELISA

IL-3 protein concentrations can be determined using a sandwich ELISA based on an affinity purified polyclonal goat anti-rhIL-3. Microtiter plates (Dynatech Immulon II) were coated with 150 $\mu$l goat-anti-rhIL-3 at a concentration of approximately 1 $\mu$g/ml in 100 mM $NaHCO_3$, pH 8.2. Plates were incubated overnight at room temperature in a chamber maintaining 100% humidity. Wells were emptied and the remaining reactive sites on the plate were blocked with 200 $\mu$l of solution containing 10 mM PBS, 3% BSA and 0.05% Tween 20, pH 7.4 for 1 hour at 37° C. and 100% humidity. Wells were emptied and washed 4× with 150 mM NaCl containing 0.05% Tween 20 (wash buffer). Each well then received 150 $\mu$l of dilution buffer (10 mM PBS containing 0.1% BSA, 0.01% Tween 20, pH 7.4), containing rhIL-3 standard, control, sample or dilution buffer alone. A standard curve was prepared with concentrations ranging from 0.125 ng/ml to 5 ng/ml using a stock solution of rhIL-3 (concentration determined by amino acid composition analysis). Plates were incubated 2.5 hours at 37° C. and 100% humidity. Wells were emptied and each plate was washed 4× with wash buffer. Each well then received 150 $\mu$l of an optimal dilution (as determined in a checkerboard assay format) of goat anti-rhIL-3 conjugated to horseradish peroxidase. Plates were incubated 1.5 hours at 37° C. and 100% humidity. Wells were emptied and each plate was washed 4× with wash buffer. Each well then received 150 μl of ABTS substrate solution (Kirkegaard and Perry). Plates were incubated at room temperature until the color of the standard wells containing 5 ng/ml rhIL-3 had developed enough to yield an absorbance between 0.5–1.0 when read at a test wavelength of 410 nm and a reference wavelength of 570 nm on a Dynatech microtiter plate reader. Concentrations of immunoreactive rhIL-3 in unknown samples were calculated from the standard curve using software supplied with the plate reader.

AML Proliferation Assay for Bioactive Human Interleukin-3

The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM/CSF supplemented medium (Lange, B., et al., (1987); Valtieri, M., et al., (1987). The ability of AML 193 cells to proliferate in the presence of human IL-3 has also been documented. (Santoli, D., et al., (1987)). A cell line variant was used, AML 193 1.3, which was adapted for long term growth in IL-3 by washing out the growth factors and starving the cytokine dependent AML 193 cells for growth factors for 24 hours. The cells were then replated at 1×10$^5$ cells/well in a 24 well plate in media containing 100 U/ml IL-3. It took approximately 2 months for the cells to grow rapidly in IL-3. These cells were maintained as AML 193 1.3 thereafter by supplementing tissue culture medium (see below) with human IL-3.

AML 193 1.3 cells were washed 6 times in cold Hanks balanced salt solution (HBSS, Gibco, Grand Island, N.Y.) by centrifuging cell suspensions at 250× g for 10 minutes followed by decantation of supernatant. Pelleted cells were resuspended in HBSS and the procedure was repeated until six wash cycles were completed. Cells washed six times by this procedure were resuspended in tissue culture medium at a density ranging from 2×10$^5$ to 5×10$^5$ viable cells/ml. This medium was prepared by supplementing Iscove's modified Dulbecco's Medium (IMDM, Hazleton, Lenexa, Kans.) with albumin, transferrin, lipids and 2-mercaptoethanol. Bovine albumin (Boehringer-Mannheim, Indianapolis, Ind.) was added at 500 μg/ml; human transferrin (Boehringer-Mannheim, Indianapolis, Ind.) was added at 100 μg/ml; soybean lipid (Boehringer-Mannheim, Indianapolis, Ind.) was added at 50 μg/ml; and 2-mercaptoethanol (Sigma, St. Louis, Mo.) was added at 5×10$^{-5}$ M.

Serial dilutions of human interleukin-3 or human interleukin-3 variant protein (hIL-3 mutein) were made in triplicate series in tissue culture medium supplemented as stated above in 96 well Costar 3596 tissue culture plates. Each well contained 50 μl of medium containing interleukin-3 or interleukin-3 variant protein once serial dilutions were completed. Control wells contained tissue culture medium alone (negative control). AML 193 1.3 cell suspensions prepared as above were added to each well by pipetting 50 μl (2.5×10$^4$ cells) into each well. Tissue culture plates were incubated at 37° C. with 5% CO$_2$ in humidified air for 3 days. On day 3, 0.5 μCi $^3$H-thymidine (2 Ci/mM, New England Nuclear, Boston, Mass.) was added in 50 μl of tissue culture medium. Cultures were incubated at 37° C. with 5% CO$_2$ in humidified air for 18–24 hours. Cellular DNA was harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats were allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) was added. Beta emissions of samples from individual tissue culture wells were counted in a LKB Betaplate model 1205 scintillation counter (Pharmacia LKB, Gaithersburg, Md.) and data was expressed as counts per minute of $^3$H-thymidine incorporated into cells from each tissue culture well. Activity of each human interleukin-3 preparation or human interleukin-3 variant preparation was quantitated by measuring cell proliferation ($^3$H-thymidine incorporation) induced by graded concentrations of interleukin-3 or interleukin-3 variant.

Typically, concentration ranges from 0.05 pM–10$^5$ pM are quantitated in these assays. Activity is determined by measuring the dose of interleukin-3 or interleukin-3 variant which provides 50% of maximal proliferation [EC$_{50}$=0.5× (maximum average counts per minute of $^3$H-thymidine incorporated per well among triplicate cultures of all concentrations of interleukin-3 tested background proliferation measured by $^3$H-thymidine incorporation observed in triplicate cultures lacking interleukin-3]. This EC$_{50}$ value is also equivalent to 1 unit of bioactivity. Every assay was performed with native interleukin-3 as a reference standard so that relative activity levels could be assigned.

Relative biological activities of IL-3 muteins of the present invention are shown in Table 1. The Relative Biological Activity of IL-3 mutants is calculated by dividing the EC$_{50}$ of (1–133) hIL-3 by the EC$_{50}$ of the mutant. The Relative Biological Activity may be the average of replicate assays.

TABLE 1

BIOLOGICAL ACTIVITY OF IL-3 MUTEINS

| Plasmid Code | Polypeptide Structure | Relative* Biological Activity |
| --- | --- | --- |
| Reference (1-133)hIL-3 | | 1 |
| pMON13298 | SEQ ID NO. 82 | 3 |
| pMON13299 | SEQ ID NO. 83 | 2 |
| pMON13300 | SEQ ID NO. 84 | 3 |
| pMON13301 | SEQ ID NO. 85 | 2 |
| pMON13302 | SEQ ID NO. 86 | 1.2 |
| pMON13303 | SEQ ID NO. 87 | 0.6 |
| pMON13287 | SEQ ID NO. 88 | 26 |
| pMON13288 | SEQ ID NO. 89 | 24 |
| pMON13289 | SEQ ID NO. 90 | 13 |
| pMON13290 | SEQ ID NO. 91 | 20 |
| pMON13292 | SEQ ID NO. 92 | 6 |
| pMON13294 | SEQ ID NO. 93 | 3 |
| pMON13295 | SEQ ID NO. 94 | 3 |
| pMON13312 | SEQ ID NO. 95 | 4 |
| pMON13313 | SEQ ID NO. 96 | 8 |
| pMON13285 | SEQ ID NO. 259 | 32 |
| pMON13286 | SEQ ID NO. 260 | 8 |
| pMON13325 | SEQ ID NO. 261 | 8 |
| pMON13326 | SEQ ID NO. 262 | 25 |
| pMON13330 | SEQ ID NO. 263 | 19 |
| pMON13329 | SEQ ID NO. 406 | 10 |
| pMON13364 | SEQ ID NO. 117 | 13 |
| pMON13475 | SEQ ID NO. 280 | 7 |
| pMON13366 | SEQ ID NO. 281 | 38 |
| pMON13367 | SEQ ID NO. 282 | 36 |
| pMON13368 | SEQ ID NO. 278 | 1.6 |
| pMON13369 | SEQ ID NO. 283 | 10 |
| pMON13370 | SEQ ID NO. 284 | 6 |
| pMON13373 | SEQ ID NO. 285 | 12 |
| pMON13374 | SEQ ID NO. 286 | 6 |
| pMON13375 | SEQ ID NO. 287 | 14 |
| pMON13376 | SEQ ID NO. 288 | 0.4 |

TABLE 1-continued

BIOLOGICAL ACTIVITY OF IL-3 MUTEINS

| Plasmid Code | Polypeptide Structure | Relative* Biological Activity |
|---|---|---|
| pMON13377 | SEQ ID NO. 289 | 0.4 |
| pMON13379 | SEQ ID NO. 291 | 0.9 |
| pMON13380 | SEQ ID NO. 279 | 0.05 |
| pMON13381 | SEQ ID NO. 293 | 10 |
| pMON13382 | SEQ ID NO. 313 | 38 |
| pMON13383 | SEQ ID NO. 294 | 0.5 |
| pMON13384 | SEQ ID NO. 295 | 0.25 |
| pMON13385 | SEQ ID NO. 292 | 1 |
| pMON13387 | SEQ ID NO. 308 | 32 |
| pMON13388 | SEQ ID NO. 296 | 23 |
| pMON13389 | SEQ ID NO. 297 | 10 |
| pMON13391 | SEQ ID NO. 298 | 30 |
| pMON13392 | SEQ ID NO. 299 | 17 |
| pMON13393 | SEQ ID NO. 300 | 32 |
| pMON13394 | SEQ ID NO. 301 | 20 |
| pMON13395 | SEQ ID NO. 302 | 11 |
| pMON13396 | SEQ ID NO. 303 | 20 |
| pMON13397 | SEQ ID NO. 304 | 16 |
| pMON13398 | SEQ ID NO. 305 | 36 |
| pMON13399 | SEQ ID NO. 306 | 18 |
| pMON13404 | SEQ ID NO. 307 | 1.3 |
| pMON13417 | SEQ ID NO. 310 | 24 |
| pMON13420 | SEQ ID NO. 311 | 19 |
| pMON13421 | SEQ ID NO. 331 | 0.5 |
| pMON13432 | SEQ ID NO. 312 | 10 |
| pMON13400 | SEQ ID NO. 317 | 0.09 |
| pMON13402 | SEQ ID NO. 318 | 20 |
| pMON13403 | SEQ ID NO. 321 | 0.03 |
| pMON13405 | SEQ ID NO. 267 | 9 |
| pMON13406 | SEQ ID NO. 264 | 5 |
| pMON13407 | SEQ ID NO. 266 | 16 |
| pMON13408 | SEQ ID NO. 269 | 7 |
| pMON13409 | SEQ ID NO. 270 | 15 |
| pMON13410 | SEQ ID NO. 271 | 0.4 |
| pMON13411 | SEQ ID NO. 322 | 1.2 |
| pMON13412 | SEQ ID NO. 323 | 0.5 |
| pMON13413 | SEQ ID NO. 324 | 0.6 |
| pMON13414 | SEQ ID NO. 265 | 4 |
| pMON13415 | SEQ ID NO. 268 | 4 |
| pMON13418 | SEQ ID NO. 326 | 0.5 |
| pMON13419 | SEQ ID NO. 325 | 0.015 |
| pMON13422 | SEQ ID NO. 272 | 0.4 |
| pMON13423 | SEQ ID NO. 273 | 0.4 |
| pMON13424 | SEQ ID NO. 274 | 3 |
| pMON13425 | SEQ ID NO. 275 | 6 |
| pMON13426 | SEQ ID NO. 276 | >0.0003 |
| pMON13429 | SEQ ID NO. 277 | >0.0002 |
| pMON13440 | SEQ ID NO. 319 | 9 |
| pMON13451 | SEQ ID NO. 320 | 0.1 |
| pMON13459 | SEQ ID NO. 328 | 0.003 |
| pMON13416 | SEQ ID NO. 309 | 19.9 |
| pMON13428 | SEQ ID NO. 327 | 0.008 |
| pMON13467 | SEQ ID NO. 329 | 0.16 |
| pMON13446 | SEQ ID NO. 315 | 21.5 |
| pMON13390 | SEQ ID NO. 316 | 20 |

*The Relative Biological Activity of IL-3 mutants is calculated by dividing the $EC_{50}$ of (1-133) hIL-3 by the $EC_{50}$ of the mutant.

The following assay is used to measure IL-3 mediated sulfidoleukotriene release from human mononuclear cells.

IL-3 mediated sulfidoleukotriene release from human mononuclear cells

Heparin-containing human blood was collected and layered onto an equal volume of Ficoll-Paque (Pharmacia # 17-0840-02) ready to use medium (density 1.077 g/ml.). The Ficoll was warmed to room temperature prior to use and clear 50 ml polystyrene tubes were utilized. The Ficoll gradient was spun at 300×g for 30 minutes at room temperature using a H1000B rotor in a Sorvall RT6000B refrigerated centrifuge. The band containing the mononuclear cells was carefully removed, the volume adjusted to 50 mls with Dulbecco's phosphate-buffered saline (Gibco Laboratories cat. # 310-4040PK), spun at 400 × g for 10 minutes at 4° C. and the supernatant was carefully removed. The cell pellet was washed twice with HA Buffer mM Hepes (Sigma # H-3375), 125 mM NaCl (Fisher # S271-500), 5 mM KCl (Sigma # P-9541), 0.5 mM glucose (Sigma # G-5000),0.025% Human Serum Albumin (Calbiochem # 126654) and spun at 300× g, 10 min., 4° C. The cells were resuspended in HACM Buffer (HA buffer supplemented with 1 mM CaCl2 (Fisher # C79-500) and 1 mM MgCl2 (Fisher # M-33) at a concentration of 1×106 cells/ml and 180 μl were transferred into each well of 96 well tissue culture plates. The cells were allowed to acclimate at 37° C. for 15 minutes. The cells were primed by adding 10 μls of a 20× stock of various concentrations of cytokine to each well (typically 100000, 20000, 4000, 800, 160, 32, 6.4, 1.28, 0 fM IL3). The cells were incubated for 15 minutes at 37° C. Sulfidoleukotriene release was activated by the addition of 10 μls of 20× (1000 nM) fmet-leu-phe (Calbiochem # 344252) final concentration 50 nM FMLP and incubated for 10 minutes at 37° C. The plates were spun at 350× g at 4° C. for 20 minutes. The supernatants were removed and assayed for sulfidoleukotrienes using Cayman's Leukotriene C4 EIA kit (Cat. #420211) according to manufacturers' directions. Native (15–125)hIL-3 was run as a standard control in each assay.

Native hIL-3 possesses considerable inflammatory activity and has been shown to stimulate synthesis of the arachidonic acid metabolites $LTC_4$, $LTD_4$, and $LTE_4$; histamine synthesis and histamine release. Human clinical trials with native hIL-3 have documented inflammatory responses (Biesma, et al., BLOOD, 80:1141–1148 (1992) and Postmus, et al., J. CLIN. ONCOL., 10:1131–1140 (1992)). A recent study indicates that leukotrienes are involved in IL-3 actions in vivo and may contribute significantly to the biological effects of IL-3 treatment (Denzlinger, C., et al., BLOOD, 81:2466–2470 (1993))

Some muteins of the present invention may have an improved therapeutic profile as compared to native hIL-3 or (15–125)hIL-3. For example, some muteins of the present invention may have a similar or more potent growth factor activity relative to native hIL-3 or (15–125)hIL-3 without having a similar or corresponding increase in the stimulation of leukotriene or histamine. These muteins would be expected to have a more favorable therapeutic profile since the amount of polypeptide which needs to be given to achieve the desired growth factor activity (e. g. cell proliferation) would have a lesser leukotriene or histamine stimulating effect. In studies with native hIL-3, the stimulation of inflammatory factors has been an undesirable side effect of the treatment. Reduction or elimination of the stimulation of mediators of inflammation would provide an advantage over the use of native hIL-3.

The pMON13288 polypeptide has demonstrated a more potent growth factor activity relative to native hIL-3 in the AML 193 cell proliferation assay ($EC_{50}$=0.8–3.8 pM for pMON13288 and $EC_{50}$=30.2 pM for native hIL-3) without demonstrating a corresponding increase in the stimulation of leukotriene C4 ($LTC_4$) production and histamine release, i. e., it stimulated $LTC_4$ production and histamine release with a potency similar to that of native hIL-3 while having an improved ability to stimulate cell proliferation compared to native hIL-3. Thus with the pMON13288 polypeptide it would be expected that one would be able to produce a desired therapeutic response, e. g., cell proliferation, with less stimulation of the undesirable inflammatory mediators.

Some muteins of the present invention have antigenic profiles which differ from that of native hIL-3. For example, in a competition ELISA with an affinity purified polyclonal goat anti-hIL-3 antibody, native hIL-3 significantly blocked the binding of labeled hIL-3 to polyclonal anti-hIL-3 antibody whereas the pMON13288 polypeptide failed to block the binding of hIL-3 to anti-hIL-3 antibody.

Table 2 lists the sequences of some oligonucleotides used in making the muteins of the present invention.

Table 3 lists the amino acid sequence of native (15–125) hIL-3 (Peptide #1) and the amino acid sequences of some mutant polypeptides of the present invention. The sequences are shown with the amino acid numbering corresponding to that of native hIL-3 [FIG. 1].

Table 4 lists the nucleotide sequences of some DNA sequences which encode mutant polypeptides of the present invention.

TABLE 2

| OLIGONUCLEOTIDES | | |
|---|---|---|
| Oligo #1 | Length: 000040<br>CATGGCTAAC TGCTCTATAA TGATCGATGA AATTATACAT | [SEQ ID NO:15] |
| Oligo #2 | Length: 000045<br>CTTTAAGTGA TGTATAATTT CATCGATCAT TATAGAGCAG TTAGC | [SEQ ID NO:16] |
| Oligo #3 | Length: 000036<br>CACTTAAAGA GACCACCTGC ACCTTTGCTG GACCCG | [SEQ ID NO:17] |
| Oligo #4 | Length: 000036<br>GAGGTTGTTC GGGTCCAGCA AAGGTGCAGG TGGTCT | [SEQ ID NO:18] |
| Oligo #5 | Length: 000036<br>CACTTAAAGA GACCACCTAA CCCTTTGCTG GACCCG | [SEQ ID NO:19] |
| Oligo #6 | Length: 000036<br>GAGGTTGTTC GGGTCCAGCA AAGGGTTAGG TGGTCT | [SEQ ID NO:20] |
| Oligo #7 | Length: 000036<br>CACTTAAAGG TTCCACCTGC ACCTTTGCTG GACAGT | [SEQ ID NO:21] |
| Oligo #8 | Length: 000036<br>GAGGTTGTTA CTGTCCAGCA AAGGTGCAGG TGGAAC | [SEQ ID NO:22] |
| Oligo #9 | Length: 000027<br>AACAACCTCA ATGCTGAAGA CGTTGAT | [SEQ ID NO:23] |
| Oligo #10 | Length: 000018<br>ATCAACGTCT TCAGCATT | [SEQ ID NO:24] |
| Oligo #11 | Length: 000027<br>AACAACCTCA ATTCTGAAGA CATGGAT | [SEQ ID NO:25] |
| Oligo #12 | Length: 000018<br>ATCCATGTCT TCAGAATT | [SEQ ID NO:26] |
| Oligo #13 | Length: 000022<br>CATGGGAACC ATATGTCAGG AT | [SEQ ID NO:27] |
| Oligo #14 | Length: 000018<br>ATCCTGACAT ATGGTTCC | [SEQ ID NO:28] |
| Oligo #15 | Length: 000016<br>TGAACCATAT GTCAGG | [SEQ ID NO:29] |
| Oligo #16 | Length: 000024<br>AATTCCTGAC ATATGGTTCA TGCA | [SEQ ID NO:30] |
| Oligo #17 | Length: 000020<br>AATTCGAACC ATATGTCAGA | [SEQ ID NO:31] |
| Oligo #18 | Length: 000020<br>AGCTTCTGAC ATATGGTTCG | [SEQ ID NO:32] |
| Oligo #19 | Length: 000022<br>ATCGAACCAT ATGTCAGATG CA | [SEQ ID NO:33] |
| Oligo #20 | Length: 000018<br>TCTGACATAT GGTTCGAT | [SEQ ID NO:34] |
| Oligo #21 | Length: 000036<br>ATCCTGATGG AACGAAACCT TCGACTTCCA AACCTG | [SEQ ID NO:35] |

TABLE 2-continued

OLIGONUCLEOTIDES

| Oligo #22 | Length: 000027<br>AAGTCGAAGG TTTCGTTCCA TCAGGAT | [SEQ ID NO:36] |
| --- | --- | --- |
| Oligo #23 | Length: 000036<br>ATCCTGATGG AACGAAACCT TCGAACTCCA AACCTG | [SEQ ID NO:37] |
| Oligo #24 | Length: 000027<br>AGTTCGAAGG TTTCGTTCCA TCAGGAT | [SEQ ID NO:38] |
| Oligo #25 | Length: 000024<br>CTCGCATTCG TAAGGGCTGT CAAG | [SEQ ID NO:39] |
| Oligo #26 | Length: 000024<br>CCTTACGAAT GCGAGCAGGT TTGG | [SEQ ID NO:40] |
| Oligo #27 | Length: 000024<br>GAGAGCTTCG TAAGGGCTGT CAAG | [SEQ ID NO:41] |
| Oligo #28 | Length: 000024<br>CCTTACGAAG CTCTCCAGGT TTGG | [SEQ ID NO:42] |
| Oligo #29 | Length: 000015<br>CACTTAGAAA ATGCA | [SEQ ID NO:43] |
| Oligo #30 | Length: 000020<br>TTTTCTAAGT GCTTGACAGC | [SEQ ID NO:44] |
| Oligo #31 | Length: 000015<br>AACTTAGAAA ATGCA | [SEQ ID NO:45] |
| Oligo #32 | Length: 000020<br>TTTTCTAAGT TCTTGACAGC | [SEQ ID NO:46] |
| Oligo #33 | Length: 000048<br>GGTGATTGGA TGTCGAGAGG GTGCGGCCGT GGCAGAGGGC AGACATGG | [SEQ ID NO:47] |
| Oligo #34 | Length: 000048<br>CTGCCCTCTG CCACGGCCGC ACCCTCTCGA CATCCAATCA CCATCAAG | [SEQ ID NO:48] |
| Oligo #35 | Length: 000048<br>GATGATTGGA TGTCGAGAGG GTGCGGCCGT GGCAGAGGGC AGACATGG | [SEQ ID NO:49] |
| Oligo #36 | Length: 000048<br>CTGCCCTCTG CCACGGCCGC ACCCTCTCGA CATCCAATCA TCATCAAG | [SEQ ID NO:50] |
| Oligo #37 | Length: 000018<br>TACGAGATTA CGAAGAAT | [SEQ ID NO:51] |
| Oligo #38 | Length: 000018<br>CGTAATCTCG TACCATGT | [SEQ ID NO:52] |
| Oligo #39 | Length: 000018<br>TTGGAGATTA CGAAGAAT | [SEQ ID NO:53] |
| Oligo #40 | Length: 000018<br>CGTAATCTCC AACCATGT | [SEQ ID NO:54] |
| Oligo #41 | Length: 000019<br>TGCCTCAATA CCTGATGCA | [SEQ ID NO:55] |
| Oligo #42 | Length: 000021<br>TCAGGTATTG AGGCAATTCT T | [SEQ ID NO:56] |
| Oligo #43 | Length: 000026<br>AATTCTTGCC AGTCACCTGC CTTGAT | [SEQ ID NO:57] |
| Oligo #44 | Length: 000016<br>GCAGGTGACT GGCAAG | [SEQ ID NO:58] |
| Oligo #45 | Length: 000032<br>AATTCCGGGA AAAACTGACG TTCTATCTGG TT | [SEQ ID NO:59] |
| Oligo #46 | Length: 000037<br>CTCAAGGGAA ACCAGATAGA ACGTCAGTTT TTCCCGG | [SEQ ID NO:60] |

TABLE 2-continued

OLIGONUCLEOTIDES

| Oligo #47 | Length: 000032<br>ACCCTTGAGC ACGCGCAGGA ACAACAGTAA TA | [SEQ ID NO:61] |
|---|---|---|
| Oligo #48 | Length: 000027<br>AGCTTATTAC TGTTGTTCCT GCGCGTG | [SEQ ID NO:62] |
| Oligo #49 | Length: 000032<br>ACCCTTGAGC AAGCGCAGGA ACAACAGTAA TA | [SEQ ID NO:63] |
| Oligo #50 | Length: 000027<br>AGCTTATTAC TGTTGTTCCT GCGCTTG | [SEQ ID NO:64] |
| Oligo #51 | Length: 000034<br>GCCGATACCGCGGCATACTCCCACCATTCAGAGA | [SEQ ID NO:155] |
| Oligo #52 | Length: 000033<br>GCCGATAAGATCTAAAACGGGTATGGAGAAACA | [SEQ ID NO:156] |
| Oligo #53 | ATAGTCTTCCCCAGATATCTAACGCTTGAG | [SEQ ID NO:157] |
| Oligo #54 | Length: 000024<br>CAATACCTGATGCGTTTTCTAAGT | [SEQ ID NO:158] |
| Oligo #55 | Length: 000033<br>GGTTTCGTTCCATCAGAATGTCCATGTCTTCAG | [SEQ ID NO:159] |
| Oligo #165 | NCOECV1.REQ  Length: 000040<br>CATGGCTAAC TGCTCTAACA TGATCGATGA AATTATAACA | [SEQ ID NO:162] |
| Oligo #166 | NCOECRV4.REQ  Length: 000045<br>CTTTAAGTGT GTTATAATTT CATCGATCAT GTTAGAGCAG TTAGC | [SEQ ID NO:163] |
| Oligo #167 | NCOECRV2.REQ  Length: 000036<br>CACTTAAAGC AGCCACCTTT GCCTTTGCTG GACTTC | [SEQ ID NO:164] |
| Oligo #168 | NCOECRV5.REQ  Length: 000036<br>GAGGTTGTTG AAGTCCAGCA AAGGCAAAGG TGGCTG | [SEQ ID NO:165] |
| Oligo #169 | 2D5M6SUP.REQ  Length: 000027<br>AACAACCTCA ATGACGAAGA CATGTCT | [SEQ ID NO:166] |
| Oligo #170 | 2D5M6SLO.REQ  Length: 000018<br>AGACATGTCT TCGTCATT | [SEQ ID NO:167] |
| Oligo #15(A) | Length: 000016<br>TGAACCATAT GTCAGG | [SEQ ID NO:168] |
| Oligo #16(A) | Length: 000024<br>AATTCCTGAC ATATGGTTCA TGCA | [SEQ ID NO:169] |
| Oligo #B1 | 19ALA1.REQ  Length: 000040<br>CATGGCAAAC TGCTCTATAG CTATCGATGA AATTATACAT | [SEQ ID NO:170] |
| Oligo #B2 | 19ALA4.REQ  Length: 000045<br>CTTTAAGTGA TGTATAATTT CATCGATAGC TATAGAGCAG TTTGC | [SEQ ID NO:171] |
| Oligo #B3 | 19ILE1.REQ  Length: 000040<br>CATGGCAAAC TGCTCTATAA TCATCGATGA AATTATACAT | [SEQ ID NO:172] |
| Oligo #B4 | 19ILE4.REQ  Length: 000045<br>CTTTAAGTGA TGTATAATTT CATCGATGAT TATAGAGCAG TTTGC | [SEQ ID NO:173] |
| Oligo #B5 | 49ASP1.REQ  Length: 000036<br>ATCCTGGACG AACGAAAACT TCGAACTCCA AACCTG | [SEQ ID NO:174] |
| Oligo #B6 | 49ASP4.REQ  Length: 000027<br>AGTTCGAAGG TTTCGTTCGT CCAGGAT | [SEQ ID NO:175] |
| Oligo #B7 | 49ILE1.REQ  Length: 000036<br>ATCCTGATCG AACGAAACCT TCGAACTCCA AACCTG | [SEQ ID NO:176] |
| Oligo #B8 | 49ILE4.REQ  Length: 000027<br>AGTTCGAAGG TTTCGTTCGA TCAGGAT | [SEQ ID NO:177] |

TABLE 2-continued

| OLIGONUCLEOTIDES | | | |
|---|---|---|---|
| Oligo #B9 | 49LEU1.REQ Length: 000036<br>ATCCTGCTGG AACGAAACCT TCGAACTCCA AACCTG | | [SEQ ID NO:178] |
| Oligo #B10 | 49LEU4.REQ Length: 000027<br>AGTTCGAAGG TTTCGTTCCA GCAGGAT | | [SEQ ID NO:179] |
| Oligo #B11 | 42S45V3.REQ Length: 000027<br>AACAACCTCA ATTCTGAAGA CGTTGAT | | [SEQ ID NO:180] |
| Oligo #B12 | 42S45V6.REQ Length: 000018<br>ATCAACGTCT TCAGAATT | | [SEQ ID NO:181] |
| Oligo #B13 | 18I23A5H.REQ Length: 000051<br>CGCGCCATGG CTAACTGCTC TATAATGATC GATGAAGCAA TACATCACTTA | | [SEQ ID NO:182] |
| Oligo #B14 | 2341HIN3.REQ Length: 000018<br>CGCGTCGATA AGCTTATT | | [SEQ ID NO:183] |
| Oligo #B15 | 2341NCO.REQ Length: 000018<br>GGAGATATAT CCATGGCT | | [SEQ ID NO:184] |
| Oligo #B16 | 2A5M6S0D.REQ Length: 000042<br>TCGGTCCATC AGAATAGACA TGTCTTCAGC ATTGAGGTTG TT | | [SEQ ID NO:185] |
| Oligo #B17 | 2A5V6S0D.REQ Length: 000042<br>TCGGTCCATC AGAATAGAAA CGTCTTCAGC ATTGAGGTTG TT | | [SEQ ID NO:186] |
| Oligo #B18 | 2D5M6S0D.REQ Length: 000042<br>TCGGTCCATC AGAATAGACA TGTCTTCGTC ATTGAGGTTG TT | | [SEQ ID NO:187] |
| Oligo #B19 | 2D5V6S0D.REQ Length: 000042<br>TCGGTCCATC AGAATAGAAA CGTCTTCGTC ATTGAGGTTG TT | | [SEQ ID NO:188] |
| Oligo #B20 | 2S5M6S0D.REQ Length: 000042<br>TCGGTCCATC AGAATAGACA TGTCTTCAGA ATTGAGGTTG TT | | [SEQ ID NO:189] |
| Oligo #B21 | 2S5V6S0D.REQ Length: 000042<br>TCGGTCCATC AGAATAGAAA CGTCTTCAGA ATTGAGGTTG TT | | [SEQ ID NO:190] |
| Oligo #B22 | 100ARG3.REQ Length: 000048<br>CTGCCCTCTG CCACGGCCGC ACCCTCTCGA CATCCAATCA TCATCCGT | | [SEQ ID NO:191] |
| Oligo #B23 | 100ARG8.REQ Length: 000026<br>AATTCTTGCC AGTCACCTGC ACGGAT | | [SEQ ID NO:192] |
| Oligo #B24 | 101MET4.REQ Length: 000016<br>ATGGGTGACT GGCAAG | | [SEQ ID NO:193] |
| Oligo #B25 | 10R01M8.REQ Length: 000026<br>AATTCTTGCC AGTCACCCAT ACGGAT | | [SEQ ID NO:194] |
| Oligo #B26 | 23ALA1.REQ Length: 000040<br>CATGGCTAAC TGCTCTATTA TGATCGATGA AGCAATACAT | | [SEQ ID NO:195] |
| Oligo #B27 | 23ALA4.REQ Length: 000045<br>CTTTAAGTGA TGTATTGCTT CATCGATCAT AATAGAGCAG TTAGC | | [SEQ ID NO:196] |
| Oligo #B28 | 29V2R4S2.REQ Length: 000036<br>CACTTAAAGG TACCACCTCG CCCTTCCCTG GACCCG | | [SEQ ID NO:197] |
| Oligo #B29 | 29V2R4S5.REQ Length: 000036<br>GAGGTTGTTC GGGTCCAGGG AAGGGCGAGG TGGTAC | | [SEQ ID NO:198] |
| Oligo #B30 | 34SER2.REQ Length: 000036<br>CACTTAAAGA GACCACCTGC ACCTTCCCTG GACCCG | | [SEQ ID NO:199] |
| Oligo #B31 | 34SER5.REQ Length: 000036<br>GAGGTTGTTC GGGTCCAGGG AAGGTGCAGG TGGTCT | | [SEQ ID NO:200] |
| Oligo #B32 | 42D45M3.REQ Length: 000027<br>AACAACCTCA ATGACGAAGA CATGGAT | | [SEQ ID NO:201] |
| Oligo #B33 | 42D45M6.REQ Length: 000018<br>ATCCATGTCT TCGTCATT | | [SEQ ID NO:202] |

TABLE 2-continued

OLIGONUCLEOTIDES

| | | |
|---|---|---|
| Oligo #B34 | 42D45V3.REQ  Length: 000027<br>AACAACCTCA ATGACGAAGA CGTCGAT | [SEQ ID NO:203] |
| Oligo #B35 | 42D45V6.REQ  Length: 000018<br>ATCGACGTCT TCGTCATT | [SEQ ID NO:204] |
| Oligo #B36 | 42D5M6S3.REQ  Length: 000027<br>AACAACCTCA ATGACGAAGA CATGTCT | [SEQ ID NO:205] |
| Oligo #B37 | 42D5M6S6.REQ  Length: 000018<br>AGACATGTCT TCGTCATT | [SEQ ID NO:206] |
| Oligo #B38 | 42D5V6S3.REQ  Length: 000027<br>AACAACCTCA ATGACGAAGA CGTCTCT | [SEQ ID NO:207] |
| Oligo #B39 | 42D5V6S6.REQ  Length: 000018<br>AGAGACGTCT TCGTCATT | [SEQ ID NO:208] |
| Oligo #B40 | 50ASP1.REQ  Length: 000036<br>ATCCTGATGG ACCGAAACCT TCGACTTCCA AACCTG | [SEQ ID NO:209] |
| Oligo #B41 | 50ASP4.REQ  Length: 000027<br>AAGTCGAAGG TTTCGGTCCA TCAGGAT | [SEQ ID NO:210] |
| Oligo #B42 | 50D56S1.REQ  Length: 000036<br>ATCCTGATGG ACCGAAACCT TCGACTTAGC AACCTG | [SEQ ID NO:211] |
| Oligo #B43 | 56SER5.REQ  Length: 000024<br>CCTTACGAAG CTCTCCAGGT TGCT | [SEQ ID NO:212] |
| Oligo #B44 | 82TRP2.REQ  Length: 000018<br>CGTAATCTCT GGCCATGT | [SEQ ID NO:213] |
| Oligo #B45 | 82TRP6.REQ  Length: 000018<br>CCAGAGATTA CGAAGAAT | [SEQ ID NO:214] |
| Oligo #B46 | 9E12Q6W1.REQ  Length: 000032<br>AATTCCGGGA AAAACTGCAA TTCTATCTGT GG | [SEQ ID NO:215] |
| Oligo #B47 | 9E12Q6W3.REQ  Length: 000037<br>CTCAAGGGTC CACAGATAGA ATTGCAGTTT TTCCCGG | [SEQ ID NO:216] |
| Oligo #B48 | 9E12Q6V1.REQ  Length: 000032<br>AATTCCGGGA AAAACTGCAA TTCTATCTGG TT | [SEQ ID NO:217] |
| Oligo #B49 | 9E12Q6V3.REQ  Length: 000037<br>CTCAAGGGTA CCAGAGATAGA ATTGCAGTTT TTCCCGG | [SEQ ID NO:218] |
| Oligo #B50 | S09E16V1.REQ  Length: 000023<br>AATTCCGGGA AAAACTGACG TTC | [SEQ ID NO:219] |
| Oligo #B51 | S09E16V3.REQ  Length: 000028<br>AACCAGATAG AACGTCAGTT TTTCCCGG | [SEQ ID NO:220] |
| Oligo #B52 | S116VD31.REQ  Length: 000023<br>TATCTGGTTA CCCTTGAGTA ATA | [SEQ ID NO:221] |
| Oligo #B53 | SECR1D33.REQ  Length: 000018<br>AGCTTATTAC TTCAAGGGT | [SEQ ID NO:222] |
| Oligo #B54 | S9E2Q6V1.REQ  Length: 000023<br>AATTCCGGGA AAAACTGCAA TTC | [SEQ ID NO:223] |
| Oligo #B55 | S9E2Q6V3.REQ  Length: 000028<br>AACCAGATAG AATTGCAGTT TTTCCCGG | [SEQ ID NO:224] |
| Oligo #B56 | Ent338.Lo  Length: 61<br>CGATCATTAT AGAGCAGTTA GCCTTGTCAT CGTCGTCCTT GTAATCAGTT TCTGGATATG C | [SEQ ID NO:225] |
| Oligo #B57 | Ent338.UP  Length: 63<br>CATGGCATAT CCAGAAACTG ATTACAAGGA CGACGATGAC AAGGCTAACT GCTCTATAAT GAT | [SEQ ID NO:226] |
| 09L2Q6S1.REQ | Length: 000032<br>AATTCCGGCT TAAACTGCAA TTCTATCTGT CT | [SEQ ID NO:227] |

TABLE 2-continued

OLIGONUCLEOTIDES

| | | |
|---|---|---|
| 09L2Q6S3.REQ | Length: 000037<br>CTCAAGGGTA GACAGATAGA ATTGCAGTTT AAGCCGG | [SEQ ID NO:228] |
| 117S2.REQ | Length: 000032<br>TCTCTTGAGC AAGCGCAGGA ACAACAGTAA TA | [SEQ ID NO:229] |
| 19I0L3A1.REQ | Length: 000040<br>CATGGCAAAC TGCTCTATAA TACTCGATGA AGCAATACAT | [SEQ ID NO:230] |
| 19I0L3A4.REQ | Length: 000045<br>CTTTAAGTGA TGTATTGCTT CATCGAGTAT TATAGAGCAG TTTGC | [SEQ ID NO:231] |
| 20P23A1.REQ | Length: 000040<br>CATGGCAAAC TGCTCTATAA TGCCAGATGA AGCAATACAT | [SEQ ID NO:232] |
| 20P23A4.REQ | Length: 000045<br>CTTTAAGTGA TGTATTGCTT CATCTGGCAT TATAGAGCAG TTTGC | [SEQ ID NO:233] |
| 23L1.REQ | Length: 000040<br>CATGGCaAAC TGCTCTATAA TGATCGATGA AactgATACAT | [SEQ ID NO:234] |
| 23L4.REQ | Length: 000045<br>CTTTAAGTGA TGTATcagTT CATCGATCAT TATAGAGCAG TTtGC | [SEQ ID NO:235] |
| 29I4S7S2.REQ | Length: 000036<br>CACTTAAAGA TACCACCTAA CCCTAGCCTG GACAGT | [SEQ ID NO:236] |
| 29I4S7S5.REQ | Length: 000036<br>GAGGTTAGCA CTGTCCAGGC TAGGGTTAGG TGGTAT | [SEQ ID NO:237] |
| 38A5V6S3.REQ | Length: 000027<br>GCTAACCTCA ATTCCGAAGA CGTCTCT | [SEQ ID NO:238] |
| 38A5V6S6.REQ | Length: 000018<br>AGAGACGTCT TCGGAATT | [SEQ ID NO:239] |
| 50D51S1.REQ | Length: 000036<br>ATCCTGATGG ACTCCAACCT TCGAACTCCA AACCTG | [SEQ ID NO:240] |
| 50D51S4.REQ | Length: 000027<br>AGTTCGAAGG TTGGAGTCCA TCAGGAT | [SEQ ID NO:241] |
| 5VYWPTT3.REQ | Length: 000048<br>GTTCCCTATT GGACGGCCCC TCCCTCTCGA ACACCAATCA CGATCAAG | [SEQ ID NO:242] |
| 5VYWPTT7.REQ | Length: 000048<br>CGTGATTGGT GTTCGAGAGG GAGGGGCCGT CCAATAGGGA ACACATGG | [SEQ ID NO:243] |
| 62P3H5S2.REQ | Length: 000024<br>CTCGCATTCC CACATGCTTC TAAG | [SEQ ID NO:244] |
| 62P63H2.REQ | Length: 000024<br>CTCGCATTCC CACATGCTGT CAAG | [SEQ ID NO:245] |
| 62P63H5.REQ | Length: 000024<br>ATGTGGGAAT GCGAGCAGGT TTGG | [SEQ ID NO:246] |
| 65S67Q6.REQ | Length: 000020<br>TTTTCTAATT GCTTAGAAGC | [SEQ ID NO:247] |
| 67Q3.REQ | Length: 000015<br>CAATTAGAAA ATGCA | [SEQ ID NO:248] |
| 67Q6.REQ | Length: 00002]<br>TTTTCTAATT GCTTGACAGC | [SEQ ID NO:249] |
| 76P1.REQ | Length: 000021<br>TCAGGTATTG AGCCAATTCT T | [SEQ ID NO:250] |
| 76P5.REQ | Length: 000019<br>TGGCTCAATA CCTGATGCA | [SEQ ID NO:251] |
| 79S2.REQ | Length: 000018<br>TCTAATCTCC AACCATGT | [SEQ ID NO:252] |

TABLE 2-continued

OLIGONUCLEOTIDES

| | | |
|---|---|---|
| 79S6.REQ | Length: 000018<br>TTGGAGATTA GAAAGAAT | [SEQ ID NO:253] |
| 9L2Q67S3.REQ | Length: 000037<br>CTCAAGAGAA GACAGATAGA ATTGCAGTTT AAGCCGG | [SEQ ID NO:254] |
| 9LQS1181.REQ | Length: 000043<br>AATTCCGGCT TAACTGCAA TTCTATCTGT CTACCCTTTA ATA | [SEQ ID NO:256] |
| 9LQS1183.REQ | Length: 000043<br>AGCTTATTAA AGGGTAGACA GATAGAATTG CAGTTTAAGC CGG | [SEQ ID NO:257] |
| S9L2Q6S1.REQ | Length: 000043<br>AATTCCGGCT TAAACTGCAA TTCTATCTGT CTACCCTTTA ATA | [SEQ ID NO:258] |

TABLE 3

POLYPEPTIDES

The numbering of the mutated amino acid positions which describe the following polypeptides corresponds to the sequence of the full-length, native (1–133)hIL-3.

PEPTIDE #1: pMON5988 (Example 43), (15–125)hIL-3 SEQ ID NO:65;
PEPTIDE #2: pMON13344 (Example 8), (15–125)hIL-3 (18I, 25H, 29R, 32A, 37P, 42A and 45V) SEQ ID NO:66;
PEPTIDE #3: pMON13345 (Example 9), (15–125)hIL-3 (18I, 25H, 29R, 32N, 37P, 42S and 45M) SEQ ID NO:67;
PEPTIDE #4: pMON13346 (Example 10), (15–125)hIL-3 (18I, 25H, 29V, 32A, 37S, 42S and 45M) SEQ ID NO:68;
PEPTIDE #5: pMON13347 (Example 12), (15–125)hIL-3 (51R, 55L, 59L, 62V, 67N and 69E) SEQ ID NO:69;
PEPTIDE #6: pMON13348 (Example 13), (15–125)hIL-3 (51R, 55L, 60S, 62V, 67N and 69E) SEQ ID NO:70;
PEPTIDE #7: pMON13349 (Example 14), (15–125)hIL-3 (51R, 55T, 59L, 62V, 67H and 69E) SEQ ID NO:71;
PEPTIDE #8: pMON13350 (Example 16), (15–125)hIL-3 (73G, 76A, 79R, 82Q, 87S, 93S, 98I, 101A and 105Q) SEQ ID NO:72;
PEPTIDE #9: pMON13355 (Example 17), (15–125)hIL-3 (73G, 76A, 79R, 82V, 87S, 93S, 98T, 101A and 105Q) SEQ ID NO:73;
PEPTIDE #10: pMON13352 (Example 19), (15–125)hIL-3 (109E, 116V, 120Q and 123E) SEQ ID NO:74;
PEPTIDE #11: pMON13354 (Example 20), (15–125)hIL-3 (109E, 116V, 117S, 120H and 123E) SEQ ID NO:75;
PEPTIDE #12: pMON13360 (Example 21), (15–125)hIL-3 (73G, 76A, 79R, 82Q, 87S, 93S, 98I, 101A, 105Q, 109E, 116V, 120Q and 123E) SEQ. ID. NO:76;
PEPTIDE #13: pMON13361 (Example 22), (15–125)hIL-3 (73G, 76A, 79R, 82V, 87S, 93S, 98T, 101A, 105Q, 109E, 116V, 120Q and 123E), SEQ ID NO:77;
PEPTIDE #14: pMON13362 (Example 23), (15–125)hIL-3 (73G, 76A, 79R, 82V, 87S, 93S, 98T, 101A, 105Q, 109E, 116V, 117S, 120H and 123E) SEQ ID NO:78;
PEPTIDE #15: pM0N13363 (Example 24), (15–125)hIL-3 (18I, 25H, 29R, 32A, 37P, 42A, 45V, 51R, 55L, 60S, 62V, 67N and 69E) SEQ ID NO:79;
PEPTIDE #16: pMON13364 (Example 25), (15–125)hIL-3 (18I, 25H, 29R, 32N, 37P, 42S, 45M, 51R, 55T, 59L, 62V, 67H and 69E) SEQ ID NO:80;
PEPTIDE #17: pMON13365 (Example 26), (15–125)hIL-3 (18I, 25H, 29V, 32A, 37S, 42S, 45M, 51R, 55L, 59L, 62V, 67N and 69E) SEQ ID NO:81;
PEPTIDE #18: pMON13298 (Example 27), Met-Ala-(15–125)hIL-3 (73G, 76A, 79R, 82Q, 87S, 93S, 98I, 101A, 105Q, 109E, 116V, 120Q and 123E) SEQ ID NO:82;
PEPTIDE #19: pMON13299 (Example 28), Met-Ala-(15–125)hIL-3 (73G, 76A, 79R, 82V, 87S, 93S, 98T, 101A, 105Q, 109E, 116V, 120Q and 123E); SEQ ID NO:83;
PEPTIDE #20: pM0N13300 (Example 29), Met-Ala-(15–125)hIL-3 (73G, 76A, 79R, 82V, 87S, 93S, 98T, 101A, 105Q, 109E, 116V, 117S, 120H and 123E) SEQ ID NO:84;

TABLE 3-continued

POLYPEPTIDES

The numbering of the mutated amino acid positions which describe the following polypeptides corresponds to the sequence of the full-length, native (1–133)hIL-3.

PEPTIDE #21: pMON13301 (Example 30), Met-Ala-(15–125)hIL-3 (18I, 25H, 29R, 32A, 37P, 42A, 45V, 51R, 55L, 60S, 62V, 67N and 69E) SEQ ID NO:85;
PEPTIDE #22: pMON13302 (Example 31), Met-Ala-(15–125)hIL-3 (18I, 25H, 29R, 32N, 37P, 42S, 45M, 51R, 55T, 59L, 62V, 67H and 69E) SEQ ID NO:86;
PEPTIDE #23: pMON13303 (Example 32), Met-Ala-(15–125)hIL-3 (18I, 25H, 29V, 32A, 37S, 42S, 45M, 51R, 55L, 59L, 62V, 67N and 69E) SEQ ID NO:87;
PEPTIDE #24: pMON13287 (Example 33), Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:88;
PEPTIDE #25: pMON13288 (Example 34), Met-Ala-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:89;
PEPTIDE #26: pMON13289 (Example 35), Met-Ala-(15–125)hIL-3 (18I, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E) SEQ ID NO:90;
PEPTIDE #27: pMON13290 (Example 36), Met-Ala-(15–125)hIL-3 (18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 120Q and 123E) SEQ ID NO:91;
PEPTIDE #28: pMON13292 (Example 37), Met-Ala-(15–125)hIL-3 (18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 120Q and 123E) SEQ ID NO:92;
PEPTIDE #29: pMON13294 (Example 38), Met-Ala-(15–125)hIL-3 (18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 117S, 120H and 123E) SEQ ID NO:93;
PEPTIDE #30: pMON13295 (Example 39), Met-Ala-(15–125)hIL-3 (18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 117S, 120H and 123E) SEQ ID NO:94;
PEPTIDE #31: pMON13312 (Example 40), Met-Ala-(15–125)hIL-3 (18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 120Q and 123E) SEQ ID NO:95;
PEPTIDE #32: pMON13313 (Example 41), Met-Ala-(15–125)hIL-3 (18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 117S, 120H and 123E) SEQ ID NO:96;
PEPTIDE #A3: pMON13285 (Example 60), Met-Ala-(15–125)hIL-3 (42D, 45M, 46S, 50D) SEQ ID NO:259;
PEPTIDE #A4: pMON13286 (Example 61), Met-Ala-(15–125)hIL-3 (42D, 45M, 46S) SEQ ID NO:260;

TABLE 3-continued

POLYPEPTIDES

The numbering of the mutated amino acid positions which describe the following polypeptides corresponds to the sequence of the full-length, native (1–133)hIL-3.

PEPTIDE #A5: pMON13325 (Example 62), Met-Ala-(15–125)hIL-3 (42D, 45M, 46S, 116W) SEQ ID NO:261;
PEPTIDE #A6: pMON13326 (Example 63), Met-Ala-(15–125)hIL-3 (42D, 45M, 46S, 50D, 116W) SEQ ID NO:262;
PEPTIDE #A7: pMON13330 (Example 65), Met-Ala-(15–125)hIL-3 (42D, 45M, 46S, 50D, 95R, 98I, 100R, 116W) SEQ ID NO:263;
PEPTIDE #A8: pMON13329 (Example 66), Met-Ala-(15–125)hIL-3, (42D, 45M, 46S, 98I, 100R, 116W) SEQ ID NO:406;
PEPTIDE #B1: pMON13406 (Example 69), Met-Ala-(15–125)hIL-3 (18I, 19A, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:264;
PEPTIDE #B2: pMON13414 (Example 70), Met-Ala-(15–125)hIL-3 (18I, 19I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:265;
PEPTIDE #B3: pMON13407 (Example 71), Met-Ala-(15–125)hIL-3 (18I, 25H, 29R, 32N, 37P, 42S, 45V, 51R, 55T, 59L, 62V, 67H, 69E, 73G, 76A, 79R, 82Q, 87S, 93S, 98I, 101A, 105Q, 109E, 116V, 120Q and 123E) SEQ ID NO:266;
PEPTIDE #B4: pMON13405 (Example 72), Met-Ala-(15–125)hIL-3 (18I, 19A, 25H, 29R, 32N, 37P, 42S, 45V, 51R, 55T, 59L, 62V, 67H, 69E, 73G, 76A, 79R, 82Q, 87S, 93S, 98I, 101A, 105Q, 109E, 116V, 120Q and 123E) SEQ ID NO:267;
PEPTIDE #B5: pMON13415 (Example 73), Met-Ala-(15–125)hIL-3 (18I, 19I, 25H, 29R, 32N, 37P, 42S, 45V, 51R, 55T, 59L, 62V, 67H, 69E, 73G, 76A, 79R, 82Q, 87S, 93S, 98I, 101A, 105Q, 109E, 116V, 120Q and 123E) SEQ ID NO:268;
PEPTIDE #B6: pMON13408 (Example 74), Met-Ala-(15–125)hIL-3 (18I, 25H, 29R, 32N, 37P, 42S, 45M, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:269;
PEPTIDE #B7: pMON13409 (Example 75), Met-Ala-(15–125)hIL-3 (18I, 25H, 29R, 32N, 37P, 42S, 45M, 49L, 51R, 55T, 59L, 62V, 67H, 69E, 73G, 76A, 79R, 82Q, 87S, 93S, 98I, 101A, 105Q, 109E, 116V, 120Q and 123E) SEQ ID NO:270;
PEPTIDE #B8: pMON13410 (Example 76), Met-Ala-(15–125)hIL-3 (18I, 25H, 29R, 32N, 37P, 42S, 45M, 49D, 51R, 55T, 59L, 62V, 67H, 69E, 73G, 76A, 79R, 82Q, 87S, 93S, 98I, 101A, 105Q, 109E, 116V, 120Q and 123E) SEQ ID NO:271;
PEPTIDE #B9: pMON13422 (Example 77), Met-Ala-(15–125)hIL-3 (18I, 19A, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:272;
PEPTIDE #B10: pMON13423 (Example 78), Met-Ala-(15–125)hIL-3 (18I, 19I, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:273;
PEPTIDE #B11: pMON13424 (Example 79), Met-Ala-(15–125)hIL-3 (18I, 19A, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:274;
PEPTIDE #B12: pMON13425 (Example 80), Met-Ala-(15–125)hIL-3 (18I, 19I, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:275;
PEPTIDE #B13: pMON13426 (Example 81), Met-Ala-(15–125)hIL-3 (18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E) SEQ ID NO:276;
PEPTIDE #B14: pMON13429 (Example 82), Met-Ala-(15–125)hIL-3 (18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E) SEQ ID NO:277;
PEPTIDE #B15: pMON13368 (Example 83), Met-Ala-(15–125)hIL-3 (18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E) SEQ ID NO:278;
PEPTIDE #B16: pMON13380 (Example 84), Met-Ala-(15–125)hIL-3 (18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E) SEQ ID NO:279;
PEPTIDE #B17: pMON13475 (Example 86), Met-Ala-(15–125)hIL-3 (18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:280;
PEPTIDE #B18: pMON13366 (Example 87), Met-Ala-(15–125)hIL-3 (18I, 25H, 29R, 32A, 37P, 42N, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:281;
PEPTIDE #B19: pMON13367 (Example 88), Met-Ala-(15–125)hIL-3 (18I, 25H, 29R, 32A, 37P, 42A, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:282;
PEPTIDE #B20: pMON13369 (Example 89), Met-Ala-(15–125)hIL-3 (18I, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:283;
PEPTIDE #B21: pMON13370 (Example 90), Met-Ala-(15–125)hIL-3 (18I, 25H, 29R, 32A, 37P, 42A, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:284;
PEPTIDE #B22: pMON13373 (Example 91), Met-Ala-(15–125)hIL-3 (18I, 25H, 29R, 32A, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:285;
PEPTIDE #B23: pMON13374 (Example 92), Met-Ala-(15–125)hIL-3 (18I, 25H, 29R, 32A, 37P, 42S, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:286;
PEPTIDE #B24: pMON13375 (Example 93), Met-Ala-(15–119)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,) SEQ ID NO:287;
PEPTIDE #B25: pMON13376 (Example 94), Met-Asp-(15–119)hIL-3 (18I, 23A, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V) SEQ ID NO:288;
PEPTIDE #B26: pMON13377 (Example 95), Met-Ala-(15–119)hIL-3 (18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V) SEQ ID NO:289;
PEPTIDE #B27: pMON13378 (Example 96), Met-Asp-(15–119)hIL-3 (18I, 23A, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V) SEQ ID NO:290;
PEPTIDE #B28: pMON13379 (Example 97), Met-Ala-(15–125)hIL-3 (18I, 25H, 29R, 32A, 37P, 42A, 45V, 46S, 50D, 51R, 55L, 60S, 62V, 67N, 69E, 73G, 76A, 79R, 82Q, 87S, 93S, 98I, 101A, 105Q, 109E, 112Q, 116V, 120Q and 123E) SEQ ID NO:291;
PEPTIDE #B29: pMON13385 (Example 98), Met-Ala-(15–125)hIL-3 (18I, 25H, 29V, 32R, 34S, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:292;
PEPTIDE #B30: pMON13381 (Example 99), Met-Ala-(15–125)hIL-3 (18I, 25H, 29R, 32A, 37P, 42A, 45V, 51R, 55L, 60S, 62V, 67N, 69E, 73G, 76A, 79R, 82W, 87S, 93S, 98I, 101A, 105Q, 109E, 116V, 120Q and 123E) SEQ ID NO:293;
PEPTIDE #B31: pMON13383 (Example 100), Met-Ala-(15–125)hIL-3 (18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V, 120Q and 123E) SEQ ID NO:294;
PEPTIDE #B32: pMON13384 (Example 101), Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V, 120Q and 123E) SEQ ID NO:295;
PEPTIDE #B33: pMON13388 (Example 102), Met-Ala-(15–125)hIL-3 (18I, 25H, 29R, 32A, 37P, 42A, 45V, 50D, 51R, 55L, 56S, 60S, 62V, 67N, 69E, 73G, 76A, 79R, 82Q, 87S, 93S, 98I, 101A, 105Q, 109E, 116V, 120Q and 123E) SEQ ID NO:296;
PEPTIDE #B34: pMON13389 (Example 103), Met-Ala-(15–125)hIL-3 (18I, 25H, 29R, 32A, 37P, 42D, 45M, 51R, 55L, 60S, 62V, 67N, 69E, 73G, 76A, 79R, 82Q, 87S, 93S, 98I, 101A, 105Q, 109E, 116V, 120Q and 123E) SEQ ID NO:297;

TABLE 3-continued

POLYPEPTIDES

The numbering of the mutated amino acid positions which describe the following polypeptides corresponds to the sequence of the full-length, native (1–133)hIL-3.

PEPTIDE #B35: pMON13391 (Example 104), Met-Ala-(15–125)hIL-3 (18I, 25H, 29R, 32A, 34S, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:298;

PEPTIDE #B36: pMON13392 (Example 105), Met-Ala-(15–125)hIL-3 (18I, 25H, 29R, 32A, 37P, 42D, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:299;

PEPTIDE #B37: pMON13393 (Example 106), Met-Ala-(15–125)hIL-3 (18I, 23A, 25H, 29R, 32A, 34S, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:300;

PEPTIDE #B38: pMON13394 (Example 107), Met-Ala-(15–125)hIL-3 (18I, 25H, 29R, 32A, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:301;

PEPTIDE #B39: pMON13395 (Example 108), Met-Ala-(15–125)hIL-3 (18I, 23A, 25H, 29V, 32R, 34S, 37P, 42D, 45V, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:302;

PEPTIDE #B40: pMON13396 (Example 109), Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 100R, 101M, 116V, 120Q and 123E) SEQ ID NO:303;

PEPTIDE #B41: pMON13397 (Example 110), Met-Ala-(15–125)hIL-3 (18I, 25H, 29R, 32A, 37P, 42A, 45V, 51R, 55L, 60S, 62V, 67N, 69E, 73G, 76A, 79R, 82W, 87S, 93S, 98I, 101A, 105Q, 109E, 100R, 101M, 116V, 120Q and 123E) SEQ ID NO:304;

PEPTIDE #B42: pMON13398 (Example 111), Met-Ala-(15–125)hIL-3 (18I, 25H, 29R, 32A, 37P, 42D, 45V, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:305;

PEPTIDE #B43: pMON13399 (Example 112), Met-Ala-(15–125)hIL-3 (18I, 23A, 25H, 29V, 32R, 34S, 37P, 42D, 45V, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:306;

PEPTIDE #B44: pMON13404 (Example 113), Met-Ala-(15–119)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V) SEQ ID NO:307;

PEPTIDE #B45: pMON13387 (Example 114), Met-Ala-(15–125)hIL-3 (18I, 25H, 29R, 32A, 37P, 42A, 45V, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:308;

PEPTIDE #B46: pMON13416 (Example 115), Met-Ala-(15–125)hIL-3 (18I, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:309;

PEPTIDE #B47: pMON13417 (Example 116), Met-Ala-(15–125)hIL-3 (18I, 25H, 29R, 32A, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:310;

PEPTIDE #B48: pMON13420 (Example 117), Met-Ala-(15–125)hIL-3 (18I, 23A, 25H, 29R, 32A, 34S, 37P, 42D, 45V, 46S, 50D, 51R, 55L, 56S, 60S, 62V, 67N, 69E, 73G, 76A, 79R, 82Q, 87S, 93S, 98I, 101A, 105Q, 109E, 116V, 120Q and 123E) SEQ ID NO:311;

PEPTIDE #B49: pMON13421 (Example 118), Met-Ala-(15–125)hIL-3 (18I, 23A, 25H, 29R, 32A, 34S, 37P, 42D, 45M, 46S, 50D, 51R, 55L, 56S, 60S, 62V, 67N, 69E, 73G, 76A, 79R, 82Q, 87S, 93S, 98I, 101A, 105Q, 109E, 116V, 120Q and 123E) SEQ ID NO:331;

PEPTIDE #B50: pMON13432 (Example 119), Met-Ala-(15–125)hIL-3 (18I, 23A, 25H, 29R, 32A, 34S, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:312;

PEPTIDE #B51: pMON13382 (Example 120), Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116W, 120Q and 123E) SEQ ID NO:313;

PEPTIDE #B52: pMON13476 (Example 85), Met-Asp-(15–125)hIL-3 (18I, 23A, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ DI NO:314;

PEPTIDE #B53: pMON13446 (Example 121), Met-Ala-Tyr-Pro-Glu-Thr-Asp-Tyr-Lys-Asp-Asp-Asp-Asp-Lys-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:315;

PEPTIDE #B54: pMON13390 (Example 122), Met-Ala-Tyr-Pro-Glu-Thr-Asp-Tyr-Lys-Asp-Asp-Asp-Asp-Lys-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:316;

PEPTIDE #C-2: pMON13400 (Example 124), Met-Ala-(15–125)hIL-3 (18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:317;

PEPTIDE #C-3: pMON13402 (Example 125), Met-Ala-(15–125)hIL-3 (18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:318;

PEPTIDE #C-10: pMON13440 (Example 131), Met-Ala-(15–125)hIL-3 (18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:319;

PEPTIDE #C-11: pMON13451 (Example 132), Met-Ala-(15–125)hIL-3 (18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:320;

PEPTIDE #C-4: pMON13403 (Example 126), Met-Ala-(15–125)hIL-3 (18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E) SEQ ID NO:321;

PEPTIDE #C-5: pMON13411 (Example 127), Met-Ala-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E) SEQ ID NO:322;

PEPTIDE #C-6: pMON13412 (Example 128), Met-Ala-(15–118)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S) SEQ ID NO:323.

TABLE 4

DNA SEQUENCES

The numbering of the mutated amino acid positions in the modified hIL-3 proteins corresponds to the sequence of the full-length, native (1–133)hIL-3.

DNA Sequence #1: pMON13287 (Example 33), encoding Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:97;

DNA Sequence #2: pMON13290 (Example 36), encoding Met-Ala-(15–125)hIL-3 (18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 120Q and 123E) SEQ ID NO:98;

DNA Sequence #3: pMON13313 (Example 41), encoding Met-Ala-(15–125)hIL-3 (18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 117S, 120H and 123E) SEQ ID NO:98;

DNA Sequence #4: pMON13288 (Example 34), encoding Met-Ala-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:100;

DNA Sequence #5: pMON13312 (Example 40), encoding Met-Ala-(15–125)hIL-3 (18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 120Q and 123E) SEQ ID NO:101;

TABLE 4-continued

DNA SEQUENCES

The numbering of the mutated amino acid positions in the modified hIL-3 proteins corresponds to the sequence of the full-length, native (1–133)hIL-3.

DNA Sequence #6: pMON13294 (Example 38), encoding Met-Ala-(15–125)hIL-3 (18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 117S, 120H and 123E) SEQ ID NO:102;
DNA Sequence #7: pMON13289 (Example 35), encoding Met-Ala-(15–125)hIL-3 (18I, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E) SEQ ID NO:103;
DNA Sequence #8: pMON13292 (Example 37), encoding Met-Ala-(15–125)hIL-3 (18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 120Q and 123E) SEQ ID NO:104;
DNA Sequence #9: pMON13295 (Example 39), encoding Met-Ala-(15–125)hIL-3 (18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 117S, 120H and 123E) SEQ ID No:105;
DNA Sequence #10: pMON13344 (Example 8), (15–125)hIL-3 (18I, 25H, 29R, 32A, 37P, 42A and 45V) SEQ ID NO:106;
DNA Sequence #11: pMON13345 (Example 9), (15–125)hIL-3 (18I, 25H, 29R, 32N, 37P, 42S and 45M) SEQ ID NO:107;
DNA Sequence #12: pMON13346 (Example 10), (15–125)hIL-3 (18I, 25H, 29V, 32A, 37S, 42S and 45M) SEQ ID NO:108;
DNA Sequence #13: pMON13347 (Example 12), (15–125)hIL-3 (51R, 55L, 59L, 62V, 67N and 69E) SEQ ID NO:109;
DNA Sequence #14: pMON13348 (Example 13), (15–125)hIL-3 (51R, 55L, 60S, 62V, 67N and 69E) SEQ ID NO:110;
DNA Sequence #15: pMON13349 (Example 14), (15–125)hIL-3 (51R, 55T, 59L, 62V, 67H and 69E) SEQ ID NO:111;
DNA Sequence #16: pMON13350 (Example 16), (15–125)hIL-3 (73G, 76A, 79R, 82Q, 87S, 93S, 98I, 101A and 105Q) SEQ ID NO:112;
DNA Sequence #17: pMON13355 (Example 17), (15–125)hIL-3 (73G, 76A, 79R, 82V, 87S, 93S, 98T, 101A and 105Q) SEQ ID NO:113;
DNA Sequence #18: pMON13352 (Example 19), (15–125)hIL-3 (109E, 116V, 120Q and 123E) SEQ ID NO:114;
DNA Sequence #19: pMON13354 (Example 20), (15–125)hIL-3 (109E, 116V, 117S, 120H and 123E) SEQ ID NO:115;
DNA Sequence #20: pMON13363 (Example 24), (15–125)hIL-3 (18I, 25H, 29R, 32A, 37P, 42A, 45V, 51R, 55L, 60S, 62V, 67N and 69E) SEQ ID NO:116;
DNA Sequence #21: pMON13364 (Example 25), (15–125)hIL-3 (18I, 25H, 29R, 32N, 37P, 42S, 45M, 51R, 55T, 59L, 62V, 67H and 69E) SEQ ID NO:117;
DNA Sequence #22: pMON13365 (Example 26), (15–125)hIL-3 (18I, 25H, 29V, 32A, 37S, 42S, 45M, 51R, 55L, 59L, 62V, 67N and 69E) SEQ ID NO:118;
DNA Sequence #23: pMON13360 (Example 21), (15–125)hIL-3 (73G, 76A, 79R, 82Q, 87S, 93S, 98I, 101A, 105Q, 109E, 116V, 120Q and 123E) SEQ ID NO:119;
DNA Sequence #24: pMON13361 (Example 22), (15–125)hIL-3 (73G, 76A, 79R, 82V, 87S, 93S, 98T, 101A, 105Q, 109E, 116V, 120Q and 123E) SEQ ID NO:120;
DNA Sequence #25: pMON13362 (Example 23), (15–125)hIL-3 (73G, 76A, 79R, 82V, 87S, 93S, 98T, 101A, 105Q, 109E, 116V, 117S, 120H and 123E) SEQ ID NO:121;
DNA Sequence #26: pMON13301 (Example 30), encoding Met-Ala-(15–125)hIL-3 (18I, 25H, 29R, 32A, 37P, 42A, 45V, 51R, 55L, 60S, 62V, 67N and 69E) SEQ ID NO:122;
DNA Sequence #27: pMON13302 (Example 31), encoding Met-Ala-(15–125)hIL-3 (18I, 25H, 29R, 32N, 37P, 42S, 45M, 51R, 55T, 59L, 62V, 67H and 69E) SEQ ID NO:123;
DNA Sequence #28: pMON13303 (Example 32), encoding Met-Ala-(15–125)hIL-3 (18I, 25H, 29V, 32A, 37S, 42S, 45M, 51R, 55L, 59L, 62V, 67N and 69E) SEQ ID NO:124;
DNA Sequence #29: pMON13298 (Example 27), encoding Met-Ala-(15–125)hIL-3 (73G, 76A, 79R, 82Q, 87S, 93S, 98I, 101A, 105Q, 109E, 116V, 120Q and 123E) SEQ ID NO:125;
DNA Sequence #30: pMON13299 (Example 28), encoding Met-Ala-(15–125)hIL-3 (73G, 76A, 79R, 82V, 87S, 93S, 98T, 101A, 105Q, 109E, 116V, 120Q and 123E); SEQ ID NO:126;
DNA Sequence #31: pMON13300 (Example 29), encoding Met-Ala-(15–125)hIL-3 (73G, 76A, 79R, 82V, 87S, 93S, 98T, 101A, 105Q, 109E, 116V, 117S, 120H and 123E) SEQ ID NO:127;

DNA Sequence #33: pMON13438 (Example 59), encoding Met-Ala-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:161;
DNA Sequence #A3: pMON13285 (Example 60), encoding Met-Ala-(15–125)hIL-3 (42D, 45M, 46S, 50D) SEQ ID NO:398;
DNA Sequence #A4: pMON13286 (Example 61), encoding Met-Ala-(15–125)hIL-3 (42D, 45M, 46S) SEQ ID NO:399;
DNA Sequence #B1: pMON13406 (Example 69), encoding Met-Ala-(15–125)hIL-3 (18I, 19A, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:332;
DNA Sequence #B2: pMON13414 (Example 70), encoding Met-Ala-(15–125)hIL-3 (18I, 19I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:333;
DNA Sequence #B3: pMON13407 (Example 71), encoding Met-Ala-(15–125)hIL-3 (18I, 25H, 29R, 32N, 37P, 42S, 45V, 51R, 55T, 59L, 62V, 67H, 69E, 73G, 76A, 79R, 82Q, 87S, 93S, 98I, 101A, 105Q, 109E, 116V, 120Q and 123E) SEQ ID NO:334;
DNA Sequence #B4: pMON13405 (Example 72), encoding Met-Ala-(15–125)hIL-3 (18I, 19A, 25H, 29R, 32N, 37P, 42S, 45V, 51R, 55T, 59L, 62V, 67H, 69E, 73G, 76A, 79R, 82Q, 87S, 93S, 98I, 101A, 105Q, 109E, 116V, 120Q and 123E) SEQ ID NO:335;
DNA Sequence #B5: pMON13415 (Example 73), encoding Met-Ala-(15–125)hIL-3 (18I, 19I, 25H, 29R, 32N, 37P, 42S, 45V, 51R, 55T, 59L, 62V, 67H, 69E, 73G, 76A, 79R, 82Q, 87S, 93S, 98I, 101A, 105Q, 109E, 116V, 120Q and 123E) SEQ ID NO:336;
DNA Sequence #B6: pMON13408 (Example 74), encoding Met-Ala-(15–125)hIL-3 (18I, 25H, 29R, 32N, 37P, 42S, 45M, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:337;
DNA Sequence #B7: pMON13409 (Example 75), encoding Met-Ala-(15–125)hIL-3 (18I, 25H, 29R, 32N, 37P, 42S, 45M, 49L, 51R, 55T, 59L, 62V, 67H, 69E, 73G, 76A, 79R, 82Q, 87S, 93S, 98I, 101A, 105Q, 109E, 116V, 120Q and 123E) SEQ ID NO:338;
DNA Sequence #B8: pMON13410 (Example 76), encoding Met-Ala-(15–125)hIL-3 (18I, 25H, 29R, 32N, 37P, 42S, 45M, 49D, 51R, 55T, 59L, 62V, 67H, 69E, 73G, 76A, 79R, 82Q, 87S, 93S, 98I, 101A, 105Q, 109E, 116V, 120Q and 123E) SEQ ID NO:339;
DNA Sequence #B9: pMON13422 (Example 77), encoding Met-Ala-(15–125)hIL-3 (18I, 19A, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:340;
DNA Sequence #B10: pMON13423 (Example 78), encoding Met-Ala-(15–125)hIL-3 (18I, 19I, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:341;
DNA Sequence #B11: pMON13424 (Example 79), encoding Met-Ala-(15–125)hIL-3 (18I, 19A, 25H, 29R, 32N, 37P, 42S, 45V, 49L, 51R, 55T, 59L, 62V, 67H, 69E, 73G, 76A, 79R, 82Q, 87S, 93S, 98I, 101A, 105Q, 109E, 116V, 120Q and 123E) SEQ ID NO:342;
DNA Sequence #B12: pMON13425 (Example 80), encoding Met-Ala-(15–125)hIL-3 (18I, 19I, 25H, 29R, 32N, 37P, 42S, 45V, 49I, 51R, 55T, 59L, 62V, 67H, 69E, 73G, 76A, 79R, 82Q, 87S, 93S, 98I, 101A, 105Q, 109E, 116V, 120Q and 123E) SEQ ID NO:343;
DNA Sequence #B13: pMON13426 (Example 81), encoding Met-Ala-(15–125)hIL-3 (18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E) SEQ ID NO:344;
DNA Sequence #B14: pMON13429 (Example 82), encoding Met-Ala-(15–125)hIL-3 (18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E) SEQ ID NO:345;
DNA Sequence #B15: pMON13368 (Example 83), encoding Met-Ala-(15–125)hIL-3 (18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E) SEQ ID NO:346;
DNA Sequence #B16: pMON13380 (Example 84), encoding Met-Ala-(15–125)hIL-3 (18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E) SEQ ID NO:347;

TABLE 4-continued

DNA SEQUENCES

The numbering of the mutated amino acid positions in the modified hIL-3 proteins corresponds to the sequence of the full-length, native (1–133)hIL-3.

DNA Sequence #B17: pMON13475 (Example 86), encoding Met-Ala-(15–125)hIL-3 (18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:348;
DNA Sequence #B18: pMON13366 (Example 87), encoding Met-Ala-(15–125)hIL-3 (18I, 25H, 29R, 32A, 37P, 42N, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:349;
DNA Sequence #B19: pMON13367 (Example 88), encoding Met-Ala-(15–125)hIL-3 (18I, 25H, 29R, 32A, 37P, 42A, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:350;
DNA Sequence #B20: pMON13369 (Example 89), encoding Met-Ala-(15–125)hIL-3 (18I, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:351;
DNA Sequence #B21: pMON13370 (Example 90), encoding Met-Ala-(15–125)hIL-3 (18I, 25H, 29R, 32A, 37P, 42A, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:352;
DNA Sequence #B22: pMON13373 (Example 91), encoding Met-Ala-(15–125)hIL-3 (18I, 25H, 29R, 32A, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:353;
DNA Sequence #B23: pMON13374 (Example 92), encoding Met-Ala-(15–125)hIL-3 (18I, 25H, 29R, 32A, 37P, 42S, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:354;
DNA Sequence #B24: pMON13375 (Example 93), encoding Met-Ala-(15–119)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,) SEQ ID NO:355;
DNA sequence #B25: pMON13376 (Example 94), Met-Asp-(15–119)hIL-3 (18I, 23A, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V) SEQ ID NO:356;
DNA Sequence #B26: pMON13377 (Example 95), encoding Met-Ala-(15–119)hIL-3 (18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V) SEQ ID NO:357;
DNA Sequence #B27: pMON13378 (Example 96), Met-Asp-(15–119)hIL-3 (18I, 23A, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V) SEQ ID NO:358;
DNA sequence #B28: pMON13379 (Example 97), encoding Met-Ala-(15–125)hIL-3 (18I, 25H, 29R, 32A, 37P, 42A, 45V, 46S, 50D, 51R, 55L, 60S, 62V, 67N, 69E, 73G, 76A, 79R, 82Q, 87S, 93S, 98I, 101A, 105Q, 109E, 112Q, 116V, 120Q and 123E) SEQ ID NO:359;
DNA sequence #B29: pMON13385 (Example 98), encoding Met-Ala-(15–125)hIL-3 (18I, 25H, 29V, 32R, 34S, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:360;
DNA Sequence #B30: pMON13381 (Example 99), encoding Met-Ala-(15–125)hIL-3 (18I, 25H, 29R, 32A, 37P, 42A, 45V, 51R, 55L, 60S, 62V, 67N, 69E, 73G, 76A, 79R, 82W, 87S, 93S, 98I, 101A, 105Q, 109E, 116V, 120Q and 123E) SEQ ID NO:361;
DNA Sequence #B31: pMON13383 (Example 100), encoding Met-Ala-(15–125)hIL-3 (18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V, 120Q and 123E) SEQ ID NO:362;
DNA Sequence #B32: pMON13384 (Example 101), encoding Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V, 120Q and 123E) SEQ ID NO:363;
DNA Sequence #B33: pMON13388 (Example 102), encoding Met-Ala-(15–125)hIL-3 (18I, 25H, 29R, 32A, 37P, 42A, 45V, 50D, 51R, 55L, 56S, 60S, 62V, 67N, 69E, 73G, 76A, 79R, 82Q, 87S, 93S, 98I, 101A, 105Q, 109E, 116V, 120Q and 123E) SEQ ID NO:346;
DNA Sequence #B34: pMON13389 (Example 103), encoding Met-Ala-(15–125)hIL-3 (18I, 25H, 29R, 32A, 37P, 42D, 45M, 51R, 55L, 60S, 62V, 67N, 69E, 73G, 76A, 79R, 82Q, 87S, 93S, 98I, 101A, 105Q, 109E, 116V, 120Q and 123E) SEQ ID NO:365;
DNA Sequence #B35: pMON13391 (Example 104), encoding Met-Ala-(15–125)hIL-3 (18I, 25H, 29R, 32A, 34S, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:366;
DNA Sequence #B36: pMON13392 (Example 105), encoding Met-Ala-(15–125)hIL-3 (18I, 25H, 29R, 32A, 37P, 42D, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:367;
DNA Sequence #B37: pMON13393 (Example 106), encoding Met-Ala-(15–125)hIL-3 (18I, 23A, 25H, 29R, 32A, 34S, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:368;
DNA Sequence #B38: pMON13394 (Example 107), encoding Met-Ala-(15–125)hIL-3 (18I, 25H, 29R, 32A, 37P, 42D, 45M, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:369;
DNA Sequence #B39: pMON13395 (Example 108), encoding Met-Ala-(15–125)hIL-3 (18I, 23A, 25H, 29V, 32R, 34S, 37P, 42D, 45V, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:370;
DNA Sequence #B40: pMON13396 (Example 109), encoding Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 100R, 101M, 116V, 120Q and 123E) SEQ ID NO:371;
DNA Sequence #B41: pMON13397 (Example 110), encoding Met-Ala-(15–125)hIL-3 (18I, 25H, 29R, 32A, 37P, 42A, 45V, 51R, 55L, 60S, 62V, 67N, 69E, 73G, 76A, 79R, 82W, 87S, 93S, 98I, 101A, 105Q, 109E, 100R, 101M, 116V, 120Q and 123E) SEQ ID NO:372;
DNA Sequence #B42: pMON13398 (Example 111), encoding Met-Ala-(15–125)hIL-3 (18I, 25H, 29R, 32A, 37P, 42D, 45V, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:373;
DNA Sequence #B43: pMON13399 (Example 112), encoding Met-Ala-(15–125)hIL-3 (18I, 23A, 25H, 29V, 32R, 34S, 37P, 42D, 45V, 46S, 51R, 55L, 60S, 62V, 67N, 69E, 73G, 76A, 79R, 82Q, 87S, 93S, 98I, 101A, 105Q, 109E, 116V, 120Q and 123E) SEQ ID NO:374;
DNA Sequence #B44: pMON13404 (Example 113), encoding Met-Ala-(15–119)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V) SEQ ID NO:375;
DNA Sequence #B45: pMON13387 (Example 114), encoding Met-Ala-(15–125)hIL-3 (18I, 25H, 29R, 32A, 37P, 42A, 45V, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:376;
DNA Sequence #B46: pMON13416 (Example 115), encoding Met-Ala-(15–125)hIL-3 (18I, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:377;
DNA Sequence #B47: pMON13417 (Example 116), encoding Met-Ala-(15–125)hIL-3 (18I, 25H, 29R, 32A, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:378;
DNA Sequence #B48: pMON13420 (Example 117), encoding Met-Ala-(15–125)hIL-3 (18I, 23A, 25H, 29R, 32A, 34S, 37P, 42D, 45V, 46S, 50D, 51R, 55L, 56S, 60S, 62V, 67N, 69E, 73G, 76A, 79R, 82Q, 87S, 93S, 98I, 101A, 105Q, 109E, 116V, 120Q and 123E) SEQ ID NO:379;
DNA Sequence #B49: pMON13421 (Example 118), encoding Met-Ala-(15–125)hIL-3 (18I, 23A, 25H, 29R, 32A, 34S, 37P, 42D, 45M, 46S, 50D, 51R, 55L, 56S, 60S, 62V, 67N, 69E, 73G, 76A, 79R, 82Q, 87S, 93S, 98I, 101A, 105Q, 109E, 116V, 120Q and 123E) SEQ ID NO:380;
DNA Sequence #B50: pMON13432 (Example 119), encoding Met-Ala-(15–125)hIL-3 (18I, 23A, 25H, 29R, 32A, 34S, 37P, 42D, 45M, 46S, 50D, 51R, 55L, 60S, 62V, 67N, 69E, 73G, 76A, 79R, 82Q, 87S, 93S, 98I, 101A, 105Q, 109E, 116V, 120Q and 123E) SEQ ID NO:381;
DNA Sequence #B51: pMON13382 (Example 120), encoding Met-Ala-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116W, 120Q and 123E) SEQ ID NO:382;
DNA Sequence #B52: pMON13476 (Example 85), Met-Asp-(15–(15–125)hIL-3 (18I, 23A, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ DI NO:383;

TABLE 4-continued

DNA SEQUENCES

The numbering of the mutated amino acid positions in the modified hIL-3 proteins corresponds to the sequence of the full-length, native (1–133)hIL-3.

DNA Sequence #B53: pMON13446 (Example 121), encoding Met-Ala-Tyr-Pro-Glu-Thr-Asp-Tyr-Lys-Asp-Asp-Asp-Asp-Lys-(15–125)hIL-3 (18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E) SEQ ID NO:404;

DNA Sequence #B54: pMON13390 (Example 122), encoding Met-Ala-Tyr-Pro-Glu-Thr-Asp-Tyr-Lys-Asp-Asp-Asp-Asp-Lys-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:405;

DNA Sequence #C-1: pMON13418 (Example 123), encoding Met-Ala-(15–125)hIL-3 (18I, 25H, 29R, 32N, 37P, 42S, 45M, 51R, 55T, 59L, 62V, 67H, 69E, 73G, 76P, 79I, 82Q, 85V, 87Y, 88W, 91P, 93S, 95T, 98T, 101A, 105Q, 109E, 116V, 120Q and 123E) SEQ ID NO:393;

DNA Sequence #C-2: pMON13400 (Example 124), encoding Met-Ala-(15–125)hIL-3 (18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:384;

DNA Sequence #C-3: pMON13402 (Example 125), encoding Met-Ala-(15–125)hIL-3 (18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:385;

DNA Sequence #C-4: pMON13403 (Example 126), encoding Met-Ala-(15–125)hIL-3 (18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E) SEQ ID NO:388;

DNA Sequence #C-5: pMON13411 (Example 127), encoding Met-Ala-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E) SEQ ID NO:390;

DNA Sequence #C-6: pMON13412 (Example 128), encoding Met-Ala-(15–118)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S) SEQ ID NO:391;

DNA Sequence #C-7: pMON13413 (Example 129), encoding Met-Ala-(15–125)hIL-3 (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E) SEQ ID NO:392;

DNA Sequence #C-8: pMON13419 (Example 126), encoding Met-Ala-(15–125)hIL-3 (18I, 25H, 29R, 32N, 37P, 42S, 45M, 50D, 51S, 55T, 59L, 62P, 63H, 65S, 67Q, 69E, 73G, 76A, 79R, 82Q, 87S, 93S, 98I, 101A, 105Q, 109E, 116V, 120Q and 123E) SEQ ID NO:389;

DNA Sequence #C-9: pMON13428 (Example 133), encoding Met-Ala-(15–125)hIL-3 (18I, 25H, 29R, 32N, 37P, 42S, 45M, 51R, 55T, 59L, 62V, 67H, 69E, 73G, 76P, 79S, 82Q, 85V, 87Y, 91P, 93S, 95T, 98T, 101A, 105Q, 109L, 112Q, 116S, 120Q and 123E) SEQ ID NO:394;

DNA Sequence #C-10: pMON13440 (Example 131), encoding Met-Ala-(15–125)hIL-3 (18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:386;

DNA Sequence #C-11: pMON13451 (Example 132), encoding Met-Ala-(15–125)hIL-3 (18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E) SEQ ID NO:387;

DNA Sequence #C-12: pMON13459 (Example 134), encoding Met-Ala-(15–125)hIL-3 (18I, 23L, 25H, 29I, 32N, 34S, 37S, 38A, 42S, 45V, 46S, 51R, 55T, 59L, 62V, 67H, 69E, 73G, 76P, 79S, 82Q, 85V, 87Y, 91P, 93S, 95T, 98T, 101A, 105Q, 109L, 112Q, 116S, 120Q and 123E) SEQ ID NO:395;

DNA Sequence #C-13: pMON13467 (Example 135), encoding Met-Ala-(15–125)hIL-3 (18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109L, 112Q, 116S, 120Q and 123E) SEQ ID NO:396;

DNA Sequence #C-14: pMON13492 (Example 136), encoding Met-Ala-(15–125)hIL-3 (18I, 23L, 25H, 29I, 32N, 34S, 37S, 38A, 42S, 45V, 46S, 51R, 55T, 59L, 62V, 67H, 69E, 73G, 76P, 79S, 82Q, 85V, 87Y, 91P, 93S, 95T, 98T, 101A, 105Q, 109E, 116V, 120Q and 123E) SEQ ID NO:397.

Polypeptides corresponding to [SEQ ID NO. 129] comprising (1–133)hIL-3 containing four or more amino acid substitutions can be made using the procedures described above and in the following examples by starting with the appropriate oligonuctiotides and then constructing the DNA encoding the polypeptide and expressing it in an appropriate host cell. In a similar manner polypeptides which correspond to [SEQ ID NO. 130] and contain four or more amino acid substitutions and wherein from 1 to 14 amino acids have been sequentially deleted from the N-terminus, or from 1 to 15 amino acids have been deleted from the C-terminus or deletions of amino acids have been made from both the N-terminus and the C-terminus can also be made by following the procedures described above and in the following examples, beginning with the appropriate starting materials.

Further details known to those skilled in the art may be found in T. Maniatis, et al., *Molecular Cloning, A Laboratory Manual*, Cold Spring Harbor Laboratory (1982) and references cited therein, incorporated herein by reference; and in J. Sambrook, et al., *Molecular Cloning, A Laboratory Manual*, 2nd edition, Cold Spring Harbor Laboratory (1989) and references cited therein, incorporated herein by reference.

The following examples will illustrate the invention in greater detail although it will be understood that the invention is not limited to these specific examples.

Amino acids are shown herein by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

References

Adams, S. P., Kavka, K. S., Wykes, E. J., Holder, S. B. and Galluppi, G. R. Hindered Dialkyamino Nucleoside Phosphate reagents in the synthesis of two DNA 51-mers. J. Am. Chem. Soc., 105, 661–663 (1983).

Atkinson, T. and Smith, M., in Gait, M. J., Oligonucleotide Sythesis (1984) (IRL Press, Oxford England).

Bachmann, B., Pedigrees of some mutant strains of Escherichia coli K-12, *Bacteriological Reviews*, 36:525–557 (1972).

Bayne, M. L., Expression of a synthetic gene encoding human insulin-like growth factor I in cultured mouse fibroblasts. *Proc. Natl. Acad. Sci. USA* 84, 2638–2642 (1987).

Ben-Bassat, A., K. Bauer, S -Y. Chang, K. Myambo, A. Boosman and S. Ching. Processing of the initiating methionine from proteins: properties of the Escherichia coli methionine aminopeptidase and its gene structure. *J. Bacteriol.,* 169: 751–757 (1987).

Biesma, B. et al., Effects of interleukin-3 after chemotherapy for advanced ovarian cancer. *Blood,* 80:1141–1148 (1992).

Birnboim, H. C. and J. Doly. A rapid alkaline extraction method for screening recombinant plasmid DNA. *Nucleic Acids Research,* 7(6): 1513–1523 (1979).

Bradford, M. M., A rapid and sensitive method for the quantitation of microgram quantities of protein utilizing the principle of protein-dye binding, *Analytical Biochemistry,* 72: 248–254 (1976).

Clark-Lewis, I., L. E. Hood and S. B. H. Kent. Role of disulfide bridges in determining the biological activity of interleukin 3, *Proc. Natl. Acad. Sci.,* 85: 7897–7901 (1988).

Clement, J. M. and Hofnung, M. Gene sequence of the receptor, an outer membrane protein of *E. coli* K12. *Cell,* 27: 507–514 (1981).

Covarrubias, L., L. Cervantes, A. Covarrubias, X. Soberon, I. Vichido, A. Blanco, Y. M. Kupersztoch-Portnoy and F. Bolivar. Construction and characterization of new cloning vehicles. V. Mobilization and coding properties of pBR322 and several deletion derivates including pBR327 and pBR328. *Gene* 13: 25–35 (1981).

Deng, W. P. & Nickoloff, J. A. Site-directed mutagenesis of virtually any plasmid by eliminating a unique site *Anal. Biochem.* 200:81 (1992).

Dente, L., G. Cesareni and R. Cortese, pEMBL: a new family of single stranded plasmids, *Nucleic Acids Research,* 11: 1645–1655 (1983).

Dunn, J. J. and Studier, F. W., Complete nucleotide sequence of bacteriophage T7 DNA and the locations of T7 genetic elements. *J. Mol. Biol.* 166:477–535 (1983).

Falk, S., G. Seipelt, A. Ganser, O. G. Ottmann, D. Hoelzer, H. J. Stutte and K. Hubner. *Hematopathology* 95: 355 (1991).

Fling, M. E., et al. Nucleotide sequence of the transposon Tn7 gene encoding an aminoglycoside-modifying enzyme, 3"(9)-O-nucleotidyltransferase. *Nucl. Acids Res.* 13:7095–7106 (1985).

Ganser, A., A. Lindemann, G. Seipelt, O. G. Ottmann, F. Herrmann, M. Eder, J. Frisch, G. Schulz, R. Mertelsmann and D. Hoelzer. Effects of Recombinant Human Interleukin-3 in Patients With Normal Hematopoiesis and in Patients with Bone Marrow Failure, *Blood* 76: 666 (1990).

Gething and Sambrook, Cell-surface expression of influenza haemagglutinin from a cloned DNA copy of the RNA gene, *Nature,* 293: 620–625 (1981).

Gillio, A. P., C. Gasparetto, J. Laver, M. Abboud, M. A. Bonilla, M. B. Garnick and R. J. O'Reilly. *J. Clin. Invest.* 85: 1560 (1990).

Gouy, M. and G. Gautier, Codon usage in bacteria: Correlation with gene expressivity, *Nucleic Acids Research,* 10: 7055–7074 (1982).

Greenfield, L., T. Boone, and G. Wilcox. DNA sequence of the araBAD promoter in Escherichia coli B/r. *Proc. Natl. Acad. Sci. USA,* 75: 4724–4728 (1978).

Higuchi, R, (1989) in *PCR Technology,* H. A. Erlich ed., Stockton Press, N.Y. chapter 2–6.

Hunkapiller, M. W., R. W. Hewick, R. J. Dreyer and L. E. Hood. High sensitivity sequencing with a gas-phase sequenator. *Methods in Enzymology* 153: 399–413 (1983).

Kaufman, et al., Coamplification and Coexpression of Human Tissue-Type Plasminogen Activator and Murine Dihydrofolate Reductase Sequences in Chinese Hamster Ovary Cells, *Mol. Cell. Biol.,* 5(7): 1750–1759 (1985).

Kaufman, R. J. High level production of proteins in mammalian cells, in *Genetic Engineering, Principles and Methods,* Vol. 9, J. K. Setlow, editor, Plenum Press, New York (1987).

Kunkel, T. A. Rapid and efficient site-specific mutagenesis without phenotypic selection. *Proc. Natl. Acad. Sci. USA,* 82: 488–492 (1985).

Laemmli, U. K., Cleavage of structural proteins during assembly of the head of bacteriophage T4, *Nature,* 227:680–685 (1970).

Lange, B., M. Valtieri, D. Santoli, D. Caracciolo, F. Mavilio, I. Gemperlein, C. Griffin, B. Emanuel, J. Finan, P. Nowell, and G. Rovera. Growth factor requirements of childhood acute leukemia: establishment of GM-CSF-defendent cell lines. *Blood* 70:192 (1987).

Mahler, H. R. and E. H. Cordes, in *Biological Chemistry,* p. 128, New York, Harper and Row (1966).

Maniatis, T., E. F. Fritsch and J. Sambrook, *Molecular Cloning, A Laboratory Manual.* Cold Spring Harbor Laboratory (1982).

Marinus, M. G. Location of DNA methylation genes on the *Escherichia coli* K-12 genetic map. *Molec. Gen. Genet.* 127: 47–55 (1973).

McBride, L. J. and Caruthers, M. H. An investigation of several deoxynucleoside phosphoramidites. Tetrahedron Lett., 24, 245–248 (1983).

Messing, J., A multipurpose cloning system based on the single-stranded DNA bacteriophage M13. *Recombinant DNA Technical Bulletin,* NIH Publication No. 79–99, Vol. 2, No. 2, pp. 43–48 (1979).

Neu, H. C. and L. A. Heppel. The release of enzymes from Escherichia coli by osmotic shock and during the formation of spheroplasts. *J. Biol. Chem.,* 240: 3685–3692 (1965).

Obukowicz, M. G., Staten, N. R. and Krivi, G. G., Enhanced Heterologous Gene Expression in Novel rpoH Mutants of Escherichia coli. *Applied and Environmental Microbiology* 58, No. 5, p. 1511–1523 (1992).

Olins, P. O., C. S. Devine, S. H. Rangwala and K. S. Kavka, The T7 phage gene 10 leader RNA, a ribosome-binding site that dramatically enhances the expression of foreign genes in *Escherichia coli, Gene,* 73:227–235 (1988).

Olins, P. O. and S. H. Rangwala, Vector for enhanced translation of foreign genes in *Escherichia coli, Methods in Enzymology,* 185: 115–119 (1990).

Postmus, et al., Effects of recombinant human interleukin-3 in patients with relapsed small-cell lung cancer treated with chemotherapy: a dose-finding study. *J. Clin. Oncol.,* 10:1131–1140 (1992).

Prober, J. M., G. L. Trainor, R. J. Dam, F. W. Hobbs, C. W. Robertson, R. J. Zagursky, A. J. Cocuzza, M. A. Jensen and K. Baumeister. A system for rapid DNA sequencing with fluorescent chain-terminating dideoxynucleotides. *Science* 238: 336–341 (1987).

Renart J., J. Reiser and G. R. Stark, Transfer of proteins from gels to diazobenzyloxymethyl-paper and detection with anti-sera: a method for studying antibody specificity and antigen structure, *Proc. Natl. Acad. Sci. USA,* 76:3116–3120 (1979).

Saiki, R. K., Schorf, S., Faloona, F., Mullis, K. B., Horn, G. T., Erlich, H. A. and Arnheim, N., Enzymatic Amplification of B-Globin Genomic Sequences and Restriction Site Analysis for Diagnosis of Sickle Cell Anemia, *Science,* 230: 1350–1354 (1985).

Sambrook, J., et al., *Molecular Cloning, A Laboratory Manual*, 2nd edition, Cold Spring Harbor Laboratory (1989).

Sancar, A., C. Stachelek, W. Konigsberg and W. D. Rupp, Sequences of the recA gene and protein, *Proc. Natl. Acad. Sci.*, 77: 2611–2615 (1980).

Sanger, F., S. Nicklen and A. R. Coulson. DNA sequencing with chain-terminating inhibitors. Proc. Natl. Acad. Sci. U. S. A. 74: 5463–5467 (1977).

Santoli, D., Y. Yang, S. C. Clark, B. L. Kreider, D. Caracciolo, and G. Rovera. Synergistic and antagonistic effects of recombinant human interleukin (IL-3), IL-1 , granulocyte and macrophage colony-stimulating factors (G-CSF and M-CSF) on the growth of GM-CSF-dependent leukemic cell lines. *J. Immuno.* 139:348 (1987).

Smith, M. In vitro mutagenesis. *Ann. Rev. Genet.*, 19:423–462 (1985).

Soberon, X., L. Covarrubias and F. Bolivar, Construction and characterization of new cloning vehicles. IV. Deletion derivatives of pBR322 and pBR325, *Gene*, 9: 211–223 (1980).

Stader, J. A. and T. J. Silhavy. Engineering *Escherichia coli* to secrete heterologous gene products, *Methods in Enzymology*, 185: 166–87 (1990).

Summers, M. D. and G. E. Smith. A manual of methods for Baculovirus vectors and insect cell culture procedures. *Texas Agricultural Experiment Station Bulletin No.* 1555 (1987).

Taylor, J. W., Ott, J. and Eckstein, F. The rapid generation of oligonucleotide-directed mutants at high frequency using phosphorothioate modified DNA. *Nucl. Acids Res.*, 13:8764–8785 (1985).

Treco, D. A., (1989) in *Current protocols in Molecular Biology*, Seidman et al., eds. J Wiley N.Y., unit 2.1.

Valtieri, M., D. Santoli, D. Caracciolo, B. L. Kreider, S. W. Altmann, D. J. Tweardy, I. Gemperlein, F. Mavilio, B. J. Lange and G. Rovera. Establishment and characterization of an undifferentiated human T leukemia cell line which requires granulocyte-macrophage colony stimulating factor for growth. *J. Immunol.* 13:4042 (1987).

Voet, D., W. B. Gatzer, R. A. Cox, P. Doty. Absorption spectra of the common bases. *Biopolymers* 1: 193 (1963).

Wells, J. A., Vasser, M., and Powers, D. B. Cassette mutagenesis: an effective method for generation of multiple mutants at defined sites. *Gene*, 34:315–323 (1985).

Wong, Y. Y., R. Seetharam, C. Kotts, R. A. Heeren, B. K. Klein, S. B. Braford, K. J. Mathis, B. F. Bishop, N. R. Siegel, C. E. Smith and W. C. Tacon. Expression of secreted IGF-1 in *Escherichia coli. Gene*, 68: 193–203 (1988).

Yanisch-Perron, C., J. Viera and J. Messing. Improved M13 phage cloning vectors and host strains: nucleotide sequences of the M13mp18 and pUC19 vectors. *Gene* 33: 103–119 (1985).

Zoller, M. J. and Smith, M. Oligonucleotide-directed mutagenesis using M13-derived vectors: an efficient and general procedure for the production of point mutations in any fragment of DNA. *Nucleic Acid Research*, 10: 6487–6500 (1982).

Zoller, M. J. and Smith, M. Oligonucleotide-directed mutagenesis of DNA fragments cloned into M13 vectors. *Methods in Enzymology*, 100:468–500 (1983).

Zoller, M. J. and Smith, M. Oligonucleotide-directed Mutagenesis: A simple method using two oligonucleotide primers and a single-stranded DNA template. *DNA*, 3: 479 (1984).

EXAMPLE 1

Construction of pMON 5846 (FIG. 4) which encodes [Met-(1–133) hIL-3 (Arg$^{129}$)]

A plasmid containing the gene for the cDNA of hIL-3 cloned into pUC18 on an EcoRI to HindIII fragment was obtained from British Biotechnology Limited (Cambridge, England). This plasmid was designated pPO518. The purified plasmid DNA was cleaved by the restriction endonucleases NheI and BamHI. Approximately 0.5 micrograms of cleaved plasmid DNA was ligated to 1.0 picomoles of a pair of annealed oligonucleotides with the following sequence:

5'-CTAGCGATCTTTTAATAAGCTTG-3' [SEQ ID NO:1]

3'-GCTAGAAAATTATTCGAACCTAG-5' [SEQ ID NO:2]

The ligation mixture was used to transform competent JM101 cells to ampicillin resistance. Colonies were picked, and plasmid DNA was purified and subjected to restriction enzyme analysis. An isolate was identified in which the above oligonucleotide sequence had replaced the portion of the gene that encodes the extreme C terminus. Within the new sequence was a new stop codon, TAA, and a recognition site for the enzyme HindIII. The new plasmid was designated pMON5846.

EXAMPLE 2

(a) Construction of expression vector plasmid pMON2341

The plasmid pMON2341 was used to supply the particular replicon and expression elements used for construction of many of the plasmids used to produce hIL-3 and hIL-3 muteins in *E. coli*. These expression elements are described in the materials and methods section. pMON2341 is derived from pMON5515 (Olins et al., 1988) and from pMON2429. pMON2429 consists of the phage mp18 (Yanisch-Perron et al., 1985) with a BclI fragment carrying the chloramphenicol acetyl transferase (cat) gene from pBR328 (Covarrubias et al., 1981) inserted into the BamHI site. The cat gene in pMON2429 has been altered from that in pBR328 by site directed mutagenesis (Kunkel, 1985). The recognition sites for NcoI and EcoRI which occur in the native gene were altered so that these two restriction enzymes no longer recognize these sites. The changes did not alter the protein specified by the gene. Also, an NcoI site was introduced at the N-terminus of the coding sequence so that it overlaps the codon for initiator methionine.

The steps involved in construction of pMON2341 are listed below:

(1) The DNAs of pMON5515 and pMON2429 were treated with NcoI and HindIII. The fragments were ligated and used to transform competent *E. coli* to ampicillin resistance. From these colonies, some were identified that were chloramphenicol resistant. From one of these colonies, plasmid DNA was isolated in which the rat atriopeptigen gene of pMON5515 had been replaced by the NcoI to HindIII fragment containing the cat gene from pMON2429. This fragment contains the recognition sites for several restriction enzymes in the portion derived from the multi-linker region of mp18. The new plasmid was designated pMON2412.

(2) pMON2412 was treated with the enzyme ClaI which cleaves at one location in the pBR327 derived portion of the DNA. The protruding ends were rendered blunt by treatment with Klenow in the presence of nucleotide precursors. This DNA was mixed with an isolated 514 bp RsaI fragment derived from pEMBL8 (Dente et al., 1983). This RsaI fragment contains the origin of replication of phage f1. This ligation mixture was used to transform competent *E. coli* cells to ampicillin resistance. Among the plasmid DNAs isolated from these cells was pMON5578. This plasmid has the structure of pMON2412 with the f1 origin region inserted into the ClaI site. This is illustrated in the Figures and in Olins and Rangwala (1990).

(3) The DNA of pMON5578 was treated with restriction enzymes HindIII and MstII. The DNA was then treated with Klenow enzyme in the presence of nucleotide precursors to render the ends blunt. This treated DNA was ligated and used to transform competent *E. coli* to ampicillin resistance. From the ampicillin resistant colonies, one plasmid was recovered from which the portion between HindIII and MstII was absent. This deletion resulted in the removal of sequences from the plasmid which are recognized by a number of restriction endonuclease sites. The new plasmid was designated pMON5582.

(4) The DNA of pMON5582 was treated with SstII and BclII and ligated in the presence of annealed oligonucleotides with the sequences shown below.

5'- GGCAACAATTTCTACAAAACACTTGATACTGTATGAGCATACAGTATAATTGCTTCAACAGAACAGATC-3' [SEQ ID NO:3]

3'-CGCCGTTGTTAAAGATGTTTTGTGAACTATGACATACTCGTATGTCATATTAACGAAGTTGTCTTGT-5' [SEQ ID NO:4]

This sequence encodes the essential elements of the recA promoter of *E. coli* including the transcription start site and the lexA repressor binding site (the operator) (Sancar et al., 1980). The plasmid recovered from the ligation mixes contained this recA promoter in place of the one in pMON5582 (and in pMON5515). The functionality of the recA promoter was illustrated by Olins and Rangwala (1990). The new plasmid was designated pMON5594.

(5) To eliminate the single EcoRI site in pMON5594, the DNA was treated with EcoRI, then with Klenow in the presence of nucleotide precursors to render the ends blunt and then the DNA was ligated. From this ligation mix a plasmid was recovered whose DNA was not cleaved with EcoRI. This plasmid was designated pMON5630.

(6) To alter the single recognition site for PstI, plasmid pMON5630 was subjected to site directed mutagensis (Kunkel, 1985). The oligonucleotide used in this procedure has the sequence shown below.

5'-CCATTGCTGCCGGCATCGTGGTC-3' [SEQ ID NO:5]

Figure 5:
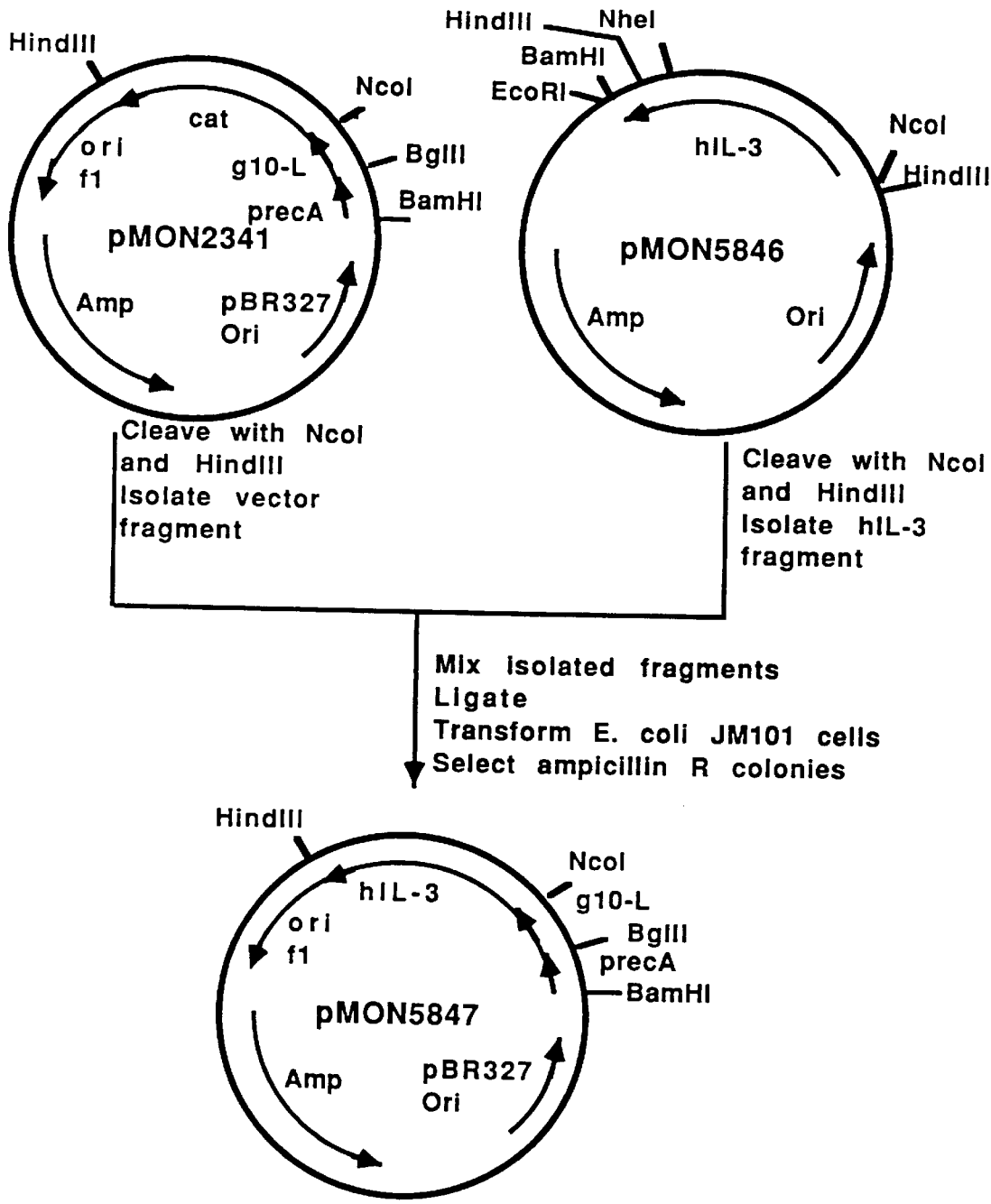
FIG. 5 shows the construction of the plasmid vector pMON5847 (ATCC 68912) which encodes [Met-(1–133) hIL-3 ($Arg^{129}$)].

The result of the procedure was to construct pMON2341 which differs from pMON5630 in that the PstI site in the beta-lactamase gene was altered so that PstI no longer recognizes the site. The single nucleotide change does not alter the amino acid sequence of the beta-lactamase protein.
(b) Construction of pMON5847 (FIG. 5) which encodes [Met-(1–133)hIL-3(Arg$^{129}$)]

Plasmid pMON2341 was used to supply the replicon, promotor, ribosome binding site, transcription terminator and antibiotic resistance marker for the plasmids used to produce hIL-3 in *E. coli* from cDNA derived hIL-3 genes.

Plasmid pMON2341 was treated with restriction enzymes NcoI and HindIII. The restriction fragment containing the replication origin was purified. The DNA of plasmid pMON5846 was treated with NcoI and HindIII. The restriction fragment containing the hIL-3 gene was gel purified. These purified restriction fragments were mixed and ligated. The ligation mixture was used to transform competent JM101 cells to ampicillin resistance. Colonies were picked, and plasmid DNA was purified and analyzed using restriction enzymes. pMON5847 was identified as a plasmid with the replicon of pMON2341 and the hIL-3 gene in place of the chloramphenicol acetyl transferase gene. JM101 cells harboring this plasmid were cultured in M9 medium and treated with nalidixic acid as described above. Samples of the culture were examined for protein content. It was found that this hIL-3 mutein was produced at about 6% of total cell protein as measured on Coomassie stained polyacrylamide gels.

EXAMPLE 3

Figure 7:
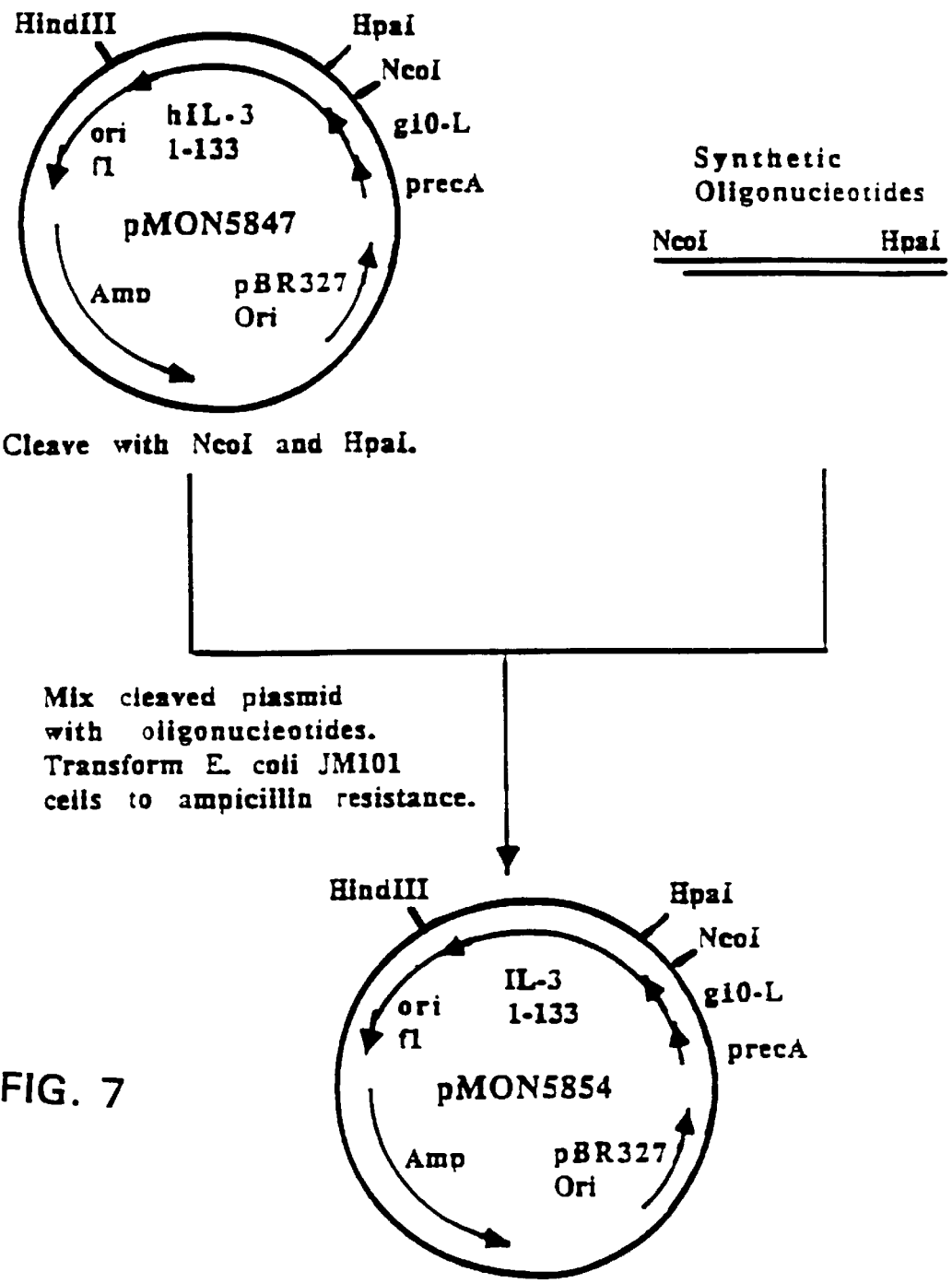
FIG. 7 shows the construction of the plasmid vector pMON5854 which encodes [Met-(1–133) hIL-3 ($Arg^{129}$)].
Figure 9:
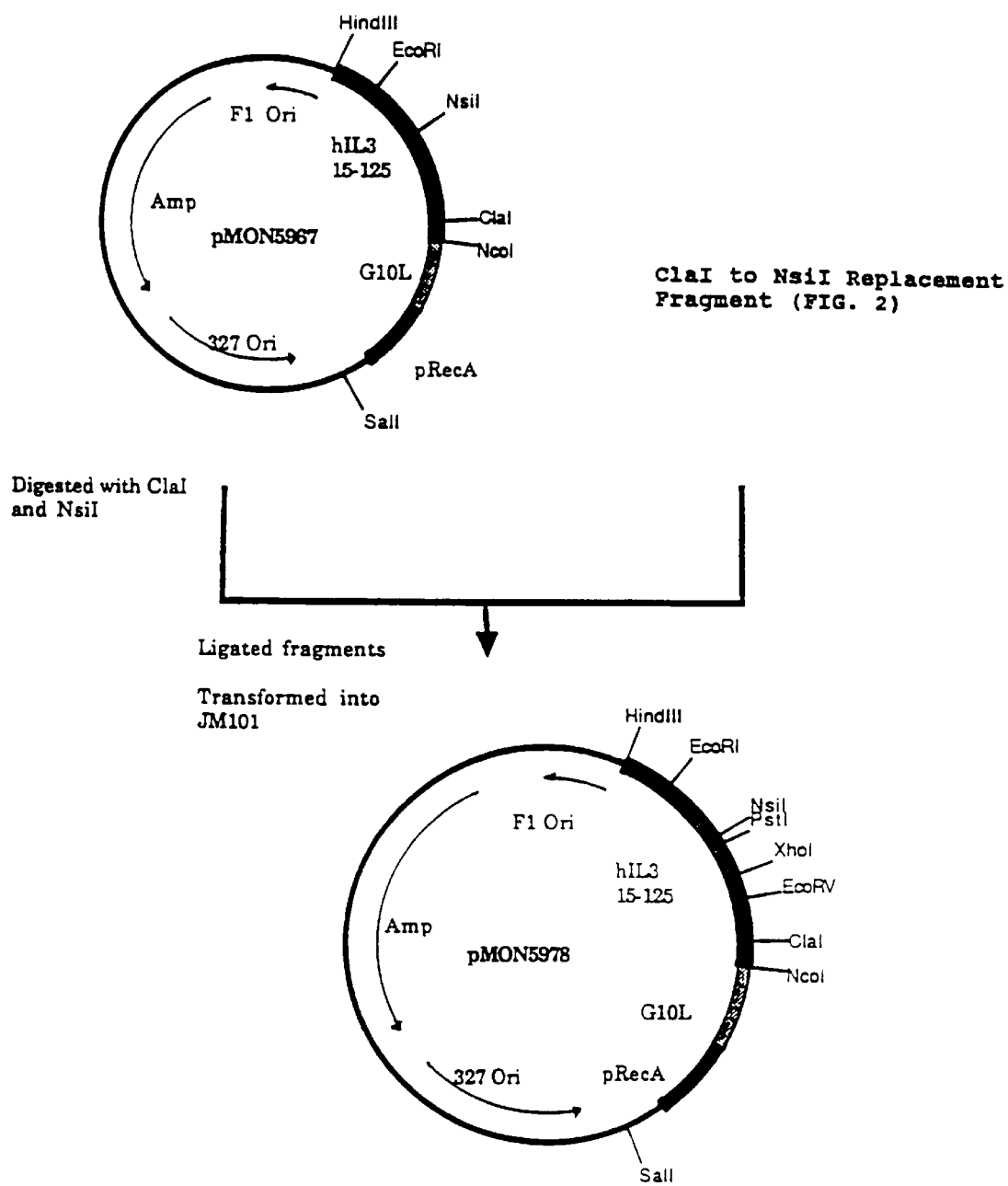
FIG. 9 shows the construction of the plasmid vector pMON5978 which encodes Met-Ala-(15–125)hIL-3.
Figure 10:
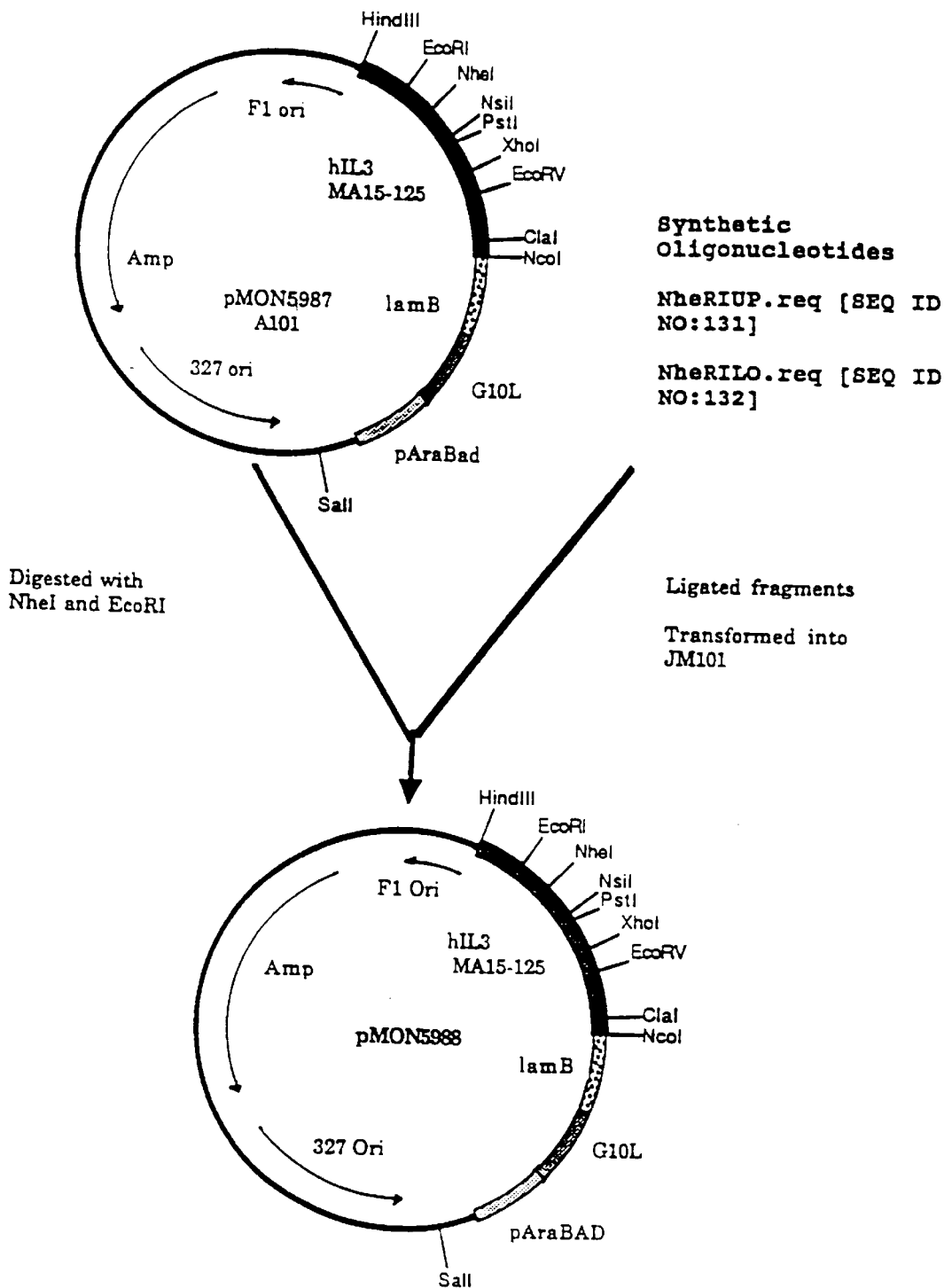
FIG. 10 shows the construction of the plasmid vector pMON5988 which encodes Met-Ala(15–125)hIL-3.
Figure 11:
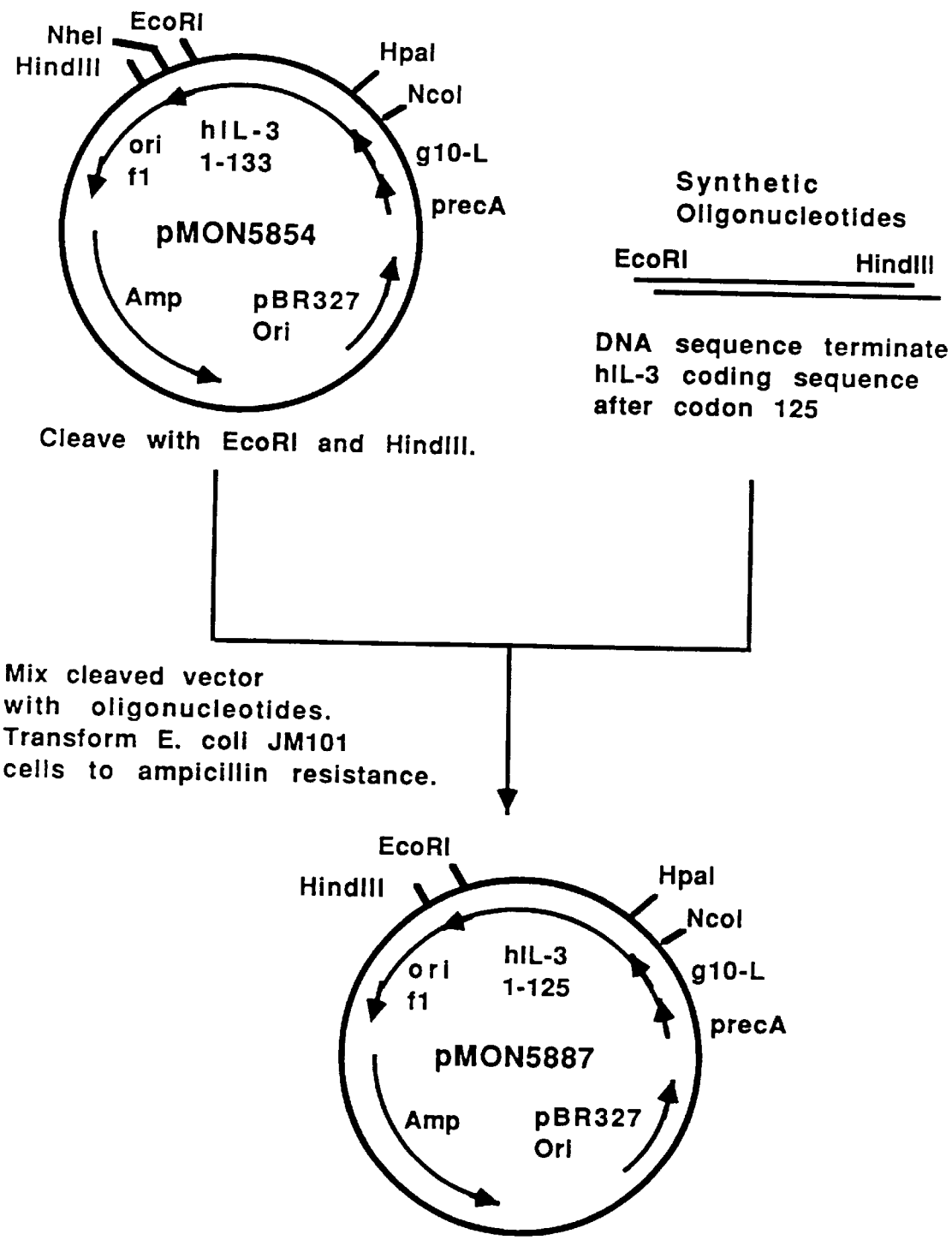
FIG. 11 shows the construction of the plasmid vector pMON5887 which encodes Met-(1–125)hIL-3.

Construction of pMON5854 (FIG. 7) which encodes [Met-(1–133)hIL-3(Arg$^{129}$)]

To increase the accumulation of hIL-3 in *E. coli*, the coding sequence of the amino terminal portion of the protein was altered to more closely reflect the codon bias found in *E. coli* genes that produce high levels of proteins (Gouy and Gautier, 1982). To change the coding sequence for the amino terminal portion of the gene, a pair of synthetic oligonucleotides were inserted between the NcoI and HpaI sites within the coding sequence. About 0.5 micrograms of DNA of the plasmid pMON5847 (Example 2) was treated with NcoI and HpaI. This DNA was mixed with an annealed pair of oligonucleotides with the following sequence:

5'-CATGGCTCCAATGACTCAGACTACTTCTCTTAAGACTTCTTGGGTT-3' [SEQ ID NO:6]

3'-CGAGGTTACTGAGTCTGATGAAGAGAATTCTGAAGAACCCAA-5' [SEQ ID NO:7]

The fragments were ligated. The ligation mixture was used to transform competent JM101 to ampicillin resistance. Colonies were picked into broth. From the cultures plasmid DNA was made and examined for the presence of a DdeI site (CTNAG) which occurs in the synthetic sequence but not between the NcoI and HpaI sites in the sequence of pMON5847. The new recombinant plasmid was designated pMON5854. The nucleotide sequence of the DNA in the coding sequence of the amino terminal portion of the hIL-3 gene in pMON5854 was determined by DNA sequencing and found to be the same as that of the synthetic oligonucleotide used in ligation. Cultures of JM101 cells harboring this plasmid were grown and treated with nalidixic acid to induce production of the hIL-3 mutant protein. Analysis of the proteins on Coomassie gels showed that the accumulation of hIL-3 mutein was about 25% of total cell protein in cultures harboring pMON5854, significantly higher than it was in cultures harboring pMON5847.

EXAMPLE 4

Figure 12:
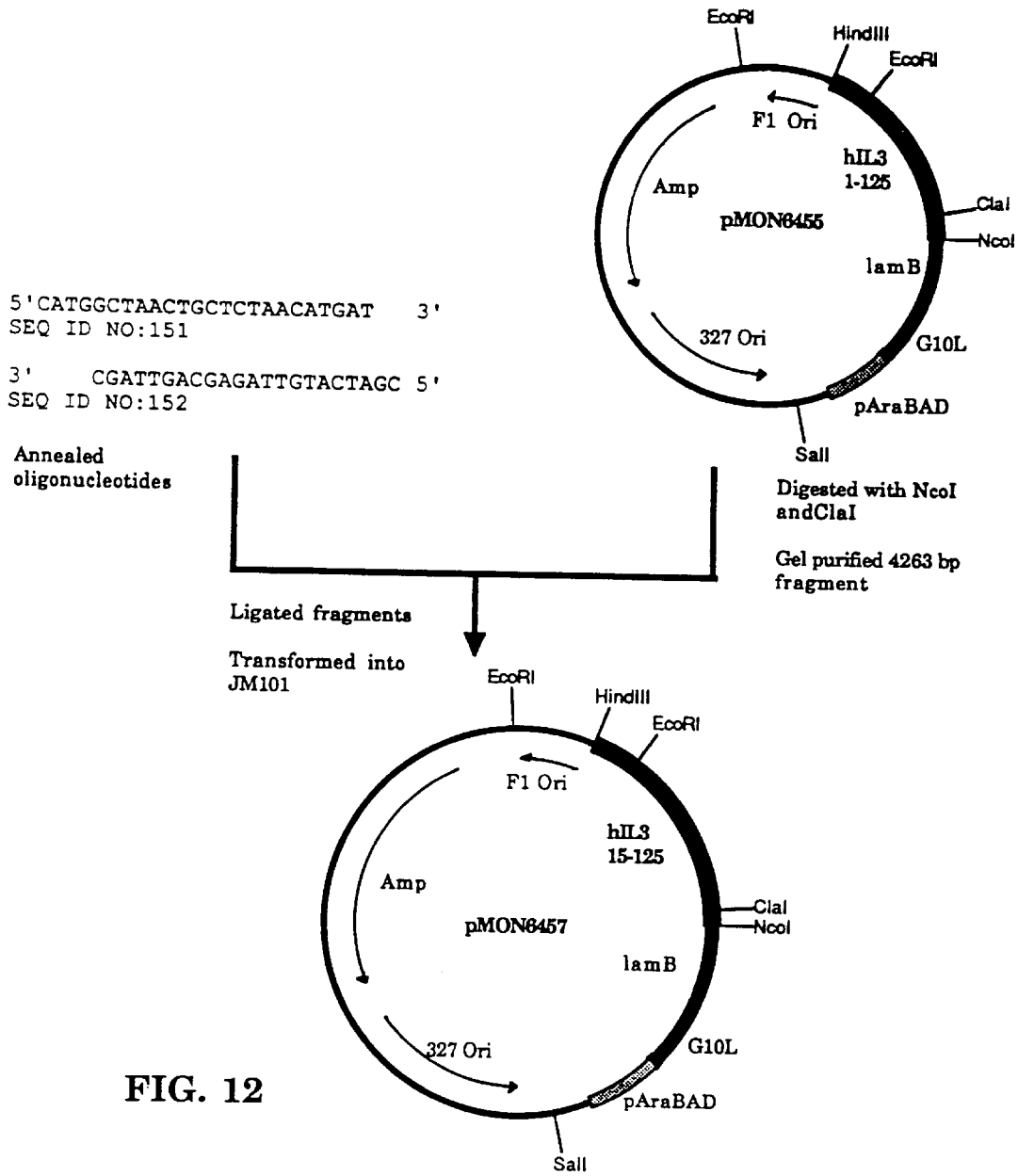
FIG. 12 shows the construction of pMON6457 which encodes (15–125)hIL-3; it contains the araBAD promoter and the LamB signal peptide fused to the variant hIL-3 amino acids 15–125.
Figure 13:
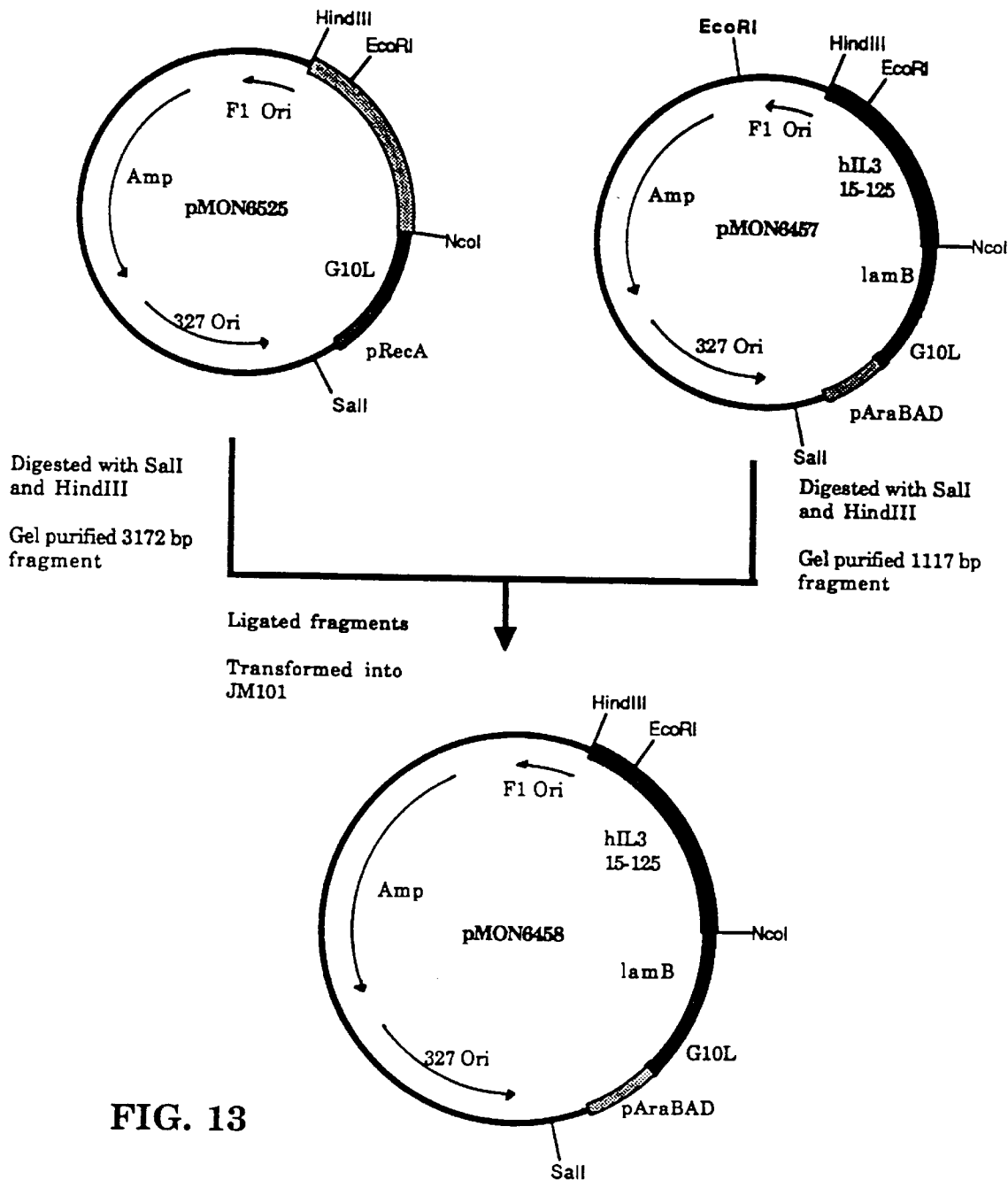
FIG. 13 shows the construction of pMON6458; it contains the araBAD promoter and the LamB signal peptide fused to the variant hIL-3 amino acids 15–125.
Figure 14:
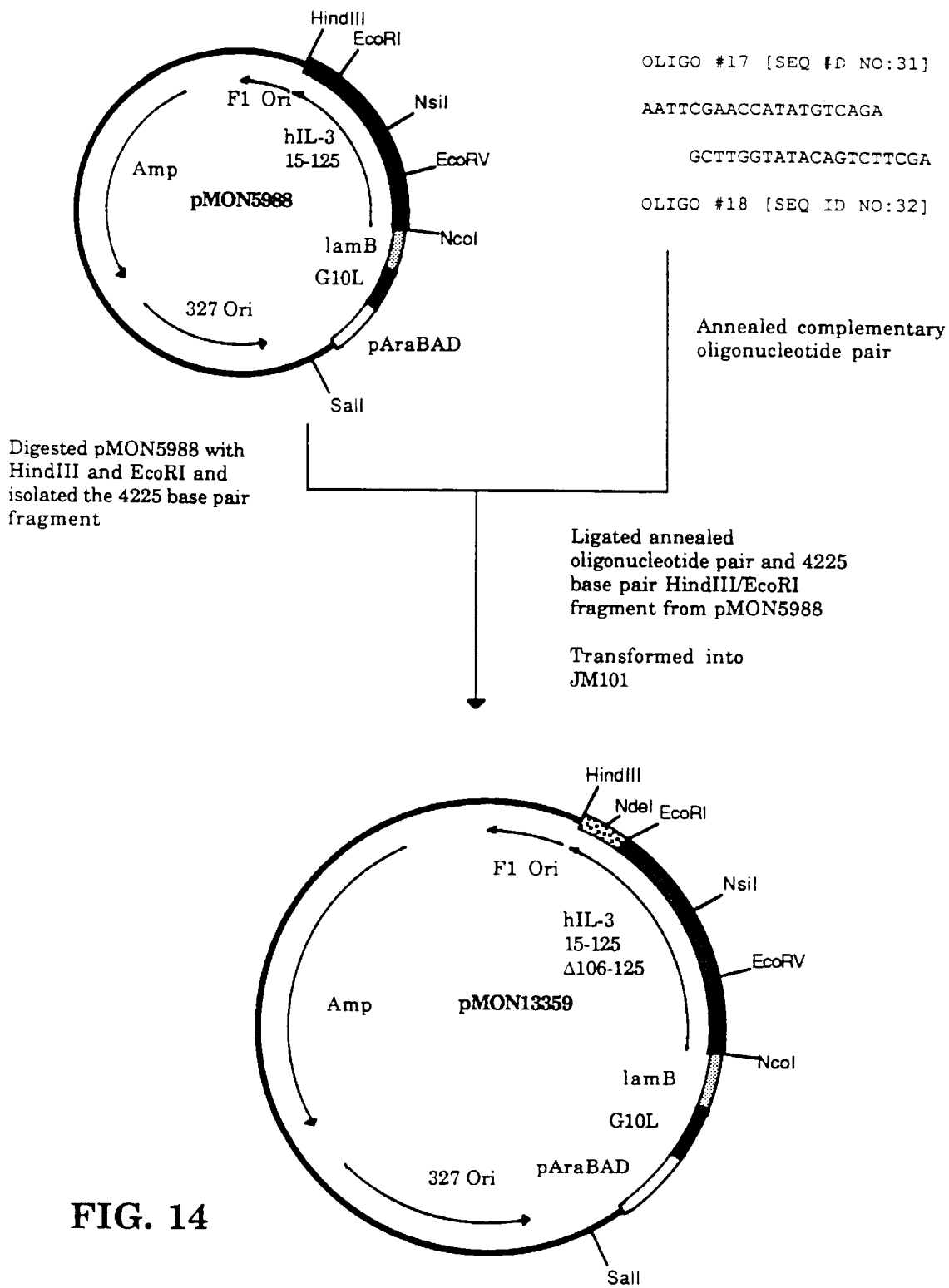
FIG. 14 shows the construction of pMON13359.
Figure 15:
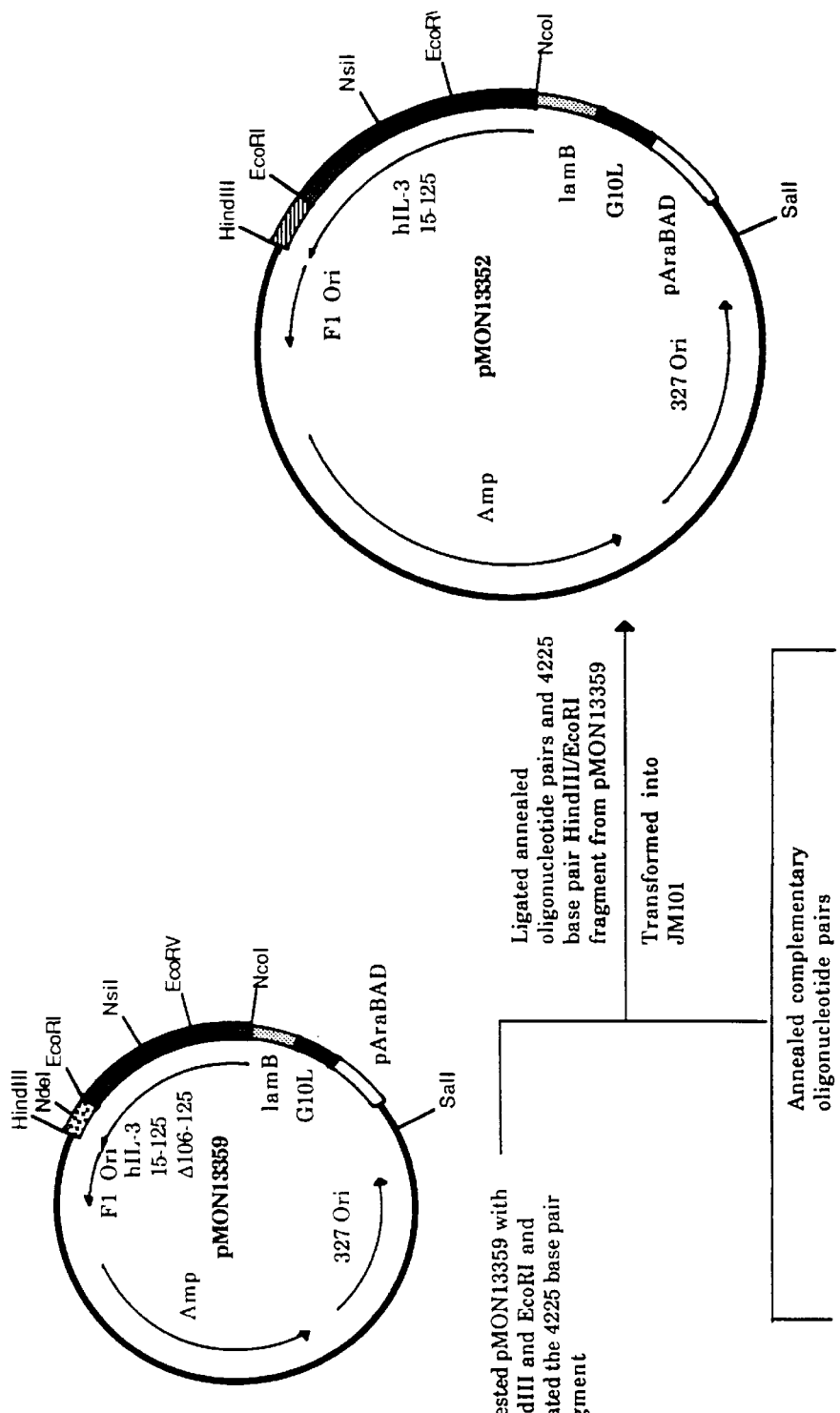
FIG. 15 shows the construction of pMON13352.
Figure 16:
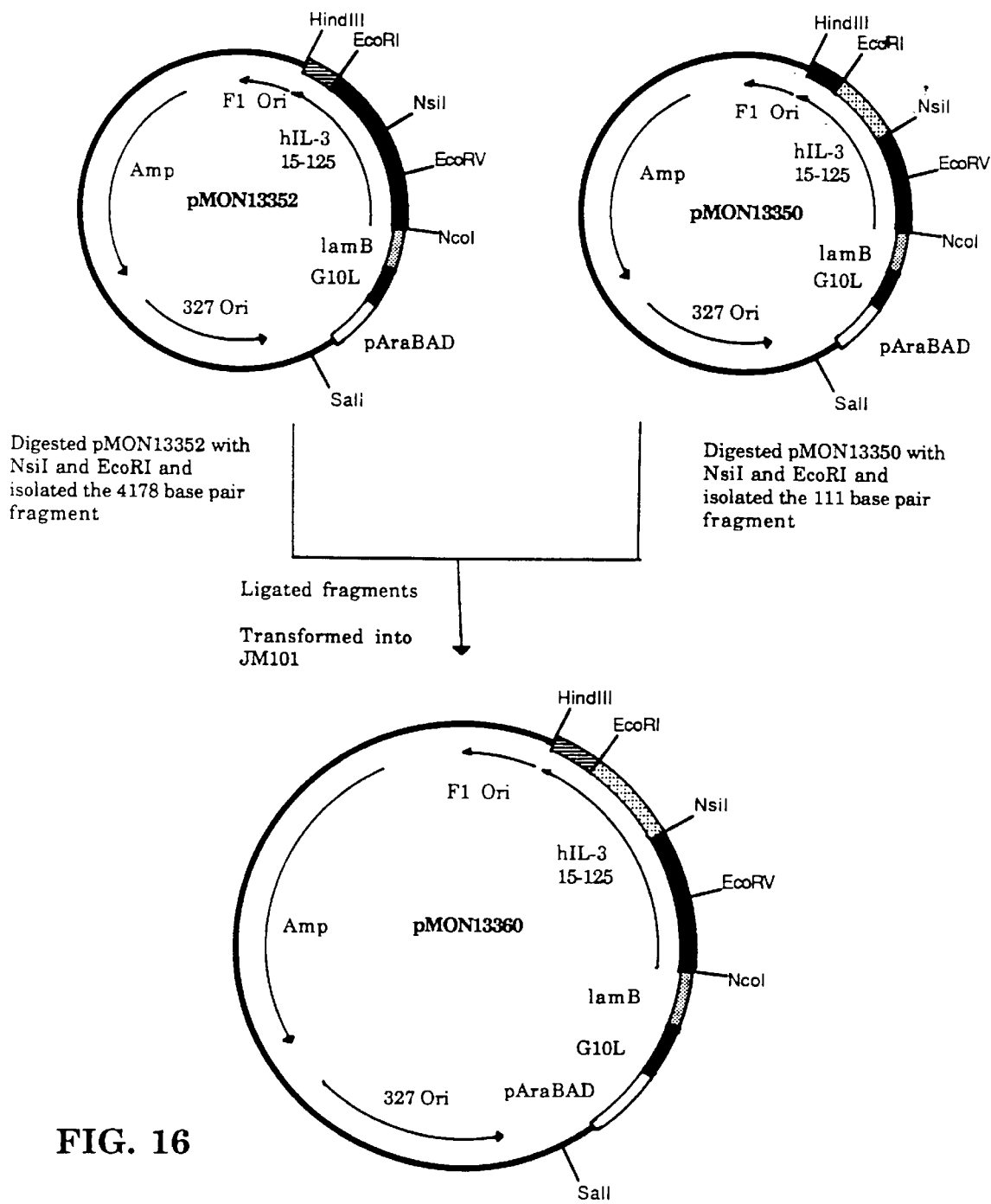
FIG. 16 shows the construction of pMON13360.
Figure 17:
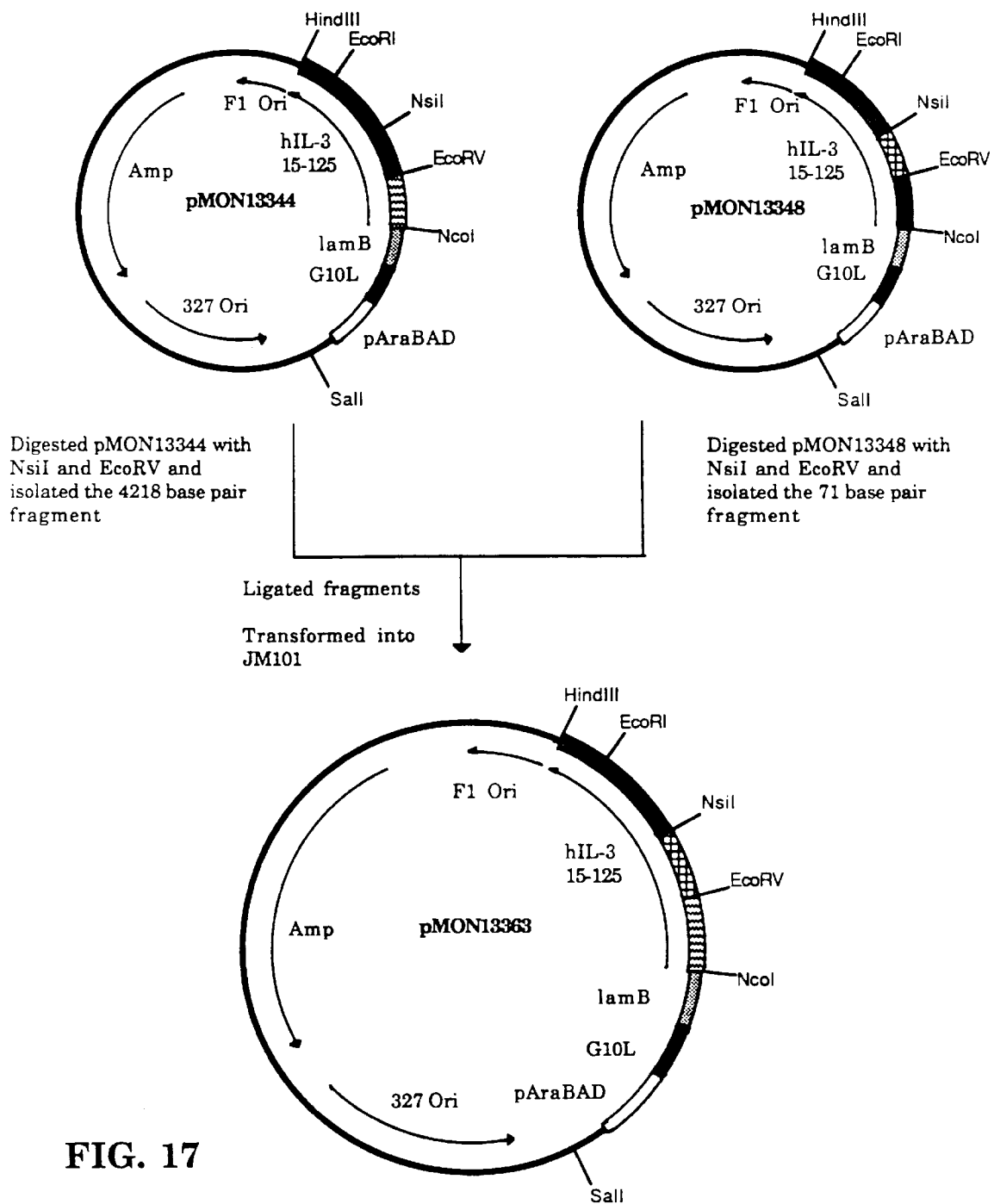
FIG. 17 shows the construction of pMON13363.
Figure 18:
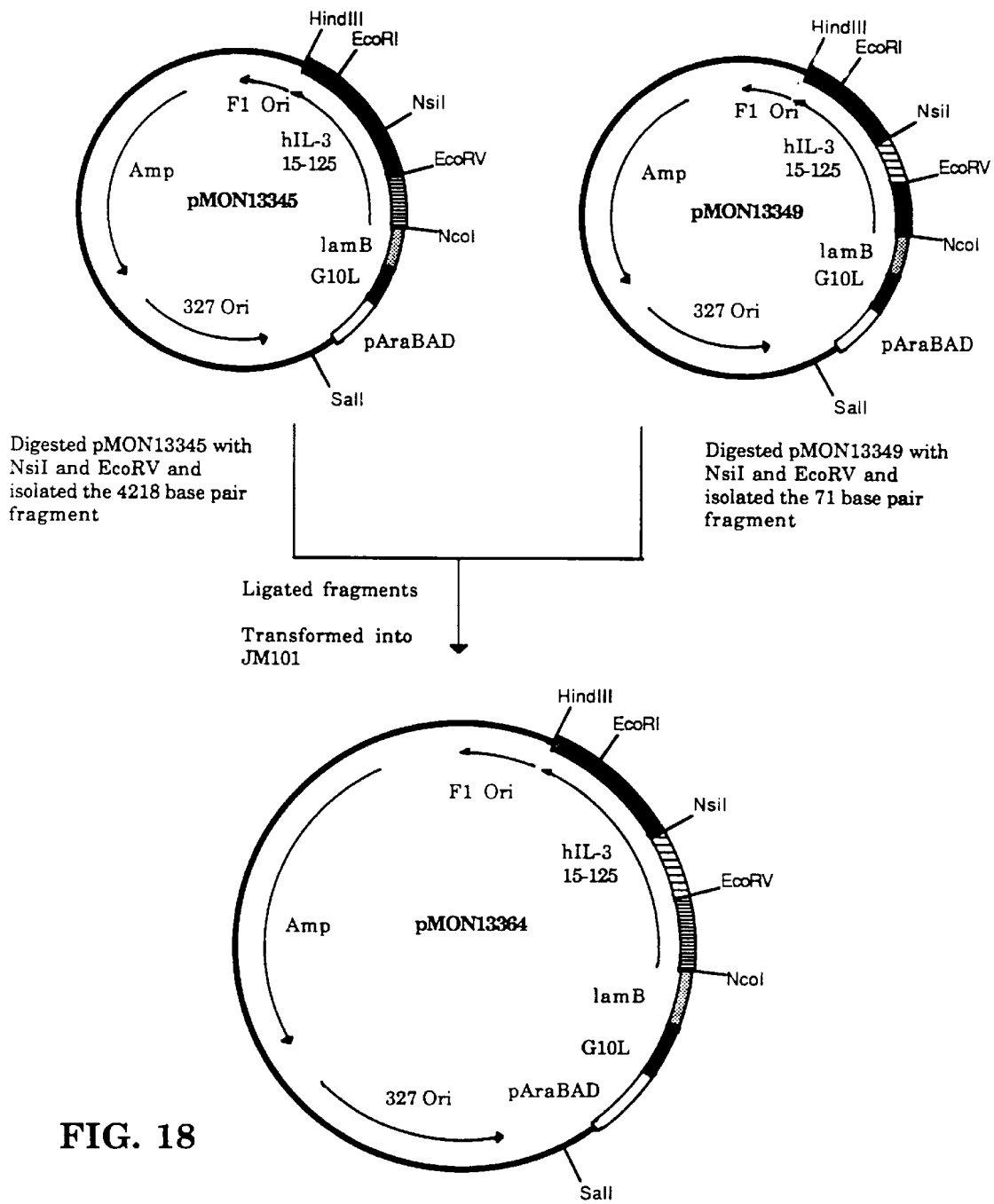
FIG. 18 shows the construction of pMON13364.
Figure 19:
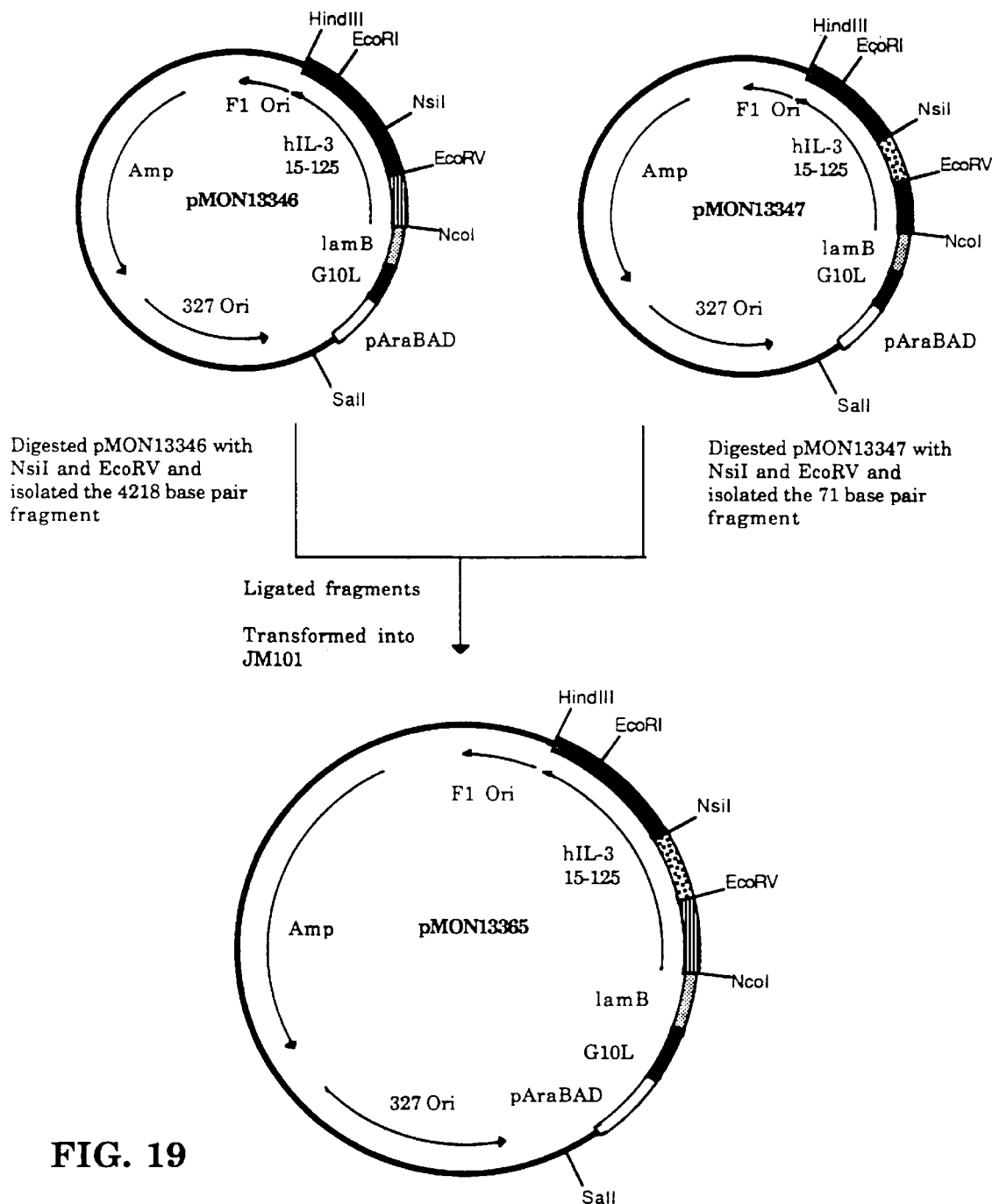
FIG. 19 shows the construction of pMON13365.
Figure 20:
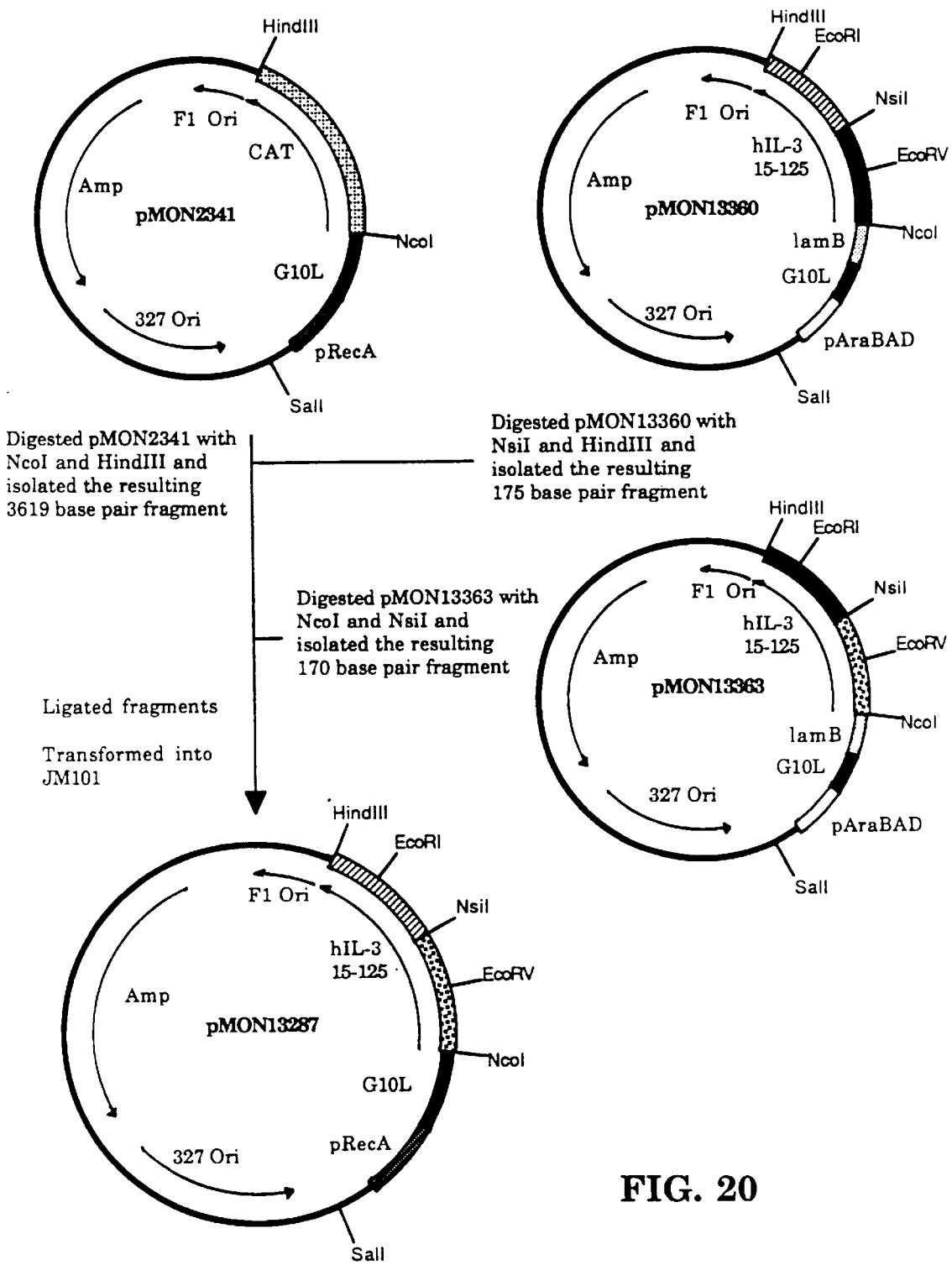
FIG. 20 shows the construction of pMON13287.
Figure 21:
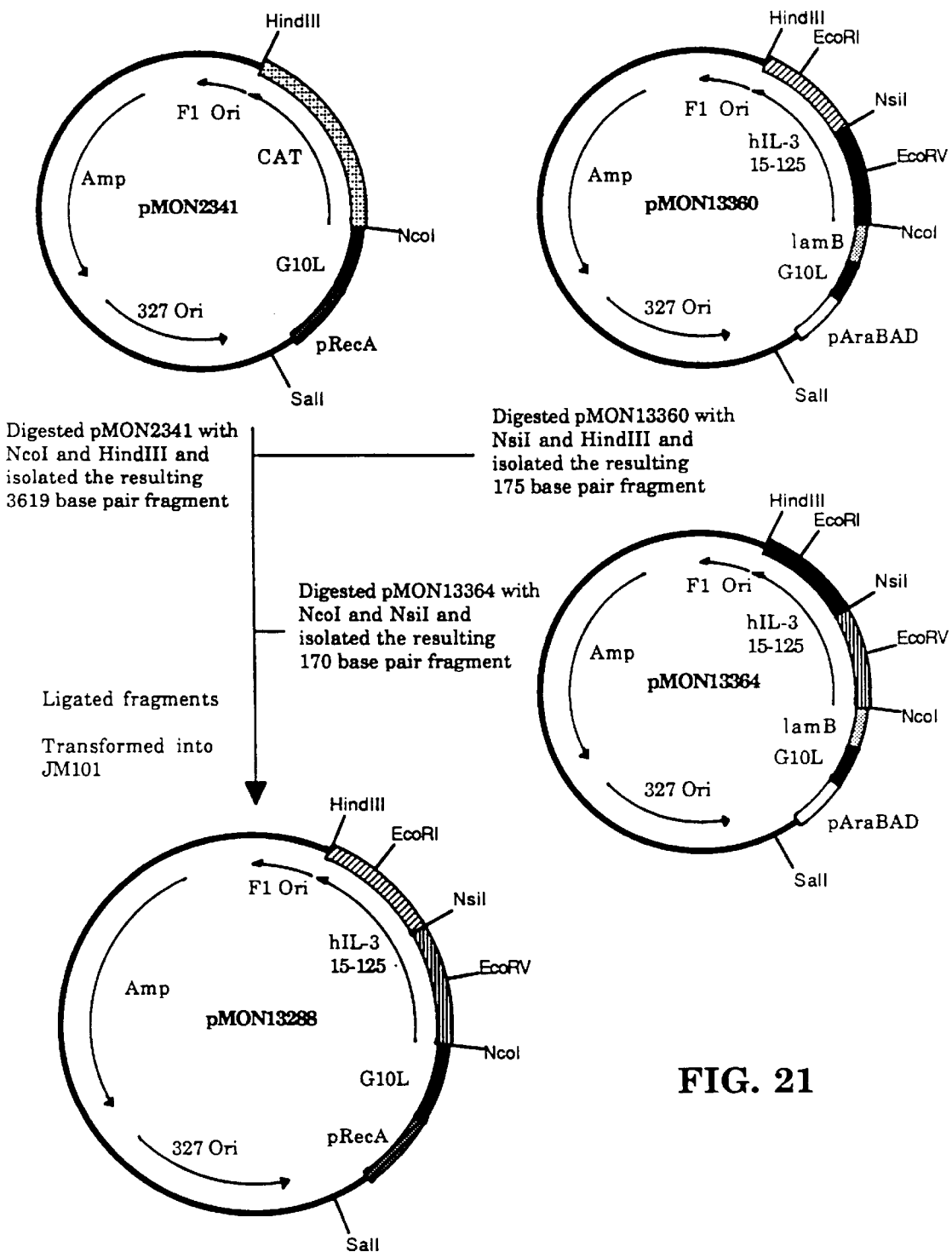
FIG. 21 shows the construction of pMON13288.
Figure 22:
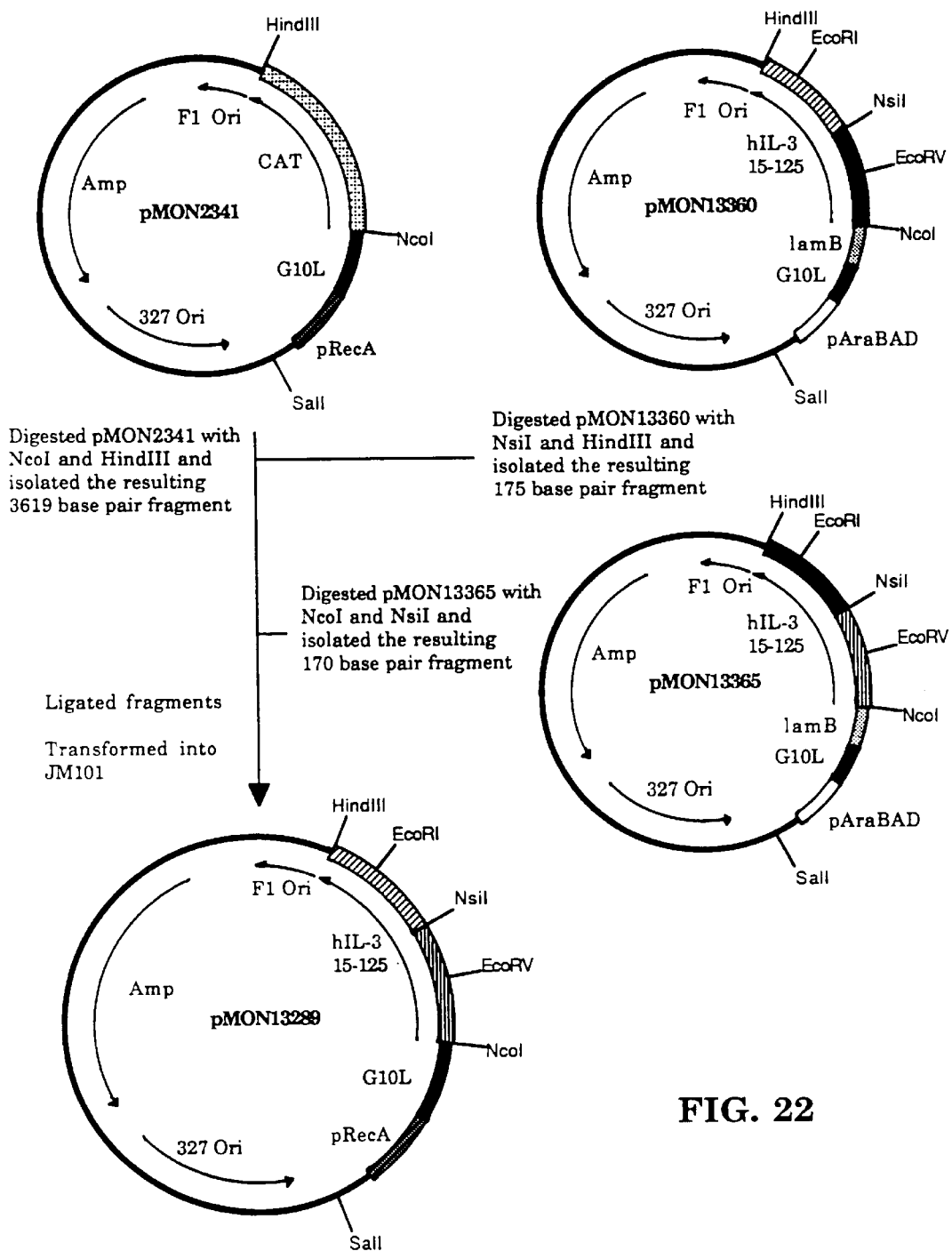
FIG. 22 shows the construction of pMON13289.
Figure 23:
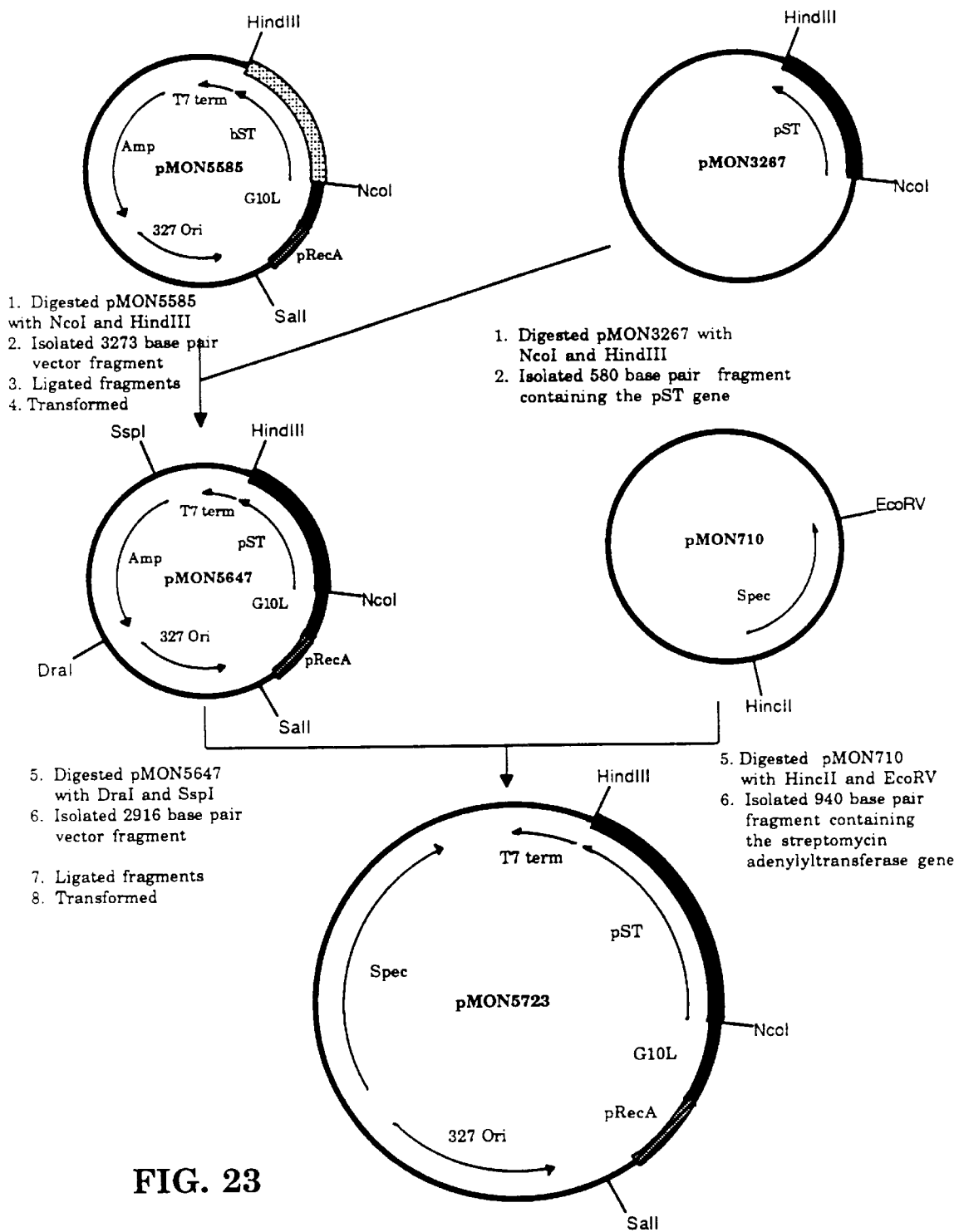
FIG. 23 shows the construction of pMON5723.
Figure 24:
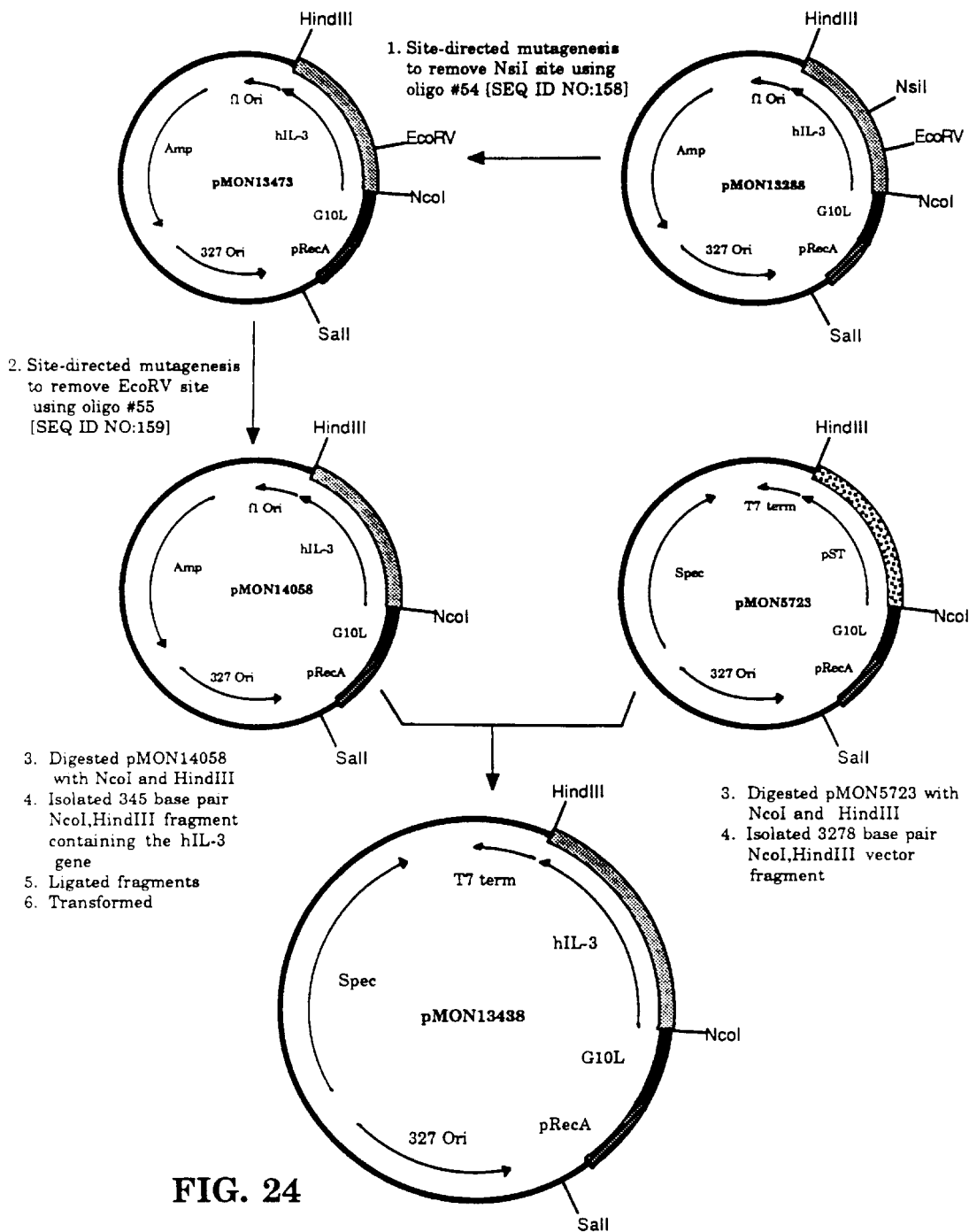
FIG. 24 shows the construction of pMON13438.

Construction of pMON5887 (FIG. 12) which encodes [Met-(1–125)hTL-3]

The plasmid DNA of pMON5854 (Example 3) was treated with EcoRI and HindIII and the larger fragment gel was purified. About 0.5 microgram of this DNA was ligated to 1 picomole of an annealed pair of oligonucleotides which encode amino acids 107 through 125 of hIL-3. The sequences of these oligonucleotides are shown below.

EcoRI to HindIII
5'-AATTCCGTCGTAAACTGACCTTCTATCTGAAAACCTTGGAGAACGCGCAGGCTCAACAGTAATA-3' [SEQ ID NO:8]

3'-GGCAGCATTTGACTGGAAGATAGACTTTTGGAACCTCTTGCGCGTCCGAGTTGTCATTATTCGA-5' [SEQ ID NO:9]

After ligation, the DNA was used to transform competent JM101 cells to ampicillin resistance. Colonies were picked into broth and plasmid DNA was isolated from each culture. Restriction analysis of the plasmid DNA showed the presence of an EcoRI to HindIII fragment smaller than that of pMON5854. The nucleotide sequence of the portion of the coding sequence between the EcoRI and HindIII sites was determined to confirm the accuracy of the replaced sequence. The new plasmid was designated pMON5887 encoding Met-(1–125)hIL-3 which has the following amino acid sequence:

Met Ala Pro Met Thr Gln Thr Thr Ser Leu Lys Thr Ser Trp Val Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:10]

EXAMPLE 5

Construction of pMON5967 which encodes [Met-Ala-(15–125)hTL-3]

Plasmid DNA of pMON5887 isolated from *E. coli* GM48 (dam-) was cleaved with NcoI and ClaI and ligated to 1 picomole of an annealed pair of oligonucleotides, encoding amino acids [Met Ala (15–20)hIL-3]. The sequence of these oligonucleotides is shown below.

5'-CATGGCTAACTGCTCTAACATGAT-3' [SEQ ID NO:11]

3'-CGATTGACGAGATTGTACTAGC-5' [SEQ ID NO:12]

The resulting ligation mix was used to transform competent *E. coli* JM101 cells to ampicillin resistant colonies. Plasmid DNA was isolated from these cells and the size of the inserted fragment was determined to be smaller than that of pMON5887 by restriction analysis using NcoI and NsiI. The nucleotide sequence of the region between NcoI and ClaI was determined and found to be that of the synthetic oligonucleotides. The new plasmid was designated pMON5967 and cells containing it were induced for protein production. Sonicated cell pellets and supernatants were used for protein purification and bio-assay.

EXAMPLE 6

Construction of gMON5978 which encodes [Met-Ala-(15–125)hTL-3]

Plasmid DNA of pMON5967 isolated from *E. coli* GM48 (dam-) was cleaved with ClaI and NsiI and ligated to 1 picomole of an annealed assembly of six oligonucleotides encoding hIL-3 amino acids 20–70 (FIG. 2). This synthetic fragment encodes three unique restriction sites, EcoRV, XhoI and PstI. The sequence of these oligonucleotides is shown in FIG. 2.

The resulting ligation mix was used to transform competent *E. coli* JM101 cells to ampicillin resistant colonies. Plasmid DNA was isolated and screened with XbaI and EcoRV for the presence of the new restriction site EcoRV. The DNA sequence of the region between ClaI and NsiI was determined and found to be the same as that of the synthetic oligonucleotides. The new plasmid was designated pMON5978, and cells containing it were induced for protein production. Sonicated cell pellets and supernatants were used for protein purification and bioassay.

Plasmid pMON5978 encodes [Met-Ala-(15–125)hIL-3] which has the following amino acid sequence:

Met Ala Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:13]

EXAMPLE 7

Construction of pMON13356

Plasmid pMON5988 DNA was digested with restriction enzymes NcoI and EcoRV, and the resulting 4190 base pair NcoI,EcoRV fragment contains the following genetic elements: beta-lactamase gene (AMP), pBR327 origin of replication, phage f1 origin of replication as the transcription terminator, pAraBAD promoter, g10L ribosome binding site, lamB secretion leader and the bases encoding amino acids 47–125 of (15–125)hIL-3. The 4190 base pair NcoI, EcoRV restriction fragment from pMON5988 was ligated to the following annealed complementary oligonucleotides from Table (2).

Oligo #13 [SEQ ID NO:27]
Oligo #14 [SEQ ID NO:28]

The ligation reaction mixture was used to transform *E. coli* K-12 strain JM101 and transformant bacteria were selected on ampicillin-containing plates. Plasmid DNA was isolated from a colony grown in LB broth and the size of the inserted fragment was determined by restriction analysis employing restriction enzymes NcoI and HindIII in double digest. In the resulting plasmid the 99 bases between the NcoI and EcoRV restriction sites in the (15–125) hIL-3 gene are replaced with 22 bases from the above mentioned oligonucleotides. This linker also contains a NdeI recognition sequence.

EXAMPLE 8

Construction of pMON13344

Plasmid pMON13356 DNA was digested with restriction enzymes NcoI and EcoRV, and the resulting 4190 base pair NcoI,EcoRV fragment contains the following genetic elements: beta-lactamase gene (AMP), pBR327 origin of replication, phage f1 origin of replication as the transcription terminator, pAraBAD promoter, g10L ribosome binding site, lamB secretion leader and the bases encoding amino acids 47–125 of (15–125)hIL-3. The second DNA fragment was generated by synthetic gene assembly using the following complementary oligonucleotide pairs that have overlapping ends:

Oligo #1 [SEQ ID NO:15]
Oligo #2 [SEQ ID NO:16]
Oligo #3 [SEQ ID NO:17]

Oligo #4 [SEQ ID NO:18]
Oligo #9 [SEQ ID NO:23]
Oligo #10 [SEQ ID NO:24]

The assembled oligonucleotides create NcoI and EcoRV restriction ends and the DNA sequence that encodes amino acids 15–46 of (15–125)hIL-3 with the following amino acid substitutions: 18I, 25H, 29R, 32A, 37P, 42A and 45V. The codons encoding amino acids 15–46 of (15–125)hIL-3 are those found in the hIL-3 cDNA sequence except at those positions where amino acid substitutions were made. The 4190 base pair NcoI,EcoRV restriction fragment from pMON13356 was ligated with the pairs of annealed oligonucleotides. The ligation reaction was digested with NdeI and subsequently used to transform E. coli K-12 str

EXAMPLE 12
Construction of pMON13347

The 4218 base pair EcoRV,NsiI restriction fragment from pMON13357 was ligated with the following pairs of annealed complementary oligonucleotides:
Oligo #21 [SEQ ID NO:35]
Oligo #22 [SEQ ID NO:36]
Oligo #25 [SEQ ID NO:39]
Oligo #26 [SEQ ID NO:40]
Oligo #31 [SEQ ID NO:45]
Oligo #32 [SEQ ID NO:46]

The assembled oligonucleotides create EcoRV and NsiI restriction ends and the DNA sequence that encodes amino acids 47–71 of (15–125)hIL-3 with the following amino acid substitutions: 51R, 55L, 59L, 62V, 67N and 69E. The codons encoding amino acids 47–71 of (15–125)hIL-3 are those found in the hIL-3 cDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides. The plasmid, pMON13347, encodes the (15–125)hIL-3 variant with the following amino acid sequence:
Peptide #5

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Leu Pro Asn Leu Leu Ala Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:69]

DNA sequence #13 [SEQ ID NO:109] codes for the foregoing pMON13347 polypeptide.

EXAMPLE 13
Construction of pMON13348

The 4218 base pair EcoRV,NsiI restriction fragment from pMON13357 was ligated with the following pairs of annealed complementary oligonucleotides:
Oligo #21 [SEQ ID NO:35]
Oligo #22 [SEQ ID NO:36]
Oligo #27 [SEQ ID NO:41]
Oligo #28 [SEQ ID NO:42]
Oligo #31 [SEQ ID NO:45]
Oligo #32 [SEQ ID NO:46]

The assembled oligonucleotides create EcoRV and NsiI restriction ends and the DNA sequence that encodes amino acids 47–71 of (15–125)hIL-3 with the following amino acid substitutions: 51R, 55L, 60S, 62V, 67N and 69E. The codons encoding amino acids 47–71 of (15–125)hIL-3 are those found in the hIL-3 cDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides. The plasmid, pMON13348, encodes the (15–125) hIL-3 variant with the following amino acid sequence:
Peptide #6

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Leu Pro Asn Leu Glu Ser Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:70]

DNA sequence #14 [SEQ ID NO:110] encodes the foregoing pMON13348 polypeptide.

EXAMPLE 14
Construction of pMON13349

The 4218 base pair EcoRV,NsiI restriction fragment from pMON13357 was ligated with the following pairs of annealed complementary oligonucleotides:
Oligo #23 [SEQ ID NO:37]
Oligo #24 [SEQ ID NO:38]
Oligo #25 [SEQ ID NO:39]
Oligo #26 [SEQ ID NO:40]
Oligo #29 [SEQ ID NO:43]
Oligo #30 [SEQ ID NO:44]

The assembled oligonucleotides create EcoRV and NsiI restriction ends and the DNA sequence that encodes amino acids 47–71 of (15–125)hIL-3 with the following amino acid substitutions: 51R, 55T, 59L, 62V, 67H and 69E. The codons encoding amino acids 47–71 of (15–125)hIL-3 are those found in the hIL-3 cDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth and the DNA was sequenced to determine that the sequence was that of the oligonucleotides. The plasmid, pMON13349, encodes the (15–125)hIL-3 variant with the following amino acid sequence:
Peptide #7

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Arg Asn Leu Arg Thr Pro Asn Leu Leu Ala Phe Val Arg Ala Val Lys His Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:71]

DNA sequence #15 [SEQ ID NO:111] encodes the foregoing pMON13349 polypeptide.

EXAMPLE 15
Construction of pMON13358

Plasmid pMON5988 DNA was digested with restriction enzymes NsiI and EcoRI and the resulting 4178 base pair NsiI,EcoRI fragment contains the following genetic elements: beta-lactamase gene (AMP), pBR327 origin of replication, phage fl origin of replication as the transcription terminator, pAraBAD promoter, g10L ribosome binding site, lamB secretion leader and the bases encoding amino acids 15–71 and 106–125 of (15–125)hIL-3. The 4178 base pair NsiI,EcoRI restriction fragment from pMON5988 was ligated to the following annealed complementary oligonucleotides.
Oligo #15 [SEQ ID NO:29]
Oligo #16 [SEQ ID NO:30]

The ligation reaction mixture was used to transform E. coli K-12 strain JM101. Transformant bacteria were selected on ampicillin-containing plates. Plasmid DNA was isolated from a colony grown in LB broth, and the size of the inserted fragment was determined by restriction analysis employing restriction enzymes NcoI and HindIII in double digest. In the resulting plasmid the 111 bases between the NsiI and EcoRI restriction sites in the (15–125) hIL-3 gene are replaced with 24 bases from the above mentioned oligonucleotides. This linker also contains a NdeI recognition sequence.

EXAMPLE 16
Construction of pMON13350

The 4178 base pair NsiI,EcoRI restriction fragment from pMON13358 was ligated with the following pairs of annealed complementary oligonucleotides:
Oligo #41 [SEQ ID NO:55]
Oligo #42 [SEQ ID NO:56]
Oligo #39 [SEQ ID NO:53]
Oligo #40 [SEQ ID NO:54]
Oligo #35 [SEQ ID NO:49]
Oligo #36 [SEQ ID NO:50]
Oligo #43 [SEQ ID NO:57]
Oligo #44 [SEQ ID NO:58]

The assembled oligonucleotides create NsiI and EcoRI restriction ends and the DNA sequence that encodes amino acids 72–105 of (15–125)hIL-3 with the following amino acid substitutions: 73G, 76A, 79R, 82Q, 87S, 93S, 98I, 101A and 105Q. The codons encoding amino acids 72–105 of (15–125)hIL-3 are those found in the hIL-3 cDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides. The plasmid, pMON13350, encodes the (15–125)hIL-3 variant with the following amino acid sequence:
Peptide #8
Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Arg Lys Leu Thr Phe Tyr Leu Lys Thr Leu Glu Asn Ala Gln Ala Gln Gln [SEQ ID NO:72]

DNA sequence #16 [SEQ ID NO:112] codes for the foregoing pMON13350 polypeptide.

EXAMPLE 17
Construction of pMON13355

The 4178 base pair NsiI,EcoRI restriction fragment from pMON13358 was ligated with the following pairs of annealed complementary oligonucleotides:
Oligo #41 [SEQ ID NO:55]
Oligo #42 [SEQ ID NO:56]
Oligo #37 [SEQ ID NO:51]
Oligo #38 [SEQ ID NO:52]
Oligo #33 [SEQ ID NO:47]
Oligo #34 [SEQ ID NO:48]
Oligo #43 [SEQ ID NO:57]
Oligo #44 [SEQ ID NO:58]

The assembled oligonucleotides create NsiI and EcoRI restriction ends and the DNA sequence that encodes amino acids 72–105 of (15–125)hIL-3 with the following amino acid substitutions: 73G, 76A, 79R, 82V, 87S, 93S, 98T, 101A and 105Q. The codons encoding amino acids 72–105 of (15–125)hIL-3 are those found in the hIL-3 CDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides. The plasmid, pMON13355, encodes the (15–125)hIL-3 variant with the following amino acid sequence:
Peptide #9
Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Arg Lys Leu Thr Phe Tyr Leu Lys Thr Leu Glu Asn Ala Gln Ala Gln Gln [SEQ ID NO:73]

DNA sequence #17 [SEQ ID NO:113] codes for the foregoing pMON13355 polypeptide.

EXAMPLE 18
Construction of pMON13359

Plasmid pMON5988 DNA was digested with restriction enzymes EcoRI and HindIII, and the resulting 4225 base pair EcoRI,HindIII fragment contains the following genetic elements: beta-lactamase gene (AMP), pBR327 origin of replication, phage f1 origin of replication as the transcription terminator, pAraBAD promoter, g10L ribosome binding site, lamB secretion leader and the bases encoding amino acids 15–105 of (15–125)hIL-3. The 4225 base pair EcoRI, HindIII restriction fragment from pMON5988 was ligated to the following annealed complementary oligonucleotides.
Oligo #17 [SEQ ID NO:31]
Oligo #18 [SEQ ID NO:32]

The ligation reaction was used to transform E. coli K-12 strain JM101. Transformant bacteria were selected on ampicillin-containing plates. Plasmid DNA was isolated from a colony grown in LB broth, and the size of the inserted fragment was determined by restriction analysis employing restriction enzymes NcoI and HindIII in double digest. In the resulting plasmid the 64 bases between the EcoRI and HindIII restriction sites in the (15–125)hIL-3 gene are replaced with 20 bases from the above mentioned oligonucleotides. This linker also contains an NdeI recognition sequence.

EXAMPLE 19
Construction of pMON13352

The 4225 base pair EcoRI,HindIII restriction fragment from pMON13359 was ligated with the following pairs of annealed complementary oligonucleotides:
Oligo #45 [SEQ ID NO:59]
Oligo #46 [SEQ ID NO:60]
Oligo #49 [SEQ ID NO:63]
Oligo #50 [SEQ ID NO:64]

The assembled oligonucleotides create EcoRI and HindIII restriction ends and the DNA sequence that encodes amino acids 106–125 of (15–125)hIL-3 with the following amino acid substitutions: 109E, 116V, 120Q and 123E. The codons encoding amino acids 106–125 of (15–125)hIL-3 are those found in the hIL-3 cDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth. The DNA was sequenced to determine that the sequence was that of the oligonucleotides. The plasmid, pMON13352, encodes the (15–125) hIL-3 variant with the following amino acid sequence:

Peptide #10

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Glu Lys Leu Thr Phe Tyr Leu Val Thr Leu Glu Gln Ala Gln Glu Gln Gln [SEQ ID NO:74]

DNA sequence #18 [SEQ ID NO:114] codes for the foregoing pMON13352 polypeptide.

EXAMPLE 20

Construction of pMON13354

The 4225 base pair EcoRI,HindIII restriction fragment from pMON13359 was ligated with the following pairs of annealed complementary oligonucleotides:

Oligo #45 [SEQ ID NO:59]
Oligo #46 [SEQ ID NO:60]
Oligo #47 [SEQ ID NO:61]
Oligo #48 [SEQ ID NO:62]

The assembled oligonucleotides create EcoRI and HindIII restriction ends and the DNA sequence that encodes amino acids 106–125 of (15–125)hIL-3 with the following amino acid substitutions: 109E, 116V, 117S, 120H and 123E. The codons encoding amino acids 106–125 of (15–125)hIL-3 are those found in the hIL-3 cDNA sequence except at those positions where amino acid substitutions were made. The ligation reaction was digested with NdeI and used to transform E. coli K-12 strain JM101. Transformant bacteria were selected on ampicillin-containing plates. Plasmid DNA was isolated from a colony grown in LB broth, and the DNA was sequenced to determine that the sequence was that of the oligonucleotides. The plasmid, pMON13354, encodes the (15–125)hIL-3 variant with the following amino acid sequence:

Peptide #11

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Glu Lys Leu Thr Phe Tyr Leu Val Ser Leu Glu His Ala Gln Glu Gln Gln [SEQ ID NO:75]

DNA sequence #19 [SEQ ID NO:115] codes for the foregoing pMON13354 polypeptide.

EXAMPLE 21

Construction of pMON13360

Plasmid pMON13352 DNA was digested with restriction enzymes NsiI and EcoRI, resulting in a 4178 base pair NsiI,EcoRI fragment. The genetic elements derived from pMON13352 are the beta-lactamase gene (AMP), pBR327 origin of replication, phage f1 origin of replication as the transcription terminator, pAraBAD promoter, g10L ribosome binding site, lamB secretion leader and the bases encoding amino acids 15–71 and 106–125 of (15–125)hIL-3. Plasmid pMON13350 DNA was digested with NsiI and EcoRI. The resulting 111 base pair NsiI, EcoRI fragment encodes amino acids 72–105 of (15–125)hIL-3. The eluted restriction fragments were concentrated and desalted using Centricon concentrators. The restriction fragments were ligated, and the ligation reaction mixture was used to transform E. coli K-12 strain JM101. Transformant bacteria were selected on ampicillin-containing plates. Plasmid DNA was isolated and analyzed by restriction analysis. Clones containing the correct insert lost a XmnI site as compared with pMON13352. Positive clones were identified by the loss of a 615 base pair XmnI fragment. The DNA was sequenced to confirm the correct insert. The resulting (15–125)hIL-3 variant has the following amino acid substitutions: 73G, 76A, 79R, 82Q, 87S, 93S, 98I, 101A, 105Q, 109E, 116V, 120Q and 123E. The codons encoding amino acids 72–125 of (15–125)hIL-3 are those found in the hIL-3 cDNA sequence except at those positions where amino acid substitutions were made. The plasmid, pMON13360, encodes the (15–125)hIL-3 variant with the following amino acid sequence:

Peptide #12

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln [SEQ. NO:76]

DNA sequence #23 [SEQ ID NO:i19] encodes the foregoing pMON13360 polypeptide.

EXAMPLE 22

Construction of pMON13361

Plasmid pMON13352 DNA was digested with restriction enzymes NsiI and EcoRI, resulting in a 4178 base pair NsiI,EcoRI fragment. The genetic elements derived from pMON13352 are the beta-lactamase gene (AMP), pBR327 origin of replication, phage f1 origin of replication as the transcription terminator, pAraBAD promoter, g10L ribosome binding site, lamB secretion leader and the bases encoding amino acids 15–71 and 106–125 of (15–125)hIL-3. Plasmid pMON13355 DNA was digested with NsiI and EcoRI. The resulting 111 base pair NsiI, EcoRI fragment encodes amino acids 72–105 of (15–125)hIL-3. The restriction fragments were ligated, and the ligation reaction mixture was used to transform E. coli K-12 strain JM101. Transformant bacteria were selected on ampicillin-containing plates. Clones containing the correct insert contained an additional RsaI site which results in a 1200 base pairs RsaI fragment. The DNA was sequenced to confirm the correct insert. The resulting (15–125)hIL-3 variant has the following amino acid substitutions: 73G, 76A, 79R, 82v, 87S, 93S, 98T, 101A, 105Q, 109E, 116V, 120Q and 123E. The codons encoding amino acids 72–125 of (15–125)hIL-3 are those found in the hIL-3 cDNA sequence except at those positions where amino acid substitutions were made. The plasmid, pMON13361, encodes the (15–125)hIL-3 variant with the following amino acid sequence:

Peptide #13

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:77]

DNA sequence #24 [SEQ ID NO:120] codes for the foregoing pMON13361 polypeptide.

EXAMPLE 23
Construction of pMON13362

Plasmid pMON13354 DNA was digested with restriction enzymes NsiI and EcoRI, resulting in a 4178 base pair NsiI,EcoRI fragment. The genetic elements derived from pMON13354 are the beta-lactamase gene (AMP), pBR327 origin of replication, phage f1 origin of replication as the transcription terminator, pAraBAD promoter, g10L ribosome binding site, lamB secretion leader and the bases encoding amino acids 15–71 and 106–125 of (15–125)hIL-3. Plasmid pMON13355 DNA was digested with NsiI and EcoRI. The resulting 111 base pair NsiI, EcoRI fragment encodes amino acids 72–105 of (15–125)hIL-3. The restriction fragments were ligated, and the ligation reaction mixture was used to transform *E. coli* K-12 strain JM101. Transformant bacteria were selected on ampicillin-containing plates. Clones containing the correct insert contained an additional RsaI site which results in a 1200 base pairs RsaI fragment. The DNA was sequenced to confirm the correct insert. The resulting (15–125)hIL-3 variant has the following amino acid substitutions: 73G, 76A, 79R, 82V, 87S, 93S, 98T, 101A, 105Q, 109E, 116V, 117S, 120H and 123E. The codons encoding amino acids 72–125 of (15–125)hIL-3 are those found in the hIL-3 cDNA sequence except at those positions where amino acid substitutions were made. The plasmid, pMON13362, encodes the (15–125)hIL-3 variant with the following amino acid sequence:

Peptide #14

Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Ser Leu Glu His Ala Gln Glu Gln Gln [SEQ ID NO:78]

DNA sequence #25 [SEQ ID NO:121] codes for the foregoing pMON13362 polypeptide.

EXAMPLE 24
Construction of pMON13363

Plasmid pMON13344 DNA was digested with restriction enzymes NsiI and EcoRV, resulting in a 4218 base pair NsiI,EcoRV fragment. The genetic elements derived from pMON13344 are the beta-lactamase gene (AMP), pBR327 origin of replication, phage f1 origin of replication as the transcription terminator, pAraBAD promoter, g10L ribosome binding site, lamB secretion leader and the bases encoding amino acids 15–46 and 72–125 of (15–125)hIL-3. Plasmid pMON13348 DNA was digested with NsiI and EcoRV. The resulting 71 base pair NsiI, EcoRV fragment encodes amino acids 47–71 of (15–125)hIL-3. The restriction fragments were ligated with T4 ligase, and the ligation reaction mixture was used to transform *E. coli* K-12 strain JM101. Transformant bacteria were selected on ampicillin-containing plates. Clones containing the correct insert contained an additional DdeI site which results in DdeI restriction fragments of 806 and 167 base pairs compared to 973 base pairs in pMON13344. The DNA was sequenced to confirm the correct insert. The resulting (15–125)hIL-3 variant has the following amino acid substitutions: 18I, 25H, 29R, 32A, 37P, 42A, 45V, 51R, 55L, 60S, 62V, 67N and 69E. The codons encoding amino acids 15–71 of (15–125) hIL-3 are those found in the hIL-3 cDNA sequence except at those positions where amino acid substitutions were made. The plasmid, pMON13363, encodes the (15–125) hIL-3 variant with the following amino acid sequence:

Peptide #15

Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Arg Asn Leu Arg Leu Pro Asn Leu Glu Ser Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:79]

DNA sequence #20 [SEQ ID NO:116] codes for the foregoing pMON13363 polypeptide.

EXAMPLE 25
Construction of pMON13364

Plasmid pMON13345 DNA was digested with restriction enzymes NsiI and EcoRV, resulting in a 4218 base pair NsiI,EcoRV fragment. The genetic elements derived from pMON13345 are the beta-lactamase gene (AMP), pBR327 origin of replication, phage f1 origin of replication as the transcription terminator, pAraBAD promoter, g10L ribosome binding site, lamB secretion leader and the bases encoding amino acids 15–46 and 72–125 of (15–125)hIL-3. Plasmid pMON13349 DNA was digested with NsiI and EcoRV. The resulting 71 base pair NsiI, EcoRV fragment encodes amino acids 47–71 of (15–125)hIL-3. The restriction fragments were ligated, and the ligation reaction mixture was used to transform *E. coli* K-12 strain JM101. Transformant bacteria were selected on ampicillin-containing plates. Clones containing the correct insert contained an additional DdeI site which results in DdeI restriction fragments of 806 and 167 base pairs compared to 973 base pairs in pMON13344. The DNA was sequenced to confirm the correct insert. The resulting (15–125)hIL-3 variant has the following amino acid substitutions: 18I, 25H, 29R, 32N, 37P, 42S, 45M, S1R, 55T, 59L, 62v, 67H and 69E. The codons encoding amino acids 15–71 of (15–125) hIL-3 are those found in the hIL-3 cDNA sequence except at those positions where amino acid substitutions were made. The plasmid, pMON13364, encodes the (15–125) hIL-3 variant with the following amino acid sequence:

Peptide #16

Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Arg Asn Leu Arg Thr Pro Asn Leu Leu Ala Phe Val Arg Ala Val Lys His Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:80]

DNA sequence #21 [SEQ ID NO:117] codes for the foregoing pMON13364 polypeptide.

EXAMPLE 26
Construction of pMON13365

Plasmid pMON13346 DNA was digested with restriction enzymes NsiI and EcoRV, resulting in a 4218 base pair NsiI,EcoRV fragment. The genetic elements derived from pMON13346 are the beta-lactamase gene (AMP), pBR327 origin of replication, phage f1 origin of replication as the transcription terminator, pAraBAD promoter, g10L ribosome binding site, lamB secretion leader and the bases encoding amino acids 15–46 and 72–125 of (15–125)hIL-3. Plasmid pMON13347 DNA was digested with NsiI and EcoRV. The resulting 71 base pair NsiI, EcoRV fragment encodes amino acids 47–71 of (15–125)hIL-3. The restriction fragments were ligated, and the ligation reaction mixture was used to transform *E. coli* K-12 strain JM101. Transformant bacteria were selected on ampicillin-containing plates. Clones containing the correct insert contained an additional DdeI site which results in DdeI restriction fragments of 806 and 167 base pairs compared to 973 base pairs in pMON13344. The DNA was sequenced to confirm the correct insert. The resulting (15–125)hIL-3 variant has the following amino acid substitutions: 18I, 25H, 29V, 32A, 37S, 42S, 45M, 51R, 55L, 59L, 62V, 67N and 69E. The codons encoding amino acids 15–71 of (15–125) hIL-3 are those found in the hIL-3 cDNA sequence except at those positions where amino acid substitutions were made. The plasmid, pMON13365, encodes the (15–125) hIL-3 variant with the following amino acid sequence:

Peptide #17

Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Arg Asn Leu Arg Leu Pro Asn Leu Leu Ala Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:81]

DNA sequence #22 [SEQ ID NO:118] codes for the foreging pMON13365 polypeptide.

EXAMPLE 27

Construction of pMON13298

Plasmid pMON5978 DNA was digested with restriction enzymes NsiI and HindIII, resulting in a 3789 base pair NsiI,HindIII fragment. The genetic elements derived from pMON5978 are the beta-lactamase gene (AMP), pBR327 origin of replication, phage f1 origin of replication as the transcription terminator, precA promoter, g10L ribosome binding site, and the bases encoding amino acids 15–71 of (15–125)hIL-3. Plasmid pMON13360 DNA was digested with NsiI and HindIII. The resulting 175 base pair NsiI, HindIII fragment encodes amino acids 72–125 of (15–125) hIL-3. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 73G, 76A, 79R, 82Q, 87S, 93S, 98I, 101A, 105Q, 109E, 116V, 120Q and 123E. The codons encoding amino acids 72–125 of (15–125)hIL-3 are those found in the hIL-3 cDNA sequence except at those positions where amino acid substitutions were made. The plasmid, pMON13298, encodes the (15–125)hIL-3 variant with the following amino acid sequence:

Peptide #18

Met Ala Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:82]

DNA sequence #29 [SEQ ID NO:125] codes for the foregoing pMON13298 polypeptide.

EXAMPLE 28

Construction of pMON13299

Plasmid pMON5978 DNA was digested with restriction enzymes NsiI and HindIII, resulting in a 3789 base pair NsiI,HindIII fragment. The genetic elements derived from pMON5978 are the beta-lactamase gene (AMP), pBR327 origin of replication, phage f1 origin of replication as the transcription terminator, precA promoter, g10L ribosome binding site and the bases encoding amino acids 15–71 of (15–125)hIL-3. Plasmid pMON13361 DNA was digested with NsiI and HindIII, the resulting 175 base pair NsiI, HindIII fragment encodes amino acids 72–125 of (15–125) hIL-3. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 73G, 76A, 79R, 82v, 87S, 93S, 98T, 101A, 105Q, 109E, 116V, 120Q and 123E. The codons encoding amino acids 72–125 of (15–125)hIL-3 are those found in the hIL-3 cDNA sequence except at those positions where amino acid substitutions were made. The plasmid, pMON13299, encodes the (15–125)hIL-3 variant with the following amino acid sequence:

Peptide #19

Met Ala Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:83]

DNA sequence #30 [SEQ ID NO:126] codes for the foregoing pMON13299 polypeptide.

EXAMPLE 29

Construction of pMON13300

Plasmid pMON5978 DNA was digested with restriction enzymes NsiI and HindIII, resulting in a 3789 base pair NsiI,HindIII fragment. The genetic elements derived from pMON5978 are the beta-lactamase gene (AMP), pBR327 origin of replication, phage f1 origin of replication as the transcription terminator, precA promoter, g10L ribosome binding site, and the bases encoding amino acids 15–71 of (15–125)hIL-3. Plasmid pMON13362 DNA was digested with NsiI and HindIII. The resulting 175 base pair NsiI, HindIII fragment encodes amino acids 72–125 of (15–125) hIL-3. The restriction fragments were ligated, and the ligation reaction mixture was used to transform *E. coli* K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 73G, 76A, 79R, 82V, 87S, 93S, 98T, 101A, 105Q, 109E, 116V, 117S, 120H and 123E. The codons encoding amino acids 72–125 of (15–125)hIL-3 are those found in the hIL-3 cDNA sequence except at those positions where amino acid substitutions were made. The plasmid, pMON13300, encodes the (15–125)hIL-3 variant with the following amino acid sequence:

Peptide #20

Met Ala Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg

Arg Pro Asn Leu Glu Ala Phe Asn Arg Ala Val Lys Ser Leu Gln Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Ser Leu Glu His Ala Gln Glu Gln Gln [SEQ ID NO:84]

DNA sequence #31 [SEQ ID NO:127] codes for the foregoing pMON13300 polypeptide.

EXAMPLE 30

Construction of pMON13301

Plasmid pMON5978 DNA was digested with restriction enzymes NcoI and NsiI, resulting in a 3794 base pair NcoI,NsiI fragment. The genetic elements derived from pMON5978 are the beta-lactamase gene (AMP), pBR327 origin of replication, phage f1 origin of replication as the transcription terminator, precA promoter, g10L ribosome binding site and the bases encoding amino acids 72–125 of (15–125)hIL-3. Plasmid pMON13363 DNA was digested with NcoI and NsiI. The resulting 170 base pair NcoI, NsiI fragment encodes amino acids 15–71 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32A, 37P, 42A, 45V, 51R, 55L, 60S, 62V, 67N and 69E. The codons encoding amino acids 15–71 of (15–125)hIL-3 are those found in the hIL-3 cDNA sequence except at those positions where amino acid substitutions were made. The plasmid, pMON13301, encodes the (15–125)hIL-3 variant with the following amino acid sequence:

Peptide #21

Met Ala Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Arg Asn Leu Arg Leu Pro Asn Leu Glu Ser Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:85]

DNA sequence #26 [SEQ ID NO:122] codes for the foregoing pMON13301 polypeptide.

EXAMPLE 31

Construction of pMON13302

Plasmid pMON5978 DNA was digested with restriction enzymes NcoI and NsiI, resulting in a 3794 base pair NcoI,NsiI fragment. The genetic elements derived from pMON5978 are the beta-lactamase gene (AMP), pBR327 origin of replication, phage f1 origin of replication as the transcription terminator, precA promoter, g10L ribosome binding site, and the bases encoding amino acids 72–125 of (15–125)hIL-3. Plasmid pMON13364 DNA was digested with NcoI and NsiI. The resulting 170 base pair NcoI, NsiI fragment encodes amino acids 15–71 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32N, 37P, 42S, 45M, 51R, 55T, 59L, 62V, 67H and 69E. The codons encoding amino acids 15–71 of (15–125)hIL-3 are those found in the hIL-3 cDNA sequence except at those positions where amino acid substitutions were made. The plasmid, pMON13302, encodes the (15–125)hIL-3 variant with the following amino acid sequence:

Peptide #22

Met Ala Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Arg Asn Leu Arg Thr Pro Asn Leu Leu Ala Phe Val Arg Ala Val Lys His Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:86]

DNA sequence #27 [SEQ ID NO:123] codes for the foregoing pMON13302 polypeptide.

EXAMPLE 32

Construction of pMON13303

Plasmid pMON5978 DNA was digested with restriction enzymes NcoI and NsiI, resulting in a 3794 base pair NcoI,NsiI fragment. The genetic elements derived from pMON5978 are the beta-lactamase gene (AMP), pBR327 origin of replication, phage f1 origin of replication as the transcription terminator, precA promoter, g10L ribosome binding site, and the bases encoding amino acids 72–125 of (15–125)hIL-3. Plasmid pMON13365 DNA was digested with NcoI and NsiI. The resulting 170 base pair NcoI, NsiI fragment encodes amino acids 15–71 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29V, 32A, 37S, 42S, 45M, 51R, 55L, 59L, 62V, 67N and 69E. The codons encoding amino acids 15–71 of (15–125)hIL-3 are those found in the hIL-3 cDNA sequence except at those positions where amino acid substitutions were made. The plasmid, pMON13303, encodes the (15–125)hIL-3 variant with the following amino acid sequence:

Peptide #23

Met Ala Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Arg Asn Leu Arg Leu Pro Asn Leu Leu Ala Phe Val Arg Ala Val Lys Asn Leu Glu Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln [SEQ ID NO:87]

DNA sequence #28 [SEQ ID NO:124] codes for the foregoing pMON13303 polypeptide.

EXAMPLE 33

Construction of pMON13287

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13363 DNA was digested with NcoI and NsiI. The resulting 170 base pair NcoI, NsiI fragment encodes amino acids 15–71 of (15–125)hIL-3. Plasmid pMON13360 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V, 120Q and 123E. The codons encoding amino acids 15–125 of (15–125)hIL-3 are those found in the hIL-3 cDNA sequence except at those positions where amino acid substitutions were made. The plasmid, pMON13287, encodes the (15–125)hIL-3 variant with the following amino acid sequence:

Peptide #24

Met Ala Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Arg Asn Leu Arg Leu Pro Asn Leu Glu Ser Phe Val Arg Ala Val Lys Asn Leu Glu Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:88]

DNA sequence #1 [SEQ ID NO:97] codes for the foregoing pMON13287 polypeptide.

EXAMPLE 34
Construction of pMON13288

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13364 DNA was digested with NcoI and NsiI. The resulting 170 base pair NcoiI, NsiI fragment encodes amino acids 15–71 of (15–125)hIL-3. Plasmid pMON13360 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109E, 116V, 120Q and 123E. The codons encoding amino acids 15–125 of (15–125)hIL-3 are those found in the hIL-3 cDNA sequence except at those positions where amino acid substitutions were made. The plasmid, pMON13288, encodes the (15–125)hIL-3 variant with the following amino acid sequence:

Peptide #25

Met Ala Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Arg Asn Leu Arg Thr Pro Asn Leu Ala Phe Val Arg Ala Val Lys His Leu Glu Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:89]

DNA sequence #4 [SEQ ID NO:100] codes for the foregoing pMON13288 polypeptide.

EXAMPLE 35
Construction of pMON13289

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13365 DNA was digested with NcoI and NsiI. The resulting 170 base pair Ncoi, NsiI fragment encodes amino acids 15–71 of (15–125)hIL-3. Plasmid pMON13360 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E. The codons encoding amino acids 15–125 of (15–125)hIL-3 are those found in the hIL-3 cDNA sequence except at those positions where amino acid substitutions were made. The plasmid, pMON13289, encodes the (15–125)hIL-3 variant with the following amino acid sequence:

Peptide #26

Met Ala Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Arg Asn Leu Arg Leu Pro Asn Leu Leu Ala Phe Val Arg Ala Val Lys Asn Leu Glu Asn Ala Ser Gly Ile Glu Ala Ile Leu Arg Asn Leu Gln Pro Cys Leu Pro Ser Ala Thr Ala Ala Pro Ser Arg His Pro Ile Ile Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:90]

DNA sequence #7 [SEQ ID NO:103] codes for the foregoing pMON13289 polypeptide.

EXAMPLE 36
Construction of pMON13290

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13363 DNA was digested with NcoI and NsiI. The resulting 170 base pair NcoI, NsiI fragment encodes amino acids 15–71 of (15–125)hIL-3. Plasmid pMON13361 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 120Q and 123E. The codons encoding amino acids 15–125 of (15–125)hIL-3 are those found in the hIL-3 cDNA sequence except at those positions where amino acid substitutions were made. The plasmid, pMON13290, encodes the (15–125)hIL-3 variant with the following amino acid sequence:

Peptide #27
Met Ala Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Arg Asn Leu Arg Leu Pro Asn Leu Glu Ser Phe Val Arg Ala Val Lys Asn Leu Glu Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:91]

DNA sequence #2 [SEQ ID NO:98] codes for the foregoing pMON13290 polypeptide.

EXAMPLE 37
Construction of pMON13292

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13365 DNA was digested with NcoI and NsiI. The resulting 170 base pair NcoI, NsiI fragment encodes amino acids 15–71 of (15–125)hIL-3. Plasmid pMON13361 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29V, 32A, 37S, 42S, 45M, 51R, 55L, 59L, 62v, 67N, 69E, 73G, 76A, 79R, 82V, 87S, 93S, 98T, 101A, 105Q, 109E, 116v, 120Q and 123E. The codons encoding amino acids 15–125 of (15–125)hIL-3 are those found in the hIL-3 cDNA sequence except at those positions where amino acid substitutions were made. The plasmid, pMON13292, encodes the (15–125)hIL-3 variant with the following amino acid sequence:
Peptide #28
Met Ala Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Arg Asn Leu Arg Leu Pro Asn Leu Leu Ala Phe Val Arg Ala Val Lys Asn Leu Glu Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Thr Leu Glu Gln Ala Gln Glu Gln Gln [SEQ ID NO:92]

DNA sequence #8 [SEQ ID NO:104] codes for the foregoing pMON13292 polypeptide.

EXAMPLE 38R
Construction of pMON13294

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13364 DNA was digested with NcoI and NsiI. The resulting 170 base pair NcoI, NsiI fragment encodes amino acids 15–71 of (15–125)hIL-3. Plasmid pMON13362 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 117S, 120H and 123E. The codons encoding amino acids 15–125 of (15–125)hIL-3 are those found in the hIL-3 cDNA sequence except at those positions where amino acid substitutions were made. The plasmid, pMON13294, encodes the (15–125)hIL-3 variant with the following amino acid sequence:
Peptide #29
Met Ala Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Arg Asn Leu Arg Thr Pro Asn Leu Leu Ala Phe Val Arg Ala Val Lys His Leu Glu Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Ser Leu Glu His Ala Gln Glu Gln Gln [SEQ ID NO:93]

DNA sequence #6 [SEQ ID NO:102] codes for the foregoing pMON13294 polypeptide.

EXAMPLE 39
Construction of pMON13295

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13365 DNA was digested with NcoI and NsiI. The resulting 170 base pair NcoI, NsiI fragment encodes amino acids 15–71 of (15–125)hIL-3. Plasmid pMON13362 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29V, 32A, 37S, 42S, 45M, 51R, 55L, 59L, 62V, 67N, 69E, 73G, 76A, 79R, 82V, 87S, 93S, 98T, 101A, 105Q, 109E, 116V, 117S, 120H and 123E. The codons encoding amino acids 15–125 of (15–125)hIL-3 are those found in the hIL-3 cDNA sequence except at those positions where amino acid substitutions were made. The plasmid, pMON13295, encodes the (15–125)hIL-3 variant with the following amino acid sequence:
Peptide #30
Met Ala Asn Cys Ser Ile Met Ile Asp Glu Ile Ile His His Leu Lys Val Pro Pro Ala Pro Leu Leu Asp Ser Asn Asn Leu Asn Ser Glu Asp Met Asp Ile Leu Met Glu Arg Asn Leu Arg Leu Pro Asn Leu Leu Ala Phe Val Arg Ala Val Lys Asn Leu Glu Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Ser Leu Glu His Ala Gln Glu Gln Gln [SEQ ID NO:94]

DNA sequence #9 [SEQ ID NO:105] codes for the foregoing pMON13295 polypeptide.

EXAMPLE 40
Construction of pMON13312

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13364 DNA was digested with NcoI and NsiI. The resulting 170 base pair NcoI, NsiI fragment encodes amino acids 15–71 of (15–125)hIL-3. Plasmid pMON13361 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32N, 37P, 42S, 45M, 51R, 55T, 59L, 62V, 67H, 69E, 73G, 76A, 79R, 82V, 87S, 93S, 98T, 101A, 105Q, 109E, 116V, 120Q and 123E. The codons encoding amino acids 15–125 of (15–125)hIL-3 are those found in the hIL-3 cDNA sequence except at those positions where amino acid substitutions were made. The plasmid, pMON13312, encodes the (15–125)hIL-3 variant with the following amino acid sequence:
Peptide #31

Met Ala Asn Cys Ser Ile Met Ile Asp Glu Ile Ile His His Leu Lys Arg Pro Pro Asn Pro Leu Leu Asp Pro Asn Asn Leu Asn Ser Glu Asp Met Asp Ile Leu Met Glu Arg Asn Leu Arg Thr Pro Asn Leu Leu Ala Phe Val Arg Ala Val Lys His Leu Glu Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Thr Leu Glu Gln Ala Gln Glu Gln Gln Gln [SEQ ID NO:95]

DNA sequence #5 [SEQ ID NO:101] codes for the foregoing pMON13312 polypeptide.

EXAMPLE 41
Construction of pMON13313

Plasmid pMON2341 DNA was digested with restriction enzymes NcoI and HindIII, resulting in a 3619 base pair NcoI,HindIII fragment. The genetic elements derived from pMON2341 are the beta-lactamase gene (AMP), pBR327 origin of replication, phage f1 origin of replication as the transcription terminator, precA promoter and g10L ribosome binding site. Plasmid pMON13363 DNA was digested with NcoI and NsiI. The resulting 170 base pair NcoI, NsiI fragment encodes amino acids 15–71 of (15–125)hIL-3. Plasmid pMON13362 DNA was digested with NsiI and HindIII. The resulting 175 base pair NsiI, HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated, analyzed by restriction analysis, and sequenced to confirm the correct insert. The resulting (15–125)hIL-3 variant has the following amino acid substitutions: 18I, 25H, 29R, 32A, 37P, 42A, 45V, 51R, 55L, 60S, 62V, 67N, 69E, 73G, 76A, 79R, 82V, 87S, 93S, 98T, 101A, 105Q, 109E, 116V, 117S, 120H and 123E. The codons encoding amino acids 15–125 of (15–125)hIL-3 are those found in the hIL-3 cDNA sequence except at those positions where amino acid substitutions were made. The plasmid, pMON13313, encodes the (15–125)hIL-3 variant with the following amino acid sequence:
Peptide #32

Met Ala Asn Cys Ser Ile Met Ile Asp Glu Ile Ile His His Leu Lys Arg Pro Pro Ala Pro Leu Leu Asp Pro Asn Asn Leu Asn Ala Glu Asp Val Asp Ile Leu Met Glu Arg Asn Leu Arg Leu Pro Asn Leu Glu Ser Phe Val Arg Ala Val Lys Asn Leu Glu Asn Ala Ser Gly Ile Glu Ala Ile Leu Arg Asn Leu Val Pro Cys Leu Pro Ser Ala Thr Ala Ala Pro Ser Arg His Pro Ile Thr Ile Lys Ala Gly Asp Trp Gln Glu Phe Arg Glu Lys Leu Thr Phe Tyr Leu Val Ser Leu Glu His Ala Gln Glu Gln Gln [SEQ ID NO:96)

DNA sequence #3 [SEQ ID NO:99] codes for the foregoing pMON13313 polypeptide.

EXAMPLE 42
Construction of pMON5987

Plasmid pMON6458 DNA was digested with restriction enzymes NcoI and HindIII, resulting in a 3940 base pair NcoI,HindIII fragment. The genetic elements derived from pMON6458 are the beta-lactamase gene (AMP), pBR327 origin of replication, phage f1 origin of replication as the transcription terminator, pAraBAD promoter, g10L ribosome binding site and lamB secretion leader. Plasmid pMON5978 DNA was digested with NcoI and NsiI. The resulting 170 base pair NcoI, NsiI fragment encodes amino acids 15–71 of (15–125)hIL-3. Plasmid pMON5976 DNA was digested with NsiI and HindIII. The resulting 175 base pair NsiI,HindIII fragment encodes amino acids 72–125 of (15–125)hIL-3. The restriction fragments were ligated, and the ligation reaction mixture was used to transform E. coli K-12 strain JM101. Transformant bacteria were selected on ampicillin-containing plates. Plasmid DNA was isolated and screened for the restriction sites EcoRV and NheI and DNA sequenced to confirm the correct insert.

EXAMPLE 43
Construction of pMON5988

The plasmid DNA of pMON5987 was digested with NheI and EcoRI, resulting in a 3903 base pair NheI, EcoRI fragment. The 3903 base pair NheI, EcoRI fragment was ligated to 1.0 picomoles of the following annealed oligonucleotides:

```
5'-CTAGCCACGGCCGCACCCACGCGACATCCAATCCATATCAAGGACGGTGACTGGAATG-3' [SEQ ID NO:131]

3'-GGTGCCGGCGTGGGTGCGCTGTAGGTTAGGTATAGTTCCTGCCACTGACCTTACAATT-5' [SEQ ID NO:132]
```

The ligation reaction mixture was used to transform E. coli K-12 strain JM101 and transformant bacteria were selected on ampicillin-containing plates. Plasmid DNA was isolated and sequenced to confirm positive clones. This plasmid was constructed to change alanine 101 to aspartic acid in the hIL-3 gene (15–125). This plasmid was designated pMON5988.

Figure 6:
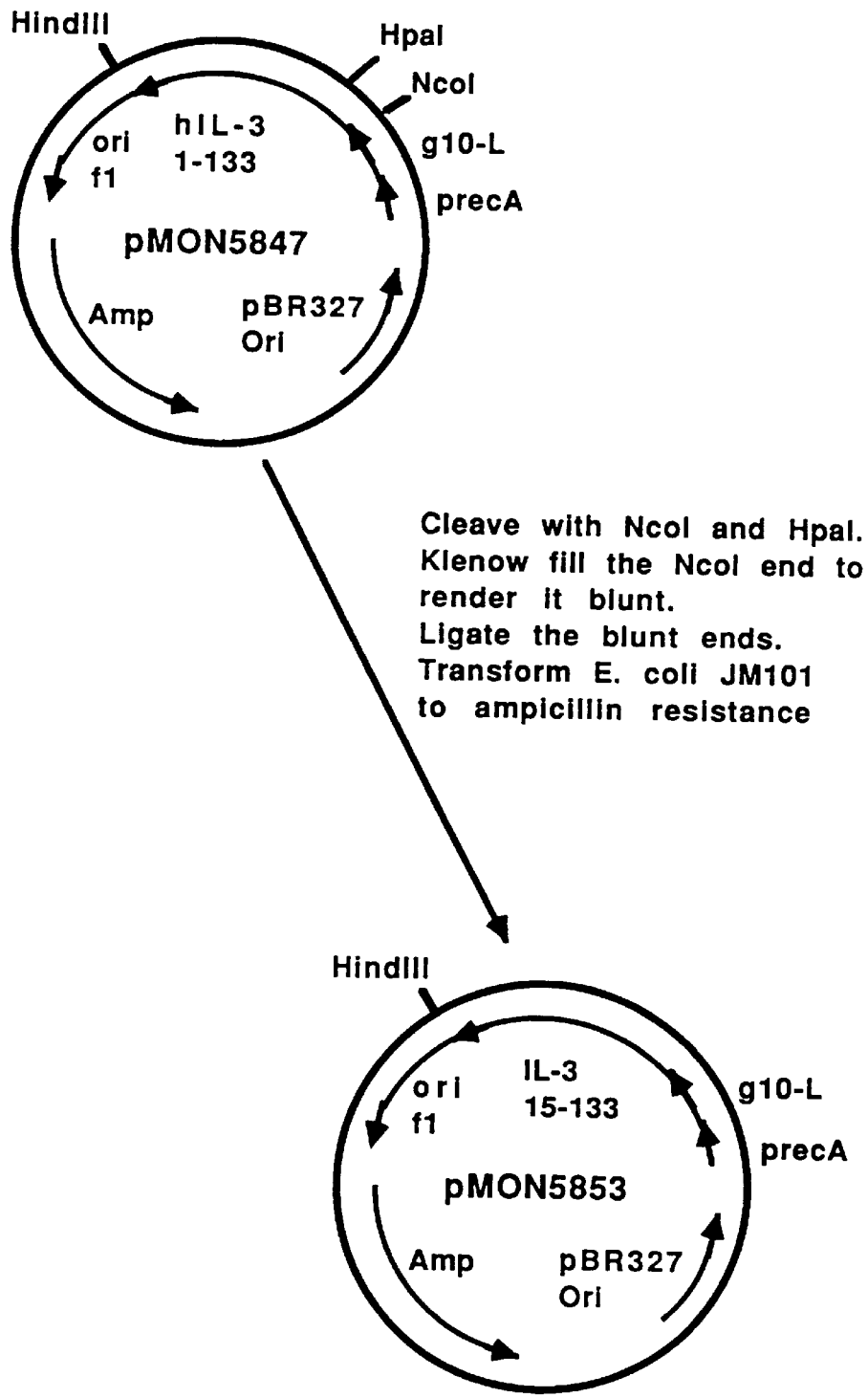
FIG. 6 shows the construction of plasmid vector pMON5853 which encodes [Met-(15–133) hIL-3 ($Arg^{129}$)].

EXAMPLE 44
Construction of pMON5853 (FIG. 6) which encodes [Met-(15–133)hIL-3(Arg$^{129}$)]

Plasmid DNA of pMON5847 (Example 2) was treated with NcoI. The restriction enzyme was inactivated by heat treatment (65° C. for 10 minutes). The DNA was then treated with large fragment of DNA polymerase I (Klenow) in the presence of all four nucleotide precursors. This produces DNA termini with non-overlapping ends. After 5 minutes at 37° C., the polymerase was inactivated by heat treatment at 65° C. for 10 minutes. The DNA was then treated with HpaI, an enzyme which produces non-overlapping termini. The DNA was ethanol precipitated and ligated. The ligation reaction mixture was used to transform competent JM101 cells to ampicillin resistance. Colonies were picked and plasmid DNA was analyzed by restriction analysis. A plasmid designated pMON5853 was identified as one containing a deletion of the amino terminal 14 codons of the hIL-3 gene. The DNA sequence for the junction of the ribosome binding site to the (15–133) hIL-3 gene was determined to be the following:

5'-AAGGAGATATATCCATGAACTGCTCTAAC-3' [SEQ ID NO:133]

M N C S N [SEQ ID NO:134]

The lower line contains the one letter code for the amino acids specified by the coding sequence of the amino terminus of the 15–133 hIL-3 gene. These are methionine, asparagine, cysteine, serine and asparagine.

When cultures of JM101 cells harboring this plasmid were induced with nalidixic acid, it was found that hIL-3 (15–133) accumulated at levels higher than hIL-3 (pMON5847).

The plasmid, pMON5853, encodes Met-(15–133) hIL-3 (Arg$^{129}$) which has the following amino acid sequence:

Met Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln Thr Thr Leu Arg Leu Ala Ile Phe [SEQ ID NO:135]

EXAMPLE 45
Construction of pMON5873 which encodes [Met-(1–133) hIL-3]

The gene obtained from British Biotechnology, Ltd. specified arginine at codon position 129. The amino acid specified in the native hIL-3 cDNA is serine. To produce a protein with the native sequence at this position, the portion of the coding sequence between the EcoRI site at codons 106 and 107 and the NheI site at codons 129 and 130 was replaced. Plasmid DNA of pMON5854 (Example 3) and pMON5853 (Example 44) were treated with EcoRI and NheI. The larger fragments of each were gel purified. These were ligated to a pair of an annealed oligonucleotides with the following sequences:

the gene in the region between EcoRI and NheI was determined and found to be that of the synthetic oligonucleotides. The new plasmids were designated pMON5873 encoding [Met-(1–133)hIL-3] and pMON5872 encoding [Met-(15–133)hIL-3].

The plasmid, pMON5873, encodes Met-(1–133)hIL-3 which has the following amino acid sequence:

Met Ala Pro Met Thr Gln Thr Thr Ser Leu Lys Thr Ser Trp Val Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Asp Gly Asp Trp Asn Glu Phe Arg Arg Lys Leu Thr Phe Tyr Leu Lys Thr Leu Glu Asn Ala Gln Ala Gln Gln Thr Thr Leu Ser Leu Ala Ile Phe [SEQ ID NO:128]

EXAMPLE 46
Construction of pMON6458

Plasmid pMON6525 was digested with restriction enzymes HindIII and SalI and the resulting 3172 base pair fragment was isolated from a 1% agarose gel by interception onto DEAE membrane. The genetic elements derived from pMON6525 are the beta-lactamase gene (AMP), pBR327 origin of replication, and phage f1 origin of replication as the transcription terminator. (The genetic elements derived from plasmid pMON6525 are identical to those in plasmid pMON2341 which could also be used to construct pMON6458.) Plasmid pMON6457 was digested with restriction enzymes HindIII and SalI and the resulting 1117 base pair fragment was isolated by PAGE and crush and soak elution. The genetic elements derived from pMON6457 are the pAraBAD promoter, g10L ribosome binding site, lamB secretion leader and the (15–125) hIL-3 gene. The restriction fragments were ligated and the ligation reaction mixture was used to transform E. coli K-12 strain JM101. Transformant bacteria were selected on ampicillin-containing plates. Plasmid DNA was isolated and the size of the inserted fragment was determined by restriction analysis employing restriction enzymes NcoI and HindIII in double digest. Clones containing the hIL-3 gene (encoding amino acids 15–125) contained a 345 base pair NcoI, HindIII restriction fragment. This construct was designated pMON6458. This plasmid was constructed to eliminate an EcoRI restriction site outside the hIL-3 gene coding region in plasmid pMON6457.

EXAMPLE 47
Construction of pMON5976 which encodes [Met-(15–125) hIL-3(Ala$^{101}$)]

The plasmid DNA of pMON5941 isolated from the dam- E. coli strain GM48 was cleaved with ClaI and NsiI and ligated to 1 picomole of an annealed assembly of six oligonucleotides encoding amino acids 20–70 of hIL-3 (FIG. 2). This synthetic fragment encodes three unique 5'-AATTCCGTCGTAAACTGACCTTCTATCTGAAAACCTTGGAGAACGCGCAGGCTCAACAGACCACTCTGTCG-3' [SEQ ID NO:136]

3'-GGCAGCATTTGACTGGAAGATAGACTTTTGGAACCTCTTGCGCGTCCGAGTTGTGAGACAGCGATC-5' [SEQ ID NO:137]

The ligation reaction mixtures were used to transform competent JM101 cells to ampicillin resistance. Colonies were picked into broth and grown. Plasmid DNA was isolated and screened for the presence of a new StyI recognition site present in the synthetic DNA and not in pMON5854 and pMON5853. The nucleotide sequence of restriction sites, EcoRV, XhoI and PstI. The sequence of these oligonucleotides is shown in FIG. 2.

The resulting ligation mix was used to transform competent E. coli JM101 cells to ampicillin resistant colonies. Plasmid DNA was isolated and the inserted fragment was determined to have both an EcoRV and NheI site. The nucleotide sequence of the region between ClaI and NsiI was determined and found to be that of the synthetic oligonucleotides. At codons 86–87 of a nucleotide sequence coding for (15–125)hIL-3, an NheI site was introduced. The plasmid with this alteration was designated pMON5941. This plasmid encodes Met-(15–125)hIL-3 which is altered at position 101 by replacement of aspartate by alanine.

Plasmid pMON5976 encodes Met-(15–125)hIL-3 (Ala$^{101}$) which has the following amino acid sequence:

Met Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala Thr Ala Ala Pro Thr Arg His Pro Ile His Ile Lys Ala Gly Asp Trp Asn Glu Phe Arg Arg Lys Leu Thr Phe Tyr Leu Lys Thr Leu Glu Asn Ala Gln Ala Gln Gln [SEQ ID NO:138]

EXAMPLE 48
Construction of pMON5917 which encodes [Met-(15–88) hIL-3]

The plasmid DNA of pMON5853 was cleaved with NsiI and HindIII and ligated to an annealed pair of oligonucleotides encoding (70–88)hIL-3 with a new NheI endonuclease restriction site at codons 86–87. The sequence of these oligonucleotides is shown in Example 18.

The ligation mixture was used to transform competent *E. coli* JM101 cells, and ampicillin resistant colonies were picked. Plasmid DNA isolated from individual colonies was screened for the presence of the new NheI restriction site. The nucleotide sequence of the substituted portion was determined and found to be that of the synthetic oligonucleotides. The new plasmid was designated pMON5917 encoding Met-(15–88)hIL-3 containing a new NheI site at codons 86–87.

Plasmid pMON5917 encodes Met-(15–88)hIL-3 which has the following amino acid sequence:

Met Asn Cys Ser Asn Met Ile Asp Glu Ile Ile Thr His Leu Lys Gln Pro Pro Leu Pro Leu Leu Asp Phe Asn Asn Leu Asn Gly Glu Asp Gln Asp Ile Leu Met Glu Asn Asn Leu Arg Arg Pro Asn Leu Glu Ala Phe Asn Arg Ala Val Lys Ser Leu Gln Asn Ala Ser Ala Ile Glu Ser Ile Leu Lys Asn Leu Leu Pro Cys Leu Pro Leu Ala [SEQ ID NO: 139]

EXAMPLE 49
Construction of pmon5941 which encodes [Met-(15–125) hIL-3 Ala$^{101}$]

The plasmid DNA of pMON5917 was cleaved with NheI and HindIII and ligated to two annealed pairs of oligonucleotides which encode amino acids 86–106 and 107–125 of hIL-3. The sequences of these oligonucleotides is shown below.

inserted fragment was determined to be larger by restriction analysis with NcoI and HindIII. The Asp to Ala 101 change is encoded on the NheI to EcoRI fragment. The nucleotide sequence of the portion of the coding region between the NheI and HindIII sites was determined and found to be that of the synthetic oligonucleotides. The new plasmid was designated pMON5941.

The plasmid, pMON5941, encodes Met-(15–125)hIL-3 (Ala$^{101}$) and contains a new NheI restriction site.

EXAMPLE 50
Construction of pMON6455

Plasmid pMON5905 was digested with restriction enzymes HindIII and NcoI resulting in a 3936 base pair fragment. The genetic elements derived from pMON5905 are the beta-lactamase gene (AMP), pBR327 origin of replication, pAraBAD promoter, g10L ribosome binding site, lamB secretion leader and phage f1 origin of replication as the transcription terminator. The following genetic elements; beta-lactamase gene (AMP), pBR327 origin of replication, g10L ribosome binding site and phage fl origin of replication as the transcription terminator, derived from plasmid pMON5905 are identical to these in plasmid pMON5594 which could also be used to construct pMON6455. The AraBAD promoter is identical to that described in pMON6235. The lamB signal peptide sequence used in pMON6455 is that shown in FIG. 8 fused to hIL-3 (15–125) at the NcoI site. Plasmid pMON5887 was digested with restriction enzymes HindIII and NcoI, resulting in a 384 base pair NcoI, HindIII fragment. The restriction fragments were ligated, and the ligation reaction mixture was used to transform into *E. coli* K-12 strain JM101. Transformant bacteria were selected on ampicillin-containing plates. Plasmid DNA was isolated and the size of the inserted fragment was determined by restriction analysis employing restriction enzymes NcoI and HindIII in double digest. Positive clones containing the hIL-3 gene (encoding amino acids 1–125) contained a 384 base pair NcoI, HindIII restriction fragment. This construct was designated pMON6455.

EXAMPLE 51
Construction of pMON6456

Plasmid pMON5905 was digested with restriction enzymes HindIII and NcoI resulting in a 3936 base pair fragment. The genetic elements derived from pMON5905 are the beta-lactamase gene (AMP), pBR327 origin of replication, phage f1 origin of replication as the transcription terminator, pAraBAD promoter, g10L ribosome binding site and the lamb secretion leader. Plasmid pMON5871 was digested with restriction enzymes HindIII and NcoI, resulting in a 330 base pair NcoI, HindIII fragment. The genetic element derived from pMON5871 encompassed the bases

```
NheI to EcoRI
5'-CTAGCCACGGCCGCACCCACGCGACATCCAATCCATATCAAGGCTGGTGACTGGAATG-3' [SEQ ID NO:140]

3'-GGTGCCGGCGTGGGTGCGCTGTAGGTTAGGTATAGTTCCGACCACTGACCTTACTTAA-5' [SEQ ID NO:141]

EcoRI to HindIII
5'-AATTCCGTCGTAAACTGACCTTCTATCTGAAAACCTTGGAGAACGCGCAGGCTCAACAGTAATA-3' [SEQ ID NO:142]

3'-GGCAGCATTTGACTGGAAGATAGACTTTTGGAACCTCTTGCGCGTCCGAGTTGTCATTATTCGA-5' [SEQ ID NO:143]
```

The ligation mixture was used to transform competent *E. coli* JM10l cells to ampicillin resistant colonies. Plasmid DNA was isolated from these cells and the size of the encoding the (1–107) hIL-3 gene. The restriction fragments were ligated, and the ligation reaction mixture was used to transform *E. coli* K-12 strain JM101. Transformant bacteria were selected on ampicillin-containing plates. Plasmid DNA was isolated and the size of the inserted fragment was determined by restriction analysis employing restriction enzymes NcoI and HindIII in double digest. Clones containing the hIL-3 gene (encoding amino acids 1–107) contained a 330 base pair NcoI, HindIII restriction fragment. This construct was designated pMON6456.

EXAMPLE 52
Construction of pMON6457

Plasmid pMON6455 DNA grown in *E. coli* strain GM48 (dam-)was digested with restriction enzymes NcoI and ClaI, resulting in a 4263 base pair NcoI, ClaI fragment. The restriction fragment was ligated to 1.0 picomoles of annealed oligonucleotides with the following sequence coding for Met Ala 14–20 hIL-3:

```
5'-CATGGCTAACTGCTCTAACATGAT-3' [SEQ ID NO:151]

3'-CGATTGACGAGATTGTACTAGC-5' [SEQ ID NO:152]
```

The resulting DNA was transformed into *E. coli* K-12 strain JM101 and transformant bacteria were selected on ampicillin-containing plates. Plasmid DNA was isolated and the size of the inserted fragment was determined by restriction analysis employing restriction enzymes XbaI and EcoRI in double digest. Positive clones containing the hIL-3 gene (encoding aa 15–125 of hIL-3) contained a 433 base pair XbaI, EcoRI restriction fragment. This construct was designated pMON6457. This plasmid was constructed to delete the first 14 amino acids of hIL-3. The coding sequence of the resulting gene begins as follows:

```
5' ATG GCT AAC TGC... 3' [SEQ ID NO:153]

Met Ala Asn Cys...   [SEQ ID NO:154]
        15
```

The first two amino acids (Methionine, Alanine) create an NcoI restriction site and a signal peptidase cleavage site between the lamB signal peptide and (15–125) hIL-3. Plasmid pMON6457 encodes (15–125) hIL-3 which has the amino acid sequence designated SEQ ID NO:65.

EXAMPLE 53
Construction of pMON6235

One of the DNA fragments used to create this plasmid was generated by site-directed mutagenesis employing PCR techniques described previously using the following oligonucleotides, Oligo #51 [SEQ ID NO:155] and Oligo #52 [SEQ ID NO:156], were used as primers in this procedure. The template for the PCR reaction was *E. coli* strain W3110 chromosomal DNA, prepared as described in Maniatis (1982). The oligonucleotide primers were designed to amplify the AraBAD promoter (Greenfield et al., 1978). The resulting DNA product was digested with the restriction enzymes SacII and BglII. The reaction mixture was purified as described previously. Plasmid, pMON5594, DNA was digested with SacII and BglII, resulting in a 4416 base pair SacII,BglII restriction fragment which contains the following genetic elements; beta-lactamase gene (AMP), pBR327 origin of replication, G10L ribosome binding site, phage f1 origin of replication as the transcription terminator and the chloramphenicol acetyl transferase (cat) gene. The 4416 base pair SacII,BglII restriction fragment from pMON5594 was ligated to the PCR-generated SacII, BglII DNA fragment. The ligation mixture was used to transform *E. coli* K-112 strain JM101. Positive clones contained a 323 base pair SacII,BglII fragment and were DNA sequenced to confirm that the SacII,BglII fragment was the AraBAD promoter. This construct was designated pMON6235.

EXAMPLE 54
Construction of pMON5647

Plasmid pMON5585 [prepared as disclosed in EP 0241446 incorporated herein by reference in its entirety] DNA was digested with restriction enzymes NcoI and HindIII resulting in a 3273 base pair NcoI,HindIII fragment. The genetic elements derived from pMON5585 are the pBR327 origin of replication, precA promoter, g10L ribosome binding protein, bovine somatotropin gene (bST), beta-lactamase gene (AMP) and T7 transcription terminator. Plasmid pMON3267 [prepared as disclosed in EP 0241446 incorporated herein by reference in its entirety] DNA was digested with NcoI and HindIII enzymes resulting in a 580 base pair NcoI,HindIII fragment which contains the porcine somatotropin (pST) gene. The restriction fragments were the ligation reaction mixture was used to transform *E. coli* strain JM101. The DraI, SspI, HincII and EcoRV restriction sites are lost as a result of the cloning. Transformant bacteria were selected on spectinomycin-containing plates. Plasmid DNA was isolated, analyzed by restriction analysis and sequenced to confirm the correct insert.

EXAMPLE 57
Construction of pMON13361

Plasmid pMON13288 was mutagenized by oligonucleotide site-directed mutagenesis (method described in Kunkel, 1985) to eliminate a NsiI site in the (15–125) hIL-3 variant coding region. Codon 70 of (15–125) hIL-3, encoding asparagine, was converted from AAT to AAC destroying the NsiI recognition site. The oligonucleotide, Oligo # 54 [SEQ ID NO:158], was used in this procedure to eliminate the NsiI site. Transformant bacteria were selected on ampicillin-containing plates. Plasmid DNA was isolated, analyzed by restriction analysis to confirm the loss of the NsiI site and sequenced to confirm the sequence of the (15–125) hIL-3 variant gene. The plasmid, pMON13361, encodes the (15–125) hIL-3 variant with the amino acid sequence of PEPTIDE #25 [SEQ ID NO:89].
DNA sequence # 32 [SEQ ID NO:160] codes for the foregoing pMON13361 polypeptide.

EXAMPLE 58
Construction of pMON14058

Plasmid pMON13361 was mutagenized by oligonucleotide site-directed mutagenesis (method described by Taylor et al., 1985 using a kit from Amersham, Arlington Heights, Ill.) to eliminate a EcoRV site in the (15–125) hIL-3 variant coding region. Codon 46 and 47 of (15–125) hIL-3, encoding asparagine and isoleucine, were converted from ligated and the ligation reaction mixture was used to transform *E. coli* strain JM101. Transformant bacteria were selected on ampicillin-containing plates. Plasmid DNA was isolated, analyzed by restriction analysis and sequenced to confirm the correct insert.

EXAMPLE 55
Construction of pMON710

Plasmid pMON709 consists of a 1614 base pair AvaI, EcoRI fragment of transposon TN7, containing the streptomycin adenylyltransferase gene (Fling et al., 1985) and a pUC9 linker (XmaI,HindIII) cloned between the HindIII and EcoRI sites of pUC19. The streptomycin adenylyltransferase gene COnfers resistance to streptomycin and spectinomycin. Plasmid pMON709 was mutagenized by oligonucleotide site-directed mutagenesis (methods described in Zoller and Smith, 1982) to introduce an EcoRV site at the 3' end of the streptomycin adenylyltransferase gene. The oligonucleotide, Oligo # 53 [SEQ ID NO:157], was used in this procedure to introduce the EcoRV site. The resulting plasmid was designated pMON710.

EXAMPLE 56

Construction of pMON5723

Plasmid pMON5647 DNA was digested with restriction enzymes DraI and SspI resulting in a 2916 base pair DraI, SspI fragment. The genetic elements derived from pMON5647 are the pBR327 origin of replication, precA promoter, g10L ribosome binding protein, porcine somatotropin gene (pST) and T7 transcription terminator (Dunn and Strudier, 1983). Plasmid pMON710 DNA was digested with restriction enzymes HincII and EcoRV resulting in 940 base pair HincII,EcoRV fragment containing the streptomycin adenylyltransferase gene which infers resistance to streptomycin and spectinomycin. The restriction fragments were ligated and GAT to GAC and ATC to ATT respectively, destroying the EcoRV recognition site. The oligonucleotide, Oligo # 55 [SEQ ID NO:159], was used in this procedure to eliminate the EcoRV site. Transformant bacteria were selected on ampicillin-containing plates. Plasmid DNA was isolated, analyzed by restriction analysis to confirm the loss of the EcoRV site and sequenced to confirm the sequence of the (15–125) hIL-3 variant gene. The plasmid, pMON14058, encodes the (15–125) hIL-3 variant with the amino acid sequence of PEPTIDE #25 [SEQ ID NO:89]. DNA sequence # 33 [SEQ ID NO:161] codes for the foregoing pMON14058 polypeptide.

EXAMPLE 59

Construction of pMON13438

Plasmid pMON5723 DNA was digested with restriction enzymes NcoI and HindIII resulting in a 3278 NcoI,HindIII fragment. The genetic elements derived from pMON5723 are the pBR327 origin of replication, precA promoter, g10L ribosome binding protein, T7 transcription terminator and streptomycin adenylyltransferase gene. Plasmid pMON14058 DNA was digested with NcoI and HindIII resulting in a 345 base pair NcoI,HindIII fragment which contains the (15–125) hIL-3 gene with the following amino acid substitutions: 18I, 25H, 29R, 32N, 37P, 42S, 45M, 51R, 55T, 59L, 62V, 67H, 69E,73G, 76A, 79R, 83Q, 87S, 93S, 98I, 101A, 105Q, 109E, 116v, 120Q and 123E. The restriction fragments were ligated and the ligation reaction mixture was used to transform E. coli strain JM101. Transformant bacteria were selected on spectinomycin-containing plates.

Plasmid DNA was isolated, analyzed by restriction analysis and sequenced to confirm the correct insert. The plasmid, pMON13438, encodes the (15–125) hIL-3 variant with the amino acid sequence of PEPTIDE #25 [SEQ ID NO:89]. DNA sequence # 33 [SEQ ID NO:161] codes for the foregoing pMON13438 polypeptide.

EXAMPLE 60

Construction of pMON13285

Plasmid pMON13252 DNA was digested with restriction enzymes NcoI and EcoRV and the resulting 3669 base pair NcoI,EcoRV fragment contains the following genetic elements; streptomycin adenyltransferase gene, pBR327 origin of replication, phage f1 origin of replication as the transcription terminator, recA promoter, g10L ribosome binding site and the bases encoding amino acids 47–125 of (15–125) hIL-3 with the following amino acid substitution, 50D. The 3669 base pair NcoI,EcoRV restriction fragment from pMON13252 was ligated to the following annealed complementary oligonucleotides.

Oligo #165 [SEQ ID NO:162]
Oligo #166 [SEQ ID NO:163]
Oligo #167 [SEQ ID NO:164]
Oligo #168 [SEQ ID NO:165]
Oligo #169 [SEQ ID NO:166]
Oligo #170 [SEQ ID NO:167]

When assembled, the oligonucleotides create NcoI and EcoRV restriction ends and the DNA sequence that encodes amino acids 15–46 of (15–125) hIL-3 with the following amino acid substitutions; 42D, 45M and 46S. The codons encoding amino acids 15–46 of (15–125) hIL-3 are those found in the hIL-3 cDNA sequence except at those positions where amino acid substitutions were made. The plasmid, pMON13285, encodes the (15–125) hIL-3 variant with the following amino acid sequence:

```
Peptide #A3 [SEQ ID NO:259]
DNA sequence #A3 pMON13285 42D, 45M 46S, 50D
ATGGCTAACT GCTCTAACAT GATCGATGAA ATCATCACCC

ACCTGAAGCA GCCACCTCTG CCGCTGCTGG ACTTCAACAA

CCTCAATGAC GAAGACATGT CTATCCTGAT GGACAATAAC

CTTCGTCGTC CAAACCTCGA GGCATTCAAC CGTGCTGTCA

AGTCTCTGCA GAATGCATCA GCAATTGAGA GCATTCTTAA

AAATCTCCTG CCATGTCTGC CCCTGGCCAC GGCCGCACCC

ACGCGACATC CAATCCATAT CAAGGACGGT GACTGGAATG

AATTCCGTCG TAAACTGACC TTCTATCTGA AAACCTTGGA

GAACGCGCAG GCTCAACAG
[SEQ ID NO:398]
```

EXAMPLE 61

Construction of pMON13286

Plasmid pMON5978 DNA was digested with restriction enzymes NcoI and EcoRV and the resulting 3865 base pair NcoI,EcoRV fragment contains the following genetic elements; beta-lactamase gene (AMP), pBR327 origin of replication, phage f1 origin of replication as the transcription terminator, precA promoter, g10L ribosome binding site and the bases encoding amino acids 47–125 of (15–125) hIL-3. The 3865 base pair NcoI,EcoRV restriction fragment from pMON5978 was ligated to the following annealed complementary oligonucleotides.

Oligo #165 [SEQ ID NO:162]
Oligo #166 [SEQ ID NO:163]
Oligo #167 [SEQ ID NO:164]
Oligo #168 [SEQ ID NO:165]
Oligo #169 [SEQ ID NO:166]
Oligo #170 [SEQ ID NO:167]

When assembled, the oligonucleotides create NcoI and EcoRV restriction ends and the DNA sequence that encodes amino acids 15–46 of (15–125) hIL-3 with the following amino acid substitutions; 42D, 45M and 46S. The codons encoding amino acids 15–46 of (15–125) hIL-3 are those found in the hIL-3 cDNA sequence except at those positions where amino acid substitutions were made. The plasmid, pMON13286, encodes the (15–125) hIL-3 variant with the following amino acid sequence:

```
Peptide #A4 [SEQ ID NO:260]
DNA sequence #A4 pMON13286 42D, 45M, 46s

ATGGCTAACT GCTCTAACAT GATCGATGAA ATCATCACCC

ACCTGAAGCA GCCACCGCTG CCGCTGCTGG ACTTCAACAA

CCTCAATGAC GAAGACATGT CTATCCTGAT GGAAAATAAC

CTTCGTCGTC CAAACCTCGA GGCATTCAAC CGTGCTGTCA

AGTCTCTGCA GAATGCATCA GCAATTGAGA GCATTCTTAA

AAATCTCCTG CCATGTCTGC CCCTGGCCAC GGCCGCACCC

ACGCGACATC CAATCCATAT CAAGGACGGT GACTGGAATG

AATTCCGTCG TAAACTGACC TTCTATCTGA AAACCTTGGA

GAACGCGCAG GCTCAACAG
[SEQ ID NO:399]
```

EXAMPLE 62

Construction of pMON13325

The 3704 base pair EcoRI, HindIII DNA fragment from plasmid pMON13286 is ligated to the 64 base pair EcoRI, HindIII DNA fragment from plasmid pMON13215. The following genetic elements are derived from pMON13286; beta-lactamase gene (AMP), pBR327 origin of replication, phage F1 origin of replication as the transcription terminator, precA promoter, g10L ribosome binding site and the bases encoding amino acids 15–105 of the (15–125) hIL-3 gene with the following changes, 42D, 45M, and 46S. The bases encoding amino acids 106–125 of the (15–125) gene with the following change, 116W, are derived from pMON13215. The resulting plasmid, pMON13325, encodes the (15–125) hIL-3 variant with the following amino acid sequence:
Peptide # A5 [SEQ ID NO:261]

EXAMPLE 63

Construction of pMON13326

The 3683 base pair NcoI, EcoRI DNA fragment from plasmid pMON13215 is ligated to the 281 base pair NcoI, EcoRI DNA fragment from plasmid pMON13285. The following genetic elements are derived from pMON13215; beta-lactamase gene (AMP), pBR327 origin of replication, phage F1 origin of replication as the transcription terminator, precA promoter, g10L ribosome binding site and the bases encoding amino acids 106–125 of the (15–125) hIL-3 gene with the following change, 116W. The bases encoding amino acids 15–105 of the (15–125) gene with the following change, 42D, 45M, 46S and 50D derived from pMON13285. The resulting plasmid, pMON13326, encodes the (15–125) hIL-3 variant with the following amino acid sequence:
Peptide # A6 [SEQ ID NO:262]

EXAMPLE 64

Construction of pMON13332

Plasmid pMON13326 DNA is digested with restriction enzymes NsiI and EcoRI and the resulting 3853 base pair NsiI,EcoRI fragment contains the following genetic elements; beta-lactamase gene (AMP), pBR327 origin of replication, phage f1 origin of replication as the transcription terminator, recA promoter, g10L ribosome binding site and the bases encoding amino acids 15–71 and 106–125 of (15–125) hIL-3 gene with the following changes 42D, 45M, 46S, 50D and 116W. The 3853 base pair NsiI,EcoRI restriction fragment from pMON13326 is ligated to the following annealed complementary oligonucleotides.
Oligo #15(A) [SEQ ID NO:168]
Oligo #16(A) [SEQ ID NO:169]

In the resulting plasmid the 111 bases between the NsiI and EcoRI restriction sites in the (15–125) hIL-3 gene are replaced with 24 bases from the above mentioned oligonucleotides. This linker also creates a NdeI recognition sequence.

EXAMPLE 65

Construction of pMON13330

The 3846 base pair PstI, EcoRI DNA fragment from plasmid pMON13332 is ligated to the 118 base pair PstI, EcoRI DNA fragment from plasmid pMON13305. The following genetic elements are derived from pMON13332; beta-lactamase gene (AMP), pBR327 origin of replication, phage f1 origin of replication as the transcription terminator, recA promoter, g10L ribosome binding site and the bases encoding amino acids 15–69 and 106–125 of the (15–125) hIL-3 gene with the following change, 42D, 45M, 46S, 50D and 116W. The bases encoding amino acids 70–105 of the (15–125) gene with the following change, 95R, 98I and 100R are derived from pMON13305. The resulting plasmid, pMON13330, encodes the (15–125) hIL-3 variant with the following amino acid sequence:
Peptide # A7 [SEQ ID NO:263]

EXAMPLE 66

Construction of pMON13329

The 3846 base pair PstI, EcoRI DNA fragment from plasmid pMON13332 is ligated to the 118 base pair PstI, EcoRI DNA fragment from plasmid pMON13304. The following genetic elements are derived from pMON13332; beta-lactamase gene (AMP), pBR327 origin of replication, phage f1 origin of replication as the transcription terminator, recA promoter, g10L ribosome binding site and the bases encoding amino acids 15–69 and 106–125 of the (15–125) hIL-3 gene with the following change, 42D, 45M, 46S, and 116W. The bases encoding amino acids 70–105 of the (15–125) gene with the following change, 98I and 100R are derived from pMON13304. The resulting plasmid, pMON13329, encodes the (15–125) hIL-3 variant with the following amino acid sequence:
Peptide # A8 [SEQ ID NO:406]

EXAMPLE 67

Construction of pMON5853 (FIG. 6) which encodes [Met-(15–133)hIL-3(Arg$^{129}$)]

Plasmid DNA of pMON5847 (Example 2) was treated with NcoI. The restriction enzyme was inactivated by heat treatment (65° C. for 10 minutes) The DNA was then treated with large fragment of DNA polymerase I (Klenow) in the presence of all four nucleotide precursors. This produces DNA termini with non-overlapping ends. After 5 minutes at 37° C., the polymerase was inactivated by heat treatment at 65° C. for 10 minutes. The DNA was then treated with HpaI, an enzyme which produces non-overlapping termini. The DNA was ethanol precipitated and ligated. The ligation reaction mixture was used to transform competent JM101 cells to ampicillin resistance. Colonies were picked and plasmid DNA was analyzed by restriction analysis. A plasmid designated pMON5853 was identified as one containing a deletion of the amino terminal 14 codons of the hIL-3 gene. The DNA sequence for the junction of the ribosome binding site to the (15–133) hIL-3 gene was determined to be the following:

5'-AAGGAGATATATCCATGAACTGCTCTAAC-3' [SEQ ID NO:400]

M  N  C  S  N [SEQ ID NO: 401]

The lower line contains the one-letter code for the amino acids specified by the coding sequence of the amino terminus of the 15–133 hIL-3 gene. These are methionine, asparagine, cysteine, serine and asparagine.

When cultures of JM101 cells harboring this plasmid were induced with nalidixic acid, it was found that hIL-3 (15–133) accumulated at levels higher than hIL-3 (pMON5847).

The plasmid, pMON5853, encodes Met-(15–133) hIL-3 (Arg$^{129}$) which has the following amino acid sequence:

```
Met Asn Cys Ser Asn Met Ile Asp Glu Ile Ile Thr
His Leu Lys Gln Pro Pro Leu Pro Leu Leu Asp Phe Asn
Asn Leu Asn Gly Glu Asp Gln Asp Ile Leu Met Glu Asn
Asn Leu Arg Arg Pro Asn Leu Glu Ala Phe Asn Arg Ala
Val Lys Ser Leu Gln Asn Ala Ser Ala Ile Glu Ser Ile
Leu Lys Asn Leu Leu Pro Cys Leu Pro Leu Ala Thr Ala
```

-continued
```
Ala Pro Thr Arg His Pro Ile His Ile Lys Asp Gly Asp
Trp Asn Glu Phe Arg Arg Lys Leu Thr Phe Tyr Leu Lys
Thr Leu Glu Asn Ala Gln Ala Gln Gln Thr Thr Leu Arg
Leu Ala Ile Phe [SEQ ID NO:402]
```

EXAMPLE 68

Construction of pMON13252

Plasmid, pMON2341, DNA was digested with restriction enzymes NcoI and HindIII resulting in a 3619 base pair NcoI/HindIII fragment. The genetic elements derived from pMON2341 are the beta-lactamase gene (AMP), pBR327 origin of replication F1 phage origin of replication as the transcription terminator, precA, g10L ribosome binding site. The plasmid encoding the hIL-3 (15–125) Asp$^{(50)}$ variant, was digested with NcoI and HindIII resulting in a 345 base pair NcoI/HindIII fragment. This 345 Base pair NcoI/HindIII fragment was ligated with the 3619 base pair fragment from pMON2341 and the ligation reaction mixture was used to transform *E. coli* K-12 strain JM101. Plasmid DNA was isolated and screened by restriction analysis using NcoI and HindIII. Positive clones contained a 345 base pair NcoI/HindIII fragment. This construct was designated pMON13252. The plasmid, pMON13252, encodes the (15–125)hIL-3 variant with the following amino acid sequence:

```
PEPTIDE A10; (15-125)HIL-3 Asp(50) pMON13252
        Asn Cys Ser Asn Met Ile Asp Glu Ile Ile Thr His Leu
        15              20                  25

Lys Gln Pro Pro Leu Pro Leu Leu Asn Phe Asn Asn Leu Asn Gly
        30                  35                  40

Glu Asp Gln Asp Ile Leu Met Asp Asn Asn Leu Arg Arg Pro Asn
        45                  50                  55

Leu Glu Ala Phe Asn Arg Ala Val Lys Ser Leu Gln Asn Ala Ser
        60                  65                  70

Ala Ile Glu Ser Ile Leu Lys Asn Leu Leu Pro Cys Leu Pro Leu
        75                  80                  85

Ala Thr Ala Ala Pro Thr Arg His Pro Ile His Ile Lys Asp Gly
        90                  95                  100

Asp Trp Asn Glu Phe Arg Arg Lys Leu Thr Phe Tyr Leu Lys Thr
        105                 110                 115

Leu Glu Asn Ala Gln Ala Gln Gln [SEQ ID NO:407]
        120                 125

DNA sequence #A10 pMON13252 50D
ATGGCTAACT GCTCTAACAT GATCGATGAA ATCATCACCC ACCTGAAGCA

GCCACCGCTG CCGCTGCTGG ACTTCAACAA CCTCAATGGT GAAGACCAAG

ATATCCTGAT GGAACAATAAC CTTCGTCGTC CAAACCTCGA GGCATTCAAC

CGTGCTGTCA ACTCTCTGCA GAATGCATCA GCAATTGAGA GCATTCTTAA

AAATCTCCTG CCATGTCTGC CCCTGGCCAC GGCCGCACCC ACGCGACATC

CAATCCATAT CAAGGACGGT GACTGGAATG AATTCCGTCG TAAACTGACC

TTCTATCTGA AAACCTTGGA GAACGCGCAG GCTCAACAG
[SEQ ID NO:408]
```

EXAMPLES 69–76

The variants in Table 5 were constructed by cassette mutagenesis using methods described in the Materials and Methods and the Examples contained herein, particularly Examples 54–58. Parental plasmid DNA (Table 5), digested with the appropriate restriction enzymes (Table 5), was ligated with the indicated annealed pairs of complementary oligonucleotides (Table 5). The assembled oligonucleotides create appropriate restriction ends and a portion of the (15–125) hIL-3 gene sequence (pMON13288 (SEQ ID NO:100]). Individual isolates were screened by restriction analysis and DNA sequenced to confirm that the desired changes in the (15–125) hIL-3 variant gene were made. The oligonucleotides create change(s) in the (15–125) hIL-3 gene which encode the corresponding amino acid substitution(s) in the variant polypeptide (Table 5). The amino acids substitutions in addition to and/or different from those in polypeptide # 25 [SEQ ID NO:89] are indicated in Table 5. The table also shows the plasmid designation (pMON number), DNA sequence identification number for the mutated hIL-3 gene and the identification number for the the resulting variant polypeptide. The biological activity (growth promoting activity in AML 193 cells) for some of the variants in Table 5 is shown in Table 1.

EXAMPLES 77–82

The variants in Table 6 were constructed by methods described in the Materials and Methods and the Examples contained herein, particularly in Examples 60 and 61. Parental plasmid DNA (Table 6), digested with the appropriate restriction enzymes (Table 6), was ligated with the indicated restriction fragment (Table 6). Individual isolates were screened by restriction analysis and DNA sequenced to confirm that the desired changes in the (15–125) hIL-3 variant gene were made. The resulting mutated (15–125) hIL-3 genes encode the corresponding amino acid substitutions in the variant polypeptides (Table 6). The amino acids substitutions in addition to and/or different from those in polypeptide # 25 [SEQ ID NO:89] are indicated in Table 6. The table also shows the plasmid designation (pMON number), DNA sequence identification number for the mutated hIL-3 gene and the identification number for the the resulting variant polypeptide. The biological activity (growth promoting activity in AML 193 cells) for some of the variants in Table 6 is shown in Table 1.

EXAMPLE 83
Construction of pMON13368

One of the DNA fragments to construct the plasmid, pMON13368, was generated by site-directed mutagenesis employing PCR techniques described in the Materials and Methods and the Examples contained herein, particularly Example 53. The template for the PCR reaction was plasmid, pMON13289, DNA using the oligonucleotides, Oligo #B13 18I23A25H [SEQ ID NO: 182] and Oligo #B14 2341HIN3 [SEQ ID NO:183], as primers. The resulting DNA product was digested with the restriction enzymes NcoI and HindIII. Upon completion, the digest was heated at 70° C. for 15 minutes to inactivate the enzymes. The restriction fragment was purified by phenol/chloroform extraction and precipitation with equal volume isopropanol in the presence of 2M NH4OAc. The oligonucleotide, Oligo #B13 18I23A25H [SEQ ID NO:182], changes the codon at position 23 of (15–125) hIL-3 variant gene pMON13289 [SEQ ID NO:103] from 'ATT' to 'GCA' (Ile to Ala). The 3619 base pair NcoI, HindIII restriction fragment from pMON2341 was ligated to the PCR-generated NcoI, HindIII restriction fragment. Individual isolates were screened by restriction analysis and DNA sequenced to confirm that the desired changes in the (15–125) hIL-3 variant gene were made. The plasmid, pMON13368, contains the (15–125) hIL-3 variant gene (DNA sequence #B15 [SEQ ID NO:346]) which encodes the (15–125) hIL-3 variant polypeptide with the following amino acid sequence:
Polypeptide #B15 [SEQ ID NO.:278]

EXAMPLE 84
Construction of pMON13380

Plasmid, pMON13368, DNA was digested with restriction enzymes EcoRI and HindIII. The resulting 3900 base pair EcoRI,HindIII fragment contains the following genetic elements; beta-lactamase gene (AMP), pBR327 origin of replication, phage Fl origin of replication as the transcription terminator, precA promoter, g10L ribosome binding site and the DNA sequence encoding amino acids 15–105 of the variant pMON13368. The 3900 base pair EcoRI,HindIII restriction fragment from pMON13368 was ligated to the following annealed complementary oligonucleotides.

| Oligo #B48 | 9E12Q6V1 | [SEQ ID NO:217] |
| Oligo #B49 | 9E12Q6V3 | [SEQ ID NO:218] |
| Oligo #49  | 12OQ123E2 | [SEQ ID NO:63] |
| Oligo #50  | 12OQ123E4 | [SEQ ID NO:64] |

When assembled, the oligonucleotides create EcoRI and HindIII restriction ends and the DNA sequence that encodes amino acids 106–125 of (15–125) hIL-3 with the following amino acid substitution; 109E, 112Q, 116V, 120Q and 123E. The codons used in the (15–125) hIL-3 gene are those found in the hIL-3 cDNA sequence except at those positions where amino acid substitutions were made. Individual isolates were screened by restriction analysis and DNA sequenced to confirm that the desired changes in the (15–125) hIL-3 variant gene were made. The plasmid, pMON13380, contains the (15–125) hIL-3 variant gene (DNA sequence #B16 [SEQ.ID NO:347]) which encodes the (15–125) hIL-3 variant polypeptide with the following amino acid sequence:
Polypeptide #B16 [SEQ ID NO.:279]

EXAMPLE 85
Construction of pMON13476

One of the DNA fragments to construct the plasmid, pMON13476, was generated by site-directed mutagenesis employing PCR techniques described in the Materials and Methods and the Examples contained herein, particularly Example 54. The template for the PCR reaction was plasmid, pMON13287, DNA using the oligonucleotides, Oligo #B13 18I23A25H [SEQ ID NO:182] and Oligo #B14 2341HIN3 [SEQ ID NO.:183] as primers. The resulting DNA product was digested with the restriction enzymes NcoI and HindIII. Upon completion, the digest was heated at 70° C. for 15 minutes to inactivate the enzymes. The restriction fragment was purified by phenol/chloroform extraction and precipitation with equal volume isopropanol in the presence of 2M NH4OAc. The oligonucleotide, Oligo #B13 18I23A25H [SEQ ID NO.:182], changes the codon at position 23 of (15–125) hIL-3 variant gene, pMON13287, [SEQ ID NO:97] from 'ATT' to 'GCA' (Ile to Ala). The 3619 base pair NcoI, HindIII restriction fragment from pMON2341 was ligated to the PCR-generated NcoI, HindIII restriction fragment. Individual isolates were screened by restriction analysis and DNA sequenced to confirm that the desired changes in the (15–125) hIL-3 variant gene were made. The resulting clone also contained a change, that was not designed in the mutagenic oligonucleotide, which changed the codon at position −1 from 'GCT' to 'GAT' which changes the amino acid from Alanine to Aspartic Acid. The plasmid, pMON13476, contains the (15–125) hIL-3 variant gene (DNA sequence #B52 [SEQ ID NO:303]) which encodes the (15–125) hIL-3 variant polypeptide with the following amino acid sequence:
Polypeptide #B52 [SEQ ID NO.:314]

EXAMPLES 86–92

The variants in Table 7 were constructed by PCR techniques using methods described in the Materials and Methods and the Example contained herein, particularly Example 51. Two sequential PCR reactions were used to create the variants. In the first PCR reaction pMON13287 plasmid DNA served as the template and the two oligonucleotides indicated in Table 7 served as the primers. Following the PCR extension reaction, the PCR product was partially purified to remove primer that was not extended. In the second PCR reaction pMON13287 plasmid DNA served as the template, the purified PCR product from the first PCR reaction served as one of the primers and the Oligo #B14 2341Hin3 [SEQ ID NO:183] as the second primer. The product from the second PCR reaction was partially purified and digested with restriction enzymes NcoI and HindIII and ligated with the 3619 base pair NcoI,HindIII fragment from pMON2341. Individual isolates were screened by restriction analysis and DNA sequenced to confirm that the desired changes in the (15–125) hIL-3 variant gene were made. The amino acids substitutions in addition to and/or different from those in polypeptide # 24 [SEQ ID NO:88] are indicated in Table 7. The table also shows the plasmid designation (pMON number), DNA sequence identification number for the mutated hIL-3 gene and the identification number for the the resulting variant polypeptide. The biological activity (growth promoting activity in AML 193 cells) for some of the variants in Table 7 is shown in Table 1.

EXAMPLES 93–120

The variants in Table 8 were constructed by cassette mutagenesis using methods described in the Materials and Methods and the Examples contained here, particularly Examples 54–58. Parental plasmid DNA (Table 8), digested with the appropriate restriction enzymes (Table 8), was ligated with the indicated annealed pairs of complementary oligonucleotides (Table 8). The assembled oligonucleotides create the appropriate restriction ends and a portion of (15–125) hIL-3 gene (pMON13288 [SEQ ID NO:100]) sequence. The oligonucleotides create change(s) in the (15–125) hIL-3 variant gene which encode the corresponding amino acid substitution(s); and/or deletions from the C-terminus of the variant polypeptide (Table 8). Individual isolates were screened by restriction analysis and DNA sequenced to confirm that the desired changes in the (15–125) hIL-3 variant gene were made. The amino acids substitutions in addition to and/or different from those in polypeptide # 25 [SEQ ID NO:88] are indicated in Table 8. The table also shows the plasmid designation (pMON number), DNA sequence identification number for the mutated hIL-3 gene and the identification number for the the resulting variant polypeptide. The biological activity (growth promoting activity in AML 193 cells) for some of the variants in Table 5 is shown in Table 1.

EXAMPLE 121
Construction of pMON13446

Plasmid, pMON13287, DNA (purified from the E. coli strain GM48 {dam-}) was digested with restriction enzymes NcoI and ClaI. The resulting 3942 base pair NcoI,ClaI fragment contains the following genetic elements; beta-lactamase gene (AMP), pBR327 origin of replication, phage F1 origin of replication as the transcription terminator, precA promoter, g10L ribosome binding site and the DNA sequence encoding amino acids 21–125 of the (15–125) hIL-3 variant pMON13287. The 3942 base pair NcoI,ClaI restriction fragment from pMON13368 was ligated to the following annealed complementary oligonucleotides.

| Oligo #B57 | 338UP | [SEQ ID NO:226] |
| Oligo #B56 | 338DOWN | [SEQ ID NO:225] |

When assembled, the oligonucleotides create NcoI and ClaI restriction ends and the DNA sequence that encodes the following 14 amino acid sequence; Met Ala Tyr Pro Glu Thr Asp Tyr Lys Asp Asp Asp Asp Lys [SEQ ID NO:403] and the DNA sequence which encodes amino acids 15–20 of the (15–125) hIL-3 variant gene, pMON13287 [SEQ ID NO:97]. The resulting variant polypeptide has a 14 amino acid N-terminal extension fused to the (15–125) hIL-3 variant polypeptide, pMON13288 [SEQ ID NO: 88]. The plasmid, pMON13446, contains the (15–125) hIL-3 variant gene (DNA sequence #B53 [SEQ ID NO:404]) which encodes the (15–125) hIL-3 variant polypeptide with the following amino acid sequence;
Polypeptide #B53 [SEQ ID NO.:315]

EXAMPLE 122
Construction of pMON13390

Plasmid, pMON13288, DNA (purified from the E. coli strain GM48 {dam-}) was digested with restriction enzymes NcoI and ClaI. The resulting 3942 base pair NcoI,ClaI fragment contains the following genetic elements; beta-lactamase gene (AMP), pBR327 origin of replication, phage F1 origin of replication as the transcription terminator, precA promoter, g10L ribosome binding site and the DNA sequence encoding amino acids 21–125 of the (15–125) hIL-3 variant pMON13288. The 3942 base pair NcoI,ClaI restriction fragment from pMON13288 was ligated to the following annealed complementary oligonucleotides.

| Oligo #B57 | 338UP | [SEQ ID NO:226] |
| Oligo #B56 | 338DOWN | [SEQ ID NO:225] |

When assembled, the oligonucleotides create NcoI and ClaI restriction ends and the DNA sequence which encodes the following 14 amino acid sequence; Met Ala Tyr Pro Glu Thr Asp Tyr Lys Asp Asp Asp Asp Lys [SEQ ID NO:403] and the DNA sequence which encodes amino acids 15–20 of the (15–125) hIL-3 variant gene pMON13288 [SEQ ID NO:100]. The resulting variant has a 14 amino acid N-terminal extension fused to the (15–125) hIL-3 variant polypeptide, pMON13288 [SEQ ID NO:88]. The plasmid, pMON13390, containes the (15–125) hIL-3 variant gene (DNA sequence #B54 [SEQ ID NO.:405] which encodes the (15–125) hIL-3 variant polypeptide with the following amino acid sequence:
Polypeptide #B54 [SEQ ID NO:316]

EXAMPLES 133–136

The variants in Table 10 were constructed by methods described in Materials and Methods and in Examples contained herein, particularly Examples 54–58. Parental plasmid DNA (Table 10), digested with the appropriate restriction enzymes (Table 10) was ligated with the indicated restriction fragment containing the changes listed (Table 10). The resulting mutated (15–125) IL-3 genes encode the corresponding amino acid substitutions in the variant polypeptides (Table 10). The amino acid substitutions in addition to and/or different from those in polypeptide #25 [SEQ ID NO: 89] are indicated in Table 10. The biological activity (growth promoting activity in AML 193 cells) for some of the variants in Table 10 is shown in Table 1.

EXAMPLES 123–132

The variants in Table 9 were constructed by cassett mutagenesis using methods described in Materials and Methods and in Examples 54–58 contained herein. Parental plasmid DNA (Table 9), digested with the appropriate restriction enzymes (Table 9), was ligated with the indicated annealed pairs of complementry oligonucleoties (Table 9). The assembled oligonucleotides create the appropriate restriction fragment which was inserted into the (15–125) hIL-3 gene (pMON13288 [SEQ ID NO:100] between these restriction sites. The deletions or substitutions encoded by the oligonucleotide in the (15–125) IL-3 gene correspond to the amino acid deletions or substitutions in the variant polypeptide (Table 9). The amino acid substitutions or deletions, in addition to and/or different from those in the polypeptide #25 [SEQ ID NO:89] are indicated in Table 9. The biological activity (growth promoting activity in AML 193 cells) for some of the variants in Table 9 is shown in Table 1.

Formula XI shown below is a representation of a [(15–125)hIL-3 mutein] with numbers in bold type added above the amino acids to represent the position at which the amino acid below the bolded number appears in native (1–133)hIL-3 [e. g. the amino acid at position 1 of Formula XI corresponds to the Asn which appears at position 15 in native (1–133)hIL-3]. The number shown in bold indicates the amino acids that correspond to the native IL-3(1–133). The non-bold members below the amino acids sequences are for Seq Id reference numbers. When the muteins are expressed the initial amino acid may be preceded by Met- or Met-Ala-.

```
           15                  20                  25
         Asn Cys Ser Asn Met Ile Asp Glu Ile Ile Thr His Leu Lys Gln
         1                 5                  10                  15

30                  35                  40
         Pro Pro Leu Pro Leu Leu Asp Phe Asn Asn Leu Asn Gly Glu Asp
                        20                  25                  30

45                  50                  55
         Gln Asp Ile Leu Met Glu Asn Asn Leu Arg Arg Pro Asn Leu Glu
                        35                  40                  45

60                  65                  70
         Ala Phe Asn Arg Ala Val Lys Ser Leu Gln Asn Ala Ser Ala Ile
                        50                  55                  60

75                  80                  85
         Glu Ser Ile Leu Lys Asn Leu Leu Pro Cys Leu Pro Leu Ala Thr
                        65                  70                  75

90                  95                 100
         Ala Ala Pro Thr Arg His Pro Ile His Ile Lys Asp Gly Asp Trp
                        80                  85                  90

105                 110                 115
         Asn Glu Phe Arg Arg Lys Leu Thr Phe Tyr Leu Lys Thr Leu Glu
                        95                 100                 105

120                 125
         Asn Ala Gln Ala Gln Gln [SEQ ID NO:23]
                       110
```

| Example | pMON number | Parental plasmid/ restriction digest | oligo pair 1,4 | oligo pair 2,5 | oligo pair 3,6 | amino acid changes | resulting polypeptide |
|---|---|---|---|---|---|---|---|
| Example 69 | pMON13406 SEQ ID NO:332 | pMON13288/ NcoI, EcoRV | 19Ala1 OLIGO# B1 SEQ ID NO:170 19Ala4 OLIGO# B2 SEQ ID NO:171 | 29R32N37P2 OLIGO# 5 SEQ ID NO:19 29R32N37P5 OLIGO# 6 SEQ ID NO:20 | 42S45M3 OLIGO# 11 SEQ ID NO:25 42S45M6 OLIGO# 12 SEQ ID NO:26 | 19Ala | polypeptide B1 SEQ ID NO:264 |
| Example 70 | pMON13414 SEQ ID NO:333 | pMON13288/ NcoI, EcoRV | 19Ile1 OLIGO# B3 SEQ ID NO:172 19Ile4 OLIGO# B4 SEQ ID NO:173 | 29RS2N37P5 OLIGO# 5 SEQ ID NO:19 29R32N37P5 OLIGO# 6 SEQ ID NO:20 | 42S45M3 OLIGO# 11 SEQ ID NO:25 42S45M6 OLIGO# 12 SEQ ID NO:26 | 19Ile | polypeptide B2 SEQ ID NO:265 |

-continued

| Example | pMON number | Parental plasmid/ restriction digest | oligo pair 1,4 | oligo pair 2,5 | oligo pair 3,6 | amino acid changes | resulting polypeptide |
| --- | --- | --- | --- | --- | --- | --- | --- |
| Example 71 | pMON13407 SEQ ID NO:334 | pMON13288/ NcoI, EcoRV | 18I25H1 OLIGO# 1 SEQ ID NO:15 18I25H4 OLIGO# 2 SEQ ID NO:16 | 29R32N37P2 OLIGO# 5 SEQ ID NO:19 29R32N37P5 OLIGO# 6 SEQ ID NO:20 | 42S45V3 OLIGO# B11 SEQ ID NO:180 42S45V6 OLIGO# B12 SEQ ID NO:181 | 45Val | polypeptide B3 SEQ ID NO:266 |
| Example 72 | pMON13405 SEQ ID NO:335 | pMON13288/ NcoI, EcoRV | 19Ala1 OLIGO# B1 SEQ ID NO:170 19Ala4 OLIGO# B2 SEQ ID NO:171 | 29R32N37P5 OLIGO# 5 SEQ ID NO:19 29R32N37P5 OLIGO# 6 SEQ ID NO:20 | 42S45V3 OLIGO# B11 SEQ ID NO:180 42S45V6 OLIGO# B12 SEQ ID NO:181 | 19Ala, 45Val | polypeptide 114 SEQ ID NO:267 |
| Example 73 | pMON13415 SEQ ID NO:336 | pMON13288/ NcoI, EcoRV | 19Ile1 OLIGO# B3 SEQ ID NO:172 19Ile4 OLIGO# B4 SEQ ID NO:173 | 29R32N37P5 OLIGO# 5 SEQ ID NO:19 29R32N37P5 OLIGO# 6 SEQ ID NO:20 | 42S45V3 OLIGO# B11 SEQ ID NO:180 42S45V6 OLIGO# B12 SEQ ID NO:181 | 19Ile, 45 Val | polypeptide B5 SEQ ID NO:268 |
| Example 74 | pMON13408 SEQ ID NO:337 | pMON13288/ EcoRV, NsiI | 49Ile1 OLIGO# B7 SEQ ID NO:176 49Ile4 OLIGO# B8 SEQ ID NO:177 | 59L62V2 OLIGO# 25 SEQ ID NO:39 59L62V5 OLIGO# 26 SEQ ID NO:40 | 67H69E3 OLIGO# 29 SEQ ID NO:43 67H69E6 OLIGO# 30 SEQ ID NO:44 | 49Ile | polypeptide B6 SEQ ID NO:269 |
| Example 75 | pMON13409 SEQ ID NO:338 | pMON13288/ EcoRV, NsiI | 49Leu1 SEQ ID NO:178 OLIGO# B9 49Leu4 OLIGO# B10 SEQ ID NO:179 | 59L62V2 OLIGO# 25 SEQ ID NO:39 59L62V5 OLIGO# 26 SEQ ID NO:40 | 67H69E3 OLIGO# 29 SEQ ID NO:43 67H69E6 OLJGO# 30 SEQ ID NO:44 | 49Leu | polypeptide B7 SEQ ID NO:270 |
| Example 76 | pMON13410 SEQ ID NO:339 | pMON13288/ EcoRV, NsiI | 49Asp1 OLIGO# B5 SEQ ID NO:174 49Asp4 OLIGO# B6 SEQ ID NO:175 | 59L62V2 OLIGO# 25 SEQ ID NO:39 59L62V5 OLIGO# 26 SEQ ID NO:40 | 67H69E3 OLIGO# 29 SEQ ID NO:43 67H69E6 OLIGO# 30 SEQ ID NO:44 | 49Asp | polypeptide BS SEQ ID NO:271 |

| Example No | plasmid pMON number | Parental plasmid/ restriction digest | restriction fragment | amino acid substitutions | resulting polypeptide |
| --- | --- | --- | --- | --- | --- |
| Example 77 | pMON13422 SEQ ID NO:340 | pMON13408/ NcoI, EcoRV | 99 base pair NcoI, EcoRV fragment from pMON13405 | 19Ala, 45Val, 49Ile | polypeptide B9 SEQ ID NO:272 |
| Example 78 | pMON13423 SEQ ID NO:341 | pMON13408/ NcoI, EcoRV | 99 base pair NcoI, EcoRV fragment from pMON13415 | 19Ile, 45Val, 49Ile | polypeptide B10 SEQ ID NO:273 |
| Example 79 | pMON13424 SEQ ID NO:342 | pMON13409/ NcoI, EcoRV | 99 base pair NcoI, EcoRV fragment from pMON13405 | 19Ala, 45Val, 49Leu | polypeptide B11 SEQ ID NO:274 |
| Example 80 | pMON13425 SEQ ID NO:343 | pMON13409/ NcoI, EcoRV | 99 base pair NcoI, EcoRV fragment from pMON13415 | 19Ile, 45Val, 49Leu | polypeptide B12 SEQ ID NO:275 |
| Example 81 | pMON13426/ SEQ ID NO:344 | pMON13410/ NcoI, EcoRV | 99 base pair NcoI, EcoRV fragment from pMON13405 | 19Ala, 45Val, 49Asp | polypeptide B13 SEQ ID NO:276 |
| Example 82 | pMON13429 SEQ ID NO:345 | pMON13410/ NcoI, EcoRV | 99 base pair NcoI, EcoRV fragment from pMON13415 | 19Ile, 45Val, 49Asp | polypeptide B14 SEQ ID NO:277 |

| Example | pMON number | template | Step one PCR primer1 | Step one PCR primer2 | Step two PCR primer1 | Step two PCR primer2 | Amino Acid Substitutions | Polypeptide |
|---|---|---|---|---|---|---|---|---|
| Example 86 | pMON13475 SEQ ID NO: 348 | pMON13287 | 18I23A25H OLIGO# B13 SEQ ID NO:182 | 42D45V46S50D OLIGO# B19 SEQ ID NO:188 | product from step one | 2341HIN3 OLIGO# B14 SEQ ID NO:183 | 42D, 46S, 50D | Polypeptide # B17 SEQ ID NO 280 |
| Example 87 | pMON13366 SEQ ID NO: 349 | pMON13287 | 2341NCO OLIGO# B15 SEQ ID NO:184 | 42D46V46S50D OLIGO# B19 SEQ ID NO:188 | product from step one | 2341HIN3 OLIGO# B14 SEQ ID NO:183 | 42N, 46S, 50D | Polypeptide # B18 SEQ ID NO 281 |
| Example 88 | pMON13367 SEQ ID NO: 350 | pMON13287 | 2341NCO OLIGO# B15 SEQ ID NO:184 | 42D45V46S50D OLIGO# B17 SEQ ID NO:186 | product from step one | 2341HIN3 OLIGO# B14 SEQ ID NO:183 | 46S, 50D | Polypeptide # B19 SEQ ID NO 282 |
| Example 89 | pMON13369 SEQ ID NO: 351 | pMON13287 | 2341NCO OLIGO# B15 SEQ ID NO:184 | 42D45V46S50D OLIGO# B21 SEQ ID NO:190 | product from step one | 2341HIN3 OLIGO# B14 SEQ ID NO:183 | 23A, 42D, 46S 50D | Polypeptide # B20 SEQ ID NO 283 |
| Example 90 | pMON13370 SEQ ID NO: 352 | pMON13287 | 2341NCO OLIGO# B15 SEQ ID NO:184 | 42D45M46S50D OLIGO# B16 SEQ ID NO:185 | product from step one | 2341HIN3 OLIGO# B14 SEQ ID NO:183 | 45M, 46S, 50D | Polypeptide # B21 SEQ ID NO 284 |
| Example 91 | pMON13373 SEQ ID NO: 353 | pMON13287 | 2341NCO OLIGO# B15 SEQ ID NO:184 | 42D45M46S50D OLIGO# B18 SEQ ID NO:187 | product from step one | 2341HIN3 OLIGO# B14 SEQ ID NO:183 | 42D, 45M, 46S 50D | Polypeptide # B22 SEQ ID NO 285 |
| Example 92 | pMON13374 SEQ ID NO: 354 | pMON13287 | 2341NCO OLIGO# B15 SEQ ID NO:184 | 42S45M46S50D OLIGO# B20 SEQ ID NO:189 | product from step one | 2341HIN3 OLIGO# B14 SEQ ID NO:183 | 42S, 45M, 46S | Polypeptide # B23 SEQ ID NO 286 |

TABLE 8

| Example | plasmid | parental plasmid | oligo pair | oligo pair | oligo pair | oligo pair | resulting amino acid sub(s). | poly-peptide |
|---|---|---|---|---|---|---|---|---|
| Example 93 | pMON13375 SEQ ID NO: 355 | pMON13287/ EcoR1, HindIII | S09E16V1 OLIGO# B50 SEQ ID NO:219 S09E16V3 OLIGO# B51 SEQ ID NO:220 | S116VD31 OLIGO# 552 SEQ ID NO:221 SECR1D33 OLIGO# 553 SEQ ID NO:222 | | | 15–119 | poly-peptide B24 SEQ ID NO: 287 |
| Example 94 | pMON1337E SEQ ID NO: 356 | pMON13476/ EcoR1, HindIII | S9E2Q6V1 OLIGO# B54 SEQ ID NO:223 S9E2Q6V3 OLIGO# B55 SEQ ID NO:224 | S116VD31 OLIGO# B52 SEQ ID NO:221 SECR1D33 OLIGO# B53 SEQ ID NO:222 | | | 15–119, 23A, 112Q | poly-peptide B25 SEQ ID NO:288 |
| Example 95 | pMON13377 SEQ ID NO: 357 | pMON13475/ EcoR1, HindIII | S9E2Q6V1 OLIGO# B54 SEQ ID NO:223 S9E2Q6V3 OLIGO# B55 SEQ ID NO:224 | S116VD31 OLIGO# B52 SEQ ID NO:221 SECR1D33 OLIGO# B53 SEQ ID NO:222 | | | 15–119, 23A, 42D, 46S, 50D 112Q | poly-peptide B2E SEQ ID NO:289 |
| Example 96 | pMON13375 SEQ ID NO: 358 | pMON13365/ EcoR1, HindIII | S09E16V1 OLIGO# B50 SEQ ID NO:219 S09E16V3 OLIGO# B51 SEQ ID NO:220 | S116VD31 OLIGO# B52 SEQ ID NO:221 SECR1D33 OLIGO# B53 SEQ ID NO:222 | | | 15–119, 23A | poly-peptide B27 SEQ ID NO:290 |
| Example 97 | pMON13379 SEQ ID NO: 359 | pMON13367/ EcoR1, HindIII | 9E12Q6V1 OLIGO# B48 SEQ ID NO:217 9E12Q6V3 OLIGO# B49 SEQ ID NO:218 | 120Q123E2 OLIGO# 49 SED ID NO:63 120Q123E4 OLIGO# 50 SED ID NO:64 | | | 46S, 50D, 112Q | poly-peptide B28 SEQ ID NO:291 |
| Example 98 | pMON13385 SEQ ID NO: 360 | pMON13287/ NcoI, EcoRV | 18I25H1 OLIGO# 1 SEQ ID NO:15 18I25H4 OLIGO# 2 SEQ ID NO:16 | 29V32R34S2 OLIGO# B28 SED ID NO:197 29V32R34AS5 OLIGO# B29 SED ID NO:198 | 42A45V3 OLIGO# 9 SEQ ID NO:23 42A45V6 OLIGO# 10 SED ID NO:24 | | 29V, 32R, 34S | poly-peptide 529 SEQ ID NO:292 |
| Example 99 | pMON13381 SEQ ID NO: 361 | pMON13287/ NsiI, EcoRI | 73G76A1 OLIGO# 41 SEQ ID NO:55 73G76A4 OLIGO# 42 SEQ ID NO:56 | 82TRP2 OLIGO# B44 SEQ ID NO:213 82TRP5 OLIGO# B45 SEQ ID NO:214 | 87S93S98I3 OLIGO# 35 SEQ ID NO:49 87S93S98I7 OLIGO# 36 SEQ ID NO:50 | 101A195Q4 OLIGO# 43 SEQ ID NO:57 101A105Q8 OLIGO# 44 SEQ ID NO:58 | 82W | poly-peptide B30 SEQ ID NO:293 |

TABLE 8-continued

| Example | plasmid | parental plasmid | oligo pair | oligo pair | oligo pair | oligo pair | resulting amino acid sub(s). | polypeptide |
|---|---|---|---|---|---|---|---|---|
| Example 100 | pMON13383 SEQ ID NO: 362 | pMON13475/ EcoR1, HindIII | 9E12Q6V1 OLIGO# B48 SEQ ID NO:217 9E12Q6V5 OLIGO# B49 SEQ ID NO:218 | 120Q123E2 OLIGO# 49 SED ID NO:63 120Q123E4 OLIGO# 50 SED ID NO:64 | | | 23A, 42D, 46S, 50D 112Q | polypeptide B31 SEQ ID NO:294 |
| Example 101 | pMON13384 SEQ ID NO: 363 | pMON13287/ EcoR1, HindIII | 9E12Q6V1 OLIGO# B48 SEQ ID NO:217 9E12Q6V5 OLIGO# B49 SEQ ID NO:218 | 120Q123E2 OLIGO# 49 SED ID NO:63 120Q123E4 OLIGO# 50 SED ID NO:64 | | | 112Q | polypeptide B32 SEQ ID NO:295 |
| Example 102 | pMON13388 SEQ ID NO: 364 | pMON13287/ EcoRV, NsiI | 50D56S1 OLIGO# B42 SEQ ID NO:211 50ASP4 OLIGO# B41 SEQ ID NO:210 | 60S62V2 OLIGO# 27 SEQ ID NO:41 56SER5 OLIGO# B43 SEQ ID NO:212 | 67N69E3 OLIGO# 31 SEQ ID NO:45 67N69E6 OLIGO# 32 SEQ ID NO:46 | | 50D, 56S | polypeptide B33 SEQ ID NO:296 |
| Example 103 | pNQN13389 SEQ ID NO: 365 | pMQN132871 NcoI, EcoRV | 18I25H1 OLIGO# 1 SEQ ID NO:15 18I25H4 OLIGO# 2 SEQ ID NO:16 | 29R32A37P2 OLIGO# 3 SEQ ID NO:17 29R32A37P5 OLIGO# 4 SEQ ID NO:18 | 42D45M3 OLIGO# B32 SEQ ID NO:201 42D45M6 OLIGO# B33 SEQ ID NO:202 | | 42D, 45M | polypeptide B34 SEQ ID NO:297 |
| Example 104 | pMON13391 SEQ ID NO: 366 | pMON13287/ NcoI, EcoRV | 18I25H1 OLIGO# 1 SEQ ID NO:15 18I25H4 OLIGO# 2 SEQ ID NO:16 | 34SER1 OLIGO# B30 SEQ ID NO:199 34SER5 OLIGO# B31 SEQ ID NO:200 | 42A45V3 OLIGO# 9 SEQ ID NO:23 42A45V6 QLIGO# 10 SEQ ID NO:24 | | 34S | polypeptide B35 SEQ ID NO:298 |
| Example 105 | pMON13392 SEQ ID NO: 367 | pMON13287/ NcoI, EcoRV | 18I25H1 OLIGO# 1 SEQ ID NO:15 18I25H4 OLIGO# 2 SEQ ID NO:16 | 29R32A37P2 OLIGA# 3 SEQ ID NO:17 29R32A37P5 OLIGO# 4 SEQ ID NO:18 | 42D45V3 QLIGO# B34 SEQ ID NO:203 42D45V6 OLIGO· B35 SEQ ID NO:204 | | 42D | polypeptide B36 SEQ ID NO:299 |
| Example 106 | pMON13393 SEQ ID NO: 368 | PMON13287/ NcoI, EcoRV | 23ALA1 OLIGO# B26 SEQ ID NO:195 23ALA4 OLIGO# B27 SEQ ID NO:196 | 34SER1 OLIGO# B30 SEQ ID NO:199 345ER5 OLIGO# B31 SEQ ID NO:200 | 42D45M46S3 OLIGO· B36 SEQ ID NO:205 42D45M46S6 OLIGO# B37 SEQ ID NO:206 | | 23A, 34S, 42D, 45N 46S | polypeptide B37 SEQ ID NO:300 |
| Example 107 | pMON13394 SEQ ID NO: 369 | pMON13287/ NcoI, EcoRV | 18I25H1 OLIGO# 1 SEQ ID NO:15 18I25N4 OLIGO# 2 SEQ ID NO:16 | 29R32A37P2 OLIGO# 3 SEQ ID NO:17 29R32A37P5 OLIGO# 4 SEQ ID NO:18 | 42D45M46S3 OLIGO# B36 SEQ ID NO:205 42D45M46S6 OLIGO# B37 SEQ ID NO:206 | | 42D, 45M, 46S | polypeptide B38 SEQ ID NO:301 |
| Example 108 | pMON13395 SEQ ID NO: 370 | pMON13287/ NcoI, EcoRV | 23ALA1 OLIGO# B26 SEQ ID NO:195 23ALA4 OLIGO# B27 SEQ ID NO:196 | 29V32R34S2 OLIGO# B28 SEQ ID NO:197 29V32R34S5 OLIGO# B29 SEQ ID NO:198 | 42D45V46S3 OLIGO# B38 SEO ID NO:207 42D45V4656 OLIGO# B39 SEQ ID NO:208 | | 23A, 29V, 32R, 34S 42D, 46S | polypeptide B39 SEQ ID NO:302 |
| Example 109 | pMON13396 SEQ ID NO: 371 | pMON13287/ NsiI, EcoRI | 73G76Q2 OLIGO# 41 SEQ ID NO:55 73G76A4 OLIGO# 42 SEQ ID NO:56 | 79R82Q2 OLIGO# 39 SEQ ID NO:53 79R8205 OLIGO# 40 SEQ ID NO:54 | 100ARG3 SEQ ID NO: 87S93S98I7 OLIGO# 36 SEQ ID NO:50 | 100MET4 OLIGO# B24 SEQ ID NO:193 10R01M8 OLIGO# B25 SEQ ID NO:194 | 100R, 101M | polypeptide B40 SEQ ID NO:303 |
| Example 110 | pMON13397 SEQ ID NO: 372 | pMON13287/ NsiI, EcoRI | 73G76A1 OLIGO# 41 SEQ ID NO:55 73G76A4 OLIGO# 42 SEQ ID NO:56 | 82TRP2 OLIGO# B44 SEQ ID NO:213 82TRP5 OLIGO# B45 SEQ ID NO:214 | 100ARG3 OLIGO# B22 SEQ ID NO:191 87S93S98I7 OLIGO# 36 SEQ ID NO:50 | 100MET4 OLIGO# B24 SEQ ID NO:193 10R01M8 OLIGO# B25 SEQ ID NO:194 | 82W, 100R, 101M | polypeptide B41 SEQ ID NO:304 |
| Example 111 | pMON13398 SEQ ID NO: 373 | pMON13287/ NcoI, EcoRV | 18I25H1 OLIGO# 1 SEQ ID NO:15 18I25N4 OLIGO# 2 SEQ ID NO:16 | 29R32A37P2 OLIGO# 3 SEQ ID NO:17 29R32A37P5 OLIGO# 4 SEQ ID NO:18 | 42D45V46S3 OLIGO# B38 SEQ ID NO:207 42D45V46S6 OLIGO# B39 SEQ ID NO:208 | | 42D, 46S | polypeptide B42 SEQ ID NO:305 |

TABLE 8-continued

| Example | plasmid | parental plasmid | oligo pair | oligo pair | oligo pair | oligo pair | resulting amino acid sub(s). | polypeptide |
|---|---|---|---|---|---|---|---|---|
| Example 112 | pMON13399 SEQ ID NO: 374 | pMON13388/ NcoI, EcoRV | 23ALA1 OLIGO# B26 SEQ ID NO:195 23ALA4 OLIGO# B27 SEQ ID NO:196 | 29V32R34S2 OLIGO# B2B SED ID NO:197 29V32R34S5 OLIGO# B29 SED ID NO:198 | 42D45V46S3 OLIGO# B38 SEQ ID NO:207 42D45V46S6 OLIGO# B39 SEQ ID NO:208 | | 23A, 29V, 32R, 34S 42D, 46S | polypeptide B43 SEQ ID NO:306 |
| Example 113 | pMON1304 SEQ ID NO: 375 | pMON13287/ EcoRI, HindIII | S9E2Q6V1 OLIGO# B54 SEQ ID NO:223 S9E2Q6V3 OLIGO# B55 SEQ ID NO:224 | SI16VD31 OLIGO# B52 SEQ ID NO:221 SECR1D33 OLIGO# 53 SEQ ID NO:222 | | | 15–119 112Q | polypeptide B44 SEQ ID NO:307 |
| Example 114 | pMON13387 SEQ ID NO: 376 | pMON13287/ EcoRV, NsiI | 50ASP1 OLIGO# B40 SEQ ID NO:209 50ASP4 OLIGO# B41 SEQ ID NO:210 | 60S62V2 OLIGO# 27 SEQ ID NO:41 60S62V5 QLIGO# 28 SEQ ID NO:42 | 67N69E3 OLIGO# 31 SEQ ID NO:45 67N69E6 OLIGO# 32 SEQ ID NO:46 | | 50D | polypeptide B45 SEQ ID NO:308 |
| Example 115 | pMON13416 SEQ ID NO: 377 | pMON13387/ NcoI/EcoRV | 18I25H1 OLIGO# 1 SEQ ID NO:15 18I25H4 OLIGO· 2 SEQ ID NO:16 | 29R32A37P2 OLIGO# 3 SEQ ID NO:17 29R32A37P5 OLIGO# 4 SEQ ID NO:18 | 42D45V4ES3 OLIGO# B38 SEQ ID NO:207 42D45V46S6 OLIGO# B39 SEQ ID NO:208 | | 42D, 46S, 50D | polypeptide B46 SEQ ID NO:309 |
| Example 116 | pMON13417 SEQ ID NO: 378 | pMON13387/ NcoI/EcoRV | 18I25H1 OLIGO# 1 SEQ ID NO:15 18I25N4 OLIGO# 2 SEQ ID NO:16 | 29R32A37P2 OLIGO# 3 SEQ ID NO:17 29R32A37P5 OLIGO# 4 SEQ ID NO:18 | 42D45M46S3 OLIGO# B36 SEQ ID NO:205 42D45M46S6 OLIGO# B37 SEQ ID NO:206 | | 42D, 45M, 46S, 50D | polypeptide B47 SEQ ID NO:310 |
| Example 117 | pMON13420 SEQ ID NO: 379 | pMON13388/ NcoI, EcoRV | 23ALA1 OLIGO# B26 SEQ ID NO:195 23ALA4 OLIGO# B27 SEQ ID NO:196 | 34SER1 OLIGO# 830 SEQ ID NO:199 34SER5 OLIGO· B31 SEQ ID NO:200 | 42D45V46S3 OLIGO# B38 SEQ ID NO:207 42D45V46S6 OLIGO# B39 SEQ ID NO:208 | | 23A, 34S, 42D, 46 50D, 56S | polypeptide B48 SEQ ID NO:311 |
| Example 118 | pMON13421 SEQ ID NO: 380 | pMON13388/ NcoI, EcoRV | 23ALA1 OLIGO# B26 SEQ ID NO:195 23ALA4 OLIGO# B27 SEQ ID NO:196 | 34SER1 OLIGO# B30 SEQ ID NO:199 34SER5 OLIGO· B31 SEQ ID NO:200 | 42D45M46S3 OLIGO# B36 SEQ ID NO:205 42D45M46S6 OLIGO# B37 SEQ ID NO:206 | | 23A, 34S, 42D, 45M 46S, 50D, 56S | polypeptide B49 SEQ ID NO:331 |
| Example 119 | pMON13432 SEQ ID NO: 381 | pMON13387/ NcoI, EcoRV | 23ALA1 OLIGO# B26 SEQ ID NO:195 23ALA4 OLIGO# B27 SEQ ID NO:196 | 34SER1 OLIGO# B30 SEQ ID NO:199 34SER5 OLIGO# B31 SEQ ID NO:200 | 42D45M46S3 OLIGO# B36 SEQ ID NO:205 42D45M46S6 OLIGO# B37 SEQ ID NO:206 | | 23A, 34S, 42D, 45M 46S, 50D | polypeptide B50 SEQ ID NO:312 |
| Example 120 | pMON13382 SEQ ID NO: 382 | pMON13287/ EcoRI, HindIII | 9E12Q6W1 OLIGO# B46 SEQ ID NO:215 9E12Q16W3 OLIGO# B41 SEQ ID NO:216 | 120Q123E2 OLIGO# 49 SED ID NO:63 120Q123E4 OLIGO# 50 SED ID NO:64 | | | 112Q, 116W | polypeptide B51 SEQ ID NO:313 |

| Example No. | Plasmid | Parental Plasmid/ Restriction Digest | Oligo pair | Oligo pair | Oligo pair | Oligo pair | Amino acid changes | Polypeptide |
|---|---|---|---|---|---|---|---|---|
| Example 124 | pMON13400 SEQ ID NO: 384 | pMON13288 Restriction NcoI-EcoRV | 20P23A1 SEQ ID NO:232 20P23A4 SEQ ID NO:233 | 29I4S7S2 SEQ ID NO:236 29I4S7S5 SEQ ID NO:237 | 38A5V6S3 SEQ ID NO:238 38A5V6S3 SEQ ID NO:239 | | 20P 23A 29I 34S 37S 38A 45V 46S | Polypeptids C-2 SEQ ID NO:317 |
| Example 125 | pMON13402 SEQ ID NO: 385 | pMON13288 Restriction NcoI-EcoRV | 23L1 SEQ ID NO:234 23L4 SEQ ID NO:235 | 29I4S7S2 SEQ ID NO:236 29I4S7S2 SEQ ID NO:237 | 38A5V6S3 SEQ ID NO:238 38A5V6S3 SEQ ID NO:239 | | 23L 29I 34S 37S 28A 45V 46S | Polypeptide C-3 SEQ ID NO:318 |

-continued

| Example No. | Plasmid | Parental Plasmid/ Restriction Digest | Oligo pair | Oligo pair | Oligo pair | Oligo pair | Amino acid changes | Polypeptide |
|---|---|---|---|---|---|---|---|---|
| Example 131 | pMON13440 SEQ ID NO: 386 | pMON13288 Restriction NcoI-EcoRV | 18I3A5H1 SEQ ID NO:195 18I3A5H4 SEQ ID NO:196 | 29I4S7S2 SEQ ID NO:236 29I148785 SEQ ID NO:237 | 38A5V6S3 SEQ ID NO:238 38A5V6S3 SEQ ID NO:239 | | 18I 23A 25H 29I 34s 37S 38A 45V 46S | Polypeptide C-10 SEQ ID NO:319 |
| Example 132 | pMON13451 SEQ ID NO: 387 | pMON13288 Restriction NcoI-EcoRV | 19I0L3A1 SEQ ID NO:230 19I0L3A4 SEQ ID NO:231 | 29I4S7S2 SEQ ID NO:236 29I4S7S2 SEQ ID NO:237 | 38A5V6S3 SEQ ID NO:238 38A5V6S3 SEQ ID NO:239 | | 19I 20L 23A 29I 34S 37S 38A 45V 46S | Polypeptide C-11 SEQ ID NO:320 |
| Example 130 | pMON13419 SEQ ID NO: 389 | pMON13288 Restriction EcoRV-NsiI | 50D51S1 SEQ ID NO:240 50D51S4 SEQ ID NO:241 | 62P3H5S2 SEQ ID NO:244 62P3H5 SEQ ID NO:246 | 67Q3 SEQ ID NO:248 65S67Q6 SEQ ID NO:247 | | 50D 51S 62P 63H 65S 67Q | Polypeptide C-8 SEQ ID NO:325 |
| Example 126 | pMON13403 SEQ ID NO: 388 | pMON13288 Restriction EcoRV-NsiI | 50D51S1 SEQ ID NO:240 50D51S4 SEQ ID NO:241 | 62P3H2 SEQ ID NO:245 62P3H5 SEQ ID NO:246 | 67Q3 SEQ ID NO:248 67Q6 SEQ ID NO:249 | | 50D 51S 62P 63H 67Q | Polypeptide CA SEQ ID NO:321 |
| Example 123 | pMON13418 SEQ ID NO: 393 | pMON13288 Restriction NsiI-EcoRI | 76P1 SEQ ID NO:250 76P5 SEQ ID NO:251 | 79S2 SEQ ID NO:252 79S6 SEQ ID NO:253 | 5VYWPTT3 SEQ ID NO:242 5VYWPTT7 SEQ ID NO:243 | 101A105Q4 SEQ ID NO:57 101A105Q8 SEQ ID NO:58 | 76P 79S 85V 87Y 88W 91P 95T 98T | Polypeptide C-1 SEQ ID NO:326 |
| Example 127 | pMON13411 SEQ ID NO: 390 | pMON13288 Restriction EcoRI- HindIII | 09L2Q6S1 Seq ID NO:227 09L2Q6S3 SEQ ID NO:228 | 120/Q123E2 SEQ ID NO:63 120Q123E4 SEQ ID NO:64 | | | 109L 112Q 116S | Polypeptide C-5 SEQ ID NO:322 |
| Example 128 | pMON13412 SEQ ID NO: 391 | pMON13288 Restriction EcoRI- HindIII | 9LQS1181 Seq ID NO:255 9LQS1183 SEQ ID NO:256 | | | | 15–118 109L 112Q 116S | Polypeptide C-6 SEQ ID NO:323 |
| Example 129 | pMON13413 SEQ ID NO: 392 | pMON13288 Restriction EcoRI- HindIII | 09L2Q6S1 Seq ID NO:227 09L2Q6S3 SEQ ID NO:228 | 117S2 SEQ ID NO:229 120Q123E4 SEQ ID NO 64 | | | 109L 112Q 116S 117S | Polypeptide C-7 SEQ ID NO:324 |

TABLE 10

| Example No | Plasmid | Parental plasmid/ Restriction digest | Restriction fragment | Amino Acid changes | Polypeptide |
|---|---|---|---|---|---|
| Example 133 | pMON13428 SEQ ID NO:394 | pMON13411 NsiI-EcoRI | 102 bp NsiI-EcoRI fragment from pMON13418 | 76P 79S 85V 87Y 91P 95T 98T 109L 112Q 116S | Polypeptide C-9 SEQ ID NO:327 |
| Example 134 | pMON13459 SEQ ID NO:395 | pMON13428 NcoI-NsiI | 170 bp NcoI-NsiI fragment from pMON13402 | 23L 29I 34S 37S 38A 45V 46S 76P 79S 85V 87Y 91P 95T 98T 109L 112Q 116S | Polypeptide C-12 SEQ ID NO:328 |
| Example 135 | pMON13467 SEQ ID NO:396 | pMON13413 NcoI-NsiI | 170 bp NcoI-NsiI fragment from pMON13402 | 23L 29I 34S 37S 38A 45V 46S 109L 112Q 116S 109L 112Q 116S 117S | Polypeptide C-13 SEQ ID NO:329 |
| Example 136 | pMON13492 SEQ ID NO:397 | pMON13418 NcoI-NsiI | 170 bp NcoI-NsiI fragment from pMON13402 | 23L 29I 34S 37S 38A 45V 46S 76P 79S 85V 87Y 91P 95T 98T | Polypeptide C-14 SEQ ID NO:330 |

SEQUENCE LISTING (1) GENERAL INFORMATION:

(iii) NUMBER OF SEQUENCES: 415

(2) INFORMATION FOR SEQ ID NO:1:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:1:

CTAGCGATCT TTTAATAAGC TTG                                          23

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:2:

GATCCAAGCT TATTAAAAGA TCG                                          23

(2) INFORMATION FOR SEQ ID NO:3:

(i) SEQUENCE CHARACTERISTICS:
       (A) LENGTH: 69 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:3:

GGCAACAATT TCTACAAAAC ACTTGATACT GTATGAGCAT ACAGTATAAT TGCTTCAACA    60

GAACAGATC                                                           69

(2) INFORMATION FOR SEQ ID NO:4:

(i) SEQUENCE CHARACTERISTICS:
       (A) LENGTH: 67 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:4:

TGTTCTGTTG AAGCAATTAT ACTGTATGCT CATACAGTAT CAAGTGTTTT GTAGAAATTG    60

TTGCCGC                                                             67

(2) INFORMATION FOR SEQ ID NO:5:

(i) SEQUENCE CHARACTERISTICS:
       (A) LENGTH: 23 base pairs
       (B) TYPE: nucleic acid

```
        (C) STRANDEDNESS: single
        (D) TOPOLOGY: linear (ii) MOLECULE TYPE: DNA (synthetic)

(xi) SEQUENCE DESCRIPTION: SEQ ID NO:5:

CCATTGCTGC CGGCATCGTG GTC                                            23

(2) INFORMATION FOR SEQ ID NO:6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

CATGGCTCCA ATGACTCAGA CTACTTCTCT TAAGACTTCT TGGGTT                   46

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

AACCCAAGAA GTCTTAAGAG AAGTAGTCTG AGTCATTGGA GC                       42

(2) INFORMATION FOR SEQ ID NO:8:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

AATTCCGTCG TAAACTGACC TTCTATCTGA AAACCTTGGA GAACGCGCAG GCTCAACAGT    60

AATA                                                                 64

(2) INFORMATION FOR SEQ ID NO:9:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

AGCTTATTAC TGTTGAGCCT GCGCGTTCTC CAAGGTTTTC AGATAGAAGG TCAGTTTACG    60

ACGG                                                                 64
```

(2) INFORMATION FOR SEQ ID NO:10:

(i) SEQUENCE CHARACTERISTICS:
        (A) LENGTH: 126 amino acids
        (B) TYPE: amino acid
        (D) TOPOLOGY: linear (ii) MOLECULE TYPE: peptide (xi) SEQUENCE DESCRIPTION: SEQ ID NO:10:

```
Met Ala Pro Met Thr Gln Thr Thr Ser Leu Lys Thr Ser Trp Val Asn
 1               5                  10                  15
Cys Ser Asn Met Ile Asp Glu Ile Ile Thr His Leu Lys Gln Pro Pro
            20                  25                  30
Leu Pro Leu Leu Asp Phe Asn Asn Leu Asn Gly Glu Asp Gln Asp Ile
        35                  40                  45
Leu Met Glu Asn Asn Leu Arg Arg Pro Asn Leu Glu Ala Phe Asn Arg
    50                  55                  60
Ala Val Lys Ser Leu Gln Asn Ala Ser Ala Ile Glu Ser Ile Leu Lys
65                  70                  75                  80
Asn Leu Leu Pro Cys Leu Pro Leu Ala Thr Ala Ala Pro Thr Arg His
                85                  90                  95
Pro Ile His Ile Lys Asp Gly Asp Trp Asn Glu Phe Arg Arg Lys Leu
            100                 105                 110
Thr Phe Tyr Leu Lys Thr Leu Glu Asn Ala Gln Ala Gln Gln
        115                 120                 125
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

CATGGCTAAC TGCTCTAACA TGAT                                              24

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

CGATCATGTT AGAGCAGTTA GC                                                22

(2) INFORMATION FOR SEQ ID NO:13:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:13:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
            20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Ala Ile Glu Ser
            50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln (2) INFORMATION FOR SEQ ID NO:14:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:14:

Met Met Ile Thr Leu Arg Lys Leu Pro Leu Ala Val Ala Val Ala Ala
1               5                   10                  15

Gly Val Met Ser Ala Gln Ala Met Ala Asn Cys
            20                  25

(2) INFORMATION FOR SEQ ID NO:15:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede the
            amino acid in position 1"

(ix) FEATURE:
        (A) NAME/KEY: Modified-site
        (B) LOCATION: 17
        (D) OTHER INFORMATION: /note= "Xaa at position 17 is Ser,
            Lys, Gly, Asp, Met, Gln, or Arg"

(ix) FEATURE:
        (A) NAME/KEY: Modified-site
        (B) LOCATION: 18
        (D) OTHER INFORMATION: /note= "Xaa at position 18 is Asn,
            His, Leu, Ile, Phe, Arg, or Gln"

(ix) FEATURE:
        (A) NAME/KEY: Modified-site
        (B) LOCATION: 19
        (D) OTHER INFORMATION: /note= "Xaa at positiion 19 is Met,
            Phe, Ile, Arg, Gly, Ala, or Cys"

```
    (ix) FEATURE:
          (A) NAME/KEY: Modified-site
          (B) LOCATION: 20
          (D) OTHER INFORMATION: /note= "Xaa at position 20 is Ile,
              Cys, Gln, Glu, Arg, Pro, or Ala"

(ix) FEATURE:
          (A) NAME/KEY: Modified-site
          (B) LOCATION: 21
          (D) OTHER INFORMATION: /note= "Xaa at position 21 is Asp,
              Phe, Lys, Arg, Ala, Gly, Glu, Gln, Asn, Thr, Ser,
              or Val"

(ix) FEATURE:
          (A) NAME/KEY: Modified-site
          (B) LOCATION: 22
          (D) OTHER INFORMATION: /note= "Xaa at position 22 is Glu,
              Trp, Pro, Ser, Ala, His, Asp, Asn, Gln, Leu, Val,
              or Gly"

(ix) FEATURE:
          (A) NAME/KEY: Modified-site
          (B) LOCATION: 23
          (D) OTHER INFORMATION: /note= "Xaa at position 23 is Ile,
              Val, Ala, Leu, Gly, Trp, Lys, Phe, Ser, or
              Arg"

(ix) FEATURE:
          (A) NAME/KEY: Modified-site
          (B) LOCATION: 24
          (D) OTHER INFORMATION: /note= "Xaa at position 24 is Ile,
              Gly, Val, Arg, Ser, Phe, or Leu"

(ix) FEATURE:
          (A) NAME/KEY: Modified-site
          (B) LOCATION: 25
          (D) OTHER INFORMATION: /note= "Xaa at position 25 is Thr,
              His, Gly, Gln, Arg, Pro, or Ala"

(ix) FEATURE:
          (A) NAME/KEY: Modified-site
          (B) LOCATION: 26
          (D) OTHER INFORMATION: /note= "Xaa at position 26 is His,
              Thr, Phe, Gly, Arg, Ala, or Trp"

(ix) FEATURE:
          (A) NAME/KEY: Modified-site
          (B) LOCATION: 27
          (D) OTHER INFORMATION: /note= "Xaa at position 27 is Leu,
              Gly, Arg, Thr, Ser, or Ala"

(ix) FEATURE:
          (A) NAME/KEY: Modified-site
          (B) LOCATION: 28
          (D) OTHER INFORMATION: /note= "Xaa at position 28 is Lys,
              Arg, Leu, Gln, Gly, Pro, Val, or Trp"

(ix) FEATURE:
          (A) NAME/KEY: Modified-site
          (B) LOCATION: 29
          (D) OTHER INFORMATION: /note= "Xaa at position 29 is Gln,
              Asn, Leu, Pro, Arg, or Val"

(ix) FEATURE:
          (A) NAME/KEY: Modified-site
          (B) LOCATION: 30
          (D) OTHER INFORMATION: /note= "Xaa at position 30 is Pro,
              His, Thr, Gly, Asp, Gln, Ser, Leu, or Lys"

(ix) FEATURE:
          (A) NAME/KEY: Modified-site
          (B) LOCATION: 31
          (D) OTHER INFORMATION: /note= "Xaa at position 31 is Pro,
              Asp, Gly, Ala, Arg, Leu, or Gln"
```

```
     (ix) FEATURE:
           (A) NAME/KEY: Modified-site
           (B) LOCATION: 32
           (D) OTHER INFORMATION: /note= "Xaa at position 32 is Leu,
               Val, Arg, Gln, Asn, Gly, Ala, or Glu"

(ix) FEATURE:
           (A) NAME/KEY: Modified-site
           (B) LOCATION: 33
           (D) OTHER INFORMATION: /note= "Xaa at position 33 is Pro,
               Leu, Gln, Ala, Thr, or Glu"

(ix) FEATURE:
           (A) NAME/KEY: Modified-site
           (B) LOCATION: 34
           (D) OTHER INFORMATION: /note= "Xaa at position 34 is Leu,
               Val, Gly, Ser, Lys, Glu, Gln, Thr, Arg, Ala, Phe,
               Ile, or Met"

(ix) FEATURE:
           (A) NAME/KEY: Modified-site
           (B) LOCATION: 35
           (D) OTHER INFORMATION: /note= "Xaa at position 35 is Leu,
               Ala, Gly, Asn, Pro, Gln, or Val"

(ix) FEATURE:
           (A) NAME/KEY: Modified-site
           (B) LOCATION: 36
           (D) OTHER INFORMATION: /note= "Xaa at position 36 is Asp,
               Leu, or Val"

(ix) FEATURE:
           (A) NAME/KEY: Modified-site
           (B) LOCATION: 37
           (D) OTHER INFORMATION: /note= "Xaa at position 37 is Phe,
               Ser, Pro, Trp, or Ile"

(ix) FEATURE:
           (A) NAME/KEY: Modified-site
           (B) LOCATION: 38
           (D) OTHER INFORMATION: /note= "Xaa at position 38 is Asn,
               or Ala"

(ix) FEATURE:
           (A) NAME/KEY: Modified-site
           (B) LOCATION: 40
           (D) OTHER INFORMATION: /note= "Xaa at position 40 is Leu,
               Trp, or Arg"

(ix) FEATURE:
           (A) NAME/KEY: Modified-site
           (B) LOCATION: 41
           (D) OTHER INFORMATION: /note= "Xaa at position 41 is Asn,
               Cys, Arg, Leu, His, Met, or Pro"

(ix) FEATURE:
           (A) NAME/KEY: Modified-site
           (B) LOCATION: 42
           (D) OTHER INFORMATION: /note= "Xaa at position 42 is Gly,
               Asp, Ser, Cys, Asn, Lys, Thr, Leu, Val, Glu, Phe, Tyr,
               Ile, Met, or Ala"

(ix) FEATURE:
           (A) NAME/KEY: Modified-site
           (B) LOCATION: 43
           (D) OTHER INFORMATION: /note= "Xaa at position 43 is Glu,
               Asn, Tyr, Leu, Phe, Asp, Ala, Cys, Gln, Arg, Thr, Gly,
               or Ser"

(ix) FEATURE:
           (A) NAME/KEY: Modified-site
           (B) LOCATION: 44
           (D) OTHER INFORMATION: /note= "Xaa at position 44 is Asp,
               Ser, Leu, Arg, Lys, Thr, Met, Trp, Glu, Asn, Gln, Ala,
               or Pro"

(ix) FEATURE:
           (A) NAME/KEY: Modified-site
           (B) LOCATION: 45
```

(D) OTHER INFORMATION: /note= "Xaa at position 45 is Gln,
                Pro, Phe, Val, Met, Leu, Thr, Lys, Trp, Asp, Asn, Arg,
                Ser, Ala, Ile, Glu, or His"

(ix) FEATURE:
            (A) NAME/KEY: Modified-site
            (B) LOCATION: 46
            (D) OTHER INFORMATION: /note= "Xaa at position 46 is Asp,
                Phe, Ser, Thr, Cys, Glu, Asn, Gln, Lys, His, Ala, Tyr,
                Ile, Val, or Gly"

(ix) FEATURE:
            (A) NAME/KEY: Modified-site
            (B) LOCATION: 47
            (D) OTHER INFORMATION: /note= "Xaa at position 47 is Ile,
                Gly, Val, Ser, Arg, Pro, or His"

(ix) FEATURE:
            (A) NAME/KEY: Modified-site
            (B) LOCATION: 48
            (D) OTHER INFORMATION: /note= "Xaa at position 48 is Leu,
                Ser, Cys, Arg, Ile, His, Phe, Glu, Lys, Thr, Ala, Met,
                Val, or Asn"

(ix) FEATURE:
            (A) NAME/KEY: Modified-site
            (B) LOCATION: 49
            (D) OTHER INFORMATION: /note= "Xaa at position 49 is Met,
                Arg, Ala, Gly, Pro, Asn, His, or Asp"

(ix) FEATURE:
            (A) NAME/KEY: Modified-site
            (B) LOCATION: 50
            (D) OTHER INFORMATION: /note= "Xaa at position 50 is Glu,
                Leu, Thr, Asp, Tyr, Lys, Asn, Ser, Ala, Ile, Val, His,
                Phe, Met, or Gln"

(ix) FEATURE:
            (A) NAME/KEY: Modified-site
            (B) LOCATION: 51
            (D) OTHER INFORMATION: /note= "Xaa at position 51 is Asn,
                Arg, Met, Pro, Ser, Thr, or His"

(ix) FEATURE:
            (A) NAME/KEY: Modified-site
            (B) LOCATION: 52
            (D) OTHER INFORMATION: /note= "Xaa at position 52 is Asn,
                His, Arg, Leu, Gly, Ser, or Thr"

(ix) FEATURE:
            (A) NAME/KEY: Modified-site
            (B) LOCATION: 53
            (D) OTHER INFORMATION: /note= "Xaa at position 53 is
                Leu, Thr, Ala, Gly, Glu, Pro, Lys, Ser, or Met"

(ix) FEATURE:
            (A) NAME/KEY: Modified-site
            (B) LOCATION: 54
            (D) OTHER INFORMATION: /note= "Xaa at position 54 is Arg,
                Asp, Ile, Ser, Val, Thr, Gln, Asn, Lys, His, Ala,
                or Leu"

(ix) FEATURE:
            (A) NAME/KEY: Modified-site
            (B) LOCATION: 55
            (D) OTHER INFORMATION: /note= "Xaa at position 55 is Arg,
                Thr, Val, Ser, Leu, or Gly"

(ix) FEATURE:
            (A) NAME/KEY: Modified-site
            (B) LOCATION: 56
            (D) OTHER INFORMATION: /note= "Xaa at position 56 is Pro,
                Gly, Cys, Ser, Gln, Glu, Arg, His, Thr, Ala, Tyr,
                Phe, Leu, Val, or Lys"

```
    (ix) FEATURE:
         (A) NAME/KEY: Modified-site
         (B) LOCATION: 57
         (D) OTHER INFORMATION: /note= "Xaa at position 57 is Asn
             or Gly"

(ix) FEATURE:
         (A) NAME/KEY: Modified-site
         (B) LOCATION: 58
         (D) OTHER INFORMATION: /note= "Xaa at position 58 is Leu,
             Ser, Asp, Arg, Gln, Val, or Cys"

(ix) FEATURE:
         (A) NAME/KEY: Modified-site
         (B) LOCATION: 59
         (D) OTHER INFORMATION: /note= "Xaa at position 59 is Glu,
             Tyr, His, Leu, Pro, or Arg"

(ix) FEATURE:
         (A) NAME/KEY: Modified-site
         (B) LOCATION: 60
         (D) OTHER INFORMATION: /note= "Xaa at position 60 is Ala,
             Ser, Pro, Tyr, Asn, or Thr"

(ix) FEATURE:
         (A) NAME/KEY: Modified-site
         (B) LOCATION: 61
         (D) OTHER INFORMATION: /note= "Xaa at position 61 is Phe,
             Asn, Glu, Pro, Lys, Arg, or Ser"

(ix) FEATURE:
         (A) NAME/KEY: Modified-site
         (B) LOCATION: 62
         (D) OTHER INFORMATION: /note= "Xaa at position 62 is Asn,
             His, Val, Arg, Pro, Thr, Asp, or Ile"

(ix) FEATURE:
         (A) NAME/KEY: Modified-site
         (B) LOCATION: 63
         (D) OTHER INFORMATION: /note= "Xaa at position 63 is Arg,
             Tyr, Trp, Lys, Ser, His, Pro, or Val"

(ix) FEATURE:
         (A) NAME/KEY: Modified-site
         (B) LOCATION: 64
         (D) OTHER INFORMATION: /note= "Xaa at position 64 is Ala,
             Asn, Pro, Ser, or Lys"

(ix) FEATURE:
         (A) NAME/KEY: Modified-site
         (B) LOCATION: 65
         (D) OTHER INFORMATION: /note= "Xaa at position 65 is Val,
             Thr, Pro, His, Leu, Phe, or Ser"

(ix) FEATURE:
         (A) NAME/KEY: Modified-site
         (B) LOCATION: 66
         (D) OTHER INFORMATION: /note= "Xaa at position 66 is Lys,
             Ile, Arg, Val, Asn, Glu, or Ser"

(ix) FEATURE:
         (A) NAME/KEY: Modified-site
         (B) LOCATION: 67
         (D) OTHER INFORMATION: /note= "Xaa at position 67 is Ser,
             Ala, Phe, Val, Gly, Asn, Ile, Pro, or His"

(ix) FEATURE:
         (A) NAME/KEY: Modified-site
         (B) LOCATION: 68
         (D) OTHER INFORMATION: /note= "Xaa at position 68 is Leu,
             Val, Trp, Ser, Ile, Phe, Thr, or His"

(ix) FEATURE:
         (A) NAME/KEY: Modified-site
         (B) LOCATION: 69
         (D) OTHER INFORMATION: /note= "Xaa at position 69 is Gln,
             Ala, Pro, Thr, Glu, Arg, Trp, Gly, or Leu"
```

```
(ix) FEATURE:
    (A) NAME/KEY: Modified-site
    (B) LOCATION: 70
    (D) OTHER INFORMATION: /note= "Xaa at position 70 is Asn,
        Leu, Val, Trp, Pro, or Ala"

(ix) FEATURE:
    (A) NAME/KEY: Modified-site
    (B) LOCATION: 71
    (D) OTHER INFORMATION: /note= "Xaa at position 71 is
        Ala,Met,Leu,Pro,Arg,Glu,Thr,Gln,Trp,or Asn"

(ix) FEATURE:
    (A) NAME/KEY: Modified-site
    (B) LOCATION: 72
    (D) OTHER INFORMATION: /note= "Xaa at position 72 is Ser,
        Glu, Met, Ala, His, Asn, Arg, or Asp"

(ix) FEATURE:
    (A) NAME/KEY: Modified-site
    (B) LOCATION: 73
    (D) OTHER INFORMATION: /note= "Xaa at position 73 is Ala,
        Glu, Asp, Leu, Ser, Gly, Thr, or Arg"

(ix) FEATURE:
    (A) NAME/KEY: Modified-site
    (B) LOCATION: 74
    (D) OTHER INFORMATION: /note= "Xaa at position 74 is Ile,
        Met, Thr, Pro, Arg, Gly, or Ala"

(ix) FEATURE:
    (A) NAME/KEY: Modified-site
    (B) LOCATION: 75
    (D) OTHER INFORMATION: /note= "Xaa at position 75 is
        Glu, Lys, Gly, Asp, Pro, Trp, Arg, Ser, Gln,
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Trp, Glu, Pro, Gly, or Asp"

(ix) FEATURE:
    (A) NAME/KEY: Modified-site
    (B) LOCATION: 77
    (D) OTHER INFORMATION: /note= "Xaa at position 77 is Ile,
        Ser, Arg, Thr, or Leu"

(ix) FEATURE:
    (A) NAME/KEY: Modified-site
    (B) LOCATION: 78
    (D) OTHER INFORMATION: /note= "Xaa at position 78 is Leu,
        Ala, Ser, Glu, Phe, Gly, or Arg"

(ix) FEATURE:
    (A) NAME/KEY: Modified-site
    (B) LOCATION: 79
    (D) OTHER INFORMATION: /note= "Xaa at position 79 is Lys, Thr,
        Asn, Met, Arg, Ile, Gly, or Asp"

(ix) FEATURE:
    (A) NAME/KEY: Modified-site
    (B) LOCATION: 80
    (D) OTHER INFORMATION: /note= "Xaa at position 80 is Asn,
        Trp, Val, Gly, Thr, Leu, Glu, or Arg"

(ix) FEATURE:
    (A) NAME/KEY: Modified-site
    (B) LOCATION: 81
    (D) OTHER INFORMATION: /note= "Xaa at position 81 is Leu,
        Gln, Gly, Ala, Trp, Arg, Val, or Lys"

(ix) FEATURE:
    (A) NAME/KEY: Modified-site
    (B) LOCATION: 82
```

```
              (D) OTHER INFORMATION: /note= "Xaa at position 82 is Leu,
                   Gln, Lys, Trp, Arg, Asp, Glu, Asn, His, Thr, Ser, Ala,
                   Tyr, Phe, Ile, Met, or Val"

(ix) FEATURE:
              (A) NAME/KEY: Modified-site
              (B) LOCATION: 83
              (D) OTHER INFORMATION: /note= "Xaa at position 83 is Pro,
                   Ala, Thr, Trp, Arg, or Met"

(ix) FEATURE:
              (A) NAME/KEY: Modified-site
              (B) LOCATION: 84
              (D) OTHER INFORMATION: /note= "Xaa at position 84 is Cys,
                   Glu, Gly, Arg, Met, or Val"

(ix) FEATURE:
              (A) NAME/KEY: Modified-site
              (B) LOCATION: 85
              (D) OTHER INFORMATION: /note= "Xaa at position 85 is Leu,
                   Asn, Val, or Gln"

(ix) FEATURE:
              (A) NAME/KEY: Modified-site
              (B) LOCATION: 86
              (D) OTHER INFORMATION: /note= "Xaa at position 86 is Pro,
                   Cys, Arg, Ala, or Lys"

(ix) FEATURE:
              (A) NAME/KEY: Modified-site
              (B) LOCATION: 87
              (D) OTHER INFORMATION: /note= "Xaa at position 87 is Leu,
                   Ser, Trp, or Gly"

(ix) FEATURE:
              (A) NAME/KEY: Modified-site
              (B) LOCATION: 88
              (D) OTHER INFORMATION: /note= "Xaa at position 88 is Ala,
                   Lys, Arg, Val, or Trp"

(ix) FEATURE:
              (A) NAME/KEY: Modified-site
              (B) LOCATION: 89
              (D) OTHER INFORMATION: /note= "Xaa at position 89 is Thr,
                   Asp, Cys, Leu, Val, Glu, His, Asn, or Ser"

(ix) FEATURE:
              (A) NAME/KEY: Modified-site
              (B) LOCATION: 90
              (D) OTHER INFORMATION: /note= "Xaa at position 90 is Ala,
                   Pro, Ser, Thr, Gly, Asp, Ile, or Met"

(ix) FEATURE:
              (A) NAME/KEY: Modified-site
              (B) LOCATION: 91
              (D) OTHER INFORMATION: /note= "Xaa at position 91 is Ala,
                   Pro, Ser, Thr, Phe, Leu, Asp, or His"

(ix) FEATURE:
              (A) NAME/KEY: Modified-site
              (B) LOCATION: 92
              (D) OTHER INFORMATION: /note= "Xaa at position 92 is Pro,
                   Phe, Arg, Ser, Lys, His, Ala, Gly, Ile, or Leu"

(ix) FEATURE:
              (A) NAME/KEY: Modified-site
              (B) LOCATION: 93
              (D) OTHER INFORMATION: /note= "Xaa at position 93 is Thr,
                   Asp, Ser, Asn, Pro, Ala, Leu, or Arg"

(ix) FEATURE:
              (A) NAME/KEY: Modified-site
              (B) LOCATION: 94
              (D) OTHER INFORMATION: /note= "Xaa at position 94 is Arg,
                   Ile, Ser, Glu, Leu, Val, Gln, Lys, His, Ala, or Pro"

(ix) FEATURE:
              (A) NAME/KEY: Modified-site
              (B) LOCATION: 95
```

-continued (D) OTHER INFORMATION: /note= "Xaa at position 95 is His,
                  Gln, Pro, Arg, Val, Leu, Gly, Thr, Asn, Lys, Ser, Ala,
                  Trp, Phe, Ile, or Tyr"

(ix) FEATURE:
              (A) NAME/KEY: Modified-site
              (B) LOCATION: 96
              (D) OTHER INFORMATION: /note= "Xaa at position 96 is Pro,
                  Lys, Tyr, Gly, Ile, or Thr"

(ix) FEATURE:
              (A) NAME/KEY: Modified-site
              (B) LOCATION: 97
              (D) OTHER INFORMATION: /note= "Xaa at position 97 is Ile,
                  Val, Lys, Ala, or Asn"

(ix) FEATURE:
              (A) NAME/KEY: Modified-site
              (B) LOCATION: 98
              (D) OTHER INFORMATION: /note= "Xaa at position 98 is His,
                  Ile, Asn, Leu, Asp, Ala, Thr, Glu, Gln, Ser, Phe, Met,
                  Val, Lys, Arg, Tyr, or Pro"

(ix) FEATURE:
              (A) NAME/KEY: Modified-site
              (B) LOCATION: 99
              (D) OTHER INFORMATION: /note= "Xaa at position 99 is Ile,
                  Leu, Arg, Asp, Val, Pro, Gln, Gly, Ser, Phe,
                  or His"

(ix) FEATURE:
              (A) NAME/KEY: Modified-site
              (B) LOCATION: 100
              (D) OTHER INFORMATION: /note= "Xaa at position 100 is
                  Lys, Tyr, Leu, His, Arg, Ile, Ser, Gln, or Pro"

(ix) FEATURE:
              (A) NAME/KEY: Modified-site
              (B) LOCATION: 101
              (D) OTHER INFORMATION: /note= "Xaa at position 101 is
                  Asp, Pro, Met, Lys, His, Thr, Val, Tyr, Glu, Asn, Ser,
                  Ala, Gly, Ile, Leu, or Gln"

(ix) FEATURE:
              (A) NAME/KEY: Modified-site
              (B) LOCATION: 102
              (D) OTHER INFORMATION: /note= "Xaa at position 102 is Gly,
                  Leu, Glu, Lys, Ser, Tyr, or Pro"

(ix) FEATURE:
              (A) NAME/KEY: Modified-site
              (B) LOCATION: 103
              (D) OTHER INFORMATION: /note= "Xaa at position 103 is Asp,
                  or Ser"

(ix) FEATURE:
              (A) NAME/KEY: Modified-site
              (B) LOCATION: 104
              (D) OTHER INFORMATION: /note= "Xaa at position 104 is
                  Trp, Val, Cys, Tyr, Thr, Met, Pro, Leu, Gln, Lys, Ala,
                  Phe, or Gly"

(ix) FEATURE:
              (A) NAME/KEY: Modified-site
              (B) LOCATION: 105
              (D) OTHER INFORMATION: /note= "Xaa at position 105 is
                  Asn, Pro, Ala, Phe, Ser, Trp, Gln, Tyr, Leu, Lys, Ile,
                  Asp, or His"

(ix) FEATURE:
              (A) NAME/KEY: Modified-site
              (B) LOCATION: 106
              (D) OTHER INFORMATION: /note= "Xaa at position 106 is Glu,
                  Ser, Ala, Lys, Thr, Ile, Gly, or Pro"

(ix) FEATURE:
        (A) NAME/KEY: Modified-site
        (B) LOCATION: 108
        (D) OTHER INFORMATION: /note= "Xaa at position 108 is Arg,
            Lys, Asp, Leu, Thr, Ile, Gln, His, Ser, Ala, or Pro"

(ix) FEATURE:
        (A) NAME/KEY: Modified-site
        (B) LOCATION: 109
        (D) OTHER INFORMATION: /note= "Xaa at position 109 is Arg,
            Thr, Pro, Glu, Tyr, Leu, Ser, or Gly"

(ix) FEATURE:
        (A) NAME/KEY: Modified-site
        (B) LOCATION: 110
        (D) OTHER INFORMATION: /note= "Xaa at position 110 is Lys,
            Ala, Asn, Thr, Leu, Arg, Gln, His, Glu, Ser,
            or Trp"

(ix) FEATURE:
        (A) NAME/KEY: Modified-site
        (B) LOCATION: 111
        (D) OTHER INFORMATION: /note= "Xaa at position 111 is Leu,
            Ile, Arg, Asp, or Met"

(ix) FEATURE:
        (A) NAME/KEY: Modified-site
        (B) LOCATION: 112
        (D) OTHER INFORMATION: /note= "Xaa at position 112 is Thr,
            Val, Gln, Tyr, Glu, His, Ser, or Phe"

(ix) FEATURE:
        (A) NAME/KEY: Modified-site
        (B) LOCATION: 113
        (D) OTHER INFORMATION: /note= "Xaa at position 113 is Phe,
            Ser, Cys, His, Gly, Trp, Tyr, Asp, Lys, Leu, Ile, Val,
            or Asn"

(ix) FEATURE:
        (A) NAME/KEY: Modified-site
        (B) LOCATION: 114
        (D) OTHER INFORMATION: /note= "Xaa at position 114 is Tyr,
            Cys, His, Ser, Trp, Arg, or Leu"

(ix) FEATURE:
        (A) NAME/KEY: Modified-site
        (B) LOCATION: 115
        (D) OTHER INFORMATION: /note= "Xaa at position 115 is
            Leu, Asn, Val, Pro, Arg, Ala, His, Thr, Trp, or
            Met"

(ix) FEATURE:
        (A) NAME/KEY: Modified-site
        (B) LOCATION: 116
        (D) OTHER INFORMATION: /note= "Xaa at position 116 is Lys,
            Leu, Pro, Thr, Met, Asp, Val, Glu, Arg, Trp, Ser,
            Asn, His, Ala, Tyr, Phe, Glu, or Ile"

(ix) FEATURE:
        (A) NAME/KEY: Modified-site
        (B) LOCATION: 117
        (D) OTHER INFORMATION: /note= "Xaa at position 117 is Thr,
            Ser, Asn, Ile, Trp, Lys, or Pro"

(ix) FEATURE:
        (A) NAME/KEY: Modified-site
        (B) LOCATION: 118
        (D) OTHER INFORMATION: /note= "Xaa at position 118 is Leu,
            Ser, Pro, Ala, Glu, Cys, Asp, or Tyr"

(ix) FEATURE:
        (A) NAME/KEY: Modified-site
        (B) LOCATION: 119
        (D) OTHER INFORMATION: /note= "Xaa at position 119 is Glu,
            Ser, Lys, Pro, Leu, Thr, Tyr, or Arg"

(ix) FEATURE:
        (A) NAME/KEY: Modified-site
        (B) LOCATION: 120

(D) OTHER INFORMATION: /note= "Xaa at position 120 is Asn,
                  Ala, Pro, Leu, His, Val, or Gln"

(ix) FEATURE:
              (A) NAME/KEY: Modified-site
              (B) LOCATION: 121
              (D) OTHER INFORMATION: /note= "Xaa at position 121 is Ala,
                  Ser, Ile, Asn, Pro, Lys, Asp, or Gly"

(ix) FEATURE:
              (A) NAME/KEY: Modified-site
              (B) LOCATION: 122
              (D) OTHER INFORMATION: /note= "Xaa at position 122 is
                  Gln, Ser, Met, Trp, Arg, Phe, Pro, His, Ile, Tyr,
                  or Cys"

(ix) FEATURE:
              (A) NAME/KEY: Modified-site
              (B) LOCATION: 123
              (D) OTHER INFORMATION: /note= "Xaa at position 123 is Ala,
                  Met, Glu, His, Ser, Pro, Tyr, or Leu"

(xi) SEQUENCE DESCRIPTION: SEQ ID NO:15:

Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Asn Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Phe Xaa Xaa Xaa Xaa Xaa
            100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
    130

(2) INFORMATION FOR SEQ ID NO:16:

(i) SEQUENCE CHARACTERISTICS:
              (A) LENGTH: 133 amino acids
              (B) TYPE: amino acid
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Met- may or may not precede
                  the amino acid in position 1"

(ix) FEATURE:
              (A) NAME/KEY: Modified-site
              (B) LOCATION: 17
              (D) OTHER INFORMATION: /note= "Xaa at position 17 is Ser,
                  Gly, Asp, Met, or Gln"

(ix) FEATURE:
              (A) NAME/KEY: Modified-site
              (B) LOCATION: 18
              (D) OTHER INFORMATION: /note= "Xaa at position 18 is Asn,
                  His, Leu, Ile, Phe, Arg, or Gln"

-continued

```
(ix) FEATURE:
    (A) NAME/KEY: Modified-site
    (B) LOCATION: 19
    (D) OTHER INFORMATION: /note= "Xaa at position 19 is Met,
        Phe, Ile, Arg, or Ala"

(ix) FEATURE:
    (A) NAME/KEY: Modified-site
    (B) LOCATION: 20
    (D) OTHER INFORMATION: /note= "Xaa at position 20 is Ile
        or Pro"

(ix) FEATURE:
    (A) NAME/KEY: Modified-site
    (B) LOCATION: 21
    (D) OTHER INFORMATION: /note; "Xaa at position 21 is Asp
        or Glu"

(ix) FEATURE:
    (A) NAME/KEY: Modified-site
    (B) LOCATION: 23
    (D) OTHER INFORMATION: /note= "Xaa at position 23 is Ile,
        Val, Ala, Leu, or Gly"

(ix) FEATURE:
    (A) NAME/KEY: Modified-site
    (B) LOCATION: 24
    (D) OTHER INFORMATION: /note= "Xaa at position 24 is Ile,
        Val, Phe, or Leu"

(ix) FEATURE:
    (A) NAME/KEY: Modified-site
    (B) LOCATION: 25
    (D) OTHER INFORMATION: /note= "Xaa at position 25 is Thr,
        His, Gly, Gln, Arg, Pro, or Ala"

(ix) FEATURE:
    (A) NAME/KEY: Modified-site
    (B) LOCATION: 26
    (D) OTHER INFORMATION: /note= "Xaa at position 26 is His,
        Phe, Gly, Arg, or Ala"

(ix) FEATURE:
    (A) NAME/KEY: Modified-site
    (B) LOCATION: 28
    (D) OTHER INFORMATION: /note= "Xaa at position 28 is Lys,
        Leu, Gln, Gly, Pro, or Val"

(ix) FEATURE:
    (A) NAME/KEY: Modified-site
    (B) LOCATION: 29
    (D) OTHER INFORMATION: /note= "Xaa at position 29 is Gln,
        Asn, Leu, Arg, or Val"

(ix) FEATURE:
    (A) NAME/KEY: Modified-site
    (B) LOCATION: 30
    (D) OTHER INFORMATION: /note= "Xaa at position 30 is Pro,
        His, Thr, Gly, or Gln"

(ix) FEATURE:
    (A) NAME/KEY: Modified-site
    (B) LOCATION: 31
    (D) OTHER INFORMATION: /note= "Xaa at position 31 is Pro,
        Asp, Gly, Ala, Arg, Leu, or Gln"

(ix) FEATURE:
    (A) NAME/KEY: Modified-site
    (B) LOCATION: 32
    (D) OTHER INFORMATION: /note= "Xaa at position 32 Leu,
        Arg, Gln, Asn, Gly, Ala, or Glu"

(ix) FEATURE:
    (A) NAME/KEY: Modified-site
    (B) LOCATION: 33
    (D) OTHER INFORMATION: /note= "Xaa at position 33 is Pro,
        Leu, Gln, Ala, or Glu"
```

```
(ix) FEATURE:
    (A) NAME/KEY: Modified-site
    (B) LOCATION: 34
    (D) OTHER INFORMATION: /note= "Xaa at position 34 is Leu,
        Val, Gly, Ser, Lys, Ala, Arg, Gln, Glu, Ile, Phe,
        Thr, or Met"

(ix) FEATURE:
    (A) NAME/KEY: Modified-site
    (B) LOCATION: 35
    (D) OTHER INFORMATION: /note= "Xaa at position 35 is Leu,
        Ala, Asn, Pro, Gln, or Val"

(ix) FEATURE:
    (A) NAME/KEY: Modified-site
    (B) LOCATION: 36
    (D) OTHER INFORMATION: /note= "Xaa at position 36 is Asp
        or Leu"

(ix) FEATURE:
    (A) NAME/KEY: Modified-site
    (B) LOCATION: 37
    (D) OTHER INFORMATION: /note= "Xaa at position 37 is Phe,
        Ser, Pro, Trp, or Ile"

(ix) FEATURE:
    (A) NAME/KEY: Modified-site
    (B) LOCATION: 38
    (D) OTHER INFORMATION: /note= "Xaa at position 38 is Asn
        or Ala"

(ix) FEATURE:
    (A) NAME/KEY: Modified-site
    (B) LOCATION: 41
    (D) OTHER INFORMATION: /note= "Xaa at position 41 is Asn,
        Cys, Arg, His, Met, or Pro"

(ix) FEATURE:
    (A) NAME/KEY: Modified-site
    (B) LOCATION: 42
    (D) OTHER INFORMATION: /note= "Xaa at position 42 is Gly,
        Asp, Ser, Cys, Ala, Asn, Ile, Leu, Met, Tyr, Val,
        or Arg"

(ix) FEATURE:
    (A) NAME/KEY:  Modified-site
    (B) LOCATION:  44
    (D) OTHER INFORMATION:  /note="Xaa at position 44 is Asp or
        Glu"

(ix) FEATURE:
    (A) NAME/KEY: Modified-site
    (B) LOCATION: 45
    (D) OTHER INFORMATION: /note= "Xaa at position 45 is Gln,
        Val, Met, Leu, Thr, Lys, Ala, Asn, Glu, Ser, or Trp"

(ix) FEATURE:
    (A) NAME/KEY: Modified-site
    (B) LOCATION: 46
    (D) OTHER INFORMATION: /note= "Xaa at position 46 is Asp,
        Phe, Ser, Thr, Cys, Ala, Asn, Gln, Glu, His, Ile, Lys,
        Tyr, Val, or Gly"

(ix) FEATURE:
    (A) NAME/KEY: Modified-site
    (B) LOCATION: 47
    (D) OTHER INFORMATION: /note= "Xaa at position 47 is Ile, Val,
        or His"

(ix) FEATURE:
    (A) NAME/KEY: Modified-site
    (B) LOCATION: 49
    (D) OTHER INFORMATION: /note= "Xaa at position 49 is Met,
        Asn, or Asp"
```

```
(ix) FEATURE:
    (A) NAME/KEY: Modified-site
    (B) LOCATION: 50
    (D) OTHER INFORMATION: /note= "Xaa at position 50 is Glu,
        Thr, Ala, Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 52
    (D) OTHER INFORMATION: /note= "Xaa at position 52 is Asn
        or Gly"

(ix) FEATURE:
    (A) NAME/KEY: Modified-site
    (B) LOCATION: 53
    (D) OTHER INFORMATION: /note= "Xaa at position 53 is Leu,
        Met, or Phe"

(ix) FEATURE:
    (A) NAME/KEY: Modified-site
    (B) LOCATION: 54
    (D) OTHER INFORMATION: /note= "Xaa at position 54 is Arg
        Ala, or Ser"

(ix) FEATURE:
    (A) NAME/KEY: Modified-site
    (B) LOCATION: 55
    (D) OTHER INFORMATION: /note= "Xaa at position 55 is Arg,
        Thr, Val, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Ala, Arg, Asn, Glu, His, Leu, Thr,
        Val, or Lys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, or Arg"

(ix) FEATURE:
    (A) NAME/KEY: Modified-site
    (B) LOCATION: 60
    (D) OTHER INFORMATION: /note= "Xaa at position 60 is Ala,
        Ser, Asn, or Thr"

(ix) FEATURE:
    (A) NAME/KEY: Modified-site
    (B) LOCATION: 61
    (D) OTHER INFORMATION: /note= "Xaa at position 61 is Phe
        or Ser"

(ix) FEATURE:
    (A) NAME/KEY: Modified-site
    (B) LOCATION: 62
    (D) OTHER INFORMATION: /note= "Xaa at position 62 is Asn,
        Val, Pro, Thr, or Ile"

(ix) FEATURE:
    (A) NAME/KEY: Modified-site
    (B) LOCATION: 63
    (D) OTHER INFORMATION: /note= "Xaa at position 63 is Arg,
        Tyr, Lys, Ser, His, or Val"

(ix) FEATURE:
    (A) NAME/KEY: Modified-site
    (B) LOCATION: 64
    (D) OTHER INFORMATION: /note= "Xaa at position 64 is Ala
        or Asn"
```

-continued

```
(ix) FEATURE:
    (A) NAME/KEY: Modified-site
    (B) LOCATION: 65
    (D) OTHER INFORMATION: /note= "Xaa at position 65 is Val,
        Thr, Leu, or Ser"

(ix) FEATURE:
    (A) NAME/KEY: Modified-site
    (B) LOCATION: 66
    (D) OTHER INFORMATION: /note= "Xaa at position 66 is Lys,
        Ile, Arg, Val, Asn, Glu, or Ser"

(ix) FEATURE:
    (A) NAME/KEY: Modified-site
    (B) LOCATION: 67
    (D) OTHER INFORMATION: /note= "Xaa at position 67 is Ser,
        Phe, Val, Gly, Asn, Ile, or His"

(ix) FEATURE:
    (A) NAME/KEY: Modified-site
    (B) LOCATION: 68
    (D) OTHER INFORMATION: /note= "Xaa at position 68 is Leu,
        Val, Ile, Phe, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, or Gly"

(ix) FEATURE:
    (A) NAME/KEY: Modified-site
    (B) LOCATION: 70
    (D) OTHER INFORMATION: /note= "Xaa at position 70 is Asn
        or Pro"

(ix) FEATURE:
    (A) NAME/KEY: Modified-site
    (B) LOCATION: 71
    (D) OTHER INFORMATION: /note= "Xaa at position 71 is Ala,
        Met, Pro, Arg, Glu, Thr, or Gln"

(ix) FEATURE:
    (A) NAME/KEY: Modified-site
    (B) LOCATION: 72
    (D) OTHER INFORMATION: /note= "Xaa at position 72 is Ser,
        Glu, Met, Ala, His, Asn, Arg, or Asp"

(ix) FEATURE:
    (A) NAME/KEY: Modified-site
    (B) LOCATION: 73
    (D) OTHER INFORMATION: /note= "Xaa at position 73 is Ala,
        Glu, Asp, Leu, Ser, Gly, Thr, Arg, or Pro"

(ix) FEATURE:
    (A) NAME/KEY: Modified-site
    (B) LOCATION: 74
    (D) OTHER INFORMATION: /note= "Xaa at position 74 is Ile
        or Met"

(ix) FEATURE:
    (A) NAME/KEY: Modified-site
    (B) LOCATION: 75
    (D) OTHER INFORMATION: /note= "Xaa at position 75 is Glu,
        Gly, Asp, Ser, or Gln"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Glu, Pro, Gly, or Asp"

(ix) FEATURE:
    (A) NAME/KEY: Modified-site
    (B) LOCATION: 77
    (D) OTHER INFORMATION: /note= "Xaa at position 77 is Ile,
        Ser, or Leu"
```

-continued (ix) FEATURE:
    (A) NAME/KEY: Modified-site
    (B) LOCATION: 79
    (D) OTHER INFORMATION: /note= "Xaa at position 79 is Lys,
        Thr, Asn, Met, Arg, Ile, Gly, or Asp"

(ix) FEATURE:
    (A) NAME/KEY: Modified-site
    (B) LOCATION: 80
    (D) OTHER INFORMATION: /note= "Xaa at position 80 is Asn,
        Val, Gly, Thr, Leu, Glu, or Arg"

(ix) FEATURE:
    (A) NAME/KEY: Modified-site
    (B) LOCATION: 81
    (D) OTHER INFORMATION: /note= "Xaa at position 81 is Leu
        or Val"

(ix) FEATURE:
    (A) NAME/KEY: Modified-site
    (B) LOCATION: 82
    (D) OTHER INFORMATION: /note= "Xaa at position 82 is Leu,
        Gln, Trp, Arg, Asp, Ala, Asn, Glu, His, Met, Phe,
        Ser, Thr, Tyr, or Val"

(ix) FEATURE:
    (A) NAME/KEY: Modified-site
    (B) LOCATION: 83
    (D) OTHER INFORMATION: /note= "Xaa at position 83 is Pro,
        Ala, Thr, Trp, or Met"

(ix) FEATURE:
    (A) NAME/KEY: Modified-site
    (B) LOCATION: 85
    (D) OTHER INFORMATION: /note= "Xaa at position 85 is Leu
        or Val"

(ix) FEATURE:
    (A) NAME/KEY: Modified-site
    (B) LOCATION: 87
    (D) OTHER INFORMATION: /note= "Xaa at position 87 is Leu
        or Ser"

(ix) FEATURE:
    (A) NAME/KEY: Modified-site
    (B) LOCATION: 88
    (D) OTHER INFORMATION: /note= "Xaa at position 88 is Ala,
        Arg, or Trp"

(ix) FEATURE:
    (A) NAME/KEY: Modified-site
    (B) LOCATION: 89
    (D) OTHER INFORMATION: /note= "Xaa at position 89 is Thr,
        Asp, Glu, His, Asn, or Ser"

(ix) FEATURE:
    (A) NAME/KEY: Modified-site
    (B) LOCATION: 90
    (D) OTHER INFORMATION: /note= "Xaa at position 90 is Ala,
        Asp, or Met"

(ix) FEATURE:
    (A) NAME/KEY: Modified-site
    (B) LOCATION: 91
    (D) OTHER INFORMATION: /note= "Xaa at position 91 is Ala,
        Pro, Ser, Thr, Phe, Leu, or Asp"

(ix) FEATURE:
    (A) NAME/KEY: Modified-site
    (B) LOCATION: 92
    (D) OTHER INFORMATION: /note= "Xaa at position 92 is Pro
        or Ser"

(ix) FEATURE:
    (A) NAME/KEY: Modified-site
    (B) LOCATION: 93
    (D) OTHER INFORMATION: /note= "Xaa at position 93 is Thr,
        Asp, Ser, Pro, Ala, Leu, or Arg"

-continued

```
(ix) FEATURE:
    (A) NAME/KEY: Modified-site
    (B) LOCATION: 95
    (D) OTHER INFORMATION: /note= "Xaa at position 95 is His,
        Pro, Arg, Val, Leu, Gly, Asn, Ile, Phe, Ser,
        or Thr"

(ix) FEATURE:
    (A) NAME/KEY: Modified-site
    (B) LOCATION: 96
    (D) OTHER INFORMATION: /note= "Xaa at position 96 is Pro
        or Tyr"

(ix) FEATURE:
    (A) NAME/KEY: Modified-site
    (B) LOCATION: 97
    (D) OTHER INFORMATION: /note= "Xaa at position 97 is Ile,
        Val, or Ala"

(ix) FEATURE:
    (A) NAME/KEY: Modified-site
    (B) LOCATION: 98
    (D) OTHER INFORMATION: /note= "Xaa at position 98 is His,
        Ile, Asn, Leu, Asp, Ala, Thr, Arg, Gln, Glu,
        Lys, Met, Ser, Tyr, Val, or Pro"

(ix) FEATURE:
    (A) NAME/KEY: Modified-site
    (B) LOCATION: 99
    (D) OTHER INFORMATION: /note= "Xaa at position 99 is Ile,
        Leu, Val, or Phe"

(ix) FEATURE:
    (A) NAME/KEY: Modified-site
    (B) LOCATION: 100
    (D) OTHER INFORMATION: /note= "Xaa at position 100 is Lys,
        Leu, His, Arg, Ile, Gln, Pro, or Ser"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, His, Thr, Val, Asn, Ile, Leu, or Tyr"

(ix) FEATURE:
    (A) NAME/KEY: Modified-site
    (B) LOCATION: 102
    (D) OTHER INFORMATION: /note= "Xaa at position 102 is Gly,
        Glu, Lys, or Ser"

(ix) FEATURE:
    (A) NAME/KEY: Modified-site
    (B) LOCATION: 104
    (D) OTHER INFORMATION: /note= "Xaa at position 104 is Trp,
        Val, Tyr, Met, or Leu"

(ix) FEATURE:
    (A) NAME/KEY: Modified-site
    (B) LOCATION: 105
    (D) OTHER INFORMATION: /note= "Xaa at position 105 is
        Asn, Pro, Ala, Phe, Ser, Trp, Gln, Tyr, Leu, Lys,
        Ile, Asp or His"

(ix) FEATURE:
    (A) NAME/KEY: Modified-site
    (B) LOCATION: 106
    (D) OTHER INFORMATION: /note= "Xaa at position 106 is Glu,
        Ser, Ala, or Gly"

(ix) FEATURE:
    (A) NAME/KEY: Modified-site
    (B) LOCATION: 108
    (D) OTHER INFORMATION: /note= "Xaa at position 108 is Arg,
        Ala, Gln, Ser, or Lys"
```

```
    (ix) FEATURE:
          (A) NAME/KEY: Modified-site
          (B) LOCATION: 109
          (D) OTHER INFORMATION: /note= "Xaa at position 109 is Arg,
              Thr, Glu, Leu, Ser, or Gly"

(ix) FEATURE:
          (A) NAME/KEY: Modified-site
          (B) LOCATION: 112
          (D) OTHER INFORMATION: /note= "Xaa at position 112 is Thr,
              Val, Gln, Glu, His, or Ser"

(ix) FEATURE:
          (A) NAME/KEY: Modified-site
          (B) LOCATION: 114
          (D) OTHER INFORMATION: /note= "Xaa at position 114 is Tyr
              or Trp"

(ix) FEATURE:
          (A) NAME/KEY: Modified-site
          (B) LOCATION: 115
          (D) OTHER INFORMATION: /note= "Xaa at position 115 is Leu
              or Ala"

(ix) FEATURE:
          (A) NAME/KEY: Modified-site
          (B) LOCATION: 116
          (D) OTHER INFORMATION: /note= "Xaa at position 116 is Lys,
              Thr, Met, Val, Trp, Ser, Leu, Ala, Asn, Gln, His, Met,
              Phe, Tyr, or Ile"

(ix) FEATURE:
          (A) NAME/KEY: Modified-site
          (B) LOCATION: 117
          (D) OTHER INFORMATION: /note= "Xaa at position 117 is Thr,
              Ser, or Asn"

(ix) FEATURE:
          (A) NAME/KEY: Modified-site
          (B) LOCATION: 119
          (D) OTHER INFORMATION: /note= "Xaa at position 119 is
              Glu, Ser, Pro, Leu, Thr, or Tyr"

(ix) FEATURE:
          (A) NAME/KEY: Modified-site
          (B) LOCATION: 120
          (D) OTHER INFORMATION: /note= "Xaa at position 120 is Asn,
              Pro, Leu, His, Val, or Gln"

(ix) FEATURE:
          (A) NAME/KEY: Modified-site
          (B) LOCATION: 121
          (D) OTHER INFORMATION: /note= "Xaa at position 121 is Ala,
              Ser, Ile, Asn, Pro, Lys, Asp, or Gly"

(ix) FEATURE:
          (A) NAME/KEY: Modified-site
          (B) LOCATION: 122
          (D) OTHER INFORMATION: /note= "Xaa at position 122 is
              Gln, Ser, Met, Trp, Arg, Phe, Pro, His, Ile, Tyr,
              or Cys"

(ix) FEATURE:
          (A) NAME/KEY: Modified-site
          (B) LOCATION: 123
          (D) OTHER INFORMATION: /note= "Xaa at position 123 is Ala,
              Met, Glu, His, Ser, Pro, Tyr, or Leu"

(xi) SEQUENCE DESCRIPTION: SEQ ID NO:16:

Ala Pro Met Thr Gln Thr Thr Ser Leu Lys Thr Ser Trp Val Asn Cys
1               5                   10                  15

Xaa Xaa Xaa Xaa Xaa Glu Xaa Xaa Xaa Xaa Leu Xaa Xaa Xaa Xaa Xaa
            20                  25                  30

Xaa Xaa Xaa Xaa Xaa Xaa Asn Leu Xaa Xaa Glu Xaa Xaa Xaa Xaa Leu
            35                  40                  45
```

```
Xaa Xaa Xaa Xaa Xaa Xaa Xaa Xaa Asn Leu Xaa Xaa Xaa Xaa Xaa Xaa
 50                      55                  60

Xaa Xaa Xaa Xaa Xaa Xaa Xaa Xaa Xaa Xaa Xaa Xaa Xaa Leu Xaa Xaa
 65                  70                  75                  80

Xaa Xaa Xaa Cys Xaa Pro Xaa Xaa Xaa Xaa Xaa Xaa Arg Xaa Xaa
                 85                  90                  95

Xaa Xaa Xaa Xaa Xaa Xaa Asp Xaa Xaa Xaa Phe Xaa Xaa Lys Leu Xaa
             100                 105                 110

Phe Xaa Xaa Xaa Xaa Leu Xaa Xaa Xaa Xaa Xaa Gln Gln Thr Thr Leu
         115                 120                 125

Ser Leu Ala Ile Phe
 130
```

(2) INFORMATION FOR SEQ ID NO:17:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, Met, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 19
        (D) OTHER INFORMATION: /note= "Xaa at position 19 is Met
            or Ile"

(ix) FEATURE:
        (A) NAME/KEY: Modified-site
        (B) LOCATION: 21
        (D) OTHER INFORMATION: /note= "Xaa at position 21 is Asp
            or Glu"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 24
        (D) OTHER INFORMATION: /note= "Xaa at position 24 is Ile,
            Val, or Leu"

(ix) FEATURE:
        (A) NAME/KEY: Modified-site
        (B) LOCATION: 25
        (D) OTHER INFORMATION: /note= "Xaa at position 25 is Thr,
            His, Gln, or Ala"

-continued (ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note= "Xaa at position 29 is Gln,
            Asn, or Val"

(ix) FEATURE:
        (A) NAME/KEY: Modified-site
        (B) LOCATION: 30
        (D) OTHER INFORMATION: /note= "Xaa at position 30 is Pro,
            Gly, or Gln"

(ix) FEATURE:
        (A) NAME/KEY: Modified-site
        (B) LOCATION: 31
        (D) OTHER INFORMATION: /note= "Xaa at position 31 is Pro,
            Asp, Gly, or Gln"

(ix) FEATURE:
        (A) NAME/KEY: Modified-site
        (B) LOCATION: 32
        (D) OTHER INFORMATION: /note= "Xaa at position 32 is Leu,
            Arg, Gln, Asn, Gly, Ala, or Glu"

(ix) FEATURE:
        (A) NAME/KEY: Modified-site
        (B) LOCATION: 33
        (D) OTHER INFORMATION: /note= "Xaa at position 33 is Pro
            or Glu"

(ix) FEATURE:
        (A) NAME/KEY: Modified-site
        (B) LOCATION: 34
        (D) OTHER INFORMATION: /note= "Xaa at position 34 is Leu,
            Val, Gly, Ser, Lys, Ala, Arg, Gln, Glu, Ile, Phe
            Thr, or Met"

(ix) FEATURE:
        (A) NAME/KEY: Modified-site
        (B) LOCATION: 35
        (D) OTHER INFORMATION: /note= "Xaa at position 35 is Leu,
            Ala, Asn, Pro, Gln, or Val"

(ix) FEATURE:
        (A) NAME/KEY: Modified-site
        (B) LOCATION: 37
        (D) OTHER INFORMATION: /note= "Xaa at position 37 is Phe,
            Ser, Pro, or Trp"

(ix) FEATURE:
        (A) NAME/KEY: Modified-site
        (B) LOCATION: 38
        (D) OTHER INFORMATION: /note= "Xaa at position 38 is Asn
            or Ala"

(ix) FEATURE:
        (A) NAME/KEY: Modified-site
        (B) LOCATION: 42
        (D) OTHER INFORMATION: /note= "Xaa at position 42 is Gly,
            Asp, Ser, Cys, Ala, Asn, Ile, Leu, Met, Tyr, or Arg"

(ix) FEATURE:
        (A) NAME/KEY: Modified-site
        (B) LOCATION: 44
        (D) OTHER INFORMATION: /note= "Xaa at position 44 is Asp
            or Glu"

(ix) FEATURE:
        (A) NAME/KEY: Modified-site
        (B) LOCATION: 45
        (D) OTHER INFORMATION: /note= "Xaa at position 45 is Gln,
            Val, Met, Leu, Thr, Ala, Asn, Glu, Ser, or Lys"

-continued (ix) FEATURE:
    (A) NAME/KEY: Modified-site
    (B) LOCATION: 46
    (D) OTHER INFORMATION: /note= "Xaa at position 46 is Asp,
        Phe, Ser, Thr, Ala, Asn, Gln, Glu, His, Ile, Lys,
        Tyr, Val, or Cys"

(ix) FEATURE:
    (A) NAME/KEY: Modified-site
    (B) LOCATION: 50
    (D) OTHER INFORMATION: /note= "Xaa at position 50 is Glu,
        Ala, Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 54
    (D) OTHER INFORMATION: /note= "Xaa at position 54 is Arg
        or Ala"

(ix) FEATURE:
    (A) NAME/KEY: Modified-site
    (B) LOCATION: 55
    (D) OTHER INFORMATION: /note= "Xaa at position 55 is Arg,
        Thr, Val, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Ser, Gln, Ala, Arg, Asn, Glu, Leu, Thr, Val,
        or Lys"

(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn,
        Pro, Thr, or Ile"

(ix) FEATURE:
    (A) NAME/KEY: Modified-site
    (B) LOCATION: 63
    (D) OTHER INFORMATION: /note= "Xaa at position 63 is Arg
        or Lys"

(ix) FEATURE:
    (A) NAME/KEY: Modified-site
    (B) LOCATION: 64
    (D) OTHER INFORMATION: /note= "Xaa at position 64 is Ala
        or Asn"

(ix) FEATURE:
    (A) NAME/KEY: Modified-site
    (B) LOCATION: 65
    (D) OTHER INFORMATION: /note= "Xaa at position 65 is Val
        or Thr"

(ix) FEATURE:
    (A) NAME/KEY: Modified-site
    (B) LOCATION: 66
    (D) OTHER INFORMATION: /note= "Xaa at position 66 is Lys
        or Arg"

```
(ix) FEATURE:
    (A) NAME/KEY: Modified-site
    (B) LOCATION: 67
    (D) OTHER INFORMATION: /note= "Xaa at position 67 is Ser
        Phe or His"

(ix) FEATURE:
    (A) NAME/KEY: Modified-site
    (B) LOCATION: 68
    (D) OTHER INFORMATION: /note= "Xaa at position 68 is Leu,
        Ile, Phe, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, or Gly"

(ix) FEATURE:
    (A) NAME/KEY: Modified-site
    (B) LOCATION: 71
    (D) OTHER INFORMATION: /note= "Xaa at position 71 is Ala,
        Pro, or Arg"

(ix) FEATURE:
    (A) NAME/KEY: Modified-site
    (B) LOCATION: 72
    (D) OTHER INFORMATION: /note= "Xaa at position 72 is Ser,
        Glu, Arg, or Asp"

(ix) FEATURE:
    (A) NAME/KEY: Modified-site
    (B) LOCATION: 73
    (D) OTHER INFORMATION: /note= "Xaa at position 73 is Ala
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Glu, Pro, or Gly"

(ix) FEATURE:
    (A) NAME/KEY: Modified-site
    (B) LOCATION: 77
    (D) OTHER INFORMATION: /note= "Xaa at position 77 is Ile
        or Leu"

(ix) FEATURE:
    (A) NAME/KEY: Modified-site
    (B) LOCATION: 79
    (D) OTHER INFORMATION: /note= "Xaa at position 79 is
        Lys, Thr, Asn, Met, Arg, Ile, Gly, or Asp"

(ix) FEATURE:
    (A) NAME/KEY: Modified-site
    (B) LOCATION: 80
    (D) OTHER INFORMATION: /note= "Xaa at position 80 is Asn,
        Gly, Glu, or Arg"

(ix) FEATURE:
    (A) NAME/KEY: Modified-site
    (B) LOCATION: 82
    (D) OTHER INFORMATION: /note= "Xaa at position 82 is Leu,
        Gln, Trp, Arg, Asp, Ala, Asn, Glu, His, Ile, Met,
        Phe, Ser, Thr, Tyr, or Val"

(ix) FEATURE:
    (A) NAME/KEY: Modified-site
    (B) LOCATION: 83
    (D) OTHER INFORMATION: /note= "Xaa at position 83 is Pro
        or Thr"

(ix) FEATURE:
    (A) NAME/KEY: Modified-site
    (B) LOCATION: 85
    (D) OTHER INFORMATION: /note= "Xaa at position 85 is Leu
        or Val"
```

```
(ix) FEATURE:
    (A) NAME/KEY: Modified-site
    (B) LOCATION: 87
    (D) OTHER INFORMATION: /note= "Xaa at position 87 is Leu
        or Ser"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Thr,
        Asp, Ser, Pro, Ala, Leu, or Arg"

(ix) FEATURE:
    (A) NAME/KEY: Modified-site
    (B) LOCATION: 95
    (D) OTHER INFORMATION: /note= "Xaa at position 95 is His,
        Pro, Arg, Val, Leu, Gly, Asn, Phe, Ser, or Thr"

(ix) FEATURE:
    (A) NAME/KEY: Modified-site
    (B) LOCATION: 96
    (D) OTHER INFORMATION: /note= "Xaa at position 96 is Pro
        or Tyr"

(ix) FEATURE:
    (A) NAME/KEY: Modified-site
    (B) LOCATION: 97
    (D) OTHER INFORMATION: /note= "Xaa at position 97 is Ile
        or Val"

(ix) FEATURE:
    (A) NAME/KEY: Modified-site
    (B) LOCATION: 98
    (D) OTHER INFORMATION: /note= "Xaa at position 98 is His,
        Ile, Asn, Leu, Ala, Thr, Arg, Gln, Lys,
        Met, Ser, Tyr, Val, or Pro"

(ix) FEATURE:
    (A) NAME/KEY: Modified-site
    (B) LOCATION: 99
    (D) OTHER INFORMATION: /note= "Xaa at position 99 is Ile,
        Leu, or Val"

(ix) FEATURE:
    (A) NAME/KEY: Modified-site
    (B) LOCATION: 100
    (D) OTHER INFORMATION: /note= "Xaa at position 100 is Lys,
        Arg, Ile, Gln, Pro, or Ser"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, His, Thr, Pro, Asn, Ile, Leu, or Tyr"

(ix) FEATURE:
    (A) NAME/KEY: Modified-site
    (B) LOCATION: 104
    (D) OTHER INFORMATION: /note= "Xaa at position 104 is Trp
        or Leu"

(ix) FEATURE:
    (A) NAME/KEY: Modified-site
    (B) LOCATION: 105
```

(D) OTHER INFORMATION: /note= "Xaa at position 105 is
                Asn, Pro, Ala, Ser, Trp, Gln, Tyr, Leu, Lys, Ile,
                Asp, or His"

(ix) FEATURE:
            (A) NAME/KEY: Modified-site
            (B) LOCATION: 106
            (D) OTHER INFORMATION: /note= "Xaa at position 106 is Glu
                or Gly"

(ix) FEATURE:
            (A) NAME/KEY: Modified-site
            (B) LOCATION: 109
            (D) OTHER INFORMATION: /note= "Xaa at position 109 is Arg,
                Thr, Glu, Leu, or Ser"

(ix) FEATURE:
            (A) NAME/KEY: Modified-site
            (B) LOCATION: 112
            (D) OTHER INFORMATION: /note= "Xaa at position 112 is Thr,
                Val, or Gln"

(ix) FEATURE:
            (A) NAME/KEY: Modified-site
            (B) LOCATION: 114
            (D) OTHER INFORMATION: /note= "Xaa at position 114 is Tyr
                or Trp"

(ix) FEATURE:
            (A) NAME/KEY: Modified-site
            (B) LOCATION: 115
            (D) OTHER INFORMATION: /note= "Xaa at position 115 is Leu
                or Ala"

(ix) FEATURE:
            (A) NAME/KEY: Modified-site
            (B) LOCATION: 116
            (D) OTHER INFORMATION: /note= "Xaa at position 116 is Lys,
                Thr, Val, Trp, Ser, Ala, His, Met, Phe, Tyr, or Ile"

(ix) FEATURE:
            (A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Pro, Leu, His, Val, or Gln"

(ix) FEATURE:
            (A) NAME/KEY: Modified-site
            (B) LOCATION: 121
            (D) OTHER INFORMATION: /note= "Xaa at position 121 is Ala,
                Ser, Ile, Asn, Pro, Asp, or Gly"

(ix) FEATURE:
            (A) NAME/KEY: Modified-site
            (B) LOCATION: 122
            (D) OTHER INFORMATION: /note= "Xaa at position 122 is
                Gln, Ser, Met, Trp, Arg, Phe, Pro, His, Ile, Tyr,
                or Cys"

(ix) FEATURE:
            (A) NAME/KEY: Modified-site
            (B) LOCATION: 123
            (D) OTHER INFORMATION: /note= "Xaa at position 123 is Ala,
                Met, Glu, His, Ser, Pro, Tyr, or Leu"

(xi) SEQUENCE DESCRIPTION: SEQ ID NO:17:

Ala Pro Met Thr Gln Thr Thr Ser Leu Lys Thr Ser Trp Val Asn Cys
1               5                   10                  15

Xaa Xaa Xaa Ile Xaa Glu Xaa Xaa Xaa Xaa Leu Lys Xaa Xaa Xaa Xaa
            20                  25                  30

```
Xaa Xaa Xaa Asp Xaa Xaa Asn Leu Asn Xaa Glu Xaa Xaa Xaa Ile Leu
        35              40              45

Met Xaa Xaa Asn Leu Xaa Xaa Xaa Asn Leu Glu Xaa Phe Xaa Xaa Xaa
    50              55              60

Xaa Xaa Xaa Xaa Xaa Asn Xaa Xaa Ile Glu Xaa Xaa Leu Xaa Xaa
65              70              75              80

Leu Xaa Xaa Cys Xaa Pro Xaa Xaa Thr Ala Xaa Pro Xaa Arg Xaa Xaa
            85              90              95

Xaa Xaa Xaa Xaa Xaa Gly Asp Xaa Xaa Xaa Phe Xaa Xaa Lys Leu Xaa
            100             105             110

Phe Xaa Xaa Xaa Xaa Leu Glu Xaa Xaa Xaa Xaa Gln Gln Thr Thr Leu
        115             120             125

Ser Leu Ala Ile Phe
    130
```

(2) INFORMATION FOR SEQ ID NO:18:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 25
        (D) OTHER INFORMATION: /note= "Xaa at position 25 is Thr,
            His, or Gln"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note="Xaa at position 29 is Gln
            or Asn"

(ix) FEATURE:
        (A) NAME/KEY: Modified-site
        (B) LOCATION: 30
        (D) OTHER INFORMATION: /note= "Xaa at position 30 is Pro
            or Gly"

-continued (ix) FEATURE:
    (A) NAME/KEY: Modified-site
    (B) LOCATION: 32
    (D) OTHER INFORMATION: /note= "Xaa at position 32 is Leu,
        Arg, Asn, or Ala"

(ix) FEATURE:
    (A) NAME/KEY: Modified-site
    (B) LOCATION: 34
    (D) OTHER INFORMATION: /note= "Xaa at position 34 is Leu,
        Val, Ser, Ala, Arg, Gln, Glu, Ile, Phe, Thr, or Met"

(ix) FEATURE:
    (A) NAME/KEY: Modified-site
    (B) LOCATION: 35
    (D) OTHER INFORMATION: /note= "Xaa at position 35 is Leu,
        Ala, Asn, or Pro"

(ix) FEATURE:
    (A) NAME/KEY: Modified-site
    (B) LOCATION: 38
    (D) OTHER INFORMATION: /note= "Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Asp, Ser, Ala, Asn, Ile, Leu, Met, Tyr, or Arg"

(ix) FEATURE:
    (A) NAME/KEY: Modified-site
    (B) LOCATION: 45
    (D) OTHER INFORMATION: /note= "Xaa at position 45 is Gln,
        Val, Met, Leu, Ala, Asn, Glu, or Lys"

(ix) FEATURE:
    (A) NAME/KEY: Modified-site
    (B) LOCATION: 46
    (D) OTHER INFORMATION: /note= "Xaa at position 46 is Asp,
        Phe, Ser, Gln, Glu, His, Val, or Thr"

(ix) FEATURE:
    (A) NAME/KEY: Modified-site
    (B) LOCATION: 50
    (D) OTHER INFORMATION: /note= "Xaa at position 50 is Glu,
        Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Pro, Thr, or His"

(ix) FEATURE:
    (A) NAME/KEY: Modified-site
    (B) LOCATION: 55
    (D) OTHER INFORMATION: /note= "Xaa at position 55 is Arg,
        Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Ser, Ala, Asn, Val, Leu, or Gln"

(ix) FEATURE:
    (A) NAME/KEY: Modified-site
    (B) LOCATION: 62
    (D) OTHER INFORMATION: /note= "Xaa at position 62 is Asn,
        Pro, or Thr"

(ix) FEATURE:
    (A) NAME/KEY: Modified-site
    (B) LOCATION: 64
    (D) OTHER INFORMATION: /note= "Xaa at position 64 is Ala
        or Asn"

-continued (ix) FEATURE:
    (A) NAME/KEY: Modified-site
    (B) LOCATION: 65
    (D) OTHER INFORMATION: /note= "Xaa at position 65 is Val
        or Thr"

(ix) FEATURE:
    (A) NAME/KEY: Modified-site
    (B) LOCATION: 67
    (D) OTHER INFORMATION: /note= "Xaa at position 67 is Ser
        or Phe"

(ix) FEATURE:
    (A) NAME/KEY: Modified-site
    (B) LOCATION: 68
    (D) OTHER INFORMATION: /note= "Xaa at position 68 is Leu
        or Phe"

(ix) FEATURE:
    (A) NAME/KEY: Modified-site
    (B) LOCATION: 69
    (D) OTHER INFORMATION: /note= "Xaa at position 69 is Gln,
        Ala, Glu, or Arg"

(ix) FEATURE:
    (A) NAME/KEY: Modified-site
    (B) LOCATION: 76
    (D) OTHER INFORMATION: /note= "Xaa at position 76 is Ser,
        Val, Asn, Pro, or Gly"

(ix) FEATURE:
    (A) NAME/KEY: Modified-site
    (B) LOCATION: 77
    (D) OTHER INFORMATION: /note= "Xaa at position 77 is Ile
        or Leu"

(ix) FEATURE:
    (A) NAME/KEY: Modified-site
    (B) LOCATION: 79
    (D) OTHER INFORMATION: /note= "Xaa at position 79 is Lys,
        Asn, Met, Arg, Ile, or Gly"

(ix) FEATURE:
    (A) NAME/KEY: Modified-site
    (B) LOCATION: 80
    (D) OTHER INFORMATION: /note= "Xaa at position 80 is Asn,
        Gly, Glu, or Arg"

(ix) FEATURE:
    (A) NAME/KEY: Modified-site
    (B) LOCATION: 82
    (D) OTHER INFORMATION: /note= "Xaa at position 82 is Leu,
        Gln, Trp, Arg, Asp, Asn, Glu, His, Met, Phe, Ser,
        Thr, Tyr, or Val"

(ix) FEATURE:
    (A) NAME/KEY: Modified-site
    (B) LOCATION: 87
    (D) OTHER INFORMATION: /note= "Xaa at position 87 is Leu
        or Ser"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Thr,
        Asp, or Ala"

```
(ix) FEATURE:
    (A) NAME/KEY: Modified-site
    (B) LOCATION: 95
    (D) OTHER INFORMATION: /note= "Xaa at position 95 is His,
        Pro, Arg, Val, Gly, Asn, Ser, or Thr"

(ix) FEATURE:
    (A) NAME/KEY: Modified-site
    (B) LOCATION: 98
    (D) OTHER INFORMATION: /note= "Xaa at position 98 is His,
        Ile, Asn, Ala, Thr, Arg, Gln, Glu, Lys, Met, Ser,
        Tyr, Val, or Leu"

(ix) FEATURE:
    (A) NAME/KEY: Modified-site
    (B) LOCATION: 99
    (D) OTHER INFORMATION: /note= "Xaa at position 99 is Ile
        or Leu"

(ix) FEATURE:
    (A) NAME/KEY: Modified-site
    (B) LOCATION: 100
    (D) OTHER INFORMATION: /note= "Xaa at position 100 is Lys
        or Arg"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, Thr, His, Pro, Asn, Ile, Leu, or Tyr"

(ix) FEATURE:
    (A) NAME/KEY: Modified-site
    (B) LOCATION: 105
    (D) OTHER INFORMATION: /note= "Xaa at position 105 is Asn,
        Pro, Ser, Ile, or Asp"

(ix) FEATURE:
    (A) NAME/KEY:  Modified-site
    (B) LOCATION:  108
    (D) OTHER INFORMATION:  /note= "Xaa at position 108 is Arg,
        Ala, or Ser"

(ix) FEATURE:
    (A) NAME/KEY: Modified-site
    (B) LOCATION: 109
    (D) OTHER INFORMATION: /note= "Xaa at position 109 is Arg,
        Thr, Glu, Leu, or Ser"

(ix) FEATURE:
    (A) NAME/KEY: Modified-site
    (B) LOCATION: 112
    (D) OTHER INFORMATION: /note= "Xaa at position 112 is Thr
        or Gln"

(ix) FEATURE:
    (A) NAME/KEY: Modified-site
    (B) LOCATION: 116
    (D) OTHER INFORMATION: /note= "Xaa at position 116 is Lys,
        Val, Trp, Ala, His, Phe, Tyr, or Ile"

(ix) FEATURE:
    (A) NAME/KEY: Modified-site
    (B) LOCATION: 117
    (D) OTHER INFORMATION: /note= "Xaa at position 117 is Thr
        or Ser"

(ix) FEATURE:
    (A) NAME/KEY: Modified-site
    (B) LOCATION: 120
    (D) OTHER INFORMATION: /note= "Xaa at position 120 is Asn,
        Pro, Leu, His, Val, or Gln"

(ix) FEATURE:
    (A) NAME/KEY: Modified-site
    (B) LOCATION: 121
    (D) OTHER INFORMATION: /note= "Xaa at position 121 is Ala,
        Ser, Ile, Pro, or Asp"
```

(ix) FEATURE:
            (A) NAME/KEY: Modified-site
            (B) LOCATION: 122
            (D) OTHER INFORMATION: /note= "Xaa at position 122 is Gln,
                Met, Trp, Phe, Pro, His, Ile, or Tyr"

(ix) FEATURE:
            (A) NAME/KEY: Modified-site
            (B) LOCATION: 123
            (D) OTHER INFORMATION: /note= "Xaa at position 123 is Ala,
                Met, Glu, Ser, or Leu"

(xi) SEQUENCE DESCRIPTION: SEQ ID NO:18:

Ala Pro Met Thr Gln Thr Thr Ser Leu Lys Thr Ser Trp Val Asn Cys
1               5                   10                  15

Xaa Xaa Met Ile Asp Glu Xaa Ile Xaa Xaa Leu Lys Xaa Xaa Pro Xaa
            20                  25                  30

Pro Xaa Xaa Asp Phe Xaa Asn Leu Asn Xaa Glu Asp Xaa Xaa Ile Leu
        35                  40                  45

Met Xaa Xaa Asn Leu Arg Xaa Xaa Asn Leu Glu Ala Phe Xaa Arg Xaa
    50                  55                  60

Xaa Lys Xaa Xaa Xaa Asn Ala Ser Ala Ile Glu Xaa Xaa Leu Xaa Xaa
65                  70                  75                  80

Leu Xaa Pro Cys Leu Pro Xaa Xaa Thr Ala Xaa Pro Xaa Arg Xaa Pro
        85                  90                  95

Ile Xaa Xaa Xaa Xaa Gly Asp Trp Xaa Glu Phe Xaa Xaa Lys Leu Xaa
            100                 105                 110

Phe Tyr Leu Xaa Xaa Leu Glu Xaa Xaa Xaa Xaa Gln Gln Thr Thr Leu
        115                 120                 125

Ser Leu Ala Ile Phe
    130

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

```
(ix) FEATURE:
    (A) NAME/KEY: Modified-site
    (B) LOCATION: 6
    (D) OTHER INFORMATION: /note= "Xaa at position 6 is Ile,
        Cys, Gln, Glu, Arg, Pro, or Ala"

(ix) FEATURE:
    (A) NAME/KEY: Modified-site
    (B) LOCATION: 7
    (D) OTHER INFORMATION: /note= "Xaa at position 7 is Asp,
        Phe, Lys, Arg, Ala, Gly, Glu, Gln, Asn, Thr, Ser,
        or Val"

(ix) FEATURE:
    (A) NAME/KEY: Modified-site
    (B) LOCATION: 8
    (D) OTHER INFORMATION: /note= "Xaa at position 8 is Glu,
        Trp, Pro, Ser, Ala, His, Asp, Asn, Gln, Leu, Val,
        or Gly"

(ix) FEATURE:
    (A) NAME/KEY: Modified-site
    (B) LOCATION: 9
    (D) OTHER INFORMATION: /note= "Xaa at position 9 is
        Ile, Val, Ala, Leu, Gly, Trp, Lys, Phe, Ser
        or Arg"

(ix) FEATURE:
    (A) NAME/KEY: Modified-site
    (B) LOCATION: 10
    (D) OTHER INFORMATION: /note= "Xaa at position 10 is Ile,
        Gly, Val, Arg, Ser, Phe, or Leu"

(ix) FEATURE:
    (A) NAME/KEY: Modified-site
    (B) LOCATION: 11
    (D) OTHER INFORMATION: /note= "Xaa at position 11 is Thr,
        His, Gly, Gln, Arg, Pro, or Ala"

(ix) FEATURE:
    (A) NAME/KEY: Modified-site
    (B) LOCATION: 12
    (D) OTHER INFORMATION: /note= "Xaa at position 12 is His,
        Thr, Phe, Gly, Arg, Ala, or Trp"

(ix) FEATURE:
    (A) NAME/KEY: Modified-site
    (B) LOCATION: 13
    (D) OTHER INFORMATION: /note= "Xaa at position 13 is Leu,
        Gly, Arg, Thr, Ser, or Ala"

(ix) FEATURE:
    (A) NAME/KEY: Modified-site
    (B) LOCATION: 14
    (D) OTHER INFORMATION: /note= "Xaa at position 14 is Lys,
        Arg, Leu, Gln, Gly, Pro, Val, or Trp"

(ix) FEATURE:
    (A) NAME/KEY: Modified-site
    (B) LOCATION: 15
    (D) OTHER INFORMATION: /note= "Xaa at position 15 is Gln,
        Asn, Leu, Pro, Arg, or Val"

(ix) FEATURE:
    (A) NAME/KEY: Modified-site
    (B) LOCATION: 16
    (D) OTHER INFORMATION: /note= "Xaa at position 16 is Pro,
        His, Thr, Gly, Asp, Gln, Ser, Leu, or Lys"

(ix) FEATURE:
    (A) NAME/KEY: Modified-site
    (B) LOCATION: 17
    (D) OTHER INFORMATION: /note= "Xaa at position 17 is Pro,
        Asp, Gly, Ala, Arg, Leu, or Gln"
```

```
(ix) FEATURE:
    (A) NAME/KEY: Modified-site
    (B) LOCATION: 18
    (D) OTHER INFORMATION: /note= "Xaa at position 18 is Leu,
        Val, Arg, Gln, Asn, Gly, Ala, or Glu"

(ix) FEATURE:
    (A) NAME/KEY: Modified-site
    (B) LOCATION: 19
    (D) OTHER INFORMATION: /note= "Xaa at position 19 is Pro,
        Leu, Gln, Ala, Thr, or Glu"

(ix) FEATURE:
    (A) NAME/KEY: Modified-site
    (B) LOCATION: 20
    (D) OTHER INFORMATION: /note= "Xaa at position 20 is Leu,
        Val, Gly, Ser, Lys, Glu, Gln, Thr, Arg, Ala, Phe,
        Ile, or Met"

(ix) FEATURE:
    (A) NAME/KEY: Modified-site
    (B) LOCATION: 21
    (D) OTHER INFORMATION: /note= "Xaa at position 21 is Leu,
        Ala, Gly, Asn, Pro, Gln, or Val"

(ix) FEATURE:
    (A) NAME/KEY: Modified-site
    (B) LOCATION: 22
    (D) OTHER INFORMATION: /note= "Xaa at position 22 is Asp,
        Leu, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, Trp, or Ile"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 26
    (D) OTHER INFORMATION: /note= "Xaa at position 26 is Leu,
        Trp, or Arg"

(ix) FEATURE:
    (A) NAME/KEY: Modified-site
    (B) LOCATION: 27
    (D) OTHER INFORMATION: /note= "Xaa at position 27 is Asn,
        Cys, Arg, Leu, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Lys, Asn, Thr, Leu, Val, Glu,
        Phe, Tyr, Ile, or Met"

(ix) FEATURE:
    (A) NAME/KEY: Modified-site
    (B) LOCATION: 29
    (D) OTHER INFORMATION: /note= "Xaa at position 29 is Glu,
        Asn, Tyr, Leu, Phe, Asp, Ala, Cys, Gln, Arg, Thr,
        Gly, or Ser"

(ix) FEATURE:
    (A) NAME/KEY: Modified-site
    (B) LOCATION: 30
    (D) OTHER INFORMATION: /note= "Xaa at position 30 is Asp,
        Ser, Leu, Arg, Lys, Thr, Met, Trp, Glu, Asn, Gln,
        Ala, or Pro"

(ix) FEATURE:
    (A) NAME/KEY: Modified-site
    (B) LOCATION: 31
```

-continued (D) OTHER INFORMATION: /note= "Xaa at position 31 is Gln,
                Pro, Phe, Val, Met, Leu, Thr, Lys, Asp, Asn, Arg,
                Ser, Ala, Ile, Glu, His, or Trp"

(ix) FEATURE:
            (A) NAME/KEY: Modified-site
            (B) LOCATION: 32
            (D) OTHER INFORMATION: /note= "Xaa at position 32 is Asp,
                Phe, Ser, Thr, Cys, Glu, Asn, Gln, Lys, His, Ala,
                Tyr, Ile, Val, or Gly"

(ix) FEATURE:
            (A) NAME/KEY: Modified-site
            (B) LOCATION: 33
            (D) OTHER INFORMATION: /note= "Xaa at position 33 is Ile,
                Gly, Val, Ser, Arg, Pro, or His"

(ix) FEATURE:
            (A) NAME/KEY: Modified-site
            (B) LOCATION: 34
            (D) OTHER INFORMATION: /note= "Xaa at position 34 is Leu,
                Ser, Cys, Arg, Ile, His, Phe, Glu, Lys, Thr, Ala,
                Met, Val, or Asn"

(ix) FEATURE:
            (A) NAME/KEY: Modified-site
            (B) LOCATION: 35
            (D) OTHER INFORMATION: /note= "Xaa at position 35 is Met,
                Arg, Ala, Gly, Pro, Asn, His, or Asp"

(ix) FEATURE:
            (A) NAME/KEY: Modified-site
            (B) LOCATION: 36
            (D) OTHER INFORMATION: /note= "Xaa at position 36 is Glu,
                Leu, Thr, Asp, Tyr, Lys, Asn, Ser, Ala, Ile, Val,
                His, Phe, Met, or Gln"

(ix) FEATURE:
            (A) NAME/KEY: Modified-site
            (B) LOCATION: 37
            (D) OTHER INFORMATION: /note= "Xaa at position 37 is Asn,
                Arg, Met, Pro, Ser, Thr, or His"

(ix) FEATURE:
            (A) NAME/KEY: Modified-site
            (B) LOCATION: 38
            (D) OTHER INFORMATION: /note= "Xaa at position 38 is Asn,
                His, Arg, Leu, Gly, Ser, or Thr"

(ix) FEATURE:
            (A) NAME/KEY: Modified-site
            (B) LOCATION: 39
            (D) OTHER INFORMATION: /note= "Xaa at position 39 is
                Leu, Thr, Ala, Gly, Glu, Pro, Lys, Ser, or Met"

(ix) FEATURE:
            (A) NAME/KEY: Modified-site
            (B) LOCATION: 40
            (D) OTHER INFORMATION: /note= "Xaa at position 40 is Arg,
                Asp, Ile, Ser, Val, Thr, Gln, Asn, Lys, His,
                Ala, or Leu"

(ix) FEATURE:
            (A) NAME/KEY: Modified-site
            (B) LOCATION: 41
            (D) OTHER INFORMATION: /note= "Xaa at position 41 is Arg,
                Thr, Val, Ser, Leu, or Gly"

(ix) FEATURE:
            (A) NAME/KEY: Modified-site
            (B) LOCATION: 42
            (D) OTHER INFORMATION: /note= "Xaa at position 42 is Pro,
                Gly, Cys, Ser, Gln, Glu, Arg, His, Thr, Ala, Tyr,
                Phe, Leu, Val, or Lys"

```
(ix) FEATURE:
    (A) NAME/KEY: Modified-site
    (B) LOCATION: 43
    (D) OTHER INFORMATION: /note= "Xaa at position 43 is Asn
        or Gly"

(ix) FEATURE:
    (A) NAME/KEY: Modified-site
    (B) LOCATION: 44
    (D) OTHER INFORMATION: /note= "Xaa at position 44 is Leu,
        Ser, Asp, Arg, Gln, Val, or Cys"

(ix) FEATURE:
    (A) NAME/KEY: Modified-site
    (B) LOCATION: 45
    (D) OTHER INFORMATION: /note= "Xaa at position 45 is Glu,
        Tyr, His, Leu, Pro, or Arg"

(ix) FEATURE:
    (A) NAME/KEY: Modified-site
    (B) LOCATION: 46
    (D) OTHER INFORMATION: /note= "Xaa at position 46 is Ala,
        Ser, Pro, Tyr, Asn, or Thr"

(ix) FEATURE:
    (A) NAME/KEY: Modified-site
    (B) LOCATION: 47
    (D) OTHER INFORMATION: /note= "Xaa at position 47 is Phe,
        Asn, Glu, Pro, Lys, Arg, or Ser"

(ix) FEATURE:
    (A) NAME/KEY: Modified-site
    (B) LOCATION: 48
    (D) OTHER INFORMATION: /note= "Xaa at position 48 is Asn,
        His, Val, Arg, Pro, Thr, Asp, or Ile"

(ix) FEATURE:
    (A) NAME/KEY: Modified-site
    (B) LOCATION: 49
    (D) OTHER INFORMATION: /note= "Xaa at position 49 is Arg,
        Tyr, Trp, Lys, Ser, His, Pro, or Val"

(ix) FEATURE:
    (A) NAME/KEY: Modified-site
    (B) LOCATION: 50
    (D) OTHER INFORMATION: /note= "Xaa at position 50 is Ala,
        Asn, Pro, Ser, or Lys"

(ix) FEATURE:
    (A) NAME/KEY: Modified-site
    (B) LOCATION: 51
    (D) OTHER INFORMATION: /note= "Xaa at position 51 is Val,
        Thr, Pro, His, Leu, Phe, or Ser"

(ix) FEATURE:
    (A) NAME/KEY: Modified-site
    (B) LOCATION: 52
    (D) OTHER INFORMATION: /note= "Xaa at position 52 is Lys,
        Ile, Arg, Val, Asn, Glu, or Ser"

(ix) FEATURE:
    (A) NAME/KEY: Modified-site
    (B) LOCATION: 53
    (D) OTHER INFORMATION: /note= "Xaa at position 53 is Ser,
        Ala, Phe, Val, Gly, Asn, Ile, Pro, or His"

(ix) FEATURE:
    (A) NAME/KEY: Modified-site
    (B) LOCATION: 54
    (D) OTHER INFORMATION: /note= "Xaa at position 54 is Leu,
        Val, Trp, Ser, Ile, Phe, Thr, or His"

(ix) FEATURE:
    (A) NAME/KEY: Modified-site
    (B) LOCATION: 55
    (D) OTHER INFORMATION: /note= "Xaa at position 55 is Gln,
        Ala, Pro, Thr, Glu, Arg, Trp, Gly, or Leu"
```

-continued

```
(ix) FEATURE:
    (A) NAME/KEY: Modified-site
    (B) LOCATION: 56
    (D) OTHER INFORMATION: /note= "Xaa at position 56 is Asn,
        Leu, Val, Trp, Pro, or Ala"

(ix) FEATURE:
    (A) NAME/KEY: Modified-site
    (B) LOCATION: 57
    (D) OTHER INFORMATION: /note= "Xaa at position 57 is Ala,
        Met, Leu, Pro, Arg, Glu, Thr, Gln, Trp, or Asn"

(ix) FEATURE:
    (A) NAME/KEY: Modified-site
    (B) LOCATION: 58
    (D) OTHER INFORMATION: /note= "Xaa at position 58 is Ser,
        Glu, Met, Ala, His, Asn, Arg, or Asp"

(ix) FEATURE:
    (A) NAME/KEY: Modified-site
    (B) LOCATION: 59
    (D) OTHER INFORMATION: /note= "Xaa at position 59 is Ala,
        Glu, Asp, Leu, Ser, Gly, Thr, or Arg"

(ix) FEATURE:
    (A) NAME/KEY: Modified-site
    (B) LOCATION: 60
    (D) OTHER INFORMATION: /note= "Xaa at position 60 is Ile,
        Met, Thr, Pro, Arg, Gly, Ala"

(ix) FEATURE:
    (A) NAME/KEY: Modified-site
    (B) LOCATION: 61
    (D) OTHER INFORMATION: /note= "Xaa at position 61 is
        Glu, Lys, Gly, Asp, Pro, Trp, Arg, Ser, Gln,
        or Leu"

(ix) FEATURE:
    (A) NAME/KEY: Modified-site
    (B) LOCATION: 62
    (D) OTHER INFORMATION: /note= "Xaa at position 62 is Ser,
        Val, Ala, Asn, Trp, Glu, Pro, Gly, or Asp"

(ix) FEATURE:
    (A) NAME/KEY: Modified-site
    (B) LOCATION: 63
    (D) OTHER INFORMATION: /note= "Xaa at position 63 is Ile,
        Ser, Arg, Thr, or Leu"

(ix) FEATURE:
    (A) NAME/KEY: Modified-site
    (B) LOCATION: 64
    (D) OTHER INFORMATION: /note= "Xaa at position 64 is Leu,
        Ala, Ser, Glu, Phe, Gly, or Arg"

(ix) FEATURE:
    (A) NAME/KEY: Modified-site
    (B) LOCATION: 65
    (D) OTHER INFORMATION: /note= "Xaa at position 65 is Lys,
        Thr, Gly, Asn, Met, Arg, Ile, or Asp"

(ix) FEATURE:
    (A) NAME/KEY: Modified-site
    (B) LOCATION: 66
    (D) OTHER INFORMATION: /note= "Xaa at position 66 is Asn,
        Trp, Val, Gly, Thr, Leu, Glu, or Arg"

(ix) FEATURE:
    (A) NAME/KEY: Modified-site
    (B) LOCATION: 67
    (D) OTHER INFORMATION: /note= "Xaa at position 67 is Leu,
        Gln, Gly, Ala, Trp, Arg, Val, or Lys"

(ix) FEATURE:
    (A) NAME/KEY: Modified-site
    (B) LOCATION: 68
```

```
            (D) OTHER INFORMATION: /note= "Xaa at position 68 is Leu,
                Gln, Lys, Trp, Arg, Asp, Glu, Asn, His, Thr, Ser, Ala,
                Tyr, Phe, Ile, Met, or Val"

(ix) FEATURE:
            (A) NAME/KEY: Modified-site
            (B) LOCATION: 69
            (D) OTHER INFORMATION: /note= "Xaa at position 69 is Pro,
                Ala, Thr, Trp, Arg, or Met"

(ix) FEATURE:
            (A) NAME/KEY: Modified-site
            (B) LOCATION: 70
            (D) OTHER INFORMATION: /note= "Xaa at position 70 is Cys,
                Glu, Gly, Arg, Met, or Val"

(ix) FEATURE:
            (A) NAME/KEY: Modified-site
            (B) LOCATION: 71
            (D) OTHER INFORMATION: /note= "Xaa at position 71 is Leu,
                Asn, Val, or Gln"

(ix) FEATURE:
            (A) NAME/KEY: Modified-site
            (B) LOCATION: 72
            (D) OTHER INFORMATION: /note= "Xaa at position 72 is Pro,
                Cys, Arg, Ala, or Lys"

(ix) FEATURE:
            (A) NAME/KEY: Modified-site
            (B) LOCATION: 73
            (D) OTHER INFORMATION: /note= "Xaa at position 73 is Leu,
                Ser, Trp, or Gly"

(ix) FEATURE:
            (A) NAME/KEY: Modified-site
            (B) LOCATION: 74
            (D) OTHER INFORMATION: /note= "Xaa at position 74 is Ala,
                Lys, Arg, Val, or Trp"

(ix) FEATURE:
            (A) NAME/KEY: Modified-site
            (B) LOCATION: 75
            (D) OTHER INFORMATION: /note= "Xaa at position 75 is Thr,
                Asp, Cys, Leu, Val, Glu, His, Asn, or Ser"

(ix) FEATURE:
            (A) NAME/KEY: Modified-site
            (B) LOCATION: 76
            (D) OTHER INFORMATION: /note= "Xaa at position 76 is Ala,
                Pro, Ser, Thr, Gly, Asp, Ile, or Met"

(ix) FEATURE:
            (A) NAME/KEY: Modified-site
            (B) LOCATION: 77
            (D) OTHER INFORMATION: /note= "Xaa at position 77 is Ala,
                Pro, Ser, Thr, Phe, Leu, Asp, or His"

(ix) FEATURE:
            (A) NAME/KEY: Modified-site
            (B) LOCATION: 78
            (D) OTHER INFORMATION: /note= "Xaa at position 78 is Pro,
                Phe, Arg, Ser, Lys, His, Ala, Gly, Ile, or Leu"

(ix) FEATURE:
            (A) NAME/KEY: Modified-site
            (B) LOCATION: 79
            (D) OTHER INFORMATION: /note= "Xaa at position 79 is Thr,
                Asp, Ser, Asn, Pro, Ala, Leu, or Arg"

(ix) FEATURE:
            (A) NAME/KEY: Modified-site
            (B) LOCATION: 80
            (D) OTHER INFORMATION: /note= "Xaa at position 80 is Arg,
                Ile, Ser, Glu, Leu, Val, Gln, Lys, His, Ala, or Pro"

(ix) FEATURE:
            (A) NAME/KEY: Modified-site
            (B) LOCATION: 81
```

(D) OTHER INFORMATION: /note= "Xaa at position 81 is His,
              Gln, Pro, Arg, Val, Leu, Gly, Thr, Asn, Lys, Ser,
              Ala, Trp, Phe, Ile, or Tyr"

(ix) FEATURE:
          (A) NAME/KEY: Modified-site
          (B) LOCATION: 82
          (D) OTHER INFORMATION: /note= "Xaa at position 82 is Pro,
              Lys, Tyr, Gly, Ile, or Thr"

(ix) FEATURE:
          (A) NAME/KEY: Modified-site
          (B) LOCATION: 83
          (D) OTHER INFORMATION: /note= "Xaa at position 83 is Ile,
              Val, Lys, Ala, or Asn"

(ix) FEATURE:
          (A) NAME/KEY: Modified-site
          (B) LOCATION: 84
          (D) OTHER INFORMATION: /note= "Xaa at position 84 is His,
              Ile, Asn, Leu, Asp, Ala, Thr, Glu, Gln, Ser,
              Phe, Met, Val, Lys, Arg, Tyr, or Pro"

(ix) FEATURE:
          (A) NAME/KEY: Modified-site
          (B) LOCATION: 85
          (D) OTHER INFORMATION: /note= "Xaa at position 85 is
              Ile, Leu, Arg, Asp, Val, Pro, Gln, Gly, Ser,
              Phe, or His"

(ix) FEATURE:
          (A) NAME/KEY: Modified-site
          (B) LOCATION: 86
          (D) OTHER INFORMATION: /note= "Xaa at position 86 is
              Lys, Tyr, Leu, His, Arg, Ile, Ser, Gln, or Pro"

(ix) FEATURE:
          (A) NAME/KEY: Modified-site
          (B) LOCATION: 87
          (D) OTHER INFORMATION: /note= "Xaa at position 87 is
              Asp, Pro, Met, Lys, His, Thr, Val, Tyr, Glu, Asn,
              Ser, Ala, Gly, Ile, Leu, or Gln"

(ix) FEATURE:
          (A) NAME/KEY: Modified-site
          (B) LOCATION: 88
          (D) OTHER INFORMATION: /note= "Xaa at position 88 Gly,
              Leu, Glu, Lys, Ser, Tyr, or Pro"

(ix) FEATURE:
          (A) NAME/KEY: Modified-site
          (B) LOCATION: 89
          (D) OTHER INFORMATION: /note= "Xaa at position 89 is Asp
              or Ser"

(ix) FEATURE:
          (A) NAME/KEY: Modified-site
          (B) LOCATION: 90
          (D) OTHER INFORMATION: /note= "Xaa at position 90 is
              Trp, Val, Cys, Tyr, Thr, Met, Pro, Leu, Gln, Lys,
              Ala, Phe, or Gly"

(ix) FEATURE:
          (A) NAME/KEY: Modified-site
          (B) LOCATION: 91
          (D) OTHER INFORMATION: /note= "Xaa at position 91 is
              Asn, Pro, Ala, Phe, Ser, Trp, Gln, Tyr, Leu, Lys,
              Ile, Asp, or His"

(ix) FEATURE:
          (A) NAME/KEY: Modified-site
          (B) LOCATION: 92
          (D) OTHER INFORMATION: /note= "Xaa at position 92 is Glu,
              Ser, Ala, Lys, Thr, Ile, Gly, or Pro"

```
(ix) FEATURE:
    (A) NAME/KEY: Modified-site
    (B) LOCATION: 94
    (D) OTHER INFORMATION: /note= "Xaa at position 94 is Arg,
        Lys, Asp, Leu, Thr, Ile, Gln, His, Ser, Ala, or Pro"

(ix) FEATURE:
    (A) NAME/KEY: Modified-site
    (B) LOCATION: 95
    (D) OTHER INFORMATION: /note= "Xaa at position 95 is Arg,
        Thr, Pro, Glu, Tyr, Leu, Ser, or Gly"

(ix) FEATURE:
    (A) NAME/KEY: Modified-site
    (B) LOCATION: 96
    (D) OTHER INFORMATION: /note= "Xaa at position 96 is Lys,
        Asn, Thr, Leu, Gln, Arg, His, Glu, Ser, Ala,
        or Trp"

(ix) FEATURE:
    (A) NAME/KEY: Modified-site
    (B) LOCATION: 97
    (D) OTHER INFORMATION: /note= "Xaa at position 97 is Leu,
        Ile, Arg, Asp, or Met"

(ix) FEATURE:
    (A) NAME/KEY: Modified-site
    (B) LOCATION: 98
    (D) OTHER INFORMATION: /note= "Xaa at position 98 is Thr,
        Val, Gln, Tyr, Glu, His, Ser, or Phe"

(ix) FEATURE:
    (A) NAME/KEY: Modified-site
    (B) LOCATION: 99
    (D) OTHER INFORMATION: /note= "Xaa at position 99 is Phe,
        Ser, Cys, His, Gly, Trp, Tyr, Asp, Lys, Leu, Ile,
        Val, or Asn"

(ix) FEATURE:
    (A) NAME/KEY: Modified-site
    (B) LOCATION: 100
    (D) OTHER INFORMATION: /note= "Xaa at position 100 is Tyr,
        Cys, His, Ser, Trp, Arg, or Leu"

(ix) FEATURE:
    (A) NAME/KEY: Modified-site
    (B) LOCATION: 101
    (D) OTHER INFORMATION: /note= "Xaa at position 101 is Leu,
        Asn, Val, Pro, Arg, Ala, His, Thr, Trp, or Met"

(ix) FEATURE:
    (A) NAME/KEY: Modified-site
    (B) LOCATION: 102
    (D) OTHER INFORMATION: /note= "Xaa at position 102 is
        Lys, Leu, Pro, Thr, Met, Asp, Val, Glu, Arg, Trp,
        Ser, Asn, His, Ala, Tyr, Phe, Gln, or Ile"

(ix) FEATURE:
    (A) NAME/KEY: Modified-site
    (B) LOCATION: 103
    (D) OTHER INFORMATION: /note= "Xaa at position 103 is Thr,
        Ser, Asn, Ile, Trp, Lys, or Pro"

(ix) FEATURE:
    (A) NAME/KEY: Modified-site
    (B) LOCATION: 104
    (D) OTHER INFORMATION: /note= "Xaa at position 104 is Leu,
        Ser, Pro, Ala, Glu, Cys, Asp, or Tyr"

(ix) FEATURE:
    (A) NAME/KEY: Modified-site
    (B) LOCATION: 105
    (D) OTHER INFORMATION: /note= "Xaa at position 105 is Glu,
        Ser, Lys, Pro, Leu, Thr, Tyr, or Arg"
```

```
    (ix) FEATURE:
         (A) NAME/KEY: Modified-site
         (B) LOCATION: 106
         (D) OTHER INFORMATION: /note= "Xaa at position 106 is Asn,
             Ala, Pro, Leu, His, Val or Gln"

(ix) FEATURE:
         (A) NAME/KEY: Modified-site
         (B) LOCATION: 107
         (D) OTHER INFORMATION: /note= "Xaa at position 107 is Ala,
             Ser, Ile, Asn, Pro, Lys, Asp, or Gly"

(ix) FEATURE:
         (A) NAME/KEY: Modified-site
         (B) LOCATION: 108
         (D) OTHER INFORMATION: /note= "Xaa at position 108 is
             Gln, Ser, Met, Trp, Arg, Phe, Pro, His, Ile, Tyr,
             or Cys"

(ix) FEATURE:
         (A) NAME/KEY: Modified-site
         (B) LOCATION: 109
         (D) OTHER INFORMATION: /note= "Xaa at position 109 is Ala,
             Met, Glu, His, Ser, Pro, Tyr, or Leu"

(xi) SEQUENCE DESCRIPTION: SEQ ID NO:19:

Asn Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Asn Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Phe Xaa Xaa Xaa
                85                  90                  95

Xaa Xaa Xaa Xaa Xaa Xaa Xaa Xaa Xaa Xaa Xaa Xaa Xaa Gln Gln
            100                 105                 110

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "Met- or Met-Ala- may or may
             not precede the amino acid in position 1"

(ix) FEATURE:
         (A) NAME/KEY: Modified-site
         (B) LOCATION: 3
         (D) OTHER INFORMATION: /note= "Xaa at position 3 is Ser,
             Gly, Asp, Met, or Gln"

(ix) FEATURE:
         (A) NAME/KEY: Modified-site
         (B) LOCATION: 4
         (D) OTHER INFORMATION: /note= "Xaa at position 4 is Asn,
             His, Leu, Ile, Phe, Arg, or Gln"
```

-continued

```
(ix) FEATURE:
     (A) NAME/KEY: Modified-site
     (B) LOCATION: 5
     (D) OTHER INFORMATION: /note= "Xaa at position 5 is Met,
         Phe, Ile, Arg, or Ala"

(ix) FEATURE:
     (A) NAME/KEY: Modified-site
     (B) LOCATION: 6
     (D) OTHER INFORMATION: /note= "Xaa at position 6 is Ile or
         Pro"

(ix) FEATURE:
     (A) NAME/KEY: Modified-site
     (B) LOCATION: 7
     (D) OTHER INFORMATION: /note= "Xaa at position 7 is Asp or
         Glu"

(ix) FEATURE:
     (A) NAME/KEY: Modified-site
     (B) LOCATION: 9
     (D) OTHER INFORMATION: /note= "Xaa at position 9 is Ile,
         Val, Ala, Leu, or Gly"

(ix) FEATURE:
     (A) NAME/KEY: Modified-site
     (B) LOCATION: 10
     (D) OTHER INFORMATION: /note= "Xaa at position 10 is Ile,
         Val, Phe, or Leu"

(ix) FEATURE:
     (A) NAME/KEY: Modified-site
     (B) LOCATION: 11
     (D) OTHER INFORMATION: /note= "Xaa at position 11 is Thr,
         His, Gly, Gln, Arg, Pro, or Ala"

(ix) FEATURE:
     (A) NAME/KEY: Modified-site
     (B) LOCATION: 12
     (D) OTHER INFORMATION: /note= "Xaa at position 12 is His,
         Phe, Gly, Arg, or Ala"

(ix) FEATURE:
     (A) NAME/KEY: Modified-site
     (B) LOCATION: 14
     (D) OTHER INFORMATION: /note= "Xaa at position 14 is Lys,
         Leu, Gln, Gly, Pro, or Val"

(ix) FEATURE:
     (A) NAME/KEY: Modified-site
     (B) LOCATION: 15
     (D) OTHER INFORMATION: /note= "Xaa at position 15 is Gln,
         Asn, Leu, Arg, or Val"

(ix) FEATURE:
     (A) NAME/KEY: Modified-site
     (B) LOCATION: 16
     (D) OTHER INFORMATION: /note= "Xaa at position 16 is Pro,
         His, Thr, Gly, or Gln"

(ix) FEATURE:
     (A) NAME/KEY: Modified-site
     (B) LOCATION: 17
     (D) OTHER INFORMATION: /note= "Xaa at position 17 is Pro,
         Asp, Gly, Ala, Arg, Leu, or Gln"

(ix) FEATURE:
     (A) NAME/KEY: Modified-site
     (B) LOCATION: 18
     (D) OTHER INFORMATION: /note= "Xaa at position 18 is Leu,
         Arg, Gln, Asn, Gly, Ala or Glu"

(ix) FEATURE:
     (A) NAME/KEY: Modified-site
     (B) LOCATION: 19
     (D) OTHER INFORMATION: /note= "Xaa at poisiton 19 is Pro,
         Leu, Gln, Ala, or Glu"
```

```
(ix) FEATURE:
    (A) NAME/KEY: Modified-site
    (B) LOCATION: 20
    (D) OTHER INFORMATION: /note= "Xaa at positon 20 is Leu,
        Val, Gly, Ser, Lys, Ala, Arg, Gln, Glu, Ile, Phe,
        Thr, or Met"

(ix) FEATURE:
    (A) NAME/KEY: Modified-site
    (B) LOCATION: 21
    (D) OTHER INFORMATION: /note= "Xaa at position 21 is Leu,
        Ala, Asn, Pro, Gln, or Val"

(ix) FEATURE:
    (A) NAME/KEY: Modified-site
    (B) LOCATION: 22
    (D) OTHER INFORMATION: /note= "Xaa at position 22 is Asp
        or Leu"

(ix) FEATURE:
    (A) NAME/KEY: Modified-site
    (B) LOCATION: 23
    (D) OTHER INFORMATION: /note= "Xaa at position 23 is Phe,
        Ser, Pro, Trp, or Ile"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 27
    (D) OTHER INFORMATION: /note= "Xaa at position 27 is Asn,
        Cys, Arg, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Asn, Ile, Leu, Met, Tyr, or Arg"

(ix) FEATURE:
    (A) NAME/KEY: Modified-site
    (B) LOCATION: 30
    (C) OTHER INFORMATION:  /note= "Xaa at position 30 is Asp
        or Glu"

(ix) FEATURE:
    (A) NAME/KEY: Modified-site
    (B) LOCATION: 31
    (D) OTHER INFORMATION: /note= "Xaa at position 31 is Gln,
        Val, Met, Leu, Thr, Lys, Ala, Asn, Glu, Ser, or Trp"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Cys, Ala, Asn, Gln, Glu, His, Ile,
        Lys, Tyr, Val, or Gly"

(ix) FEATURE:
    (A) NAME/KEY: Modified-site
    (B) LOCATION: 33
    (D) OTHER INFORMATION: /note= "Xaa at position 33 is Ile,
        Val, or His"

(ix) FEATURE:
    (A) NAME/KEY: Modified-site
    (B) LOCATION: 35
    (D) OTHER INFORMATION: /note= "Xaa at position 35 is Met,
        Asn, or Asp"
```

```
(ix) FEATURE:
      (A) NAME/KEY: Modified-site
      (B) LOCATION: 36
      (D) OTHER INFORMATION: /note= "Xaa at position 36 is Glu,
          Thr, Ala, Asn, Ser, or Asp"

(ix) FEATURE:
      (A) NAME/KEY: Modified-site
      (B) LOCATION: 37
      (D) OTHER INFORMATION: /note= "Xaa at position 37 is Asn,
          Arg, Met, Pro, Ser, Thr, or His"

(ix) FEATURE:
      (A) NAME/KEY: Modified-site
      (B) LOCATION: 38
      (D) OTHER INFORMATION: /note= "Xaa at position 38 is Asn
          or Gly"

(ix) FEATURE:
      (A) NAME/KEY: Modified-site
      (B) LOCATION: 39
      (D) OTHER INFORMATION: /note= "Xaa at position 39 is Leu,
          Met, or Phe"

(ix) FEATURE:
      (A) NAME/KEY: Modified-site
      (B) LOCATION: 40
      (D) OTHER INFORMATION: /note= "Xaa at position 40 is Arg,
          Ala, or Ser"

(ix) FEATURE:
      (A) NAME/KEY: Modified-site
      (B) LOCATION: 41
      (D) OTHER INFORMATION: /note= "Xaa at position 41 is Arg,
          Thr, Val, Leu, or Gly"

(ix) FEATURE:
      (A) NAME/KEY: Modified-site
      (B) LOCATION: 42
      (D) OTHER INFORMATION: /note= "Xaa at position 42 is Pro,
          Gly, Cys, Ser, Gln, Ala, Arg, Asn, Glu, His, Leu,
          Thr, Val, or Lys"

(ix) FEATURE:
      (A) NAME/KEY: Modified-site
      (B) LOCATION: 45
      (D) OTHER INFORMATION: /note= "Xaa at position 45 is Glu,
          Tyr, His, Leu, or Arg"

(ix) FEATURE:
      (A) NAME/KEY: Modified-site
      (B) LOCATION: 46
      (D) OTHER INFORMATION: /note= "Xaa at position 46 is Ala,
          Ser, Asn, or Thr"

(ix) FEATURE:
      (A) NAME/KEY: Modified-site
      (B) LOCATION: 47
      (D) OTHER INFORMATION: /note= "Xaa at position 47 is Phe
          or Ser"

(ix) FEATURE:
      (A) NAME/KEY: Modified-site
      (B) LOCATION: 48
      (D) OTHER INFORMATION: /note= "Xaa at position 48 is Asn,
          Val, Pro, Thr, or Ile"

(ix) FEATURE:
      (A) NAME/KEY: Modified-site
      (B) LOCATION: 49
      (D) OTHER INFORMATION: /note= "Xaa at position 49 is Arg,
          Tyr, Lys, Ser, His, or Val"

(ix) FEATURE:
      (A) NAME/KEY: Modified-site
      (B) LOCATION: 50
      (D) OTHER INFORMATION: /note= "Xaa at position 50 is Ala
          or Asn"
```

```
(ix) FEATURE:
    (A) NAME/KEY: Modified-site
    (B) LOCATION: 51
    (D) OTHER INFORMATION: /note= "Xaa at position 51 is Val,
        Thr, Leu, or Ser"

(ix) FEATURE:
    (A) NAME/KEY: Modified-site
    (B) LOCATION: 52
    (D) OTHER INFORMATION: /note= "Xaa at position 52 is Lys,
        Ile, Arg, Val, Asn, Glu, or Ser"

(ix) FEATURE:
    (A) NAME/KEY: Modified-site
    (B) LOCATION: 53
    (D) OTHER INFORMATION: /note= "Xaa at position 53 is Ser,
        Phe, Val, Gly, Asn, Ile, or His"

(ix) FEATURE:
    (A) NAME/KEY: Modified-site
    (B) LOCATION: 54
    (D) OTHER INFORMATION: /note= "Xaa at position 54 is Leu,
        Val, Ile, Phe, or His"

(ix) FEATURE:
    (A) NAME/KEY: Modified-site
    (B) LOCATION: 55
    (D) OTHER INFORMATION: /note= "Xaa at position 55 is Gln,
        Ala, Pro, Thr, Glu, Arg, or Gly"

(ix) FEATURE:
    (A) NAME/KEY: Modified-site
    (B) LOCATION: 56
    (D) OTHER INFORMATION: /note= "Xaa at position 56 is Asn
        or Pro"

(ix) FEATURE:
    (A) NAME/KEY: Modified-site
    (B) LOCATION: 57
    (D) OTHER INFORMATION: /note= "Xaa at position 57 is Ala,
        Met, Pro, Arg, Glu, Thr, or Gln"

(ix) FEATURE:
    (A) NAME/KEY: Modified-site
    (B) LOCATION: 58
    (D) OTHER INFORMATION: /note= "Xaa at position 58 is Ser,
        Glu, Met, Ala, His, Asn, Arg, or Asp"

(ix) FEATURE:
    (A) NAME/KEY: Modified-site
    (B) LOCATION: 59
    (D) OTHER INFORMATION: /note= "Xaa at position 59 is Ala,
        Glu, Asp, Leu, Ser, Gly, Thr, Arg, or Pro"

(ix) FEATURE:
    (A) NAME/KEY: Modified-site
    (B) LOCATION: 60
    (D) OTHER INFORMATION: /note= "Xaa at position 60 is Ile
        or Met"

(ix) FEATURE:
    (A) NAME/KEY: Modified-site
    (B) LOCATION: 61
    (D) OTHER INFORMATION: /note= "Xaa at position 61 is Glu,
        Gly, Asp, Ser, or Gln"

(ix) FEATURE:
    (A) NAME/KEY: Modified-site
    (B) LOCATION: 62
    (D) OTHER INFORMATION: /note= "Xaa at position 62 is Ser,
        Val, Ala, Asn, Glu, Pro, Gly, or Asp"

(ix) FEATURE:
    (A) NAME/KEY: Modified-site
    (B) LOCATION: 63
    (D) OTHER INFORMATION: /note= "Xaa at position 63 is Ile,
        Ser, or Leu"
```

```
(ix) FEATURE:
    (A) NAME/KEY: Modified-site
    (B) LOCATION: 65
    (D) OTHER INFORMATION: /note= "Xaa at position 65 is Lys,
        Thr, Gly, Asn, Met, Arg, Ile, or Asp"

(ix) FEATURE:
    (A) NAME/KEY: Modified-site
    (B) LOCATION: 66
    (D) OTHER INFORMATION: /note= "Xaa at position 66 is Asn,
        Val, Gly, Thr, Leu, Glu, or Arg"

(ix) FEATURE:
    (A) NAME/KEY: Modified-site
    (B) LOCATION: 67
    (D) OTHER INFORMATION: /note= "Xaa at position 67 is Leu
        or Val"

(ix) FEATURE:
    (A) NAME/KEY: Modified-site
    (B) LOCATION: 68
    (D) OTHER INFORMATION: /note= "Xaa at position 68 is Leu,
        Gln, Trp, Arg, Asp, Ala, Asn, Glu, His, Met, Phe,
        Ser, Thr, Tyr, or Val"

(ix) FEATURE:
    (A) NAME/KEY: Modified-site
    (B) LOCATION: 69
    (D) OTHER INFORMATION: /note= "Xaa at position 69 is Pro,
        Ala, Thr, Trp, or Met"

(ix) FEATURE:
    (A) NAME/KEY: Modified-site
    (B) LOCATION: 71
    (D) OTHER INFORMATION: /note= "Xaa at position 71 is Leu
        or Val"

(ix) FEATURE:
    (A) NAME/KEY: Modified-site
    (B) LOCATION: 73
    (D) OTHER INFORMATION: /note= "Xaa at position 73 is Leu
        or Ser"

(ix) FEATURE:
    (A) NAME/KEY: Modified-site
    (B) LOCATION: 74
    (D) OTHER INFORMATION: /note= "Xaa at position 74 is Ala,
        Arg, or Trp"

(ix) FEATURE:
    (A) NAME/KEY: Modified-site
    (B) LOCATION: 75
    (D) OTHER INFORMATION: /note= "Xaa at position 75 is Thr,
        Asp, Glu, His, Asn, or Ser"

(ix) FEATURE:
    (A) NAME/KEY: Modified-site
    (B) LOCATION: 76
    (D) OTHER INFORMATION: /note= "Xaa at position 76 is Ala,
        Asp, or Met"

(ix) FEATURE:
    (A) NAME/KEY: Modified-site
    (B) LOCATION: 77
    (D) OTHER INFORMATION: /note= "Xaa at position 77 is Ala,
        Pro, Ser, Thr, Phe, Leu, or Asp"

(ix) FEATURE:
    (A) NAME/KEY: Modified-site
    (B) LOCATION: 78
    (D) OTHER INFORMATION: /note= "Xaa at position 78 is Pro
        or Ser"

(ix) FEATURE:
    (A) NAME/KEY: Modified-site
    (B) LOCATION: 79
    (D) OTHER INFORMATION: /note= "Xaa at position 79 is Thr,
        Asp, Ser, Pro, Ala, Leu, or Arg"
```

-continued (ix) FEATURE:
 (A) NAME/KEY: Modified-site
 (B) LOCATION: 81
 (D) OTHER INFORMATION: /note= "Xaa at position 81 is His,
  Pro, Arg, Val, Leu, Gly, Asn, Ile, Phe, Ser, or Thr"

(ix) FEATURE:
 (A) NAME/KEY: Modified-site
 (B) LOCATION: 82
 (D) OTHER INFORMATION: /note= "Xaa at position 82 is Pro
  or Tyr"

(ix) FEATURE:
 (A) NAME/KEY: Modified-site
 (B) LOCATION: 83
 (D) OTHER INFORMATION: /note= "Xaa at position 83 is Ile,
  Val, or Ala"

(ix) FEATURE:
 (A) NAME/KEY: Modified-site
 (B) LOCATION: 84
 (D) OTHER INFORMATION: /note= "Xaa at position 84 is His,
  Ile, Asn, Leu, Asp, Ala, Thr, Arg, Gln, Glu, Lys,
  Met, Ser, Tyr, Val, or Pro"

(ix) FEATURE:
 (A) NAME/KEY: Modified-site
 (B) LOCATION: 85
 (D) OTHER INFORMATION: /note= "Xaa at position 85 is Ile,
  Leu, Val, or Phe"

(ix) FEATURE:
 (A) NAME/KEY: Modified-site
 (B) LOCATION: 86
 (D) OTHER INFORMATION: /note= "Xaa at position 86 is Lys,
  Leu, His, Arg, Ile, Gln, Pro, or Ser"

(ix) FEATURE:
 (A) NAME/KEY: Modified-site
 (B) LOCATION: 87
 (D) OTHER INFORMATION: /note= "Xaa at position 87 is Asp,
  Pro, Met, Lys, His, Thr, Val, Asn, Ile, Leu, or Tyr"

(ix) FEATURE:
 (A) NAME/KEY: Modified-site
 (B) LOCATION: 88
 (D) OTHER INFORMATION: /note= "Xaa at position 88 is Gly,
  Glu, Lys, or Ser"

(ix) FEATURE:
 (A) NAME/KEY: Modified-site
 (B) LOCATION: 90
 (D) OTHER INFORMATION: /note= "Xaa at position 90 is Trp,
  Val, Tyr, Met, or Leu"

(ix) FEATURE:
 (A) NAME/KEY: Modified-site
 (B) LOCATION: 91
 (D) OTHER INFORMATION: /note=
  "Xaa at position 91 is Asn, Pro, Ala, Phe, Ser,
  Trp, Gln, Tyr, Leu, Lys, Ile, Asp, or His"

(ix) FEATURE:
 (A) NAME/KEY: Modified-site
 (B) LOCATION: 92
 (D) OTHER INFORMATION: /note= "Xaa at position 92 is Glu,
  Ser, Ala, or Gly"

(ix) FEATURE:
 (A) NAME/KEY: Modified-site
 (B) LOCATION: 94
 (D) OTHER INFORMATION: /note= "Xaa at position 94 is Arg,
  Ala, Gln, Ser, or Lys"

(ix) FEATURE:
   (A) NAME/KEY: Modified-site
   (B) LOCATION: 95
   (D) OTHER INFORMATION: /note= "Xaa at position 95 Arg,
        Thr, Glu, Leu, Ser, or Gly"

(ix) FEATURE:
   (A) NAME/KEY: Modified-site
   (B) LOCATION: 98
   (D) OTHER INFORMATION: /note= "Xaa at position 98 is Thr,
        Val, Gln, Glu, His, or Ser"

(ix) FEATURE:
   (A) NAME/KEY: Modified-site
   (B) LOCATION: 100
   (D) OTHER INFORMATION: /note= "Xaa at position 100 is Tyr
        or Trp"

(ix) FEATURE:
   (A) NAME/KEY: Modified-site
   (B) LOCATION: 101
   (D) OTHER INFORMATION: /note= "Xaa at position 101 is Leu
        or Ala"

(ix) FEATURE:
   (A) NAME/KEY: Modified-site
   (B) LOCATION: 102
   (D) OTHER INFORMATION: /note= "Xaa at position 102 is Lys,
        Thr, Met, Val, Trp, Ser, Leu, Ala, Asn, Gln, His,
        Met, Phe, Tyr, or Ile"

(ix) FEATURE:
   (A) NAME/KEY: Modified-site
   (B) LOCATION: 103
   (D) OTHER INFORMATION: /note= "Xaa at position 103 is Thr,
        Ser, or Asn"

(ix) FEATURE:
   (A) NAME/KEY: Modified-site
   (B) LOCATION: 105
   (D) OTHER INFORMATION: /note= "Xaa at position 105 is Glu,
        Ser, Pro, Leu, Thr, or Tyr"

(ix) FEATURE:
   (A) NAME/KEY: Modified-site
   (B) LOCATION: 106
   (D) OTHER INFORMATION: /note= "Xaa at position 106 is Asn,
        Pro, Leu, His, Val, or Gln"

(ix) FEATURE:
   (A) NAME/KEY: Modified-site
   (B) LOCATION: 107
   (D) OTHER INFORMATION: /note= "Xaa at position 107 is Ala,
        Ser, Ile, Asn, Pro, Lys, Asp, or Gly"

(ix) FEATURE:
   (A) NAME/KEY: Modified-site
   (B) LOCATION: 108
   (D) OTHER INFORMATION: /note=
        "Xaa at position 108 is Gln, Ser, Met, Trp, Arg, Phe,
        Pro, His, Ile, Tyr, or Cys"

(ix) FEATURE:
   (A) NAME/KEY: Modified-site
   (B) LOCATION: 109
   (D) OTHER INFORMATION: /note= "Xaa at position 109 is Ala,
        Met, Glu, His, Ser, Pro, Tyr, or Leu"

(xi) SEQUENCE DESCRIPTION: SEQ ID NO:20:

```
Asn Cys Xaa Xaa Xaa Xaa Xaa Glu Xaa Xaa Xaa Xaa Leu Xaa Xaa Xaa
1               5                   10                  15

Xaa Xaa Xaa Xaa Xaa Xaa Xaa Xaa Asn Leu Xaa Xaa Glu Xaa Xaa Xaa
            20                  25                  30

Xaa Leu Xaa Xaa Xaa Xaa Xaa Xaa Xaa Xaa Asn Leu Xaa Xaa Xaa Xaa
        35                  40                  45
```

```
Xaa Xaa Xaa Xaa Xaa Xaa Xaa Xaa Xaa Xaa Xaa Xaa Xaa Xaa Leu
 50                  55                  60

Xaa Xaa Xaa Xaa Xaa Cys Xaa Pro Xaa Xaa Xaa Xaa Xaa Xaa Arg
 65                  70                  75                  80

Xaa Xaa Xaa Xaa Xaa Xaa Xaa Asp Xaa Xaa Xaa Phe Xaa Xaa Lys
             85                  90                  95

Leu Xaa Phe Xaa Xaa Xaa Xaa Leu Xaa Xaa Xaa Xaa Xaa Gln Gln
            100                 105                 110
```

(2) INFORMATION FOR SEQ ID NO:21:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, Met, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 5
        (D) OTHER INFORMATION: /note= "Xaa at position 5 is Met
            or Ile"

(ix) FEATURE:
        (A) NAME/KEY: Modified-site
        (B) LOCATION: 7
        (C) OTHER INFORMATION: /note= "Xaa at position 7 is Asp or
            Glu"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 10
        (D) OTHER INFORMATION: /note= "Xaa at position 10 is Ile,
            Val, or Leu"

(ix) FEATURE:
        (A) NAME/KEY: Modified-site
        (B) LOCATION: 11
        (D) OTHER INFORMATION: /note= "Xaa at position 11 is Thr,
            His, Gln, or Ala"

(ix) FEATURE:
        (A) NAME/KEY: Modified-site
        (B) LOCATION: 12
        (D) OTHER INFORMATION: /note= "Xaa at position 12 is His
            or Ala"

(ix) FEATURE:
      (A) NAME/KEY: Modified-site
      (B) LOCATION: 15
      (D) OTHER INFORMATION: /note= "Xaa at position 15 is Gln,
          Asn, or Val"

(ix) FEATURE:
      (A) NAME/KEY: Modified-site
      (B) LOCATION: 16
      (D) OTHER INFORMATION: /note= "Xaa at position 16 is Pro,
          Gly, or Gln"

(ix) FEATURE:
      (A) NAME/KEY: Modified-site
      (B) LOCATION: 17
      (D) OTHER INFORMATION: /note= "Xaa at position 17 is Pro,
          Asp, Gly, or Gln"

(ix) FEATURE:
      (A) NAME/KEY: Modified-site
      (B) LOCATION: 18
      (D) OTHER INFORMATION: /note= "Xaa at position 18 is Leu,
          Arg, Gln, Asn, Gly, Ala, or Glu"

(ix) FEATURE:
      (A) NAME/KEY: Modified-site
      (B) LOCATION: 19
      (D) OTHER INFORMATION: /note= "Xaa at position 19 is Pro
          or Glu"

(ix) FEATURE:
      (A) NAME/KEY: Modified-site
      (B) LOCATION: 20
      (D) OTHER INFORMATION: /note= "Xaa at position 20 is Leu,
          Val, Gly, Ser, Lys, Ala, Arg, Gln, Glu, Ile, Phe,
          Thr, or Met"

(ix) FEATURE:
      (A) NAME/KEY: Modified-site
      (B) LOCATION: 21
      (D) OTHER INFORMATION: /note= "Xaa at position 21 is Leu,
          Ala, Asn, Pro, Gln, or Val"

(ix) FEATURE:
      (A) NAME/KEY: Modified-site
      (B) LOCATION: 23
      (D) OTHER INFORMATION: /note= "Xaa at position 23 is Phe,
          Ser, Pro, or Trp"

(ix) FEATURE:
      (A) NAME/KEY: Modified-site
      (B) LOCATION: 24
      (D) OTHER INFORMATION: /note= "Xaa at position 24 is Asn
          or Ala"

(ix) FEATURE:
      (A) NAME/KEY: Modified-site
      (B) LOCATION: 28
      (D) OTHER INFORMATION: /note= "Xaa at position 28 is Gly,
          Asp, Ser, Cys, Ala, Asn, Ile, Leu, Met, Tyr, or Arg"

(ix) FEATURE:
      (A) NAME/KEY: Modified-site
      (B) LOCATION: 30
      (D) OTHER INFORMATION: /note= "Xaa at position 30 is Asp
          or Glu"

(ix) FEATURE:
      (A) NAME/KEY: Modified-site
      (B) LOCATION: 31
      (D) OTHER INFORMATION: /note= "Xaa at position 31 is Gln,
          Val, Met, Leu, Thr, Ala, Asn, Glu, Ser, or Lys"

(ix) FEATURE:
      (A) NAME/KEY: Modified-site
      (B) LOCATION: 32

```
      (D) OTHER INFORMATION: /note= "Xaa at position 32 is Asp,
          Phe, Ser, Thr, Ala, Asn, Gln, Glu, His, Ile, Lys,
          Tyr, Val, or Cys"

(ix) FEATURE:
      (A) NAME/KEY: Modified-site
      (B) LOCATION: 36
      (D) OTHER INFORMATION: /note= "Xaa at position 36 is Glu,
          Ala, Asn, Ser, or Asp"

(ix) FEATURE:
      (A) NAME/KEY: Modified-site
      (B) LOCATION: 37
      (D) OTHER INFORMATION: /note= "Xaa at position 37 is Asn,
          Arg, Met, Pro, Ser, Thr, or His"

(ix) FEATURE:
      (A) NAME/KEY: Modified-site
      (B) LOCATION: 40
      (D) OTHER INFORMATION: /note= "Xaa at position 40 is Arg
          or Ala"

(ix) FEATURE:
      (A) NAME/KEY: Modified-site
      (B) LOCATION: 41
      (D) OTHER INFORMATION: /note= "Xaa at position 41 is Arg,
          Thr, Val, Leu, or Gly"

(ix) FEATURE:
      (A) NAME/KEY: Modified-site
      (B) LOCATION: 42
      (D) OTHER INFORMATION: /note= "Xaa at position 42 is Pro,
          Gly, Ser, Gln, Ala, Arg, Asn, Glu, Leu, Thr, Val,
          or Lys"

(ix) FEATURE:
      (A) NAME/KEY: Modified-site
      (B) LOCATION: 46
      (D) OTHER INFORMATION: /note= "Xaa at position 46 is Ala
          or Ser"

(ix) FEATURE:
      (A) NAME/KEY: Modified-site
      (B) LOCATION: 48
      (D) OTHER INFORMATION: /note= "Xaa at position 48 is Asn,
          Pro,  Thr, or Ile"

(ix) FEATURE:
      (A) NAME/KEY: Modified-site
      (B) LOCATION: 49
      (D) OTHER INFORMATION: /note= "Xaa at position 49 is Arg
          or Lys"

(ix) FEATURE:
      (A) NAME/KEY: Modified-site
      (B) LOCATION: 50
      (D) OTHER INFORMATION: /note= "Xaa at position 50 is Ala
          or Asn"

(ix) FEATURE:
      (A) NAME/KEY: Modified-site
      (B) LOCATION: 51
      (D) OTHER INFORMATION: /note= "Xaa at position 51 is Val
          or Thr"

(ix) FEATURE:
      (A) NAME/KEY: Modified-site
      (B) LOCATION: 52
      (D) OTHER INFORMATION: /note= "Xaa at position 52 is Lys
          or Arg"

(ix) FEATURE:
      (A) NAME/KEY: Modified-site
      (B) LOCATION: 53
      (D) OTHER INFORMATION: /note= "Xaa at position 53 is Ser,
          Phe, or His"
```

```
     (ix) FEATURE:
           (A) NAME/KEY: Modified-site
           (B) LOCATION: 54
           (D) OTHER INFORMATION: /note= "Xaa at position 54 is Leu,
               Ile, Phe, or His"

(ix) FEATURE:
           (A) NAME/KEY: Modified-site
           (B) LOCATION: 55
           (D) OTHER INFORMATION: /note= "Xaa at position 55 is Gln,
               Ala, Pro, Thr, Glu, Arg, or Gly"

(ix) FEATURE:
           (A) NAME/KEY: Modified-site
           (B) LOCATION: 57
           (D) OTHER INFORMATION: /note= "Xaa at position 57 is Ala,
               Pro, or Arg"

(ix) FEATURE:
           (A) NAME/KEY: Modified-site
           (B) LOCATION: 58
           (D) OTHER INFORMATION: /note= "Xaa at position 58 is Ser,
               Glu, Arg, or Asp"

(ix) FEATURE:
           (A) NAME/KEY: Modified-site
           (B) LOCATION: 59
           (D) OTHER INFORMATION: /note= "Xaa at position 59 is Ala
               or Leu"

(ix) FEATURE:
           (A) NAME/KEY: Modified-site
           (B) LOCATION: 62
           (D) OTHER INFORMATION: /note= "Xaa at position 62 is Ser,
               Val, Ala, Asn, Glu, Pro, or Gly"

(ix) FEATURE:
           (A) NAME/KEY: Modified-site
           (B) LOCATION: 63
           (D) OTHER INFORMATION: /note= "Xaa at position 63 is Ile
               or Leu"

(ix) FEATURE:
           (A) NAME/KEY: Modified-site
           (B) LOCATION: 65
           (D) OTHER INFORMATION: /note= "Xaa at position 65 is Lys,
               Thr, Gly, Asn, Met, Arg, Ile, Gly, or Asp"

(ix) FEATURE:
           (A) NAME/KEY: Modified-site
           (B) LOCATION: 66
           (D) OTHER INFORMATION: /note= "Xaa at position 66 is Asn,
               Gly, Glu, or Arg"

(ix) FEATURE:
           (A) NAME/KEY: Modified-site
           (B) LOCATION: 68
           (D) OTHER INFORMATION: /note= "Xaa at position 68 is Leu,
               Gln, Trp, Arg, Asp, Ala, Asn, Glu, His, Ile, Met,
               Phe, Ser, Thr, Tyr, or Val"

(ix) FEATURE:
           (A) NAME/KEY: Modified-site
           (B) LOCATION: 69
           (D) OTHER INFORMATION: /note= "Xaa at position 69 is Pro
               or Thr"

(ix) FEATURE:
           (A) NAME/KEY: Modified-site
           (B) LOCATION: 71
           (D) OTHER INFORMATION: /note= "Xaa at position 71 is Leu
               or Val"

(ix) FEATURE:
           (A) NAME/KEY: Modified-site
           (B) LOCATION: 73
           (D) OTHER INFORMATION: /note= "Xaa at position 73 is Leu
               or Ser"
```

```
  (ix) FEATURE:
        (A) NAME/KEY: Modified-site
        (B) LOCATION: 74
        (D) OTHER INFORMATION: /note= "Xaa at position 74 is Ala
            or Trp"

(ix) FEATURE:
        (A) NAME/KEY: Modified-site
        (B) LOCATION: 77
        (D) OTHER INFORMATION: /note= "Xaa at position 77 is Ala
            or Pro"

(ix) FEATURE:
        (A) NAME/KEY: Modified-site
        (B) LOCATION: 79
        (D) OTHER INFORMATION: /note= "Xaa at position 79 is Thr,
            Asp, Ser, Pro, Ala, Leu, or Arg"

(ix) FEATURE:
        (A) NAME/KEY: Modified-site
        (B) LOCATION: 81
        (D) OTHER INFORMATION: /note= "Xaa at position 81 is His,
            Pro, Arg, Val, Leu, Gly, Asn, Phe, Ser, or Thr"

(ix) FEATURE:
        (A) NAME/KEY: Modified-site
        (B) LOCATION: 82
        (D) OTHER INFORMATION: /note= "Xaa at position 82 is Pro
            or Tyr"

(ix) FEATURE:
        (A) NAME/KEY: Modified-site
        (B) LOCATION: 83
        (D) OTHER INFORMATION: /note= "Xaa at position 83 is Ile
            or Val"

(ix) FEATURE:
        (A) NAME/KEY: Modified-site
        (B) LOCATION: 84
        (D) OTHER INFORMATION: /note= "Xaa at position 84 is His,
            Ile, Asn, Leu, Ala, Thr, Arg, Gln, Lys,
            Met, Ser, Tyr, Val, or Pro"

(ix) FEATURE:
        (A) NAME/KEY: Modified-site
        (B) LOCATION: 85
        (D) OTHER INFORMATION: /note= "Xaa at position 85 is Ile,
            Leu, or Val"

(ix) FEATURE:
        (A) NAME/KEY: Modified-site
        (B) LOCATION: 86
        (D) OTHER INFORMATION: /note= "Xaa at position 86 is Lys,
            Arg, Ile, Gln, Pro, or Ser"

(ix) FEATURE:
        (A) NAME/KEY: Modified-site
        (B) LOCATION: 87
        (D) OTHER INFORMATION: /note= "Xaa at position 87 is Asp,
            Pro, Met, Lys, His, Thr, Asn, Ile, Leu, or Tyr"

(ix) FEATURE:
        (A) NAME/KEY: Modified-site
        (B) LOCATION: 90
        (D) OTHER INFORMATION: /note= "Xaa at position 90 is Trp
            or Leu"

(ix) FEATURE:
        (A) NAME/KEY: Modified-site
        (B) LOCATION: 91
        (D) OTHER INFORMATION: /note="Xaa at position 91 is Asn,
            Pro, Ala, Ser, Trp, Gln, Tyr, Leu, Lys, Ile, Asp,
            or His"
```

```
    (ix) FEATURE:
         (A) NAME/KEY: Modified-site
         (B) LOCATION: 92
         (D) OTHER INFORMATION: /note= "Xaa at position 92 is Glu
             or Gly"

(ix) FEATURE:
         (A) NAME/KEY: Modified-site
         (B) LOCATION: 94
         (C) OTHER INFORMATION: /note= "Xaa at position 94 is Arg,
             Ala, or Ser"

(ix) FEATURE:
         (A) NAME/KEY: Modified-site
         (B) LOCATION: 95
         (D) OTHER INFORMATION: /note= "Xaa at position 95 is Arg,
             Thr, Glu, Leu, or Ser"

(ix) FEATURE:
         (A) NAME/KEY: Modified-site
         (B) LOCATION: 98
         (D) OTHER INFORMATION: /note= "Xaa at position 98 is Thr,
             Val, or Gln"

(ix) FEATURE:
         (A) NAME/KEY: Modified-site
         (B) LOCATION: 100
         (D) OTHER INFORMATION: /note= "Xaa at position 100 is Tyr
             or Trp"

(ix) FEATURE:
         (A) NAME/KEY: Modified-site
         (B) LOCATION: 101
         (D) OTHER INFORMATION: /note= "Xaa at position 101 is Leu
             or Ala"

(ix) FEATURE:
         (A) NAME/KEY: Modified-site
         (B) LOCATION: 102
         (D) OTHER INFORMATION: /note= "Xaa at position 102 is Lys,
             Thr, Val, Trp, Ser, Ala, His, Met, Phe, Tyr, or Ile"

(ix) FEATURE:
         (A) NAME/KEY: Modified-site
         (B) LOCATION: 103
         (D) OTHER INFORMATION: /note= "Xaa at position 103 is Thr
             or Ser"

(ix) FEATURE:
         (A) NAME/KEY: Modified-site
         (B) LOCATION: 106
         (D) OTHER INFORMATION: /note= "Xaa at position 106 is Asn,
             Pro, Leu, His, Val, or Gln"

(ix) FEATURE:
         (A) NAME/KEY: Modified-site
         (B) LOCATION: 107
         (D) OTHER INFORMATION: /note= "Xaa at position 107 is Ala,
             Ser, Ile, Asn, Pro, Asp, or Gly"

(ix) FEATURE:
         (A) NAME/KEY: Modified-site
         (B) LOCATION: 108
         (D) OTHER INFORMATION: /note= "Xaa at position 108 is Gln,
             Ser, Met, Trp, Arg, Phe, Pro, His, Ile, Tyr, or Cys"

(ix) FEATURE:
         (A) NAME/KEY: Modified-site
         (B) LOCATION: 109
         (D) OTHER INFORMATION: /note= "Xaa at position 109 is Ala,
             Met, Glu, His, Ser, Pro, Tyr, or Leu"

(xi) SEQUENCE DESCRIPTION: SEQ ID NO:21:

Asn Cys Xaa Xaa Xaa Ile Xaa Glu Xaa Xaa Xaa Xaa Leu Lys Xaa Xaa
1               5                   10                  15
```

```
Xaa Xaa Xaa Xaa Xaa Asp Xaa Xaa Asn Leu Asn Xaa Glu Xaa Xaa Xaa
                20              25              30

Ile Leu Met Xaa Xaa Asn Leu Xaa Xaa Xaa Asn Leu Glu Xaa Phe Xaa
            35              40              45

Xaa Xaa Xaa Xaa Xaa Xaa Xaa Asn Xaa Xaa Xaa Ile Glu Xaa Xaa Leu
50              55                      60

Xaa Xaa Leu Xaa Xaa Cys Xaa Pro Xaa Xaa Thr Ala Xaa Pro Xaa Arg
65              70              75              80

Xaa Xaa Xaa Xaa Xaa Xaa Xaa Gly Asp Xaa Xaa Xaa Phe Xaa Xaa Lys
            85              90              95

Leu Xaa Phe Xaa Xaa Xaa Xaa Leu Glu Xaa Xaa Xaa Xaa Gln Gln
        100             105             110
```

(2) INFORMATION FOR SEQ ID NO:22:

(i) SEQUENCE CHARACTERISTICS:
       (A) LENGTH: 111 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Met- or Met-Ala- may or may
           not precede the amino acid in position 1"

(ix) FEATURE:
       (A) NAME/KEY: Modified-site
       (B) LOCATION: 3
       (D) OTHER INFORMATION: /note= "Xaa at position 3 is Ser,
           Gly, Asp, or Gln"

(ix) FEATURE:
       (A) NAME/KEY: Modified-site
       (B) LOCATION: 4
       (D) OTHER INFORMATION: /note= "Xaa at position 4 is Asn,
           His, or Ile"

(ix) FEATURE:
       (A) NAME/KEY: Modified-site
       (B) LOCATION: 9
       (D) OTHER INFORMATION: /note= "Xaa at position 9 is Ile,
           Ala, Leu, or Gly"

(ix) FEATURE:
       (A) NAME/KEY: Modified-site
       (B) LOCATION: 11
       (D) OTHER INFORMATION: /note= "Xaa at position 11 is Thr,
           His, or Gln"

(ix) FEATURE:
       (A) NAME/KEY: Modified-site
       (B) LOCATION: 12
       (D) OTHER INFORMATION: /note= "Xaa at position 12 is His
           or Ala"

(ix) FEATURE:
       (A) NAME/KEY: Modified-site
       (B) LOCATION: 15
       (D) OTHER INFORMATION: /note= "Xaa at position 15 is Gln
           or Asn"

(ix) FEATURE:
       (A) NAME/KEY: Modified-site
       (B) LOCATION: 16
       (D) OTHER INFORMATION: /note= "Xaa at position 16 is Pro
           or Gly"

-continued

```
(ix) FEATURE:
     (A) NAME/KEY: Modified-site
     (B) LOCATION: 18
     (D) OTHER INFORMATION: /note= "Xaa at position 18 is Leu,
         Arg, Asn, or Ala"

(ix) FEATURE:
     (A) NAME/KEY: Modified-site
     (B) LOCATION: 20
     (D) OTHER INFORMATION: /note= "Xaa at position 20 is Leu,
         Val, Ser, Ala, Arg, Gln, Glu, Ile, Phe, Thr, or Met"

(ix) FEATURE:
     (A) NAME/KEY: Modified-site
     (B) LOCATION: 21
     (D) OTHER INFORMATION: /note= "Xaa at position 21 is Leu,
         Ala, Asn, or Pro"

(ix) FEATURE:
     (A) NAME/KEY: Modified-site
     (B) LOCATION: 24
     (D) OTHER INFORMATION: /note= "Xaa at position 24 is Asn
         or Ala"

(ix) FEATURE:
     (A) NAME/KEY: Modified-site
     (B) LOCATION: 28
     (D) OTHER INFORMATION: /note= "Xaa at position 28 is Gly,
         Asp, Ser, Ala, Asn, Ile, Leu, Met, Tyr, or Arg"

(ix) FEATURE:
     (A) NAME/KEY: Modified-site
     (B) LOCATION: 31
     (D) OTHER INFORMATION: /note= "Xaa at position 31 is Gln,
         Val, Met, Leu, Ala, Asn, Glu, or Lys"

(ix) FEATURE:
     (A) NAME/KEY: Modified-site
     (B) LOCATION: 32
     (D) OTHER INFORMATION: /note= "Xaa at position 32 is Asp,
         Phe, Ser, Ala, Gln, Glu, His, Val, or Thr"

(ix) FEATURE:
     (A) NAME/KEY: Modified-site
     (B) LOCATION: 36
     (D) OTHER INFORMATION: /note= "Xaa at position 36 is Glu,
         Asn, Ser, or Asp"

(ix) FEATURE:
     (A) NAME/KEY: Modified-site
     (B) LOCATION: 37
     (D) OTHER INFORMATION: /note= "Xaa at position 37 is Asn,
         Arg, Pro, Thr, or His"

(ix) FEATURE:
     (A) NAME/KEY: Modified-site
     (B) LOCATION: 41
     (D) OTHER INFORMATION: /note= "Xaa at position 41 is Arg,
         Leu, or Gly"

(ix) FEATURE:
     (A) NAME/KEY: Modified-site
     (B) LOCATION: 42
     (D) OTHER INFORMATION: /note= "Xaa at position 42 is Pro,
         Gly, Ser, Ala, Asn, Val, Leu, or Gln"

(ix) FEATURE:
     (A) NAME/KEY: Modified-site
     (B) LOCATION: 48
     (D) OTHER INFORMATION: /note= "Xaa at position 48 is Asn,
         Pro, or Thr"

(ix) FEATURE:
     (A) NAME/KEY: Modified-site
     (B) LOCATION: 50
     (D) OTHER INFORMATION: /note= "Xaa at position 50 is Ala
         or Asn"
```

-continued (ix) FEATURE:
         (A) NAME/KEY: Modified-site
         (B) LOCATION: 51
         (D) OTHER INFORMATION: /note= "Xaa at position 51 is Val
             or Thr"

(ix) FEATURE:
         (A) NAME/KEY: Modified-site
         (B) LOCATION: 53
         (D) OTHER INFORMATION: /note= "Xaa at position 53 is Ser
             or Phe"

(ix) FEATURE:
         (A) NAME/KEY: Modified-site
         (B) LOCATION: 54
         (D) OTHER INFORMATION: /note= "Xaa at position 54 is Leu
             or Phe"

(ix) FEATURE:
         (A) NAME/KEY: Modified-site
         (B) LOCATION: 55
         (D) OTHER INFORMATION: /note= "Xaa at position 55 is Gln,
             Ala, Glu, or Arg"

(ix) FEATURE:
         (A) NAME/KEY: Modified-site
         (B) LOCATION: 62
         (D) OTHER INFORMATION: /note= "Xaa at position 62 is Ser,
             Val, Asn, Pro, or Gly"

(ix) FEATURE:
         (A) NAME/KEY: Modified-site
         (B) LOCATION: 63
         (D) OTHER INFORMATION: /note= "Xaa at position 63 is Ile
             or Leu"

(ix) FEATURE:
         (A) NAME/KEY: Modified-site
         (B) LOCATION: 65
         (D) OTHER INFORMATION: /note= "Xaa at position 65 is Lys,
             Asn, Met, Arg, Ile, or Gly"

(ix) FEATURE:
         (A) NAME/KEY: Modified-site
         (B) LOCATION: 66
         (D) OTHER INFORMATION: /note= "Xaa at position 66 is Asn,
             Gly, Glu, or Arg"

(ix) FEATURE:
         (A) NAME/KEY: Modified-site
         (B) LOCATION: 68
         (D) OTHER INFORMATION: /note= "Xaa at position 68 is Leu,
             Gln, Trp, Arg, Asp, Asn, Glu, His, Met, Phe, Ser,
             Thr, Tyr, or Val"

(ix) FEATURE:
         (A) NAME/KEY: Modified-site
         (B) LOCATION: 73
         (D) OTHER INFORMATION: /note= "Xaa at position 73 is Leu
             or Ser"

(ix) FEATURE:
         (A) NAME/KEY: Modified-site
         (B) LOCATION: 74
         (D) OTHER INFORMATION: /note= "Xaa at position 74 is Ala
             or Trp"

(ix) FEATURE:
         (A) NAME/KEY: Modified-site
         (B) LOCATION: 77
         (D) OTHER INFORMATION: /note= "Xaa at position 77 is Ala
             or Pro"

(ix) FEATURE:
         (A) NAME/KEY: Modified-site
         (B) LOCATION: 79
         (D) OTHER INFORMATION: /note= "Xaa at position 79 is Thr,
             Asp, or Ala"

```
(ix) FEATURE:
    (A) NAME/KEY: Modified-site
    (B) LOCATION: 81
    (D) OTHER INFORMATION: /note= "Xaa at position 81 is His,
        Pro, Arg, Val, Gly, Asn, Ser, or Thr"

(ix) FEATURE:
    (A) NAME/KEY: Modified-site
    (B) LOCATION: 84
    (D) OTHER INFORMATION: /note= "Xaa at position 84 is His,
        Ile, Asn, Ala, Thr, Arg, Gln, Glu, Lys, Met,
        Ser, Tyr, Val, or Leu"

(ix) FEATURE:
    (A) NAME/KEY: Modified-site
    (B) LOCATION: 85
    (D) OTHER INFORMATION: /note= "Xaa at position 85 is Ile
        or Leu"

(ix) FEATURE:
    (A) NAME/KEY: Modified-site
    (B) LOCATION: 86
    (D) OTHER INFORMATION: /note= "Xaa at position 86 is Lys
        or Arg"

(ix) FEATURE:
    (A) NAME/KEY: Modified-site
    (B) LOCATION: 87
    (D) OTHER INFORMATION: /note= "Xaa at position 87 is Asp,
        Pro, Met, Lys, His, Pro, Asn, Ile, Leu, or Tyr"

(ix) FEATURE:
    (A) NAME/KEY: Modified-site
    (B) LOCATION: 91
    (D) OTHER INFORMATION: /note= "Xaa at position 91 is Asn,
        Pro, Ser, Ile, or Asp"

(ix) FEATURE:
    (A) NAME/KEY: Modified-site
    (B) LOCATION: 94
    (D) OTHER INFORMATION: /note= "Xaa at position 94 is Arg,
        Ala, or Ser"

(ix) FEATURE:
    (A) NAME/KEY: Modified-site
    (B) LOCATION: 95
    (D) OTHER INFORMATION: /note= "Xaa at position 95 is Arg,
        Thr, Glu, Leu, or Ser"

(ix) FEATURE:
    (A) NAME/KEY: Modified-site
    (B) LOCATION: 98
    (D) OTHER INFORMATION: /note= "Xaa at position 98 is Thr
        or Gln"

(ix) FEATURE:
    (A) NAME/KEY: Modified-site
    (B) LOCATION: 102
    (D) OTHER INFORMATION: /note= "Xaa at position 102 is Lys,
        Val, Trp, or Ile"

(ix) FEATURE:
    (A) NAME/KEY: Modified-site
    (B) LOCATION: 103
    (D) OTHER INFORMATION: /note= "Xaa at position 103 is Thr,
        Ala, His, Phe, Tyr, or Ser"

(ix) FEATURE:
    (A) NAME/KEY: Modified-site
    (B) LOCATION: 106
    (D) OTHER INFORMATION: /note= "Xaa at position 106 is Asn,
        Pro, Leu, His, Val, or Gln"

(ix) FEATURE:
    (A) NAME/KEY: Modified-site
    (B) LOCATION: 107
    (D) OTHER INFORMATION: /note= "Xaa at position 107 is Ala,
        Ser, Ile, Pro, or Asp"
```

(ix) FEATURE:
    (A) NAME/KEY: Modified-site
    (B) LOCATION: 108
    (D) OTHER INFORMATION: /note= "Xaa at position 108 is Gln,
        Met, Trp, Phe, Pro, His, Ile, or Tyr"

(ix) FEATURE:
    (A) NAME/KEY: Modified-site
    (B) LOCATION: 109
    (D) OTHER INFORMATION: /note= "Xaa at position 109 is Ala,
        Met, Glu, Ser, or Leu"

(xi) SEQUENCE DESCRIPTION: SEQ ID NO:22:

```
Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa
            20                  25                  30

Ile Leu Met Xaa Xaa Asn Leu Arg Xaa Xaa Asn Leu Glu Ala Phe Xaa
            35                  40                  45

Arg Xaa Xaa Lys Xaa Xaa Xaa Asn Ala Ser Ala Ile Glu Xaa Xaa Leu
    50                  55                  60

Xaa Xaa Leu Xaa Pro Cys Leu Pro Xaa Xaa Thr Ala Xaa Pro Xaa Arg
65                  70                  75                  80

Xaa Pro Ile Xaa Xaa Xaa Xaa Gly Asp Trp Xaa Glu Phe Xaa Xaa Lys
            85                  90                  95

Leu Xaa Phe Tyr Leu Xaa Xaa Leu Glu Xaa Xaa Xaa Xaa Gln Gln
            100                 105                 110
```

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

AACAACCTCA ATGCTGAAGA CGTTGAT                                      27

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

ATCAACGTCT TCAGCATT                                                18

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

AACAACCTCA ATTCTGAAGA CATGGAT                                27

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

ATCCATGTCT TCAGAATT                                          18

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:27:

CATGGGAACC ATATGTCAGG AT                                     22

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:28:

ATCCTGACAT ATGGTTCC                                          18

(2) INFORMATION FOR SEQ ID NO:29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:29:

TGAACCATAT GTCAGG                                            16

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:30:

AATTCCTGAC ATATGGTTCA TGCA                                                  24

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:31:

AATTCGAACC ATATGTCAGA                                                       20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:32:

AGCTTCTGAC ATATGGTTCG                                                       20

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:33:

ATCGAACCAT ATGTCAGATG CA                                                    22

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:34:

TCTGACATAT GGTTCGAT                                                         18

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:35:

ATCCTGATGG AACGAAACCT TCGACTTCCA AACCTG        36

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:36:

AAGTCGAAGG TTTCGTTCCA TCAGGAT        27

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:37:

ATCCTGATGG AACGAAACCT TCGAACTCCA AACCTG        36

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:38:

AGTTCGAAGG TTTCGTTCCA TCAGGAT        27

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:39:

CTCGCATTCG TAAGGGCTGT CAAG        24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

```
      (xi) SEQUENCE DESCRIPTION: SEQ ID NO:40:

CCTTACGAAT GCGAGCAGGT TTGG                                            24

(2) INFORMATION FOR SEQ ID NO:41:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:41:

GAGAGCTTCG TAAGGGCTGT CAAG                                            24

(2) INFORMATION FOR SEQ ID NO:42:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:42:

CCTTACGAAG CTCTCCAGGT TTGG                                            24

(2) INFORMATION FOR SEQ ID NO:43:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:43:

CACTTAGAAA ATGCA                                                      15

(2) INFORMATION FOR SEQ ID NO:44:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:44:

TTTTCTAAGT GCTTGACAGC                                                 20

(2) INFORMATION FOR SEQ ID NO:45:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (synthetic)
```

(xi) SEQUENCE DESCRIPTION: SEQ ID NO:45:

AACTTAGAAA ATGCA                                                                    15

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:46:

TTTTCTAAGT TCTTGACAGC                                                               20

(2) INFORMATION FOR SEQ ID NO:47:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:47:

GGTGATTGGA TGTCGAGAGG GTGCGGCCGT GGCAGAGGGC AGACATGG                                 48

(2) INFORMATION FOR SEQ ID NO:48:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:48:

CTGCCCTCTG CCACGGCCGC ACCCTCTCGA CATCCAATCA CCATCAAG                                 48

(2) INFORMATION FOR SEQ ID NO:49:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:49:

GATGATTGGA TGTCGAGAGG GTGCGGCCGT GGCAGAGGGC AGACATGG                                 48

(2) INFORMATION FOR SEQ ID NO:50:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:50:

CTGCCCTCTG CCACGGCCGC ACCCTCTCGA CATCCAATCA TCATCAAG          48

(2) INFORMATION FOR SEQ ID NO:51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:51:

TACGAGATTA CGAAGAAT          18

(2) INFORMATION FOR SEQ ID NO:52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:52:

CGTAATCTCG TACCATGT          18

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:53:

TTGGAGATTA CGAAGAAT          18

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:54:

CGTAATCTCC AACCATGT          18

(2) INFORMATION FOR SEQ ID NO:55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:55:

TGCCTCAATA CCTGATGCA                                                      19

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:56:

TCAGGTATTG AGGCAATTCT T                                                   21

(2) INFORMATION FOR SEQ ID NO:57:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:57:

AATTCTTGCC AGTCACCTGC CTTGAT                                              26

(2) INFORMATION FOR SEQ ID NO:58:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:58:

GCAGGTGACT GGCAAG                                                         16

(2) INFORMATION FOR SEQ ID NO:59:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:59:

AATTCCGGGA AAAACTGACG TTCTATCTGG TT                                       32

(2) INFORMATION FOR SEQ ID NO:60:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:60:

CTCAAGGGAA ACCAGATAGA ACGTCAGTTT TTCCCGG 37

(2) INFORMATION FOR SEQ ID NO:61:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:61:

ACCCTTGAGC ACGCGCAGGA ACAACAGTAA TA 32

(2) INFORMATION FOR SEQ ID NO:62:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:62:

AGCTTATTAC TGTTGTTCCT GCGCGTG 27

(2) INFORMATION FOR SEQ ID NO:63:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:63:

ACCCTTGAGC AAGCGCAGGA ACAACAGTAA TA 32

(2) INFORMATION FOR SEQ ID NO:64:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:64:

AGCTTATTAC TGTTGTTCCT GCGCTTG 27

(2) INFORMATION FOR SEQ ID NO:65:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:65:

Asn Cys Ser Asn Met Ile Asp Glu Ile Ile Thr His Leu Lys Gln Pro
1               5                   10              15

-continued

```
Pro Leu Pro Leu Leu Asp Phe Asn Asn Leu Asn Gly Glu Asp Gln Asp
              20                  25                  30

Ile Leu Met Glu Asn Asn Leu Arg Arg Pro Asn Leu Glu Ala Phe Asn
              35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110
```

(2) INFORMATION FOR SEQ ID NO:66:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:66:

```
Asn Cys Ser Ile Met Ile Asp Glu Ile Ile His His Leu Lys Arg Pro
 1               5                  10                  15

Pro Ala Pro Leu Leu Asp Pro Asn Asn Leu Asn Ala Glu Asp Val Asp
              20                  25                  30

Ile Leu Met Glu Asn Asn Leu Arg Arg Pro Asn Leu Glu Ala Phe Asn
              35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
                100                 105                 110
```

(2) INFORMATION FOR SEQ ID NO:67:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:67:

```
Asn Cys Ser Ile Met Ile Asp Glu Ile Ile His His Leu Lys Arg Pro
 1               5                  10                  15

Pro Asn Pro Leu Leu Asp Pro Asn Asn Leu Asn Ser Glu Asp Met Asp
              20                  25                  30

Ile Leu Met Glu Asn Asn Leu Arg Arg Pro Asn Leu Glu Ala Phe Asn
              35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80
```

```
His Pro Ile His Ile Lys Asp Gly Asp Trp Asn Glu Phe Arg Arg Lys
            85                  90                  95

Leu Thr Phe Tyr Leu Lys Thr Leu Glu Asn Ala Gln Ala Gln Gln
            100                 105                 110

(2) INFORMATION FOR SEQ ID NO:68:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:68:

Asn Cys Ser Ile Met Ile Asp Glu Ile Ile His His Leu Lys Val Pro
1               5                   10                  15

Pro Ala Pro Leu Leu Asp Ser Asn Asn Leu Asn Ser Glu Asp Met Asp
                20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
            85                  90                  95

Leu Thr Phe Tyr Leu Lys Thr Leu Glu Asn Ala Gln Ala Gln Gln
            100                 105                 110

(2) INFORMATION FOR SEQ ID NO:69:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:69:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Arg Asn Leu Arg Leu Pro Asn Leu Leu Ala Phe Val
            35                  40                  45

Arg Ala Val Lys Asn Leu Glu Asn Ala Ser Ala Ile Glu Ser Ile Leu
50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
            85                  90                  95

Leu Thr Phe Tyr Leu Lys Thr Leu Glu Asn Ala Gln Ala Gln Gln
            100                 105                 110
```

(2) INFORMATION FOR SEQ ID NO:70:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:70:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:71:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:71:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Arg Asn Leu Arg Thr Pro Asn Leu Leu Ala Phe Val
            35                  40                  45

Arg Ala Val Lys His Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:72:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:72:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
    50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:73:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:73:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
    50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:74:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:74:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

```
Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Glu Lys
                 85                  90                  95

Leu Thr Phe Tyr Leu Val Thr Leu Glu Gln Ala Gln Glu Gln Gln
                100                 105                 110
```

(2) INFORMATION FOR SEQ ID NO:75:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:75:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
                 35                  40                  45

Arg Ala Val Lys Ser Leu Gln Asn Ala Ser Ala Ile Glu Ser Ile Leu
 50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Glu Lys
                 85                  90                  95

Leu Thr Phe Tyr Leu Val Ser Leu Glu His Ala Gln Glu Gln Gln
                100                 105                 110
```

(2) INFORMATION FOR SEQ ID NO:76:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:76:

```
Asn Cys Ser Asn Met Ile Asp Glu Ile Ile Thr His Leu Lys Gln Pro
 1               5                  10                  15

Pro Leu Pro Leu Leu Asp Phe Asn Asn Leu Asn Gly Glu Asp Gln Asp
                 20                  25                  30

Ile Leu Met Glu Asn Asn Leu Arg Arg Pro Asn Leu Glu Ala Phe Asn
                 35                  40                  45

Arg Ala Val Lys Ser Leu Gln Asn Ala Ser Gly Ile Glu Ala Ile Leu
 50                  55                  60

Arg Asn Leu Gln Pro Cys Leu Pro Ser Ala Thr Ala Ala Pro Ser Arg
 65                  70                  75                  80

His Pro Ile Ile Ile Lys Ala Gly Asp Trp Gln Glu Phe Arg Glu Lys
                 85                  90                  95

Leu Thr Phe Tyr Leu Val Thr Leu Glu Gln Ala Gln Glu Gln Gln
                100                 105                 110
```

(2) INFORMATION FOR SEQ ID NO:77:

(i) SEQUENCE CHARACTERISTICS:
  (A) LENGTH: 111 amino acids
  (B) TYPE: amino acid
  (D) TOPOLOGY: linear (ii) MOLECULE TYPE: peptide (xi) SEQUENCE DESCRIPTION: SEQ ID NO:77:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Gly Ile Glu Ala Ile Leu
    50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:78:

(i) SEQUENCE CHARACTERISTICS:
  (A) LENGTH: 111 amino acids
  (B) TYPE: amino acid
  (D) TOPOLOGY: linear (ii) MOLECULE TYPE: peptide (xi) SEQUENCE DESCRIPTION: SEQ ID NO:78:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Gly Ile Glu Ala Ile Leu
    50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Glu Lys
                85                  90                  95

Leu Thr Phe Tyr Leu Val Ser Leu Glu His Ala Gln Glu Gln Gln
                100                 105                 110
```

(2) INFORMATION FOR SEQ ID NO:79:

(i) SEQUENCE CHARACTERISTICS:
  (A) LENGTH: 111 amino acids
  (B) TYPE: amino acid
  (D) TOPOLOGY: linear (ii) MOLECULE TYPE: peptide (xi) SEQUENCE DESCRIPTION: SEQ ID NO:79:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
                20                  25                  30

Ile Leu Met Glu Arg Asn Leu Arg Leu Pro Asn Leu Glu Ser Phe Val
            35                  40                  45

Arg Ala Val Lys Asn Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:80:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:80:

Asn Cys Ser Ile Met Ile Asp Glu Ile Ile His His Leu Lys Arg Pro
1               5                   10                  15

Pro Asn Pro Leu Leu Asp Pro Asn Asn Leu Asn Ser Glu Asp Met Asp
                20                  25                  30

Ile Leu Met Glu Arg Asn Leu Arg Thr Pro Asn Leu Leu Ala Phe Val
            35                  40                  45

Arg Ala Val Lys His Leu Glu Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:81:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:81:

Asn Cys Ser Ile Met Ile Asp Glu Ile Ile His His Leu Lys Val Pro
1               5                   10                  15

Pro Ala Pro Leu Leu Asp Ser Asn Asn Leu Asn Ser Glu Asp Met Asp
                20                  25                  30

Ile Leu Met Glu Arg Asn Leu Arg Leu Pro Asn Leu Leu Ala Phe Val
            35                  40                  45

```
Arg Ala Val Lys Asn Leu Glu Asn Ala Ser Ala Ile Glu Ser Ile Leu
         50                  55                  60

Lys Asn Leu Leu Pro Cys Leu Pro Leu Ala Thr Ala Ala Pro Thr Arg
 65              70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
            100                 105                 110
```

(2) INFORMATION FOR SEQ ID NO:82:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:82:

```
Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Gly Glu Asp
             20                  25                  30

Gln Asp Ile Leu Met Glu Asn Asn Leu Arg Arg Pro Asn Leu Glu Ala
             35                  40                  45

Phe Asn Arg Ala Val Lys Ser Leu Gln Asn Ala Ser Gly Ile Glu Ala
 50                  55                  60

Ile Leu Arg Asn Leu Gln Pro Cys Leu Pro Ser Ala Thr Ala Ala Pro
 65              70                  75                  80

Ser Arg His Pro Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:83:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:83:

```
Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Gly Glu Asp
             20                  25                  30

Gln Asp Ile Leu Met Glu Asn Asn Leu Arg Arg Pro Asn Leu Glu Ala
             35                  40                  45

Phe Asn Arg Ala Val Lys Ser Leu Gln Asn Ala Ser Gly Ile Glu Ala
 50                  55                  60

Ile Leu Arg Asn Leu Val Pro Cys Leu Pro Ser Ala Thr Ala Ala Pro
 65              70                  75                  80

Ser Arg His Pro Ile Thr Ile Lys Ala Gly Asp Trp Gln Glu Phe Arg
                 85                  90                  95
```

```
Glu Lys Leu Thr Phe Tyr Leu Val Thr Leu Glu Gln Ala Gln Glu Gln
            100                 105                 110

Gln
```

(2) INFORMATION FOR SEQ ID NO:84:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:84:

```
Met Ala Asn Cys Ser Asn Met Ile Asp Glu Ile Ile Thr His Leu Lys
 1               5                  10                  15

Gln Pro Pro Leu Pro Leu Asp Phe Asn Asn Leu Asn Gly Glu Asp
            20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
 50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:85:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:85:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Ala Ile Glu Ser
 50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:86:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:86:

```
Met Ala Asn Cys Ser Ile Met Ile Asp Glu Ile Ile His His Leu Lys
1               5                  10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:87:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:87:

```
Met Ala Asn Cys Ser Ile Met Ile Asp Glu Ile Ile His His Leu Lys
1               5                  10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln
```

(2) INFORMATION FOR SEQ ID NO:88:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:88:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:89:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:89:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:90:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:90:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

```
Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:91:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:91:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Gln Ala Gln Glu Gln
            100                 105                 110

Gln
```

(2) INFORMATION FOR SEQ ID NO:92:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:92:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80
```

```
Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:93:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:93:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln (2) INFORMATION FOR SEQ ID NO:94:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:94:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:95:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:95:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:96:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:96:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
                100                 105                 110

Gln
```

(2) INFORMATION FOR SEQ ID NO:97:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:97:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGCT GAAGACGTCG ATATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:98:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:98:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGCT GAAGACGTCG ATATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCGTA CCATGTCTGC CCTCTGCCAC GGCCGCACCC | 240 |
| TCTCGACATC CAATCACCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:99:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:99:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGCT GAAGACGTCG ATATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCGTA CCATGTCTGC CCTCTGCCAC GGCCGCACCC | 240 |
| TCTCGACATC CAATCACCAT CAAGGCAGGT GACTGGCAAG AATTCCGGGA AAAACTGACG | 300 |
| TTCTATCTGG TTTCCCTTGA GCACGCGCAG GAACAACAG | 339 |

(2) INFORMATION FOR SEQ ID NO:100:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:100:

```
ATGGCTAACT GCTCTATAAT GATCGATGAA ATTATACATC ACTTAAAGAG ACCACCTAAC    60

CCTTTGCTGG ACCCGAACAA CCTCAATTCT GAAGACATGG ATATCCTGAT GGAACGAAAC   120

CTTCGAACTC CAAACCTGCT CGCATTCGTA AGGGCTGTCA AGCACTTAGA AAATGCATCA   180

GGTATTGAGG CAATTCTTCG TAATCTCCAA CCATGTCTGC CCTCTGCCAC GGCCGCACCC   240

TCTCGACATC CAATCATCAT CAAGGCAGGT GACTGGCAAG AATTCCGGGA AAAACTGACG   300

TTCTATCTGG TTACCCTTGA GCAAGCGCAG GAACAACAG                          339
```

(2) INFORMATION FOR SEQ ID NO:101:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:101:

```
ATGGCTAACT GCTCTATAAT GATCGATGAA ATTATACATC ACTTAAAGAG ACCACCTAAC    60

CCTTTGCTGG ACCCGAACAA CCTCAATTCT GAAGACATGG ATATCCTGAT GGAACGAAAC   120

CTTCGAACTC CAAACCTGCT CGCATTCGTA AGGGCTGTCA AGCACTTAGA AAATGCATCA   180

GGTATTGAGG CAATTCTTCG TAATCTCGTA CCATGTCTGC CCTCTGCCAC GGCCGCACCC   240

TCTCGACATC CAATCACCAT CAAGGCAGGT GACTGGCAAG AATTCCGGGA AAAACTGACG   300

TTCTATCTGG TTACCCTTGA GCAAGCGCAG GAACAACAG                          339
```

(2) INFORMATION FOR SEQ ID NO:102:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:102:

```
ATGGCTAACT GCTCTATAAT GATCGATGAA ATTATACATC ACTTAAAGAG ACCACCTAAC    60

CCTTTGCTGG ACCCGAACAA CCTCAATTCT GAAGACATGG ATATCCTGAT GGAACGAAAC   120

CTTCGAACTC CAAACCTGCT CGCATTCGTA AGGGCTGTCA AGCACTTAGA AAATGCATCA   180

GGTATTGAGG CAATTCTTCG TAATCTCGTA CCATGTCTGC CCTCTGCCAC GGCCGCACCC   240

TCTCGACATC CAATCACCAT CAAGGCAGGT GACTGGCAAG AATTCCGGGA AAAACTGACG   300

TTCTATCTGG TTTCCCTTGA GCACGCGCAG GAACAACAG                          339
```

(2) INFORMATION FOR SEQ ID NO:103:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:103:

```
ATGGCTAACT GCTCTATAAT GATCGATGAA ATTATACATC ACTTAAAGGT TCCACCTGCA    60
```

```
CCTTTGCTGG ACAGTAACAA CCTCAATTCC GAAGACATGG ATATCCTGAT GGAACGAAAC        120

CTTCGACTTC CAAACCTGCT CGCATTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                               339

(2) INFORMATION FOR SEQ ID NO:104:

(i) SEQUENCE CHARACTERISTICS:
         (A) LENGTH: 339 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:104:

ATGGCTAACT GCTCTATAAT GATCGATGAA ATTATACATC ACTTAAAGGT TCCACCTGCA         60

CCTTTGCTGG ACAGTAACAA CCTCAATTCC GAAGACATGG ATATCCTGAT GGAACGAAAC        120

CTTCGACTTC CAAACCTGCT CGCATTCGTA AGGGCTGTCA AGAACTTAGA AAATGCATCA        180

GGTATTGAGG CAATTCTTCG TAATCTCGTA CCATGTCTGC CCTCTGCCAC GGCCGCACCC        240

TCTCGACATC CAATCACCAT CAAGGCAGGT GACTGGCAAG AATTCCGGGA AAAACTGACG        300

TTCTATCTGG TTACCCTTGA GCAAGCGCAG GAACAACAG                               339

(2) INFORMATION FOR SEQ ID NO:105:

(i) SEQUENCE CHARACTERISTICS:
         (A) LENGTH: 339 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:105:

ATGGCTAACT GCTCTATAAT GATCGATGAA ATTATACATC ACTTAAAGGT TCCACCTGCA         60

CCTTTGCTGG ACAGTAACAA CCTCAATTCC GAAGACATGG ATATCCTGAT GGAACGAAAC        120

CTTCGACTTC CAAACCTGCT CGCATTCGTA AGGGCTGTCA AGAACTTAGA AAATGCATCA        180

GGTATTGAGG CAATTCTTCG TAATCTCGTA CCATGTCTGC CCTCTGCCAC GGCCGCACCC        240

TCTCGACATC CAATCACCAT CAAGGCAGGT GACTGGCAAG AATTCCGGGA AAAACTGACG        300

TTCTATCTGG TTTCCCTTGA GCACGCGCAG GAACAACAG                               339

(2) INFORMATION FOR SEQ ID NO:106:

(i) SEQUENCE CHARACTERISTICS:
         (A) LENGTH: 333 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:106:

AACTGCTCTA TAATGATCGA TGAAATTATA CATCACTTAA AGAGACCACC TGCACCTTTG         60

CTGGACCCGA ACAACCTCAA TGCTGAAGAC GTCGATATCC TGATGGAAAA TAACCTTCGT        120

CGTCCAAACC TCGAGGCATT CAACCGTGCT GTCAAGTCTC TGCAGAATGC ATCAGCAATT        180
```

```
GAGAGCATTC TTAAAAATCT CCTGCCATGT CTGCCCCTGG CCACGGCCGC ACCCACGCGA      240

CATCCAATCC ATATCAAGGA CGGTGACTGG AATGAATTCC GTCGTAAACT GACCTTCTAT      300

CTGAAAACCT TGGAGAACGC GCAGGCTCAA CAG                                   333

(2) INFORMATION FOR SEQ ID NO:107:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:107:

AACTGCTCTA TAATGATCGA TGAAATTATA CATCACTTAA AGAGACCACC TAACCCTTTG       60

CTGGACCCGA ACAACCTCAA TTCTGAAGAC ATGGATATCC TGATGGAAAA TAACCTTCGT      120

CGTCCAAACC TCGAGGCATT CAACCGTGCT GTCAAGTCTC TGCAGAATGC ATCAGCAATT      180

GAGAGCATTC TTAAAAATCT CCTGCCATGT CTGCCCCTGG CCACGGCCGC ACCCACGCGA      240

CATCCAATCC ATATCAAGGA CGGTGACTGG AATGAATTCC GTCGTAAACT GACCTTCTAT      300

CTGAAAACCT TGGAGAACGC GCAGGCTCAA CAG                                   333

(2) INFORMATION FOR SEQ ID NO:108:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:108:

AACTGCTCTA TAATGATCGA TGAAATTATA CATCACTTAA AGGTTCCACC TGCACCTTTG       60

CTGGACAGTA ACAACCTCAA TTCCGAAGAC ATGGATATCC TGATGGAAAA TAACCTTCGT      120

CGTCCAAACC TCGAGGCATT CAACCGTGCT GTCAAGTCTC TGCAGAATGC ATCAGCAATT      180

GAGAGCATTC TTAAAAATCT CCTGCCATGT CTGCCCCTGG CCACGGCCGC ACCCACGCGA      240

CATCCAATCC ATATCAAGGA CGGTGACTGG AATGAATTCC GTCGTAAACT GACCTTCTAT      300

CTGAAAACCT TGGAGAACGC GCAGGCTCAA CAG                                   333

(2) INFORMATION FOR SEQ ID NO:109:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:109:

AACTGCTCTA ACATGATCGA TGAAATCATC ACCCACCTGA AGCAGCCACC GCTGCCGCTG       60

CTGGACTTCA ACAACCTCAA TGGTGAAGAC CAAGATATCC TGATGGAACG AAACCTTCGA      120

CTTCCAAACC TGCTCGCATT CGTAAGGGCT GTCAAGAACT TAGAAAATGC ATCAGCAATT      180

GAGAGCATTC TTAAAAATCT CCTGCCATGT CTGCCCCTGG CCACGGCCGC ACCCACGCGA      240

CATCCAATCC ATATCAAGGA CGGTGACTGG AATGAATTCC GTCGTAAACT GACCTTCTAT      300
```

CTGAAAACCT TGGAGAACGC GCAGGCTCAA CAG                                333

(2) INFORMATION FOR SEQ ID NO:110:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:110:

AACTGCTCTA ACATGATCGA TGAAATCATC ACCCACCTGA AGCAGCCACC GCTGCCGCTG    60

CTGGACTTCA ACAACCTCAA TGGTGAAGAC CAAGATATCC TGATGGAACG AAACCTTCGA   120

CTTCCAAACC TGGAGAGCTT CGTAAGGGCT GTCAAGAACT TAGAAAATGC ATCAGCAATT   180

GAGAGCATTC TTAAAAATCT CCTGCCATGT CTGCCCCTGG CCACGGCCGC ACCCACGCGA   240

CATCCAATCC ATATCAAGGA CGGTGACTGG AATGAATTCC GTCGTAAACT GACCTTCTAT   300

CTGAAAACCT TGGAGAACGC GCAGGCTCAA CAG                                333

(2) INFORMATION FOR SEQ ID NO:111:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:111:

AACTGCTCTA ACATGATCGA TGAAATCATC ACCCACCTGA AGCAGCCACC GCTGCCGCTG    60

CTGGACTTCA ACAACCTCAA TGGTGAAGAC CAAGATATCC TGATGGAACG AAACCTTCGA   120

ACTCCAAACC TGCTCGCATT CGTAAGGGCT GTCAAGCACT TAGAAAATGC ATCAGCAATT   180

GAGAGCATTC TTAAAAATCT CCTGCCATGT CTGCCCCTGG CCACGGCCGC ACCCACGCGA   240

CATCCAATCC ATATCAAGGA CGGTGACTGG AATGAATTCC GTCGTAAACT GACCTTCTAT   300

CTGAAAACCT TGGAGAACGC GCAGGCTCAA CAG                                333

(2) INFORMATION FOR SEQ ID NO:112:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:112:

AACTGCTCTA ACATGATCGA TGAAATCATC ACCCACCTGA AGCAGCCACC GCTGCCGCTG    60

CTGGACTTCA ACAACCTCAA TGGTGAAGAC CAAGATATCC TGATGGAAAA TAACCTTCGT   120

CGTCCAAACC TCGAGGCATT CAACCGTGCT GTCAAGTCTC TGCAGAATGC ATCAGGTATT   180

GAGGCAATTC TTCGTAATCT CCAACCATGT CTGCCCTCTG CCACGGCCGC ACCCTCTCGA   240

CATCCAATCA TCATCAAGGC AGGTGACTGG CAAGAATTCC GTCGTAAACT GACCTTCTAT   300

CTGAAAACCT TGGAGAACGC GCAGGCTCAA CAG                                333

(2) INFORMATION FOR SEQ ID NO:113:

(i) SEQUENCE CHARACTERISTICS:
       (A) LENGTH: 333 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:113:

```
AACTGCTCTA ACATGATCGA TGAAATCATC ACCCACCTGA AGCAGCCACC GCTGCCGCTG      60

CTGGACTTCA ACAACCTCAA TGGTGAAGAC CAAGATATCC TGATGGAAAA TAACCTTCGT     120

CGTCCAAACC TCGAGGCATT CAACCGTGCT GTCAAGTCTC TGCAGAATGC ATCAGGTATT     180

GAGGCAATTC TTCGTAATCT CGTACCATGT CTGCCCTCTG CCACGGCCGC ACCCTCTCGA     240

CATCCAATCA CCATCAAGGC AGGTGACTGG CAAGAATTCC GTCGTAAACT GACCTTCTAT     300

CTGAAAACCT TGGAGAACGC GCAGGCTCAA CAG                                  333
```

(2) INFORMATION FOR SEQ ID NO:114:

(i) SEQUENCE CHARACTERISTICS:
       (A) LENGTH: 333 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:114:

```
AACTGCTCTA ACATGATCGA TGAAATCATC ACCCACCTGA AGCAGCCACC GCTGCCGCTG      60

CTGGACTTCA ACAACCTCAA TGGTGAAGAC CAAGATATCC TGATGGAAAA TAACCTTCGT     120

CGTCCAAACC TCGAGGCATT CAACCGTGCT GTCAAGTCTC TGCAGAATGC ATCAGCAATT     180

GAGAGCATTC TTAAAAATCT CCTGCCATGT CTGCCCCTGG CCACGGCCGC ACCCACGCGA     240

CATCCAATCC ATATCAAGGA CGGTGACTGG AATGAATTCC GGGAAAAACT GACGTTCTAT     300

CTGGTTACCC TTGAGCAAGC GCAGGAACAA CAG                                  333
```

(2) INFORMATION FOR SEQ ID NO:115:

(i) SEQUENCE CHARACTERISTICS:
       (A) LENGTH: 333 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:115:

```
AACTGCTCTA ACATGATCGA TGAAATCATC ACCCACCTGA AGCAGCCACC GCTGCCGCTG      60

CTGGACTTCA ACAACCTCAA TGGTGAAGAC CAAGATATCC TGATGGAAAA TAACCTTCGT     120

CGTCCAAACC TCGAGGCATT CAACCGTGCT GTCAAGTCTC TGCAGAATGC ATCAGCAATT     180

GAGAGCATTC TTAAAAATCT CCTGCCATGT CTGCCCCTGG CCACGGCCGC ACCCACGCGA     240

CATCCAATCC ATATCAAGGA CGGTGACTGG AATGAATTCC GGGAAAAACT GACGTTCTAT     300

CTGGTTTCCC TTGAGCACGC GCAGGAACAA CAG                                  333
```

(2) INFORMATION FOR SEQ ID NO:116:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:116:

```
AACTGCTCTA TAATGATCGA TGAAATTATA CATCACTTAA AGAGACCACC TGCACCTTTG      60

CTGGACCCGA ACAACCTCAA TGCTGAAGAC GTCGATATCC TGATGGAACG AAACCTTCGA     120

CTTCCAAACC TGGAGAGCTT CGTAAGGGCT GTCAAGAACT TAGAAAATGC ATCAGCAATT     180

GAGAGCATTC TTAAAAATCT CCTGCCATGT CTGCCCCTGG CCACGGCCGC ACCCACGCGA     240

CATCCAATCC ATATCAAGGA CGGTGACTGG AATGAATTCC GTCGTAAACT GACCTTCTAT     300

CTGAAAACCT TGGAGAACGC GCAGGCTCAA CAG                                  333
```

(2) INFORMATION FOR SEQ ID NO:117:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:117:

```
AACTGCTCTA TAATGATCGA TGAAATTATA CATCACTTAA AGAGACCACC TAACCCTTTG      60

CTGGACCCGA ACAACCTCAA TTCTGAAGAC ATGGATATCC TGATGGAACG AAACCTTCGA     120

ACTCCAAACC TGCTCGCATT CGTAAGGGCT GTCAAGCACT TAGAAAATGC ATCAGCAATT     180

GAGAGCATTC TTAAAAATCT CCTGCCATGT CTGCCCCTGG CCACGGCCGC ACCCACGCGA     240

CATCCAATCC ATATCAAGGA CGGTGACTGG AATGAATTCC GTCGTAAACT GACCTTCTAT     300

CTGAAAACCT TGGAGAACGC GCAGGCTCAA CAG                                  333
```

(2) INFORMATION FOR SEQ ID NO:118:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:118:

```
AACTGCTCTA TAATGATCGA TGAAATTATA CATCACTTAA AGGTTCCACC TGCACCTTTG      60

CTGGACAGTA ACAACCTCAA TTCCGAAGAC ATGGATATCC TGATGGAACG AAACCTTCGA     120

CTTCCAAACC TGCTCGCATT CGTAAGGGCT GTCAAGAACT TAGAAAATGC ATCAGCAATT     180

GAGAGCATTC TTAAAAATCT CCTGCCATGT CTGCCCCTGG CCACGGCCGC ACCCACGCGA     240

CATCCAATCC ATATCAAGGA CGGTGACTGG AATGAATTCC GTCGTAAACT GACCTTCTAT     300

CTGAAAACCT TGGAGAACGC GCAGGCTCAA CAG                                  333
```

(2) INFORMATION FOR SEQ ID NO:119:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:119:

```
AACTGCTCTA ACATGATCGA TGAAATCATC ACCCACCTGA AGCAGCCACC GCTGCCGCTG      60

CTGGACTTCA ACAACCTCAA TGGTGAAGAC CAAGATATCC TGATGGAAAA TAACCTTCGT     120

CGTCCAAACC TCGAGGCATT CAACCGTGCT GTCAAGTCTC TGCAGAATGC ATCAGGTATT     180

GAGGCAATTC TTCGTAATCT CCAACCATGT CTGCCCTCTG CCACGGCCGC ACCCTCTCGA     240

CATCCAATCA TCATCAAGGC AGGTGACTGG CAAGAATTCC GGGAAAAACT GACGTTCTAT     300

CTGGTTACCC TTGAGCAAGC GCAGGAACAA CAG                                   333
```

(2) INFORMATION FOR SEQ ID NO:120:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:120:

```
AACTGCTCTA ACATGATCGA TGAAATCATC ACCCACCTGA AGCAGCCACC GCTGCCGCTG      60

CTGGACTTCA ACAACCTCAA TGGTGAAGAC CAAGATATCC TGATGGAAAA TAACCTTCGT     120

CGTCCAAACC TCGAGGCATT CAACCGTGCT GTCAAGTCTC TGCAGAATGC ATCAGGTATT     180

GAGGCAATTC TTCGTAATCT CGTACCATGT CTGCCCTCTG CCACGGCCGC ACCCTCTCGA     240

CATCCAATCA CCATCAAGGC AGGTGACTGG CAAGAATTCC GGGAAAAACT GACGTTCTAT     300

CTGGTTACCC TTGAGCAAGC GCAGGAACAA CAG                                   333
```

(2) INFORMATION FOR SEQ ID NO:121:

(i) SEQUENCE CHARACTERISTICS:
        (A) LENGTH: 333 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:121:

```
AACTGCTCTA ACATGATCGA TGAAATCATC ACCCACCTGA AGCAGCCACC GCTGCCGCTG      60

CTGGACTTCA ACAACCTCAA TGGTGAAGAC CAAGATATCC TGATGGAAAA TAACCTTCGT     120

CGTCCAAACC TCGAGGCATT CAACCGTGCT GTCAAGTCTC TGCAGAATGC ATCAGGTATT     180

GAGGCAATTC TTCGTAATCT CGTACCATGT CTGCCCTCTG CCACGGCCGC ACCCTCTCGA     240

CATCCAATCA CCATCAAGGC AGGTGACTGG CAAGAATTCC GGGAAAAACT GACGTTCTAT     300

CTGGTTTCCC TTGAGCACGC GCAGGAACAA CAG                                   333
```

(2) INFORMATION FOR SEQ ID NO:122:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:122:

```
ATGGCTAACT GCTCTATAAT GATCGATGAA ATTATACATC ACTTAAAGAG ACCACCTGCA      60
CCTTTGCTGG ACCCGAACAA CCTCAATGCT GAAGACGTCG ATATCCTGAT GGAACGAAAC     120
CTTCGACTTC CAAACCTGGA GAGCTTCGTA AGGGCTGTCA AGAACTTAGA AAATGCATCA     180
GCAATTGAGA GCATTCTTAA AAATCTCCTG CCATGTCTGC CCCTGGCCAC GGCCGCACCC     240
ACGCGACATC CAATCCATAT CAAGGACGGT GACTGGAATG AATTCCGTCG TAAACTGACC     300
TTCTATCTGA AAACCTTGGA GAACGCGCAG GCTCAACAG                            339
```

(2) INFORMATION FOR SEQ ID NO:123:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:123:

```
ATGGCTAACT GCTCTATAAT GATCGATGAA ATTATACATC ACTTAAAGAG ACCACCTAAC      60
CCTTTGCTGG ACCCGAACAA CCTCAATTCT GAAGACATGG ATATCCTGAT GGAACGAAAC     120
CTTCGAACTC CAAACCTGCT CGCATTCGTA AGGGCTGTCA AGCACTTAGA AAATGCATCA     180
GCAATTGAGA GCATTCTTAA AAATCTCCTG CCATGTCTGC CCCTGGCCAC GGCCGCACCC     240
ACGCGACATC CAATCCATAT CAAGGACGGT GACTGGAATG AATTCCGTCG TAAACTGACC     300
TTCTATCTGA AAACCTTGGA GAACGCGCAG GCTCAACAG                            339
```

(2) INFORMATION FOR SEQ ID NO:124:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:124:

```
ATGGCTAACT GCTCTATAAT GATCGATGAA ATTATACATC ACTTAAAGGT TCCACCTGCA      60
CCTTTGCTGG ACAGTAACAA CCTCAATTCC GAAGACATGG ATATCCTGAT GGAACGAAAC     120
CTTCGACTTC CAAACCTGCT CGCATTCGTA AGGGCTGTCA AGAACTTAGA AAATGCATCA     180
GCAATTGAGA GCATTCTTAA AAATCTCCTG CCATGTCTGC CCCTGGCCAC GGCCGCACCC     240
ACGCGACATC CAATCCATAT CAAGGACGGT GACTGGAATG AATTCCGTCG TAAACTGACC     300
TTCTATCTGA AAACCTTGGA GAACGCGCAG GCTCAACAG                            339
```

(2) INFORMATION FOR SEQ ID NO:125:

(i) SEQUENCE CHARACTERISTICS:
  (A) LENGTH: 339 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:125:

```
ATGGCTAACT GCTCTAACAT GATCGATGAA ATCATCACCC ACCTGAAGCA GCCACCGCTG    60

CCGCTGCTGG ACTTCAACAA CCTCAATGGT GAAGACCAAG ATATCCTGAT GGAAAATAAC   120

CTTCGTCGTC CAAACCTCGA GGCATTCAAC CGTGCTGTCA AGTCTCTGCA GAATGCATCA   180

GGTATTGAGG CAATTCTTCG TAATCTCCAA CCATGTCTGC CCTCTGCCAC GGCCGCACCC   240

TCTCGACATC CAATCATCAT CAAGGCAGGT GACTGGCAAG AATTCCGGGA AAAACTGACG   300

TTCTATCTGG TTACCCTTGA GCAAGCGCAG GAACAACAG                         339
```

(2) INFORMATION FOR SEQ ID NO:126:

(i) SEQUENCE CHARACTERISTICS:
  (A) LENGTH: 339 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:126:

```
ATGGCTAACT GCTCTAACAT GATCGATGAA ATCATCACCC ACCTGAAGCA GCCACCGCTG    60

CCGCTGCTGG ACTTCAACAA CCTCAATGGT GAAGACCAAG ATATCCTGAT GGAAAATAAC   120

CTTCGTCGTC CAAACCTCGA GGCATTCAAC CGTGCTGTCA AGTCTCTGCA GAATGCATCA   180

GGTATTGAGG CAATTCTTCG TAATCTCGTA CCATGTCTGC CCTCTGCCAC GGCCGCACCC   240

TCTCGACATC CAATCACCAT CAAGGCAGGT GACTGGCAAG AATTCCGGGA AAAACTGACG   300

TTCTATCTGG TTACCCTTGA GCAAGCGCAG GAACAACAG                         339
```

(2) INFORMATION FOR SEQ ID NO:127:

(i) SEQUENCE CHARACTERISTICS:
  (A) LENGTH: 339 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:127:

```
ATGGCTAACT GCTCTAACAT GATCGATGAA ATCATCACCC ACCTGAAGCA GCCACCGCTG    60

CCGCTGCTGG ACTTCAACAA CCTCAATGGT GAAGACCAAG ATATCCTGAT GGAAAATAAC   120

CTTCGTCGTC CAAACCTCGA GGCATTCAAC CGTGCTGTCA AGTCTCTGCA GAATGCATCA   180

GGTATTGAGG CAATTCTTCG TAATCTCGTA CCATGTCTGC CCTCTGCCAC GGCCGCACCC   240

TCTCGACATC CAATCACCAT CAAGGCAGGT GACTGGCAAG AATTCCGGGA AAAACTGACG   300

TTCTATCTGG TTTCCCTTGA GCACGCGCAG GAACAACAG                         339
```

(2) INFORMATION FOR SEQ ID NO:128:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:128:

```
Met Ala Pro Met Thr Gln Thr Thr Ser Leu Lys Thr Ser Trp Val Asn
 1               5                  10                  15
Cys Ser Asn Met Ile Asp Glu Ile Ile Thr His Leu Lys Gln Pro Pro
                 20                  25                  30
Leu Pro Leu Leu Asp Phe Asn Asn Leu Asn Gly Glu Asp Gln Asp Ile
             35                  40                  45
Leu Met Glu Asn Asn Leu Arg Arg Pro Asn Leu Glu Ala Phe Asn Arg
 50                      55                  60
Ala Val Lys Ser Leu Gln Asn Ala Ser Ala Ile Glu Ser Ile Leu Lys
 65                  70                  75                  80
Asn Leu Leu Pro Cys Leu Pro Leu Ala Thr Ala Ala Pro Thr Arg His
                 85                  90                  95
Pro Ile His Ile Lys Asp Gly Asp Trp Asn Glu Phe Arg Arg Lys Leu
                100                 105                 110
Thr Phe Tyr Leu Lys Thr Leu Glu Asn Ala Gln Ala Gln Gln Thr Thr
             115                 120                 125
Leu Ser Leu Ala Ile Phe
            130
```

(2) INFORMATION FOR SEQ ID NO:129:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 18
        (D) OTHER INFORMATION: /note= "Xaa at position 18 is Asn
            or Ile"

(ix) FEATURE:
        (A) NAME/KEY: Modified-site
        (B) LOCATION: 19
        (D) OTHER INFORMATION: /note= "Xaa at position 19 is Met,
            Ala, or Ile"

(ix) FEATURE:
        (A) NAME/KEY: Modified-site
        (B) LOCATION: 20
        (D) OTHER INFORMATION: /note= "Xaa at position 20 is Ile,
            Pro, or Leu"

(ix) FEATURE:
        (A) NAME/KEY: Modified-site
        (B) LOCATION: 23
        (D) OTHER INFORMATION: /note= "Xaa at position 23 is Ile,
            Ala, or Leu"

```
(ix) FEATURE:
    (A) NAME/KEY: Modified-site
    (B) LOCATION: 25
    (D) OTHER INFORMATION: /note= "Xaa at position 25 is Thr
        or His"

(ix) FEATURE:
    (A) NAME/KEY: Modified-site
    (B) LOCATION: 29
    (D) OTHER INFORMATION: /note= "Xaa at position 29 is Gln,
        Arg, Val, or Leu"

(ix) FEATURE:
    (A) NAME/KEY: Modified-site
    (B) LOCATION: 32
    (D) OTHER INFORMATION: /note= "Xaa at position 32 is Leu,
        Ala, Asn, or Arg"

(ix) FEATURE:
    (A) NAME/KEY: Modified-site
    (B) LOCATION: 34
    (D) OTHER INFORMATION: /note= "Xaa at position 34 is Leu
        or Ser"

(ix) FEATURE:
    (A) NAME/KEY: Modified-site
    (B) LOCATION: 37
    (D) OTHER INFORMATION: /note= "Xaa at position 37 is Phe,
        Pro, or Ser"

(ix) FEATURE:
    (A) NAME/KEY: Modified-site
    (B) LOCATION:; 38
    (D) OTHER INFORMATION: /note= "Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Ala, Ser, Asp, or Asn"

(ix) FEATURE:
    (A) NAME/KEY: Modified-site
    (B) LOCATION: 45
    (D) OTHER INFORMATION: /note= "Xaa at position 45 is Gln,
        Val, or Met"

(ix) FEATURE:
    (A) NAME/KEY: Modified-site
    (B) LOCATION: 46
    (D) OTHER INFORMATION: /note= "Xaa at position 46 is Asp
        or Ser"

(ix) FEATURE:
    (A) NAME/KEY: Modified-site
    (B) LOCATION: 49
    (D) OTHER INFORMATION: /note= "Xaa at position 49 is Met,
        Ile, Leu, or Asp"

(ix) FEATURE:
    (A) NAME/KEY: Modified-site
    (B) LOCATION: 50
    (D) OTHER INFORMATION: /note= "Xaa at position 50 is Glu
        or Asp"

(ix) FEATURE:
    (A) NAME/KEY: Modified-site
    (B) LOCATION: 51
    (D) OTHER INFORMATION: /note= "Xaa at position 51 is Asn,
        Arg, or Ser"

(ix) FEATURE:
    (A) NAME/KEY: Modified-site
    (B) LOCATION: 55
    (D) OTHER INFORMATION: /note= "Xaa at position 55 is Arg,
        Leu, or Thr"
```

(ix) FEATURE:
              (A) NAME/KEY: Modified-site
              (B) LOCATION: 56
              (D) OTHER INFORMATION: /note= "Xaa at position 56 is Pro
                  or Ser"

(ix) FEATURE:
              (A) NAME/KEY: Modified-site
              (B) LOCATION: 59
              (D) OTHER INFORMATION: /note= "Xaa at position 59 is Glu
                  or Leu"

(ix) FEATURE:
              (A) NAME/KEY: Modified-site
              (B) LOCATION: 60
              (D) OTHER INFORMATION: /note= "Xaa at position 60 is Ala
                  or Ser"

(ix) FEATURE:
              (A) NAME/KEY: Modified-site
              (B) LOCATION: 62
              (D) OTHER INFORMATION: /note= "Xaa at position 62 is Asn
                  Val, or Pro"

(ix) FEATURE:
              (A) NAME/KEY: Modified-site
              (B) LOCATION: 63
              (D) OTHER INFORMATION: /note= "Xaa at position 63 is Arg
                  or His"

(ix) FEATURE:
              (A) NAME/KEY: Modified-site
              (B) LOCATION: 65
              (D) OTHER INFORMATION: /note= "Xaa at position 65 is Val
                  or Ser"

(ix) FEATURE:
              (A) NAME/KEY: Modified-site
              (B) LOCATION: 67
              (D) OTHER INFORMATION: /note= "Xaa at position 67 is Ser,
                  Asn, His, or Gly"

(ix) FEATURE:
              (A) NAME/KEY: Modified-site
              (B) LOCATION: 69
              (D) OTHER INFORMATION: /note= "Xaa at position 69 is Gln
                  or Glu"

(ix) FEATURE:
              (A) NAME/KEY: Modified-site
              (B) LOCATION: 73
              (D) OTHER INFORMATION: /note= "Xaa at position 73 is Ala
                  or Gly"

(ix) FEATURE:
              (A) NAME/KEY: Modified-site
              (B) LOCATION: 76
              (D) OTHER INFORMATION: /note= "Xaa at position 76 is Ser,
                  Ala, or Pro"

(ix) FEATURE:
              (A) NAME/KEY: Modified-site
              (B) LOCATION: 79
              (D) OTHER INFORMATION: /note= "Xaa at position 79 is Lys,
                  Arg, or Ser"

(ix) FEATURE:
              (A) NAME/KEY: Modified-site
              (B) LOCATION: 82
              (D) OTHER INFORMATION: /note= "Xaa at position 82 is Leu,
                  Glu, Val, or Trp"

(ix) FEATURE:
              (A) NAME/KEY: Modified-site
              (B) LOCATION: 85
              (D) OTHER INFORMATION: /note= "Xaa at position 85 is Leu
                  or Val"

-continued

```
(ix) FEATURE:
    (A) NAME/KEY: Modified-site
    (B) LOCATION: 87
    (D) OTHER INFORMATION: /note= "Xaa at position 87 is Leu,
        Ser, or Trp"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Pro
        or Ser"

(ix) FEATURE:
    (A) NAME/KEY: Modified-site
    (B) LOCATION: 95
    (D) OTHER INFORMATION: /note= "Xaa at position 95 is His
        or Thr"

(ix) FEATURE:
    (A) NAME/KEY: Modified-site
    (B) LOCATION: 98
    (D) OTHER INFORMATION: /note= "Xaa at position 98 is His,
        Ile, or Thr"

(ix) FEATURE:
    (A) NAME/KEY: Modified-site
    (B) LOCATION: 100
    (D) OTHER INFORMATION: /note= "Xaa at position 100 is Lys
        or Arg"

(ix) FEATURE:
    (A) NAME/KEY: Modified-site
    (B) LOCATION: 101
    (D) OTHER INFORMATION: /note= "Xaa at position 101 is Asp,
        Ala, or Met"

(ix) FEATURE:
    (A) NAME/KEY: Modified-site
    (B) LOCATION: 105
    (D) OTHER INFORMATION: /note= "Xaa at position 105 is Asn
        or Gln"

(ix) FEATURE:
    (A) NAME/KEY: Modified-site
    (B) LOCATION: 109
    (D) OTHER INFORMATION: /note= "Xaa at position 109 is Arg,
        Glu, or Leu"

(ix) FEATURE:
    (A) NAME/KEY: Modified-site
    (B) LOCATION: 112
    (D) OTHER INFORMATION: /note= "Xaa at position 112 is Thr
        or Gln"

(ix) FEATURE:
    (A) NAME/KEY: Modified-site
    (B) LOCATION: 116
    (D) OTHER INFORMATION: /note= "Xaa at position 116 is Lys,
        Val, Trp, or Ser"

(ix) FEATURE:
    (A) NAME/KEY: Modified-site
    (B) LOCATION: 117
    (D) OTHER INFORMATION: /note= "Xaa at position 117 is Thr
        or Ser"
```

```
        (ix) FEATURE:
              (A) NAME/KEY: Modified-site
              (B) LOCATION: 120
              (D) OTHER INFORMATION: /note= "Xaa at position 120 is Asn,
                  Gln, or His"

(ix) FEATURE:
              (A) NAME/KEY: Modified-site
              (B) LOCATION: 123
              (D) OTHER INFORMATION: /note= "Xaa at position 123 is Ala
                  or Glu"

(xi) SEQUENCE DESCRIPTION: SEQ ID NO:129:

Ala Pro Met Thr Gln Thr Thr Ser Leu Lys Thr Ser Trp Val Asn Cys
1               5                   10                  15

Ser Xaa Xaa Xaa Asp Glu Xaa Ile Xaa His Leu Lys Xaa Pro Pro Xaa
            20                  25                  30

Pro Xaa Leu Asp Xaa Xaa Asn Leu Asn Xaa Glu Asp Xaa Xaa Ile Leu
        35                  40                  45

Xaa Xaa Xaa Asn Leu Arg Xaa Xaa Asn Leu Xaa Xaa Phe Xaa Xaa Ala
50                  55                  60

Xaa Lys Xaa Leu Xaa Asn Ala Ser Xaa Ile Glu Xaa Ile Leu Xaa Asn
65                  70                  75                  80

Leu Xaa Pro Cys Xaa Pro Xaa Xaa Thr Ala Xaa Pro Xaa Arg Xaa Pro
            85                  90                  95

Ile Xaa Ile Xaa Xaa Gly Asp Trp Xaa Glu Phe Arg Xaa Lys Leu Xaa
        100                 105                 110

Phe Tyr Leu Xaa Xaa Leu Glu Xaa Ala Gln Xaa Gln Gln Thr Thr Leu
        115                 120                 125

Ser Leu Ala Ile Phe
        130

(2) INFORMATION FOR SEQ ID NO:130:

(i) SEQUENCE CHARACTERISTICS:
            (A) LENGTH: 111 amino acids
            (B) TYPE: amino acid
            (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Met- or Met-Ala may or may
                  not precede the amino acid in position 1"

(ix) FEATURE:
              (A) NAME/KEY: Modified-site
              (B) LOCATION: 4
              (D) OTHER INFORMATION: /note= "Xaa at position 4 is Asn or
                  Ile"

(ix) FEATURE:
              (A) NAME/KEY: Modified-site
              (B) LOCATION: 5
              (D) OTHER INFORMATION: /note= "Xaa at position 5 is Met,
                  Ala, or Ile"

(ix) FEATURE:
              (A) NAME/KEY: Modified-site
              (B) LOCATION: 6
              (D) OTHER INFORMATION: /note= "Xaa at position 6 is Ile,
                  Pro, or Leu"
```

```
(ix) FEATURE:
    (A) NAME/KEY: Modified-site
    (B) LOCATION: 9
    (D) OTHER INFORMATION: /note= "Xaa at position 9 is Ile,
        Ala, or Leu"

(ix) FEATURE:
    (A) NAME/KEY: Modified-site
    (B) LOCATION: 11
    (D) OTHER INFORMATION: /note= "Xaa at position 11 is Thr
        or His"

(ix) FEATURE:
    (A) NAME/KEY: Modified-site
    (B) LOCATION: 15
    (D) OTHER INFORMATION: /note= "Xaa at position 15 is Gln,
        Arg, Val, or Leu"

(ix) FEATURE:
    (A) NAME/KEY: Modified-site
    (B) LOCATION: 18
    (D) OTHER INFORMATION: /note= "Xaa at position 18 is Leu,
        Ala, Asn, or Arg"

(ix) FEATURE:
    (A) NAME/KEY: Modified-site
    (B) LOCATION: 20
    (D) OTHER INFORMATION: /note= "Xaa at position 20 is Leu
        or Ser"

(ix) FEATURE:
    (A) NAME/KEY: Modified-site
    (B) LOCATION: 23
    (D) OTHER INFORMATION: /note= "Xaa at position 23 is Phe,
        Pro, or Ser"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 28
    (D) OTHER INFORMATION: /note= "Xaa at position 28 is Gly,
        Ala, Ser, Asp, or Asn"

(ix) FEATURE:
    (A) NAME/KEY: Modified-site
    (B) LOCATION: 31
    (D) OTHER INFORMATION: /note= "Xaa at position 31 is Gln,
        Val, or Met"

(ix) FEATURE:
    (A) NAME/KEY: Modified-site
    (B) LOCATION: 32
    (D) OTHER INFORMATION: /note= "Xaa at position 32 is Asp
        or Ser"

(ix) FEATURE:
    (A) NAME/KEY: Modified-site
    (B) LOCATION: 35
    (D) OTHER INFORMATION: /note= "Xaa at position 35 is Met,
        Ile, Leu, or Asp"

(ix) FEATURE:
    (A) NAME/KEY: Modified-site
    (B) LOCATION: 36
    (D) OTHER INFORMATION: /note= "Xaa at position 36 is Glu
        or Asp"

(ix) FEATURE:
    (A) NAME/KEY: Modified-site
    (B) LOCATION: 37
    (D) OTHER INFORMATION: /note= "Xaa at position 37 is Asn,
        Arg, or Ser"
```

```
(ix) FEATURE:
    (A) NAME/KEY: Modified-site
    (B) LOCATION: 41
    (D) OTHER INFORMATION: /note= "Xaa at position 41 is Arg,
        Leu, or Thr"

(ix) FEATURE:
    (A) NAME/KEY: Modified-site
    (B) LOCATION: 42
    (D) OTHER INFORMATION: /note= "Xaa at position 42 is Pro
        or Ser"

(ix) FEATURE:
    (A) NAME/KEY: Modified-site
    (B) LOCATION: 45
    (D) OTHER INFORMATION: /note= "Xaa at position 45 is Glu
        or Leu"

(ix) FEATURE:
    (A) NAME/KEY: Modified-site
    (B) LOCATION: 46
    (D) OTHER INFORMATION: /note= "Xaa at position 46 is Ala
        or Ser"

(ix) FEATURE:
    (A) NAME/KEY: Modified-site
    (B) LOCATION: 48
    (D) OTHER INFORMATION: /note= "Xaa at position 48 is Asn,
        Val, or Pro"

(ix) FEATURE:
    (A) NAME/KEY: Modified-site
    (B) LOCATION: 49
    (D) OTHER INFORMATION: /note= "Xaa at position 49 is Arg
        or His"

(ix) FEATURE:
    (A) NAME/KEY: Modified-site
    (B) LOCATION: 51
    (D) OTHER INFORMATION: /note= "Xaa at position 51 is Val
        or Ser"

(ix) FEATURE:
    (A) NAME/KEY: Modified-site
    (B) LOCATION: 53
    (D) OTHER INFORMATION: /note= "Xaa at position 53 is Ser,
        Asn, His, or Gly"

(ix) FEATURE:
    (A) NAME/KEY: Modified-site
    (B) LOCATION: 55
    (D) OTHER INFORMATION: /note= "Xaa at position 55 is Gln
        or Glu"

(ix) FEATURE:
    (A) NAME/KEY: Modified-site
    (B) LOCATION: 59
    (D) OTHER INFORMATION: /note= "Xaa at position 59 is Ala
        or Gly"

(ix) FEATURE:
    (A) NAME/KEY: Modified-site
    (B) LOCATION: 62
    (D) OTHER INFORMATION: /note= "Xaa at position 62 is Ser,
        Ala, or Pro"

(ix) FEATURE:
    (A) NAME/KEY: Modified-site
    (B) LOCATION: 65
    (D) OTHER INFORMATION: /note= "Xaa at position 65 is Lys,
        Arg, or Ser"

(ix) FEATURE:
    (A) NAME/KEY: Modified-site
    (B) LOCATION: 67
    (D) OTHER INFORMATION: /note= "Xaa at position 67 is Leu,
        Glu, or Val"
```

-continued

```
(ix) FEATURE:
    (A) NAME/KEY: Modified-site
    (B) LOCATION: 68
    (D) OTHER INFORMATION: /note= "Xaa at position 68 is Leu,
        Glu, Val, or Trp"

(ix) FEATURE:
    (A) NAME/KEY: Modified-site
    (B) LOCATION: 71
    (D) OTHER INFORMATION: /note= "Xaa at position 71 is Leu
        or Val"

(ix) FEATURE:
    (A) NAME/KEY: Modified-site
    (B) LOCATION: 73
    (D) OTHER INFORMATION: /note= "Xaa at position 73 is Leu,
        Ser, or Trp"

(ix) FEATURE:
    (A) NAME/KEY: Modified-site
    (B) LOCATION: 74
    (D) OTHER INFORMATION: /note= "Xaa at position 74 is Ala
        or Trp"

(ix) FEATURE:
    (A) NAME/KEY: Modified-site
    (B) LOCATION: 77
    (D) OTHER INFORMATION: /note= "Xaa at position 77 is Ala
        or Pro"

(ix) FEATURE:
    (A) NAME/KEY: Modified-site
    (B) LOCATION: 79
    (D) OTHER INFORMATION: /note= "Xaa at position 79 is Pro
        or Ser"

(ix) FEATURE:
    (A) NAME/KEY: Modified-site
    (B) LOCATION: 81
    (D) OTHER INFORMATION: /note= "Xaa at position 81 is His
        or Thr"

(ix) FEATURE:
    (A) NAME/KEY: Modified-site
    (B) LOCATION: 84
    (D) OTHER INFORMATION: /note= "Xaa at position 84 is His,
        Ile, or Thr"

(ix) FEATURE:
    (A) NAME/KEY: Modified-site
    (B) LOCATION: 86
    (D) OTHER INFORMATION: /note= "Xaa at position 86 is Lys
        or Arg"

(ix) FEATURE:
    (A) NAME/KEY: Modified-site
    (B) LOCATION: 87
    (D) OTHER INFORMATION: /note= "Xaa at position 87 is Asp,
        Ala, or Met"

(ix) FEATURE:
    (A) NAME/KEY: Modified-site
    (B) LOCATION: 91
    (D) OTHER INFORMATION: /note= "Xaa at position 91 is Asn
        or Glu"

(ix) FEATURE:
    (A) NAME/KEY: Modified-site
    (B) LOCATION: 95
    (D) OTHER INFORMATION: /note= "Xaa at position 95 is Arg,
        Glu, or Leu"

(ix) FEATURE:
    (A) NAME/KEY: Modified-site
    (B) LOCATION: 98
    (D) OTHER INFORMATION: /note= "Xaa at position 98 is Thr
        or Gln"
```

```
    (ix) FEATURE:
         (A) NAME/KEY: Modified-site
         (B) LOCATION: 102
         (D) OTHER INFORMATION: /note= "Xaa at position 102 is Lys,
             Val, Trp, or Ser"

(ix) FEATURE:
         (A) NAME/KEY: Modified-site
         (B) LOCATION: 103
         (D) OTHER INFORMATION: /note= "Xaa at position 103 is Thr
             or Ser"

(ix) FEATURE:
         (A) NAME/KEY: Modified-site
         (B) LOCATION: 106
         (D) OTHER INFORMATION: /note= "Xaa at position 106 is Asn,
             Gln, or His"

(ix) FEATURE:
         (A) NAME/KEY: Modified-site
         (B) LOCATION: 109
         (D) OTHER INFORMATION: /note= "Xaa at position 109 is Ala
             or Glu"

(xi) SEQUENCE DESCRIPTION: SEQ ID NO:130:

Asn Cys Ser Xaa Xaa Xaa Asp Glu Xaa Ile Xaa His Leu Lys Xaa Pro
1               5                   10                  15

Pro Xaa Pro Xaa Leu Asp Xaa Xaa Asn Leu Asn Xaa Glu Asp Xaa Xaa
            20                  25                  30

Ile Leu Xaa Xaa Xaa Asn Leu Arg Xaa Xaa Asn Leu Xaa Xaa Phe Xaa
            35                  40                  45

Xaa Ala Xaa Lys Xaa Leu Xaa Asn Ala Ser Xaa Ile Glu Xaa Ile Leu
        50                  55                  60

Xaa Asn Xaa Xaa Pro Cys Xaa Pro Xaa Xaa Thr Ala Xaa Pro Xaa Arg
65                  70                  75                  80

Xaa Pro Ile Xaa Ile Xaa Xaa Gly Asp Trp Xaa Glu Phe Arg Xaa Lys
            85                  90                  95

Leu Xaa Phe Tyr Leu Xaa Xaa Leu Glu Xaa Ala Gln Xaa Gln Gln
            100                 105                 110

(2) INFORMATION FOR SEQ ID NO:131:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:131:

CTAGCCACGG CCGCACCCAC GCGACATCCA ATCCATATCA AGGACGGTGA CTGGAATG         58

(2) INFORMATION FOR SEQ ID NO:132:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:132:

TTAACATTCC AGTCACCGTC CTTGATATGG ATTGGATGTC GCGTGGGTGC GGCCGTGG         58
```

(2) INFORMATION FOR SEQ ID NO:133:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:133:

AAGGAGATAT ATCCATGAAC TGCTCTAAC                                                29

(2) INFORMATION FOR SEQ ID NO:134:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:134:

Met Asn Cys Ser Asn
1               5

(2) INFORMATION FOR SEQ ID NO:135:

(i) SEQUENCE CHARACTERISTICS:
        (A) LENGTH: 120 amino acids
        (B) TYPE: amino acid
        (D) TOPOLOGY: linear (ii) MOLECULE TYPE: peptide (xi) SEQUENCE DESCRIPTION: SEQ ID NO:135:

Met Asn Cys Ser Asn Met Ile Asp Glu Ile Ile Thr His Leu Lys Gln
1               5                  10                  15

Pro Pro Leu Pro Leu Leu Asp Phe Asn Asn Leu Asn Gly Glu Asp Gln
            20                  25                  30

Asp Ile Leu Met Glu Asn Asn Leu Arg Arg Pro Asn Leu Glu Ala Phe
        35                  40                  45

Asn Arg Ala Val Lys Ser Leu Gln Asn Ala Ser Ala Ile Glu Ser Ile
    50                  55                  60

Leu Lys Asn Leu Leu Pro Cys Leu Pro Leu Ala Thr Ala Ala Pro Thr
65                  70                  75                  80

Arg His Pro Ile His Ile Lys Asp Gly Asp Trp Asn Glu Phe Arg Arg
                85                  90                  95

Lys Leu Thr Phe Tyr Leu Lys Thr Leu Glu Asn Ala Gln Ala Gln Gln
            100                 105                 110

Thr Thr Leu Arg Leu Ala Ile Phe
            115                 120

(2) INFORMATION FOR SEQ ID NO:136:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:136:

```
AATTCCGTCG TAAACTGACC TTCTATCTGA AAACCTTGGA GAACGCGCAG GCTCAACAGA        60

CCACTCTGTC G                                                             71
```

(2) INFORMATION FOR SEQ ID NO:137:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:137:

```
CTAGCGACAG AGTGGTCTGT TGAGCCTGCG CGTTCTCCAA GGTTTTCAGA TAGAAGGTCA        60

GTTTACGACG G                                                             71
```

(2) INFORMATION FOR SEQ ID NO:138:

(i) SEQUENCE CHARACTERISTICS:
        (A) LENGTH: 112 amino acids
        (B) TYPE: amino acid
        (D) TOPOLOGY: linear (ii) MOLECULE TYPE: peptide (xi) SEQUENCE DESCRIPTION: SEQ ID NO:138:

```
Met Asn Cys Ser Asn Met Ile Asp Glu Ile Ile Thr His Leu Lys Gln
1               5                   10                  15

Pro Pro Leu Pro Leu Leu Asp Phe Asn Asn Leu Asn Gly Glu Asp Gln
            20                  25                  30

Asp Ile Leu Met Glu Asn Asn Leu Arg Arg Pro Asn Leu Glu Ala Phe
        35                  40                  45

Asn Arg Ala Val Lys Ser Leu Gln Asn Ala Ser Ala Ile Glu Ser Ile
    50                  55                  60

Leu Lys Asn Leu Leu Pro Cys Leu Pro Leu Ala Thr Ala Ala Pro Thr
65                  70                  75                  80

Arg His Pro Ile His Ile Lys Ala Gly Asp Trp Asn Glu Phe Arg Arg
                85                  90                  95

Lys Leu Thr Phe Tyr Leu Lys Thr Leu Glu Asn Ala Gln Ala Gln Gln
                100                 105                 110
```

(2) INFORMATION FOR SEQ ID NO:139:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (xi) SEQUENCE DESCRIPTION: SEQ ID NO:139:

```
Met Asn Cys Ser Asn Met Ile Asp Glu Ile Ile Thr His Leu Lys Gln
1               5                   10                  15

Pro Pro Leu Pro Leu Leu Asp Phe Asn Asn Leu Asn Gly Glu Asp Gln
            20                  25                  30

Asp Ile Leu Met Glu Asn Asn Leu Arg Arg Pro Asn Leu Glu Ala Phe
        35                  40                  45
```

```
      Asn Arg Ala Val Lys Ser Leu Gln Asn Ala Ser Ala Ile Glu Ser Ile
       50                  55                  60

Leu Lys Asn Leu Leu Pro Cys Leu Pro Leu Ala
      65                  70                  75
```

(2) INFORMATION FOR SEQ ID NO:140:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:140:

```
CTAGCCACGG CCGCACCCAC GCGACATCCA ATCCATATCA AGGCTGGTGA CTGGAATG      58
```

(2) INFORMATION FOR SEQ ID NO:141:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:141:

```
AATTCATTCC AGTCACCAGC CTTGATATGG ATTGGATGTC GCGTGGGTGC GGCCGTGG      58
```

(2) INFORMATION FOR SEQ ID NO:142:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:142:

```
AATTCCGTCG TAAACTGACC TTCTATCTGA AAACCTTGGA GAACGCGCAG GCTCAACAGT    60

AATA                                                                 64
```

(2) INFORMATION FOR SEQ ID NO:143:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:143:

```
AGCTTATTAC TGTTGAGCCT GCGCGTTCTC CAAGGTTTTC AGATAGAAGG TCAGTTTACG    60

ACGG                                                                 64
```

(2) INFORMATION FOR SEQ ID NO:144:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:144:

```
ATGGCTCCAA TGACTCAGAC TACTTCTCTT AAGACTTCTT GGGTTAACTG CTCTAACATG       60

ATCGATGAAA TTATAACACA CTTAAAGCAG CCACCTTTGC CTTTGCTGGA CTTCAACAAC      120

CTCAATGGGG AAGACCAAGA CATTCTGATG GAAAATAACC TTCGAAGGCC AAACCTGGAG      180

GCATTCAACA GGGCTGTCAA GAGTTTACAG AATGCATCAG CAATTGAGAG CATTCTTAAA      240

AATCTCCTGC CATGTCTGCC CCTGGCCACG GCCGCACCCA CGCGACATCC AATCCATATC      300

AAGGACGGTG ACTGGAATGA ATTCCGTCGT AAACTGACCT TCTATCTGAA AACCTTGGAG      360

AACGCGCAGG CTCAACAGAC CACTCTGTCG CTAGCGATCT TTTAATAA                   408
```

(2) INFORMATION FOR SEQ ID NO:145:

(i) SEQUENCE CHARACTERISTICS:
        (A) LENGTH: 157 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..156

(xi) SEQUENCE DESCRIPTION: SEQ ID NO:145:

```
ATC GAT GAA ATC ATC ACC CAC CTG AAG CAG CCA CCG CTG CCG CTG CTG         48
Ile Asp Glu Ile Ile Thr His Leu Lys Gln Pro Pro Leu Pro Leu Leu
 1               5                  10                  15

GAC TTC AAC AAC CTC AAT GGT GAA GAC CAA GAT ATC CTG ATG GAA AAT         96
Asp Phe Asn Asn Leu Asn Gly Glu Asp Gln Asp Ile Leu Met Glu Asn
                20                  25                  30

AAC CTT CGT CGT CCA AAC CTC GAG GCA TTC AAC CGT GCT GTC AAG TCT        144
Asn Leu Arg Arg Pro Asn Leu Glu Ala Phe Asn Arg Ala Val Lys Ser
            35                  40                  45

CTG CAG AAT GCA T                                                      157
Leu Gln Asn Ala
    50
```

(2) INFORMATION FOR SEQ ID NO:146:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:146:

```
Ile Asp Glu Ile Ile Thr His Leu Lys Gln Pro Pro Leu Pro Leu Leu
 1               5                  10                  15

Asp Phe Asn Asn Leu Asn Gly Glu Asp Gln Asp Ile Leu Met Glu Asn
                20                  25                  30

Asn Leu Arg Arg Pro Asn Leu Glu Ala Phe Asn Arg Ala Val Lys Ser
            35                  40                  45

Leu Gln Asn Ala
    50
```

(2) INFORMATION FOR SEQ ID NO:147:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:147:

```
CCATGGCTCC AATGACTCAG ACTACTTCTC TTAAGACTTC TTGGGTTAAC TGCTCTAACA     60

TGATCGATGA AATTATAACA CACTTAAAGC AGCCACCTTT GCCTTTGCTG GACTTCAACA    120

ACCTCAATGG GGAAGACCAA GACATTCTGA TGGAAAATAA CCTTCGAAGG CCAAACCTGG    180

AGGCATTCAA CAGGGCTGTC AAGAGTTTAC AGAATGCATC AGCAATTGAG AGCATTCTTA    240

AAAATCTCCT GCCATGTCTG CCCCTGGCCA CGGCCGCACC CACGCGACAT CCAATCCATA    300

TCAAGGACGG TGACTGGAAT GAATTCCGTC GTAAACTGAC CTTCTATCTG AAAACCTTGG    360

AGAACGCGCA GGCTCAACAG ACCACTCTGT CGCTAGCGAT CTTTTAATAA GCTT          414
```

(2) INFORMATION FOR SEQ ID NO:148:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:148:

```
AAGCTTATTA AAAGATCGCT AGCGACAGAG TGGTCTGTTG AGCCTGCGCG TTCTCCAAGG     60

TTTTCAGATA GAAGGTCAGT TTACGACGGA ATTCATTCCA GTCACCGTCC TTGATATGGA    120

TTGGATGTCG CGTGGGTGCG GCCGTGGCCA GGGGCAGACA TGGCAGGAGA TTTTTAAGAA    180

TGCTCTCAAT TGCTGATGCA TTCTGTAAAC TCTTGACAGC CCTGTTGAAT GCCTCCAGGT    240

TTGGCCTTCG AAGGTTATTT TCCATCAGAA TGTCTTGGTC TTCCCCATTG AGGTTGTTGA    300

AGTCCAGCAA AGGCAAAGGT GGCTGCTTTA AGTGTGTTAT AATTTCATCG ATCATGTTAG    360

AGCAGTTAAC CCAAGAAGTC TTAAGAGAAG TAGTCTGAGT CATTGGAGCC ATGG          414
```

(2) INFORMATION FOR SEQ ID NO:149:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:149:

```
ATGATGATTA CTCTGCGCAA ACTTCCTCTG GCGGTTGCCG TCGCAGCGGG CGTAATGTCT     60

GCTCAGGCCA TGGCTAACTG C                                               81
```

(2) INFORMATION FOR SEQ ID NO:150:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:150:

GCAGTTAGCC ATGGCCTGAG CAGACATTAC GCCCGCTGCG ACGGCAACCG CCAGAGGAAG          60

TTTGCGCAGA GTAATCATCA T                                                   81

(2) INFORMATION FOR SEQ ID NO:151:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:151:

CATGGCTAAC TGCTCTAACA TGAT                                                24

(2) INFORMATION FOR SEQ ID NO:152:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:152:

CGATCATGTT AGAGCAGTTA GC                                                  22

(2) INFORMATION FOR SEQ ID NO:153:

(i) SEQUENCE CHARACTERISTICS:
            (A) LENGTH: 12 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:153:

ATGGCTAACT GC                                                             12

(2) INFORMATION FOR SEQ ID NO:154:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:154:

Met Ala Asn Cys
1

(2) INFORMATION FOR SEQ ID NO:155:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:155:

GCCGATACCG CGGCATACTC CCACCATTCA GAGA                                    34

(2) INFORMATION FOR SEQ ID NO:156:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:156:

GCCGATAAGA TCTAAAACGG GTATGGAGAA ACA                                     33

(2) INFORMATION FOR SEQ ID NO:157:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:157:

ATAGTCTTCC CCAGATATCT AACGCTTGAG                                         30

(2) INFORMATION FOR SEQ ID NO:158:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:158:

CAATACCTGA TGCGTTTTCT AAGT                                               24

(2) INFORMATION FOR SEQ ID NO:159:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:159:

GGTTTCGTTC CATCAGAATG TCCATGTCTT CAG                                     33

(2) INFORMATION FOR SEQ ID NO:160:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:160:

ATGGCTAACT GCTCTATAAT GATCGATGAA ATTATACATC ACTTAAAGAG ACCACCTAAC        60

```
CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAACGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                             339

(2) INFORMATION FOR SEQ ID NO:161:

(i) SEQUENCE CHARACTERISTICS:
        (A) LENGTH: 338 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:161:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ACATTTGATG GAACGAAACC      120

TTCGAACTCC AAACCTGCTC GCATTCGTAA GGGCTGTCAA GCACTTAGAA AACGCATCAG      180

GTATTGAGGC AATTCTTCGT AATCTCCAAC CATGTCTGCC CTCTGCCACG GCCGCACCCT      240

CTCGACATCC AATCATCATC AAGGCAGGTG ACTGGCAAGA ATTCCGGGAA AAACTGACGT      300

TCTATCTGGT TACCCTTGAG CAAGCGCAGG AACAACAG                             338

(2) INFORMATION FOR SEQ ID NO:162:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:162:

CATGGCTAAC TGCTCTAACA TGATCGATGA AATTATAACA                             40

(2) INFORMATION FOR SEQ ID NO:163:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:163:

CTTTAAGTGT GTTATAATTT CATCGATCAT GTTAGAGCAG TTAGC                       45

(2) INFORMATION FOR SEQ ID NO:164:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)
```

(xi) SEQUENCE DESCRIPTION: SEQ ID NO:164:

CACTTAAAGC AGCCACCTTT GCCTTTGCTG GACTTC					36

(2) INFORMATION FOR SEQ ID NO:165:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:165:

GAGGTTGTTG AAGTCCAGCA AAGGCAAAGG TGGCTG					36

(2) INFORMATION FOR SEQ ID NO:166:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:166:

AACAACCTCA ATGACGAAGA CATGTCT						27

(2) INFORMATION FOR SEQ ID NO:167:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:167:

AGACATGTCT TCGTCATT							18

(2) INFORMATION FOR SEQ ID NO:168:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:168:

TGAACCATAT GTCAGG							16

(2) INFORMATION FOR SEQ ID NO:169:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:169:

AATTCCTGAC ATATGGTTCA TGCA                                          24

(2) INFORMATION FOR SEQ ID NO:170:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:170:

CATGGCAAAC TGCTCTATAG CTATCGATGA AATTATACAT                         40

(2) INFORMATION FOR SEQ ID NO:171:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:171:

CTTTAAGTGA TGTATAATTT CATCGATAGC TATAGAGCAG TTTGC                   45

(2) INFORMATION FOR SEQ ID NO:172:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:172:

CATGGCAAAC TGCTCTATAA TCATCGATGA AATTATACAT                         40

(2) INFORMATION FOR SEQ ID NO:173:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:173:

CTTTAAGTGA TGTATAATTT CATCGATGAT TATAGAGCAG TTTGC                   45

(2) INFORMATION FOR SEQ ID NO:174:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:174:

ATCCTGGACG AACGAAACCT TCGAACTCCA AACCTG                36

(2) INFORMATION FOR SEQ ID NO:175:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:175:

AGTTCGAAGG TTTCGTTCGT CCAGGAT                          27

(2) INFORMATION FOR SEQ ID NO:176:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:176:

ATCCTGATCG AACGAAACCT TCGAACTCCA AACCTG                36

(2) INFORMATION FOR SEQ ID NO:177:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:177:

AGTTCGAAGG TTTCGTTCGA TCAGGAT                          27

(2) INFORMATION FOR SEQ ID NO:178:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:178:

ATCCTGCTGG AACGAAACCT TCGAACTCCA AACCTG                36

(2) INFORMATION FOR SEQ ID NO:179:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:179:

AGTTCGAAGG TTTCGTTCCA GCAGGAT                                                27

(2) INFORMATION FOR SEQ ID NO:180:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:180:

AACAACCTCA ATTCTGAAGA CGTTGAT                                                27

(2) INFORMATION FOR SEQ ID NO:181:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:181:

ATCAACGTCT TCAGAATT                                                          18

(2) INFORMATION FOR SEQ ID NO:182:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:182:

CGCGCCATGG CTAACTGCTC TATAATGATC GATGAAGCAA TACATCACTT A                     51

(2) INFORMATION FOR SEQ ID NO:183:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:183:

CGCGTCGATA AGCTTATT                                                          18

(2) INFORMATION FOR SEQ ID NO:184:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:184:

GGAGATATAT CCATGGCT                                                  18

(2) INFORMATION FOR SEQ ID NO:185:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:185:

TCGGTCCATC AGAATAGACA TGTCTTCAGC ATTGAGGTTG TT                        42

(2) INFORMATION FOR SEQ ID NO:186:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:186:

TCGGTCCATC AGAATAGAAA CGTCTTCAGC ATTGAGGTTG TT                        42

(2) INFORMATION FOR SEQ ID NO:187:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:187:

TCGGTCCATC AGAATAGACA TGTCTTCGTC ATTGAGGTTG TT                        42

(2) INFORMATION FOR SEQ ID NO:188:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:188:

TCGGTCCATC AGAATAGAAA CGTCTTCGTC ATTGAGGTTG TT                        42

(2) INFORMATION FOR SEQ ID NO:189:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:189:

TCGGTCCATC AGAATAGACA TGTCTTCAGA ATTGAGGTTG TT  42

(2) INFORMATION FOR SEQ ID NO:190:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:190:

TCGGTCCATC AGAATAGAAA CGTCTTCAGA ATTGAGGTTG TT  42

(2) INFORMATION FOR SEQ ID NO:191:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:191:

CTGCCCTCTG CCACGGCCGC ACCCTCTCGA CATCCAATCA TCATCCGT  48

(2) INFORMATION FOR SEQ ID NO:192:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:192:

AATTCTTGCC AGTCACCTGC ACGGAT  26

(2) INFORMATION FOR SEQ ID NO:193:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:193:

ATGGGTGACT GGCAAG  16

(2) INFORMATION FOR SEQ ID NO:194:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

-continued (xi) SEQUENCE DESCRIPTION: SEQ ID NO:194:

AATTCTTGCC AGTCACCCAT ACGGAT                                          26

(2) INFORMATION FOR SEQ ID NO:195:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:195:

CATGGCTAAC TGCTCTATTA TGATCGATGA AGCAATACAT                           40

(2) INFORMATION FOR SEQ ID NO:196:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:196:

CTTTAAGTGA TGTATTGCTT CATCGATCAT AATAGAGCAG TTAGC                     45

(2) INFORMATION FOR SEQ ID NO:197:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:197:

CACTTAAAGG TACCACCTCG CCCTTCCCTG GACCCG                               36

(2) INFORMATION FOR SEQ ID NO:198:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:198:

GAGGTTGTTC GGGTCCAGGG AAGGGCGAGG TGGTAC                               36

(2) INFORMATION FOR SEQ ID NO:199:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (synthetic)

-continued

```
    (xi) SEQUENCE DESCRIPTION: SEQ ID NO:199:

CACTTAAAGA GACCACCTGC ACCTTCCCTG GACCCG                                  36

(2) INFORMATION FOR SEQ ID NO:200:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:200:

GAGGTTGTTC GGGTCCAGGG AAGGTGCAGG TGGTCT                                  36

(2) INFORMATION FOR SEQ ID NO:201:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:201:

AACAACCTCA ATGACGAAGA CATGGAT                                            27

(2) INFORMATION FOR SEQ ID NO:202:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:202:

ATCCATGTCT TCGTCATT                                                      18

(2) INFORMATION FOR SEQ ID NO:203:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (synthetic)

(xi) SEQUENCE DESCRIPTION: SEQ ID NO:203:

AACAACCTCA ATGACGAAGA CGTCGAT                                            27

(2) INFORMATION FOR SEQ ID NO:204:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (synthetic)
```

(xi) SEQUENCE DESCRIPTION: SEQ ID NO:204:

ATCGACGTCT TCGTCATT                                                        18

(2) INFORMATION FOR SEQ ID NO:205:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:205:

AACAACCTCA ATGACGAAGA CATGTCT                                              27

(2) INFORMATION FOR SEQ ID NO:206:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:206:

AGACATGTCT TCGTCATT                                                        18

(2) INFORMATION FOR SEQ ID NO:207:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:207:

AACAACCTCA ATGACGAAGA CGTCTCT                                              27

(2) INFORMATION FOR SEQ ID NO:208:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:208:

AGAGACGTCT TCGTCATT                                                        18

(2) INFORMATION FOR SEQ ID NO:209:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

-continued (xi) SEQUENCE DESCRIPTION: SEQ ID NO:209:

ATCCTGATGG ACCGAAACCT TCGACTTCCA AACCTG                    36

(2) INFORMATION FOR SEQ ID NO:210:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:210:

AAGTCGAAGG TTTCGGTCCA TCAGGAT                             27

(2) INFORMATION FOR SEQ ID NO:211:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:211:

ATCCTGATGG ACCGAAACCT TCGACTTAGC AACCTG                    36

(2) INFORMATION FOR SEQ ID NO:212:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:212:

CCTTACGAAG CTCTCCAGGT TGCT                                24

(2) INFORMATION FOR SEQ ID NO:213:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:213:

CGTAATCTCT GGCCATGT                                      18

(2) INFORMATION FOR SEQ ID NO:214:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:214:

CCAGAGATTA CGAAGAAT                                              18

(2) INFORMATION FOR SEQ ID NO:215:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:215:

AATTCCGGGA AAAACTGCAA TTCTATCTGT GG                               32

(2) INFORMATION FOR SEQ ID NO:216:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:216:

CTCAAGGGTC CACAGATAGA ATTGCAGTTT TTCCCGG                          37

(2) INFORMATION FOR SEQ ID NO:217:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:217:

AATTCCGGGA AAAACTGCAA TTCTATCTGG TT                               32

(2) INFORMATION FOR SEQ ID NO:218:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:218:

CTCAAGGGTA ACCAGATAGA ATTGCAGTTT TTCCCGG                          37

(2) INFORMATION FOR SEQ ID NO:219:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:219:

AATTCCGGGA AAAACTGACG TTC                                              23

(2) INFORMATION FOR SEQ ID NO:220:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:220:

AACCAGATAG AACGTCAGTT TTTCCCGG                                         28

(2) INFORMATION FOR SEQ ID NO:221:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:221:

TATCTGGTTA CCCTTGAGTA ATA                                              23

(2) INFORMATION FOR SEQ ID NO:222:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:222:

AGCTTATTAC TTCAAGGGT                                                   19

(2) INFORMATION FOR SEQ ID NO:223:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:223:

AATTCCGGGA AAAACTGCAA TTC                                              23

(2) INFORMATION FOR SEQ ID NO:224:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:224:

AACCAGATAG AATTGCAGTT TTTCCCGG                                        28

(2) INFORMATION FOR SEQ ID NO:225:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:225:

CGATCATTAT AGAGCAGTTA GCCTTGTCAT CGTCGTCCTT GTAATCAGTT TCTGGATATG     60

C                                                                    61

(2) INFORMATION FOR SEQ ID NO:226:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:226:

CATGGCATAT CCAGAAACTG ATTACAAGGA CGACGATGAC AAGGCTAACT GCTCTATAAT     60

GAT                                                                  63

(2) INFORMATION FOR SEQ ID NO:227:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:227:

AATTCCGGCT TAAACTGCAA TTCTATCTGT CT                                   32

(2) INFORMATION FOR SEQ ID NO:228:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:228:

CTCAAGGGTA GACAGATAGA ATTGCAGTTT AAGCCGG                              37

(2) INFORMATION FOR SEQ ID NO:229:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:229:

TCTCTTGAGC AAGCGCAGGA ACAACAGTAA TA						32

(2) INFORMATION FOR SEQ ID NO:230:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:230:

CATGGCAAAC TGCTCTATAA TACTCGATGA AGCAATACAT						40

(2) INFORMATION FOR SEQ ID NO:231:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:231:

CTTTAAGTGA TGTATTGCTT CATCGAGTAT TATAGAGCAG TTTGC						45

(2) INFORMATION FOR SEQ ID NO:232:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:232:

CATGGCAAAC TGCTCTATAA TGCCAGATGA AGCAATACAT						40

(2) INFORMATION FOR SEQ ID NO:233:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:233:

CTTTAAGTGA TGTATTGCTT CATCTGGCAT TATAGAGCAG TTTGC						45

(2) INFORMATION FOR SEQ ID NO:234:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:234:

CATGGCAAAC TGCTCTATAA TGATCGATGA AACTGATACA T         41

(2) INFORMATION FOR SEQ ID NO:235:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:235:

CTTTAAGTGA TGTATCAGTT CATCGATCAT TATAGAGCAG TTTGC         45

(2) INFORMATION FOR SEQ ID NO:236:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:236:

CACTTAAAGA TACCACCTAA CCCTAGCCTG GACAGT         36

(2) INFORMATION FOR SEQ ID NO:237:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:237:

GAGGTTAGCA CTGTCCAGGC TAGGGTTAGG TGGTAT         36

(2) INFORMATION FOR SEQ ID NO:238:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:238:

GCTAACCTCA ATTCCGAAGA CGTCTCT         27

(2) INFORMATION FOR SEQ ID NO:239:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:239:

AGAGACGTCT TCGGAATT                                                    18

(2) INFORMATION FOR SEQ ID NO:240:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:240:

ATCCTGATGG ACTCCAACCT TCGAACTCCA AACCTG                                36

(2) INFORMATION FOR SEQ ID NO:241:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:241:

AGTTCGAAGG TTGGAGTCCA TCAGGAT                                          27

(2) INFORMATION FOR SEQ ID NO:242:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:242:

GTTCCCTATT GGACGGCCCC TCCCTCTCGA ACACCAATCA CGATCAAG                   48

(2) INFORMATION FOR SEQ ID NO:243:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:243:

CGTGATTGGT GTTCGAGAGG GAGGGGCCGT CCAATAGGGA ACACATGG                   48

(2) INFORMATION FOR SEQ ID NO:244:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:244:

CTCGCATTCC CACATGCTTC TAAG                                                  24

(2) INFORMATION FOR SEQ ID NO:245:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:245:

CTCGCATTCC CACATGCTGT CAAG                                                  24

(2) INFORMATION FOR SEQ ID NO:246:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:246:

ATGTGGGAAT GCGAGCAGGT TTGG                                                  24

(2) INFORMATION FOR SEQ ID NO:247:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:247:

TTTTCTAATT GCTTAGAAGC                                                       20

(2) INFORMATION FOR SEQ ID NO:248:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:248:

CAATTAGAAA ATGCA                                                            15

(2) INFORMATION FOR SEQ ID NO:249:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:249:

TTTTCTAATT GCTTGACAGC                                        20

(2) INFORMATION FOR SEQ ID NO:250:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:250:

TCAGGTATTG AGCCAATTCT T                                      21

(2) INFORMATION FOR SEQ ID NO:251:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:251:

TGGCTCAATA CCTGATGCA                                         19

(2) INFORMATION FOR SEQ ID NO:252:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:252:

TCTAATCTCC AACCATGT                                          18

(2) INFORMATION FOR SEQ ID NO:253:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:253:

TTGGAGATTA GAAAGAAT                                          18

(2) INFORMATION FOR SEQ ID NO:254:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:254:

CTCAAGAGAA GACAGATAGA ATTGCAGTTT AAGCCGG                                       37

(2) INFORMATION FOR SEQ ID NO:255:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:255:

CATGGCTAAC TGCTCTATAA TGATCGATGA AATTATACAT                                   40

(2) INFORMATION FOR SEQ ID NO:256:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:256:

AATTCCGGCT TAAACTGCAA TTCTATCTGT CTACCCTTTA ATA                               43

(2) INFORMATION FOR SEQ ID NO:257:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:257:

AGCTTATTAA AGGGTAGACA GATAGAATTG CAGTTTAAGC CGG                               43

(2) INFORMATION FOR SEQ ID NO:258:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:258:

AATTCCGGCT TAAACTGCAA TTCTATCTGT CTACCCTTTA ATA                               43

(2) INFORMATION FOR SEQ ID NO:259:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:259:

Met Ala Asn Cys Ser Asn Met Ile Asp Glu Ile Ile Thr His Leu Lys
1               5                   10                  15

-continued

```
Gln Pro Pro Leu Pro Leu Leu Asp Phe Asn Asn Leu Asn Asp Glu Asp
            20                  25                  30

Met Ser Ile Leu Met Asp Asn Asn Leu Arg Arg Pro Asn Leu Glu Ala
            35                  40                  45

Phe Asn Arg Ala Val Lys Ser Leu Gln Asn Ala Ser Ala Ile Glu Ser
            50                  55                  60

Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                    85                  90                  95

Arg Lys Leu Thr Phe Tyr Leu Lys Thr Leu Glu Asn Ala Gln Ala Gln
            100                 105                 110

Gln (2) INFORMATION FOR SEQ ID NO:260:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:260:

Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Asp Glu Asp
            20                  25                  30

Met Ser Ile Leu Met Glu Asn Asn Leu Arg Arg Pro Asn Leu Glu Ala
            35                  40                  45

Phe Asn Arg Ala Val Lys Ser Leu Gln Asn Ala Ser Ala Ile Glu Ser
            50                  55                  60

Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                    85                  90                  95

Arg Lys Leu Thr Phe Tyr Leu Lys Thr Leu Glu Asn Ala Gln Ala Gln
            100                 105                 110

Gln (2) INFORMATION FOR SEQ ID NO:261:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:261:

Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Asp Glu Asp
            20                  25                  30

Met Ser Ile Leu Met Glu Asn Asn Leu Arg Arg Pro Asn Leu Glu Ala
            35                  40                  45

Phe Asn Arg Ala Val Lys Ser Leu Gln Asn Ala Ser Ala Ile Glu Ser
            50                  55                  60
```

-continued

```
Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                 85                  90                  95

Arg Lys Leu Thr Phe Tyr Leu Trp Thr Leu Glu Asn Ala Gln Ala Gln
                100                 105                 110

Gln (2) INFORMATION FOR SEQ ID NO:262:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:262:

Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Asp Glu Asp
                 20                  25                  30

Met Ser Ile Leu Met Asp Asn Asn Leu Arg Arg Pro Asn Leu Glu Ala
                 35                  40                  45

Phe Asn Arg Ala Val Lys Ser Leu Gln Asn Ala Ser Ala Ile Glu Ser
 50                  55                  60

Ile Leu Lys Asn Leu Leu Pro Cys Leu Pro Leu Ala Thr Ala Ala Pro
 65                  70                  75                  80

Thr Arg His Pro Ile His Ile Lys Asp Gly Asp Trp Asn Glu Phe Arg
                 85                  90                  95

Arg Lys Leu Thr Phe Tyr Leu Trp Thr Leu Glu Asn Ala Gln Ala Gln
                100                 105                 110

Gln (2) INFORMATION FOR SEQ ID NO:263:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:263:

Met Ala Asn Cys Ser Asn Met Ile Asp Glu Ile Ile Thr His Leu Lys
 1               5                  10                  15

Gln Pro Pro Leu Pro Leu Leu Asp Phe Asn Asn Leu Asn Asp Glu Asp
                 20                  25                  30

Met Ser Ile Leu Met Asp Asn Asn Leu Arg Arg Pro Asn Leu Glu Ala
                 35                  40                  45

Phe Asn Arg Ala Val Lys Ser Leu Gln Asn Ala Ser Ala Ile Glu Ser
 50                  55                  60

Ile Leu Lys Asn Leu Leu Pro Cys Leu Pro Leu Ala Thr Ala Ala Pro
 65                  70                  75                  80

Thr Arg Arg Pro Ile Ile Ile Arg Asp Gly Asp Trp Asn Glu Phe Arg
                 85                  90                  95
```

-continued

```
Arg Lys Leu Thr Phe Tyr Leu Trp Thr Leu Glu Asn Ala Gln Ala Gln
            100                 105                 110

Gln
```

(2) INFORMATION FOR SEQ ID NO:264:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:264:

```
Met Ala Asn Cys Ser Ile Ala Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:265:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:265:

```
Met Ala Asn Cys Ser Ile Ile Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:266:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:266:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Val Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:267:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:267:

```
Met Ala Asn Cys Ser Ile Ala Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Val Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:268:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:268:

Met Ala Asn Cys Ser Ile Ile Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Val Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:269:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:269:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Ile Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:270:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:270:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

-continued

```
Met Asp Ile Leu Leu Glu Arg Asn Leu Arg Thr Pro Asn Leu Leu Ala
         35                  40                  45

Phe Val Arg Ala Val Lys His Leu Glu Asn Ala Ser Gly Ile Glu Ala
         50                  55                  60

Ile Leu Arg Asn Leu Gln Pro Cys Leu Pro Ser Ala Thr Ala Ala Pro
65                   70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
             100                 105                 110

Gln
```

(2) INFORMATION FOR SEQ ID NO:271:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:271:

```
Met Ala Asn Cys Ser Ile Met Ile Asp Glu Ile Ile His His Leu Lys
1                5                  10                  15

Arg Pro Pro Asn Pro Leu Leu Asp Pro Asn Asn Leu Asn Ser Glu Asp
                 20                  25                  30

Met Asp Ile Leu Asp Glu Arg Asn Leu Arg Thr Pro Asn Leu Leu Ala
         35                  40                  45

Phe Val Arg Ala Val Lys His Leu Glu Asn Ala Ser Gly Ile Glu Ala
         50                  55                  60

Ile Leu Arg Asn Leu Gln Pro Cys Leu Pro Ser Ala Thr Ala Ala Pro
65                   70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
             100                 105                 110

Gln
```

(2) INFORMATION FOR SEQ ID NO:272:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:272:

```
Met Ala Asn Cys Ser Ile Ala Ile Asp Glu Ile Ile His His Leu Lys
1                5                  10                  15

Arg Pro Pro Asn Pro Leu Leu Asp Pro Asn Asn Leu Asn Ser Glu Asp
                 20                  25                  30

Val Asp Ile Leu Ile Glu Arg Asn Leu Arg Thr Pro Asn Leu Leu Ala
         35                  40                  45

Phe Val Arg Ala Val Lys His Leu Glu Asn Ala Ser Gly Ile Glu Ala
         50                  55                  60

Ile Leu Arg Asn Leu Gln Pro Cys Leu Pro Ser Ala Thr Ala Ala Pro
65                   70                  75                  80
```

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:273:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:273:

```
Met Ala Asn Cys Ser Ile Ile Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Val Asp Ile Leu Ile Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:274:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:274:

```
Met Ala Asn Cys Ser Ile Ala Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Val Asp Ile Leu Leu Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:275:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:275:

```
Met Ala Asn Cys Ser Ile Ile Ile Asp Glu Ile Ile His His Leu Lys
1               5                   10                  15
Arg Pro Pro Asn Pro Leu Leu Asp Pro Asn Asn Leu Asn Ser Glu Asp
            20                  25                  30
Val Asp Ile Leu Leu Glu Arg Asn Leu Arg Thr Pro Asn Leu Leu Ala
        35                  40                  45
Phe Val Arg Ala Val Lys His Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:276:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:276:

```
Met Ala Asn Cys Ser Ile Ala Ile Asp Glu Ile Ile His His Leu Lys
1               5                   10                  15
Arg Pro Pro Asn Pro Leu Leu Asp Pro Asn Asn Leu Asn Ser Glu Asp
            20                  25                  30
Val Asp Ile Leu Asp Glu Arg Asn Leu Arg Thr Pro Asn Leu Leu Ala
        35                  40                  45
Phe Val Arg Ala Val Lys His Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:277:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:277:

Met Ala Asn Cys Ser Ile Ile Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Val Asp Ile Leu Asp Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:278:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:278:

Met Ala Asn Cys Ser Ile Met Ile Asp Glu Ala Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:279:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:279:

Met Ala Asn Cys Ser Ile Met Ile Asp Glu Ala Ile His His Leu Lys
1               5                   10                  15

Val Pro Pro Ala Pro Leu Leu Asp Ser Asn Asn Leu Asn Ser Glu Asp
                20                  25                  30

-continued

```
Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Gln Phe Tyr Leu Val Thr Leu Glu Gln Ala Gln Glu Gln
            100                 105                 110

Gln
```

(2) INFORMATION FOR SEQ ID NO:280:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:280:

```
Met Ala Asn Cys Ser Ile Met Ile Asp Glu Ala Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:281:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:281:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asn Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80
```

-continued

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:282:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:282:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:283:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:283:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:284:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:284:

```
Met Ala Asn Cys Ser Ile Met Ile Asp Glu Ile Ile His His Leu Lys
1               5                   10                  15
Arg Pro Pro Ala Pro Leu Leu Asp Pro Asn Asn Leu Asn Ala Glu Asp
            20                  25                  30
Met Ser Ile Leu Met Asp Arg Asn Leu Arg Leu Pro Asn Leu Glu Ser
        35                  40                  45
Phe Val Arg Ala Val Lys Asn Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:285:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:285:

```
Met Ala Asn Cys Ser Ile Met Ile Asp Glu Ile Ile His His Leu Lys
1               5                   10                  15
Arg Pro Pro Ala Pro Leu Leu Asp Pro Asn Asn Leu Asn Asp Glu Asp
            20                  25                  30
Met Ser Ile Leu Met Asp Arg Asn Leu Arg Leu Pro Asn Leu Glu Ser
        35                  40                  45
Phe Val Arg Ala Val Lys Asn Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln
```

(2) INFORMATION FOR SEQ ID NO:286:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:286:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ser Glu Asp
                20                  25                  30

Met Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:287:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO:287:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu
                100                 105

(2) INFORMATION FOR SEQ ID NO:288:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO:288:

Met Asp Asn Cys Ser Ile Met Ile Asp Glu Ala Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

```
Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Pro
65                  70                  75                  80

Ser Arg His Pro Ile Ile Ile Lys Ala Gly Asp Trp Gln Glu Phe Arg
                    85                  90                  95

Glu Lys Leu Gln Phe Tyr Leu Val Thr Leu Glu
                100                 105
```

(2) INFORMATION FOR SEQ ID NO:289:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:289:

```
Met Ala Asn Cys Ser Ile Met Ile Asp Glu Ala Ile His His Leu Lys
1                   5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
                35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Pro
65                  70                  75                  80

Ser Arg His Pro Ile Ile Ile Lys Ala Gly Asp Trp Gln Glu Phe Arg
                    85                  90                  95

Glu Lys Leu Gln Phe Tyr Leu Val Thr Leu Glu Gln Ala Gln Glu Gln
                100                 105                 110

Gln
```

(2) INFORMATION FOR SEQ ID NO:290:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO:290:

```
Met Asp Asn Cys Ser Ile Met Ile Asp Glu Ala Ile His His Leu Lys
1                   5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
                35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Pro
65                  70                  75                  80
```

```
Ser Arg His Pro Ile Ile Ile Lys Ala Gly Asp Trp Gln Glu Phe Arg
            85                  90                  95

Glu Lys Leu Thr Phe Tyr Leu Val Thr Leu Glu
            100                 105

(2) INFORMATION FOR SEQ ID NO:291:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:291:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
            85                  90                  95

Glu Lys Leu Gln Phe Tyr Leu Val Thr Leu Glu Gln Ala Gln Glu Gln
            100                 105                 110

Gln (2) INFORMATION FOR SEQ ID NO:292:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:292:

Met Ala Asn Cys Ser Ile Met Ile Asp Glu Ile Ile His His Leu Lys
1               5                   10                  15

Val Pro Pro Arg Pro Ser Leu Asp Pro Asn Asn Leu Asn Ala Glu Asp
            20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
            85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:293:

(i) SEQUENCE CHARACTERISTICS:
       (A) LENGTH: 113 amino acids
       (B) TYPE: amino acid
       (D) TOPOLOGY: linear (ii) MOLECULE TYPE: peptide (xi) SEQUENCE DESCRIPTION: SEQ ID NO:293:

```
Met Ala Asn Cys Ser Ile Met Ile Asp Glu Ile Ile His His Leu Lys
1               5                  10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Trp Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:294:

(i) SEQUENCE CHARACTERISTICS:
       (A) LENGTH: 113 amino acids
       (B) TYPE: amino acid
       (D) TOPOLOGY: linear (ii) MOLECULE TYPE: peptide (xi) SEQUENCE DESCRIPTION: SEQ ID NO:294:

```
Met Ala Asn Cys Ser Ile Met Ile Asp Glu Ala Ile His His Leu Lys
1               5                  10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Gln Phe Tyr Leu Val Thr Leu Glu Gln Ala Gln Glu Gln
            100                 105                 110

Gln
```

(2) INFORMATION FOR SEQ ID NO:295:

(i) SEQUENCE CHARACTERISTICS:
       (A) LENGTH: 113 amino acids
       (B) TYPE: amino acid
       (D) TOPOLOGY: linear (ii) MOLECULE TYPE: peptide (xi) SEQUENCE DESCRIPTION: SEQ ID NO:295:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Gln Phe Tyr Leu Val Thr Leu Glu Gln Ala Gln Glu Gln
                100                 105                 110

Gln (2) INFORMATION FOR SEQ ID NO:296:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:296:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Ser Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Gln Gln Ala Gln Glu Gln
                100                 105                 110

Gln (2) INFORMATION FOR SEQ ID NO:297:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:297:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

```
Met Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:298:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:298:

```
Met Ala Asn Cys Ser Ile Met Ile Asp Glu Ile Ile His His Leu Lys
 1               5                  10                  15

Arg Pro Pro Ala Pro Ser Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:299:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:299:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Asp Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
 65                  70                  75                  80
```

```
Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln
```

(2) INFORMATION FOR SEQ ID NO:300:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:300:

```
Met Ala Asn Cys Ser Ile Met Ile Asp Glu Ala Ile His His Leu Lys
1               5                   10                  15

Arg Pro Pro Ala Pro Ser Leu Asp Pro Asn Asn Leu Asn Asp Glu Asp
                20                  25                  30

Met Ser Ile Leu Met Glu Arg Asn Leu Arg Leu Pro Asn Leu Glu Ser
                35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln
```

(2) INFORMATION FOR SEQ ID NO:301:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:301:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Met Ser Ile Leu Met Glu Arg Asn Leu Arg Leu Pro Asn Leu Glu Ser
                35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln
```

(2) INFORMATION FOR SEQ ID NO:302:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:302:

Met Ala Asn Cys Ser Ile Met Ile Asp Glu Ala Ile His His Leu Lys
1               5                   10                  15

Val Pro Pro Arg Pro Ser Leu Asp Pro Asn Asn Leu Asn Asp Glu Asp
                20                  25                  30

Val Ser Ile Leu Met Glu Arg Asn Leu Arg Leu Pro Asn Leu Glu Ser
                35                  40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:303:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:303:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
                35                  40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Arg Met Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:304:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:304:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Trp Pro Cys Leu Pro Ser Ala Thr Ala Ala Pro
65                  70                  75                  80

Ser Arg His Pro Ile Ile Ile Arg Met Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:305:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:305:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:306:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:306:

```
Met Ala Asn Cys Ser Ile Met Ile Asp Glu Ala Ile His His Leu Lys
1               5                   10                  15

Val Pro Pro Arg Pro Ser Leu Asp Pro Asn Asn Leu Asn Asp Glu Asp
            20                  25                  30
```

Val Ser Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:307:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO:307:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Gln Phe Tyr Leu Val Thr Leu Glu
            100                 105

(2) INFORMATION FOR SEQ ID NO:308:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:308:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

-continued

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln (2) INFORMATION FOR SEQ ID NO:309:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:309:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Glu Arg Asn Leu Arg Leu Pro Asn Leu Glu Ser
               35                   40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln (2) INFORMATION FOR SEQ ID NO:310:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:310:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Met Ser Ile Leu Met Glu Arg Asn Leu Arg Leu Pro Asn Leu Glu Ser
               35                   40                  45

Phe Val Arg Ala Val Lys Asn Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
               100                 105                 110

Gln

-continued (2) INFORMATION FOR SEQ ID NO:311:

(i) SEQUENCE CHARACTERISTICS:
       (A) LENGTH: 113 amino acids
       (B) TYPE: amino acid
       (D) TOPOLOGY: linear (ii) MOLECULE TYPE: peptide (xi) SEQUENCE DESCRIPTION: SEQ ID NO:311:

```
Met Ala Asn Cys Ser Ile Met Ile Asp Glu Ala Ile His His Leu Lys
1               5                   10                  15

Arg Pro Pro Ala Pro Ser Leu Asp Pro Asn Asn Leu Asn Asp Glu Asp
            20                  25                  30

Val Ser Ile Leu Met Asp Arg Asn Leu Arg Leu Ser Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:312:

(i) SEQUENCE CHARACTERISTICS:
       (A) LENGTH: 113 amino acids
       (B) TYPE: amino acid
       (D) TOPOLOGY: linear (ii) MOLECULE TYPE: peptide (xi) SEQUENCE DESCRIPTION: SEQ ID NO:312:

```
Met Ala Asn Cys Ser Ile Met Ile Asp Glu Ala Ile His His Leu Lys
1               5                   10                  15

Arg Pro Pro Ala Pro Ser Leu Asp Pro Asn Asn Leu Asn Asp Glu Asp
            20                  25                  30

Met Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:313:

(i) SEQUENCE CHARACTERISTICS:
       (A) LENGTH: 113 amino acids
       (B) TYPE: amino acid
       (D) TOPOLOGY: linear (ii) MOLECULE TYPE: peptide (xi) SEQUENCE DESCRIPTION: SEQ ID NO:313:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Gln Phe Tyr Leu Trp Thr Leu Glu Gln Ala Gln Glu Gln
                100                 105                 110

Gln
```

(2) INFORMATION FOR SEQ ID NO:314:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:314:

```
Met Asp Asn Cys Ser Ile Met Ile Asp Glu Ala Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln
```

(2) INFORMATION FOR SEQ ID NO:315:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:315:

```
Met Ala Tyr Pro Glu Thr Asp Tyr Lys Asp Asp Asp Lys Asn Cys
1               5                   10                  15

Ser Ile Met Ile Asp Glu Ile Ile His His Leu Lys Arg Pro Pro Ala
                20                  25                  30
```

```
Pro Leu Leu Asp Pro Asn Asn Leu Asn Ala Glu Asp Val Asp Ile Leu
             35                  40                  45

Met Glu Arg Asn Leu Arg Leu Pro Asn Leu Glu Ser Phe Val Arg Ala
 50                  55                  60

Val Lys Asn Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                 85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
            115                 120                 125
```

(2) INFORMATION FOR SEQ ID NO:316:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:316:

```
Met Ala Tyr Pro Glu Thr Asp Tyr Lys Asp Asp Asp Lys Asn Cys
 1               5                  10                  15

Ser Ile Met Ile Asp Glu Ile Ile His His Leu Lys Arg Pro Pro Asn
                 20                  25                  30

Pro Leu Leu Asp Pro Asn Asn Leu Asn Ser Glu Asp Met Asp Ile Leu
             35                  40                  45

Met Glu Arg Asn Leu Arg Thr Pro Asn Leu Leu Ala Phe Val Arg Ala
 50                  55                  60

Val Lys His Leu Glu Asn Ala Ser Gly Ile Glu Ala Ile Leu Arg Asn
 65                  70                  75                  80

Leu Gln Pro Cys Leu Pro Ser Ala Thr Ala Ala Pro Ser Arg His Pro
                 85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
            115                 120                 125
```

(2) INFORMATION FOR SEQ ID NO:317:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:317:

```
Met Ala Asn Cys Ser Ile Met Pro Asp Glu Ala Ile His His Leu Lys
 1               5                  10                  15

Ile Pro Pro Asn Pro Ser Leu Asp Ser Ala Asn Leu Asn Ser Glu Asp
                 20                  25                  30

Val Ser Ile Leu Met Glu Arg Asn Leu Arg Thr Pro Asn Leu Leu Ala
             35                  40                  45

Phe Val Arg Ala Val Lys His Leu Glu Asn Ala Ser Gly Ile Glu Ala
 50                  55                  60
```

```
Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Gln Ala Gln Glu Gln
            100                 105                 110

Gln
```

(2) INFORMATION FOR SEQ ID NO:318:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:318:

```
Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
                20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Gln Ala Gln Glu Gln
            100                 105                 110

Gln
```

(2) INFORMATION FOR SEQ ID NO:319:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:319:

```
Met Ala Asn Cys Ser Ile Met Ile Asp Glu Ala Ile His His Leu Lys
1               5                   10                  15

Ile Pro Pro Asn Pro Ser Leu Asp Ser Ala Asn Leu Asn Ser Glu Asp
                20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Pro
50                  55                  60

Ile Leu Arg Asn Leu Gln Pro Cys Leu Pro Ser Ala Thr Ala Ala Pro
65                  70                  75                  80

Ser Arg Thr Pro Ile Ile Ile Lys Ala Gly Asp Trp Gln Glu Phe Arg
                85                  90                  95
```

```
Glu Lys Leu Thr Phe Tyr Leu Val Thr Leu Glu Gln Ala Gln Glu Gln
            100                 105                 110

Gln
```

(2) INFORMATION FOR SEQ ID NO:320:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:320:

```
Met Ala Asn Cys Ser Ile Ile Leu Asp Glu Ala Ile His His Leu Lys
1               5                   10                  15

Ile Pro Pro Asn Pro Ser Leu Asp Ser Ala Asn Leu Asn Ser Glu Asp
                20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Pro
    50                  55                  60

Ile Leu Arg Asn Leu Gln Pro Cys Leu Pro Ser Ala Thr Ala Ala Pro
65                  70                  75                  80

Ser Arg Thr Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:321:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:321:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Asp Ser Asn Leu Arg Thr Pro Asn Leu Leu Ala
            35                  40                  45

Phe Pro His Ala Ser Lys Gln Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:322:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:322:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Leu Lys Leu Gln Phe Tyr Leu Ser Thr Leu Glu Gln Ala Gln Glu Gln
            100                 105                 110

Gln
```

(2) INFORMATION FOR SEQ ID NO:323:

(i) SEQUENCE CHARACTERISTICS:
        (A) LENGTH: 106 amino acids
        (B) TYPE: amino acid
        (D) TOPOLOGY: linear (ii) MOLECULE TYPE: peptide (xi) SEQUENCE DESCRIPTION: SEQ ID NO:323:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Leu Lys Leu Gln Phe Tyr Leu Ser Thr Leu
            100                 105
```

(2) INFORMATION FOR SEQ ID NO:324:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:324:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Leu Lys Leu Gln Phe Tyr Leu Ser Ser Leu Glu Gln Ala Gln Glu Gln
            100                 105                 110

Gln (2) INFORMATION FOR SEQ ID NO:325:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:325:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Asp Ser Asn Leu Leu Thr Pro Asn Leu Leu Ala
            35                  40                  45

Phe Pro His Ala Ser Lys Gln Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Leu Lys Leu Gln Phe Tyr Leu Ser Ser Leu Glu Gln Ala Gln Glu Gln
            100                 105                 110

Gln (2) INFORMATION FOR SEQ ID NO:326:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:326:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

-continued

Met Asp Ile Leu Met Glu Arg Asn Leu Arg Thr Pro Asn Leu Leu Ala
         35                  40                  45

Phe Val Arg Ala Val Lys His Leu Glu Asn Ala Ser Gly Ile Glu Pro
 50                      55                  60

Ile Leu Ser Asn Leu Gln Pro Cys Val Pro Tyr Trp Thr Ala Pro Pro
 65                  70                  75                  80

Ser Arg Thr Pro Ile Thr Ile Lys Ala Gly Asp Trp Gln Glu Phe Arg
                 85                  90                      95

Glu Lys Leu Thr Phe Tyr Leu Val Thr Leu Glu Gln Ala Gln Glu Gln
             100                 105                 110

Gln (2) INFORMATION FOR SEQ ID NO:327:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:327:

Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
                 20                  25                  30

Met Asp Ile Leu Met Glu Arg Asn Leu Arg Thr Pro Asn Leu Leu Ala
         35                  40                  45

Phe Val Arg Ala Val Lys His Leu Glu Asn Ala Ser Gly Ile Glu Pro
 50                      55                  60

Ile Leu Ser Asn Leu Gln Pro Cys Val Pro Tyr Trp Thr Ala Pro Pro
 65                  70                  75                  80

Ser Arg Thr Pro Ile Thr Ile Lys Ala Gly Asp Trp Gln Glu Phe Arg
                 85                  90                      95

Leu Lys Leu Gln Phe Tyr Leu Ser Thr Leu Glu Gln Ala Gln Glu Gln
             100                 105                 110

Gln (2) INFORMATION FOR SEQ ID NO:328:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:328:

Met Ala Asn Cys Ser Ile Met Ile Asp Glu Leu Ile His His Leu Lys
 1               5                  10                  15

Ile Pro Pro Asn Pro Ser Leu Asp Ser Ala Asn Leu Asn Ser Glu Asp
                 20                  25                  30

Val Ser Ile Leu Met Glu Arg Asn Leu Arg Thr Pro Asn Leu Leu Ala
         35                  40                  45

Phe Val Arg Ala Val Lys His Leu Glu Asn Ala Ser Gly Ile Glu Pro
 50                      55                  60

Ile Leu Ser Asn Leu Gln Pro Cys Val Pro Tyr Trp Thr Ala Pro Pro
 65                  70                  75                  80

```
Ser Arg Thr Pro Ile Thr Ile Lys Ala Gly Asp Trp Gln Glu Phe Arg
                85                  90                  95

Leu Lys Leu Gln Phe Tyr Leu Ser Thr Leu Glu Gln Ala Gln Glu Gln
            100                 105                 110

Gln
```

(2) INFORMATION FOR SEQ ID NO:329:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:329:

```
Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
            20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Leu Lys Leu Gln Phe Tyr Leu Ser Ser Leu Glu Gln Ala Gln Glu Gln
            100                 105                 110

Gln
```

(2) INFORMATION FOR SEQ ID NO:330:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:330:

```
Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
            20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Pro
        50                  55                  60

Ile Leu Ser Asn Leu Gln Pro Cys Val Pro Tyr Trp Thr Ala Pro Pro
65                  70                  75                  80

Ser Arg Thr Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:331:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:331:

```
Met Ala Asn Cys Ser Ile Met Ile Asp Glu Ala Ile His His Leu Lys
1               5                  10                  15

Arg Pro Pro Ala Pro Ser Leu Asp Pro Asn Asn Leu Asn Asp Glu Asp
                20                  25                  30

Met Ser Ile Leu Met Asp Arg Asn Leu Arg Leu Ser Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:332:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:332:

```
ATGGCAAACT GCTCTATAGC TATCGATGAA ATTATACATC ACTTAAAGAG ACCACCTAAC    60
CCTTTGCTGG ACCCGAACAA CCTCAATTCC GAAGACATGG ATATCCTGAT GGAACGAAAC   120
CTTCGAACTC CAAACCTGCT CGCATTCGTA AGGGCTGTCA AGCACTTAGA AAATGCATCA   180
GGTATTGAGG CAATTCTTCG TAATCTCCAA CCATGTCTGC CCTCTGCCAC GGCCGCACCC   240
TCTCGACATC CAATCATCAT CAAGGCAGGT GACTGGCAAG AATTCCGGGA AAAACTGACG   300
TTCTATCTGG TTACCCTTGA GCAAGCGCAG GAACAACAG                          339
```

(2) INFORMATION FOR SEQ ID NO:333:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:333:

```
ATGGCAAACT GCTCTATAAT CATCGATGAA ATTATACATC ACTTAAAGAG ACCACCTAAC    60
CCTTTGCTGG ACCCGAACAA CCTCAATTCC GAAGACATGG ATATCCTGAT GGAACGAAAC   120
CTTCGAACTC CAAACCTGCT CGCATTCGTA AGGGCTGTCA AGCACTTAGA AAATGCATCA   180
```

```
GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:334:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:334:

ATGGCTAACT GCTCTATAAT GATCGATGAA ATTATACATC ACTTAAAGAG ACCACCTAAC         60

CCTTTGCTGG ACCCGAACAA CCTCAATTCT GAAGACGTTG ATATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:335:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:335:

ATGGCAAACT GCTCTATAGC TATCGATGAA ATTATACATC ACTTAAAGAG ACCACCTAAC         60

CCTTTGCTGG ACCCGAACAA CCTCAATTCT GAAGACGTTG ATATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:336:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:336:

ATGGCAAACT GCTCTATAAT GATCCATGAA ATTATACATC ACTTAAAGAG ACCACCTAAC         60

CCTTTGCTGG ACCCGAACAA CCTCAATTCT GAAGACGTTG ATATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240
```

```
TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                            339

(2) INFORMATION FOR SEQ ID NO:337:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:337:

ATGGCTAACT GCTCTATAAT GATCGATGAA ATTATACATC ACTTAAAGAG ACCACCTAAC       60

CCTTTGCTGG ACCCGAACAA CCTCAATTCC GAAGACATGG ATATCCTGAT CGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                            339

(2) INFORMATION FOR SEQ ID NO:338:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:338:

ATGGCTAACT GCTCTATAAT GATCGATGAA ATTATACATC ACTTAAAGAG ACCACCTAAC       60

CCTTTGCTGG ACCCGAACAA CCTCAATTCC GAAGACATGG ATATCCTGCT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                            339

(2) INFORMATION FOR SEQ ID NO:339:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:339:

ATGGCTAACT GCTCTATAAT GATCGATGAA ATTATACATC ACTTAAAGAG ACCACCTAAC       60

CCTTTGCTGG ACCCGAACAA CCTCAATTCC GAAGACATGG ATATCCTGGA CGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240
```

```
TCTCGACATC CAATCATCAT CAAGGCAGGT GACTGGCAAG AATTCCGGGA AAAACTGACG    300

TTCTATCTGG TTACCCTTGA GCAAGCGCAG GAACAACAG                          339

(2) INFORMATION FOR SEQ ID NO:340:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:340:

ATGGCAAACT GCTCTATAGC TATCGATGAA ATTATACATC ACTTAAAGAG ACCACCTAAC     60

CCTTTGCTGG ACCCGAACAA CCTCAATTCT GAAGACGTTG ATATCCTGAT CGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAG                          339

(2) INFORMATION FOR SEQ ID NO:341:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:341:

ATGGCAAACT GCTCTATAAT CATCGATGAA ATTATACATC ACTTAAAGAG ACCACCTAAC     60

CCTTTGCTGG ACCCGAACAA CCTCAATTCT GAAGACGTTG ATATCCTGAT CGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAG                          339

(2) INFORMATION FOR SEQ ID NO:342:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:342:

ATGGCAAACT GCTCTATAGC TATCGATGAA ATTATACATC ACTTAAAGAG ACCACCTAAC     60

CCTTTGCTGG ACCCGAACAA CCTCAATTCT GAAGACGTTG ATATCCTGCT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240
```

```
TCTCGACATC CAATCATCAT CAAGGCAGGT GACTGGCAAG AATTCCGGGA AAAACTGACG         300

TTCTATCTGG TTACCCTTGA GCAAGCGCAG GAACAACAG                                339

(2) INFORMATION FOR SEQ ID NO:343:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:343:

ATGGCAAACT GCTCTATAAT CATCGATGAA ATTATACATC ACTTAAAGAG ACCACCTAAC          60

CCTTTGCTGG ACCCGAACAA CCTCAATTCT GAAGACGTTG ATATCCTGCT GGAACGAAAC         120

CTTCGAACTC CAAACCTGCT CGCATTCGTA AGGGCTGTCA AGCACTTAGA AAATGCATCA         180

GGTATTGAGG CAATTCTTCG TAATCTCCAA CCATGTCTGC CCTCTGCCAC GGCCGCACCC         240

TCTCGACATC CAATCATCAT CAAGGCAGGT GACTGGCAAG AATTCCGGGA AAAACTGACG         300

TTCTATCTGG TTACCCTTGA GCAAGCGCAG GAACAACAG                                339

(2) INFORMATION FOR SEQ ID NO:344:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:344:

ATGGCAAACT GCTCTATAGC TATCGATGAA ATTATACATC ACTTAAAGAG ACCACCTAAC          60

CCTTTGCTGG ACCCGAACAA CCTCAATTCT GAAGACGTTG ATATCCTGGA CGAACGAAAC         120

CTTCGAACTC CAAACCTGCT CGCATTCGTA AGGGCTGTCA AGCACTTAGA AAATGCATCA         180

GGTATTGAGG CAATTCTTCG TAATCTCCAA CCATGTCTGC CCTCTGCCAC GGCCGCACCC         240

TCTCGACATC CAATCATCAT CAAGGCAGGT GACTGGCAAG AATTCCGGGA AAAACTGACG         300

TTCTATCTGG TTACCCTTGA GCAAGCGCAG GAACAACAG                                339

(2) INFORMATION FOR SEQ ID NO:345:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:345:

ATGGCAAACT GCTCTATAAT CATCGATGAA ATTATACATC ACTTAAAGAG ACCACCTAAC          60

CCTTTGCTGG ACCCGAACAA CCTCAATTCT GAAGACGTTG ATATCCTGGA CGAACGAAAC         120

CTTCGAACTC CAAACCTGCT CGCATTCGTA AGGGCTGTCA AGCACTTAGA AAATGCATCA         180

GGTATTGAGG CAATTCTTCG TAATCTCCAA CCATGTCTGC CCTCTGCCAC GGCCGCACCC         240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339
```

(2) INFORMATION FOR SEQ ID NO:346:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:346:

```
ATGGCTAACT GCTCTATTAT GATCGATGAA GCAATACATC ACTTAAAGGT TCCACCTGCA        60

CCTTTGCTGG ACAGTAACAA CCTCAATTCC GAAGACATGG ATATCCTGAT GGAACGAAAC       120

CTTCGACTTC CAAACCTGCT CGCATTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAG                              339
```

(2) INFORMATION FOR SEQ ID NO:347:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:347:

```
ATGGCTAACT GCTCTATAAT GATCGATGAA GCAATACATC ACTTAAAGGT TCCACCTGCA        60

CCTTTGCTGG ACAGTAACAA CCTCAATTCC GAAGACATGG ATATCCTGAT GGAACGAAAC       120

CTTCGACTTC CAAACCTGCT CGCATTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGCAA       300

TTCTATCTGG TTACCCTTGA GCAAGCGCAG GAACAACAG                              339
```

(2) INFORMATION FOR SEQ ID NO:348:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:348:

```
ATGGCTAACT GCTCTATAAT GATCGATGAA GCAATACATC ACTTAAAGAG ACCACCTGCA        60

CCTTTGCTGG ACCCGAACAA CCTCAATGAC GAAGACGTTT CTATTCTGAT GGACCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:349:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:349:

ATGGCTAACT GCTCTATAAT GATCGATGAA ATTATACATC ACTTAAAGAG ACCACCTGCA         60

CCTTTGCTGG ACCCGAACAA CCTCAATAAC GAAGACGTTT CTATTCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:350:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:350:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACGTTT CTATTCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:351:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:351:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACGTTT CTATTCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                                339

(2) INFORMATION FOR SEQ ID NO:352:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:352:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACATGT CTATTCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                                339

(2) INFORMATION FOR SEQ ID NO:353:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:353:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACATGT CTATTCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                                339

(2) INFORMATION FOR SEQ ID NO:354:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:354:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                               339

(2) INFORMATION FOR SEQ ID NO:355:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:355:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA G                                                 321

(2) INFORMATION FOR SEQ ID NO:356:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:356:

ATGGATAACT GCTCTATAAT GATCGATGAA GCAATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGCAA        300

TTCTATCTGG TTACCCTTGA G                                                 321

(2) INFORMATION FOR SEQ ID NO:357:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:357:

ATGGCTAACT GCTCTATAAT GATCGATGAA GCAATACATC ACTTAAAGAG ACCACCTGCA         60

CCTTTGCTGG ACCCGAACAA CCTCAATGAC GAAGACGTCT CTATTCTGAT GGACCGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240
```

| | |
|---|---|
| TCTCGACATC CAATCATCAT CAAGGCAGGT GACTGGCAAG AATTCCGGGA AAAACTGCAA | 300 |
| TTCTATCTGG TTACCCTTGA G | 321 |

(2) INFORMATION FOR SEQ ID NO:358:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:358:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGCT GAAGACGTCG ATATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA G | 321 |

(2) INFORMATION FOR SEQ ID NO:359:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:359:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGCT GAAGACGTTT CTATCCTGAT GGACCGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGCAA | 300 |
| TTCTATCTGG TTACCCTTGA GCAAGCGCAG GAACAACAG | 339 |

(2) INFORMATION FOR SEQ ID NO:360:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:360:

| | |
|---|---|
| ATGGCTAACT GCTCTATAAT GATCGATGAA ATTATACATC ACTTAAAGGT ACCACCTCGC | 60 |
| CCTTCCCTGG ACCCGAACAA CCTCAATGCT GAAGACGTCG ATATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339
```

(2) INFORMATION FOR SEQ ID NO:361:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:361:

```
ATGGCTAACT GCTCTATAAT GATCGATGAA ATTATACATC ACTTAAAGAG ACCACCTGCA        60

CCTTTGCTGG ACCCGAACAA CCTCAATGCT GAAGACGTCG ATATCCTGAT GGAACGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCTGG CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAG                              339
```

(2) INFORMATION FOR SEQ ID NO:362:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:362:

```
ATGGCTAACT GCTCTATAAT GATCGATGAA GCAATACATC ACTTAAAGAG ACCACCTGCA        60

CCTTTGCTGG ACCCGAACAA CCTCAATGAC GAAGACGTTT CTATTCTGAT GGACCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGCAA       300

TTCTATCTGG TTACCCTTGA GCAAGCGCAG GAACAACAG                              339
```

(2) INFORMATION FOR SEQ ID NO:363:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:363:

```
ATGGCTAACT GCTCTATAAT GATCGATGAA ATTATACATC ACTTAAAGAG ACCACCTGCA        60

CCTTTGCTGG ACCCGAACAA CCTCAATGCT GAAGACGTCG ATATCCTGAT GGAACGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240
```

```
TCTCGACATC CAATCATCAT CAAGGCAGGT GACTGGCAAG AATTCCGGGA AAAACTGCAA      300

TTCTATCTGG TTACCCTTGA GCAAGCGCAG GAACAACAG                            339

(2) INFORMATION FOR SEQ ID NO:364:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:364:

ATGGCTAACT GCTCTATAAT GATCGATGAA ATTATACATC ACTTAAAGAG ACCACCTGCA       60

CCTTTGCTGG ACCCGAACAA CCTCAATGCT GAAGACGTCG ATATCCTGAT GGACCGAAAC      120

CTTCGACTTA GCAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                            339

(2) INFORMATION FOR SEQ ID NO:365:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:365:

ATGGCTAACT GCTCTATAAT GATCGATGAA ATTATACATC ACTTAAAGAG ACCACCTGCA       60

CCTTTGCTGG ACCCGAACAA CCTCAATGAC GAAGACATGG ATATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                            339

(2) INFORMATION FOR SEQ ID NO:366:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:366:

ATGGCTAACT GCTCTATAAT GATCGATGAA ATTATACATC ACTTAAAGAG ACCACCTGCA       60

CCTTCCCTGG ACCCGAACAA CCTCAATGCT GAAGACGTCG ATATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:367:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:367:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:368:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:368:

ATGGCTAACT GCTCTATAAT GATCGATGAA GCAATACATC ACTTAAAGAG ACCACCTGCA         60

CCTTCCCTGG ACCCGAACAA CCTCAATGAC GAAGACATGT CTATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:369:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:369:

ATGGCTAACT GCTCTATAAT GATCGATGAA ATTATACATC ACTTAAAGAG ACCACCTGCA         60

CCTTTGCTGG ACCCGAACAA CCTCAATGAC GAAGACATGT CTATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:370:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:370:

ATGGCTAACT GCTCTATAAT GATCGATGAA GCAATACATC ACTTAAAGGT ACCACCTCGC         60

CCTTCCCTGG ACCCGAACAA CCTCAATGAC GAAGACGTCT CTATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:371:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:371:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CCGTATGGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:372:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:372:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCTGG CCATGTCTGC CCTCTGCCAC GGCCGCACCC        240
```

| | |
|---|---|
| TCTCGACATC CAATCATCAT CCGTATGGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:373:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:373:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:374:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:374:

| | |
|---|---|
| ATGGCTAACT GCTCTATAAT GATCGATGAA GCAATACATC ACTTAAAGGT ACCACCTCGC | 60 |
| CCTTCCCTGG ACCCGAACAA CCTCAATGAC GAAGACGTCT CTATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:375:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:375:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGCT GAAGACGTCG ATATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |

```
TCTCGACATC CAATCATCAT CAAGGCAGGT GACTGGCAAG AATTCCGGGA AAAACTGCAA        300

TTCTATCTGG TTACCCTTGA G                                                 321
```

(2) INFORMATION FOR SEQ ID NO:376:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:376:

```
ATGGCTAACT GCTCTATAAT GATCGATGAA ATTATACATC ACTTAAAGAG ACCACCTGCA        60

CCTTTGCTGG ACCCGAACAA CCTCAATGCT GAAGACGTCG ATATCCTGAT GGACCGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAG                              339
```

(2) INFORMATION FOR SEQ ID NO:377:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:377:

```
ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCG ATTCTCTGAT GGAACGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAG                              339
```

(2) INFORMATION FOR SEQ ID NO:378:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:378:

```
ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCA TGTCTCTGAT GGAACGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240
```

| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:379:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:379:

| ATGGCTAACT GCTCTATAAT GATCGATGAA GCAATACATC ACTTAAAGAG ACCACCTGAC | 60 |
| CTTTCCCTGG ACCCGAACAA CCTCAATGAC GAAGACGTCT CTATCCTGAT GGACCGAAAC | 120 |
| CTTCGACTTA GCAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:380:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:380:

| ATGGCTAACT GCTCTATAAT GATCGATGAA GCAATACATC ACTTAAAGAG ACCACCTGCA | 60 |
| CCTTCCCTGG ACCCGAACAA CCTCAATGAC GAAGACATGT CTATCCTGAT GGACCGAAAC | 120 |
| CTTCGACTTA GCAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAG | 339 |

(2) INFORMATION FOR SEQ ID NO:381:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:381:

| ATGGCTAACT GCTCTATAAT GATCGATGAA GCAATACATC ACTTAAAGAG ACCACCTGCA | 60 |
| CCTTCCCTGG ACCCGAACAA CCTCAATGAC GAAGACATGT CTATCCTGAT GGACCGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:382:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:382:

ATGGCTAACT GCTCTATAAT GATCGATGAA ATTATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGCAA        300

TTCTATCTGT GGACCCTTGA GCAAGCGCAG GAACAACAG                              339

(2) INFORMATION FOR SEQ ID NO:383:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:383:

ATGGATAACT GCTCTATTAT GATCGATGAA GCAATACATC ACTTAAAGAG ACCACCTGCA         60

CCTTTGCTGG ACCCGAACAA CCTCAATGCT GAAGACGTCG ATATCCTGAT GGAACGAAAC        120

CTTCGACTTC CAAACCTGGA GAGCTTCGTA AGGGCTGTCA AGAACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:384:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:384:

ATGGCTAACT GCTCTATAAT GCCAGATGAA GCAATACATC ACTTAAAGAT ACCACCTAAC         60

CCTAGCCTGG ACAGTGCTAA CCTCAATTCC GAAGACGTCT CTATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240
```

```
TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:385:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:385:

ATGGCTAACT GCTCTATAAT GATCGATGAA ATTATACATC ACTTAAAGAT ACCACCTAAC         60

CCTAGCCTGG ACAGTGCTAA CCTCAATTCC GAAGACGTCT CTATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:386:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:386:

ATGGCTAACT GCTCTATTAT GATCGATGAA GCAATACATC ACTTAAAGAT ACCACCTAAC         60

CCTAGCCTGG ACAGTGCTAA CCTCAATTCC GAAGACGTCT CTATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240

TCTCGACATC CAATCATCAT CAAGGCAGGT GACTGGCAAG AATTCCGGGA AAAACTGACG        300

TTCTATCTGG TTACCCTTGA GCAAGCGCAG GAACAACAG                              339

(2) INFORMATION FOR SEQ ID NO:387:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:387:

ATGGCTAACT GCTCTATAAT ACTCGATGAA GCAATACATC ACTTAAAGAT ACCACCTAAC         60

CCTAGCCTGG ACAGTGCTAA CCTCAATTCC GAAGACGTCT CTATCCTGAT GGAACGAAAC        120

CTTCGAACTC CAAACCTGCT CGCATTCGTA AGGGCTGTCA AGCACTTAGA AAATGCATCA        180

GGTATTGAGG CAATTCTTCG TAATCTCCAA CCATGTCTGC CCTCTGCCAC GGCCGCACCC        240
```

```
TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                              339

(2) INFORMATION FOR SEQ ID NO:388:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:388:

ATGGCTAACT GCTCTATAAT GATCGATGAA ATTATACATC ACTTAAAGAG ACCACCTAAC       60

CCTTTGCTGG ACCCGAACAA CCTCAATTCC GAAGACATGG ATATCCTGAT GGACTCCAAC      120

CTTCGAACTC CAAACCTGCT CGCATTCCCA CATGCTGTCA AGCAATTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                              339

(2) INFORMATION FOR SEQ ID NO:389:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:389:

ATGGCTAACT GCTCTATAAT GATCGATGAA ATTATACATC ACTTAAAGAG ACCACCTAAC       60

CCTTTGCTGG ACCCGAACAA CCTCAATTCC GAAGACATGG ATATCCTGAT GGACTCCAAC      120

CTTCGAACTC CAAACCTGCT CGCATTCCCA CATGCTTCTA AGCAATTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAG                              339

(2) INFORMATION FOR SEQ ID NO:390:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:390:

ATGGCTAACT GCTCTATAAT GATCGATGAA ATTATACATC ACTTAAAGAG ACCACCTAAC       60

CCTTTGCTGG ACCCGAACAA CCTCAATTCC GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240
```

```
TCTCGACATC CAATCATCAT CAAGGCAGGT GACTGGCAAG AATTCCGGCT TAAACTGCAA      300

TTCTATCTGT CTACCCTTGA GCAAGCGCAG GAACAACAG                            339
```

(2) INFORMATION FOR SEQ ID NO:391:

(i) SEQUENCE CHARACTERISTICS:
        (A) LENGTH: 318 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:391:

```
ATGGCTAACT GCTCTATAAT GATCGATGAA ATTATACATC ACTTAAAGAG ACCACCTAAC      60

CCTTTGCTGG ACCCGAACAA CCTCAATTCC GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGCT TAAACTGCAA     300

TTCTATCTGT CTACCCTT                                                    318
```

(2) INFORMATION FOR SEQ ID NO:392:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:392:

```
ATGGCTAACT GCTCTATAAT GATCGATGAA ATTATACATC ACTTAAAGAG ACCACCTAAC      60

CCTTTGCTGG ACCCGAACAA CCTCAATTCC GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGCT TAAACTGCAA     300

TTCTATCTGT CTTCTCTTGA GCAAGCGCAG GAACAACAG                            339
```

(2) INFORMATION FOR SEQ ID NO:393:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:393:

```
ATGGCTAACT GCTCTATAAT GATCGATGAA ATTATACATC ACTTAAAGAG ACCACCTAAC      60

CCTTTGCTGG ACCCGAACAA CCTCAATTCC GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGC CAATTCTTTC TAATCTCCAA CCATGTGTTC CCTATTGGAC GGCCCCTCCC     240
```

```
TCTCGAACAC CAATCACGAT CAAGGCAGGT GACTGGCAAG AATTCCGGGA AAAACTGACG    300

TTCTATCTGG TTACCCTTGA GCAAGCGCAG GAACAACAG                          339
```

(2) INFORMATION FOR SEQ ID NO:394:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:394:

```
ATGGCTAACT GCTCTATAAT GATCGATGAA ATTATACATC ACTTAAAGAG ACCACCTAAC     60

CCTTTGCTGG ACCCGAACAA CCTCAATTCC GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGC CAATTCTTTC TAATCTCCAA CCATGTGTTC CCTATTGGAC GGCCCCTCCC    240

TCTCGAACAC CAATCACGAT CAAGGCAGGT GACTGGCAAG AATTCCGGCT TAAACTGCAA    300

TTCTATCTGT CTACCCTTGA GCAAGCGCAG GAACAACAG                           339
```

(2) INFORMATION FOR SEQ ID NO:395:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:395:

```
ATGGCTAACT GCTCTATAAT GATCGATGAA ATTATACATC ACTTAAAGAT ACCACCTAAC     60

CCTAGCCTGG ACAGTGCTAA CCTCAATTCC GAAGACGTCT CTATCCTGAT GGAACGAAAC    120

CTTCGAACTC CAAACCTGCT CGCATTCGTA AGGGCTGTCA AGCACTTAGA AAATGCATCA    180

GGTATTGAGC CAATTCTTTC TAATCTCCAA CCATGTGTTC CCTATTGGAC GGCCCCTCCC    240

TCTCGAACAC CAATCACGAT CAAGGCAGGT GACTGGCAAG AATTCCGGCT TAAACTGCAA    300

TTCTATCTGT CTACCCTTGA GCAAGCGCAG GAACAACAG                           339
```

(2) INFORMATION FOR SEQ ID NO:396:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:396:

```
ATGGCTAACT GCTCTATAAT GATCGATGAA ATTATACATC ACTTAAAGAT ACCACCTAAC     60

CCTAGCCTGG ACAGTGCTAA CCTCAATTCC GAAGACGTCT CTATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240
```

```
TCTCGACATC CAATCATCAT CAAGGCAGGT GACTGGCAAG AATTCCGGCT TAAACTGCAA      300

TTCTATCTGT CTTCTCTTGA GCAAGCGCAG GAACAACAG                            339
```

(2) INFORMATION FOR SEQ ID NO:397:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:397:

```
ATGGCTAACT GCTCTATAAT GATCGATGAA ATTATACATC ACTTAAAGAT ACCACCTAAC      60

CCTAGCCTGG ACAGTGCTAA CCTCAATTCC GAAGACGTCT CTATCCTGAT GGAACGAAAC     120

CTTCGAACTC CAAACCTGCT CGCATTCGTA AGGGCTGTCA AGCACTTAGA AAATGCATCA     180

GGTATTGAGC CAATTCTTTC TAATCTCCAA CCATGTGTTC CCTATTGGAC GGCCCCTCCC     240

TCTCGAACAC CAATCACGAT CAAGGCAGGT GACTGGCAAG AATTCCGGGA AAAACTGACG     300

TTCTATCTGG TTACCCTTGA GCAAGCGCAG GAACAACAG                            339
```

(2) INFORMATION FOR SEQ ID NO:398:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:398:

```
ATGGCTAACT GCTCTAACAT GATCGATGAA ATCATCACCC ACCTGAAGCA GCCACCGCTG      60

CCGCTGCTGG ACTTCAACAA CCTCAATGAC GAAGACATGT CTATCCTGAT GGACAATAAC     120

CTTCGTCGTC CAAACCTCGA GGCATTCAAC CGTGCTGTCA AGTCTCTGCA GAATGCATCA     180

GCAATTGAGA GCATTCTTAA AAATCTCCTG CCATGTCTGC CCCTGGCCAC GGCCGCACCC     240

ACGCGACATC CAATCCATAT CAAGGACGGT GACTGGAATG AATTCCGTCG TAAACTGACC     300

TTCTATCTGA AAACCTTGGA GAACGCGCAG GCTCAACAG                            339
```

(2) INFORMATION FOR SEQ ID NO:399:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:399:

```
ATGGCTAACT GCTCTAACAT GATCGATGAA ATCATCACCC ACCTGAAGCA GCCACCGCTG      60

CCGCTGCTGG ACTTCAACAA CCTCAATGAC GAAGACATGT CTATCCTGAT GGAAAATAAC     120

CTTCGTCGTC CAAACCTCGA GGCATTCAAC CGTGCTGTCA AGTCTCTGCA GAATGCATCA     180

GCAATTGAGA GCATTCTTAA AAATCTCCTG CCATGTCTGC CCCTGGCCAC GGCCGCACCC     240
```

```
ACGCGACATC CAATCCATAT CAAGGACGGT GACTGGAATG AATTCCGTCG TAAACTGACC         300

TTCTATCTGA AAACCTTGGA GAACGCGCAG GCTCAACAG                               339
```

(2) INFORMATION FOR SEQ ID NO:400:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:400:

```
AAGGAGATAT ATCCATGAAC TGCTCTAAC                                          29
```

(2) INFORMATION FOR SEQ ID NO:401:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:401:

```
Met Asn Cys Ser Asn
1               5
```

(2) INFORMATION FOR SEQ ID NO:402:

(i) SEQUENCE CHARACTERISTICS:
        (A) LENGTH: 120 amino acids
        (B) TYPE: amino acid
        (D) TOPOLOGY: linear (ii) MOLECULE TYPE: peptide (xi) SEQUENCE DESCRIPTION: SEQ ID NO:402:

```
Met Asn Cys Ser Asn Met Ile Asp Glu Ile Ile Thr His Leu Lys Gln
1               5                   10                  15

Pro Pro Leu Pro Leu Leu Asp Phe Asn Asn Leu Asn Gly Glu Asp Gln
                20                  25                  30

Asp Ile Leu Met Glu Asn Asn Leu Arg Arg Pro Asn Leu Glu Ala Phe
            35                  40                  45

Asn Arg Ala Val Lys Ser Leu Gln Asn Ala Ser Ala Ile Glu Ser Ile
        50                  55                  60

Leu Lys Asn Leu Leu Pro Cys Leu Pro Leu Ala Thr Ala Ala Pro Thr
65                  70                  75                  80

Arg His Pro Ile His Ile Lys Asp Gly Asp Trp Asn Glu Phe Arg Arg
                85                  90                  95

Lys Leu Thr Phe Tyr Leu Lys Thr Leu Glu Asn Ala Gln Ala Gln Gln
            100                 105                 110

Thr Thr Leu Arg Leu Ala Ile Phe
        115                 120
```

(2) INFORMATION FOR SEQ ID NO:403:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:403:

Met Ala Tyr Pro Glu Thr Asp Tyr Lys Asp Asp Asp Lys
1               5                  10

(2) INFORMATION FOR SEQ ID NO:404:

(i) SEQUENCE CHARACTERISTICS:
            (A) LENGTH: 378 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:404:

```
ATGGCATATC CAGAAACTGA TTACAAGGAC GACGATGACA AGGCTAACTG CTCTATAATG    60

ATCGATGAAA TTATACATCA CTTAAAGAGA CCACCTGCAC CTTTGCTGGA CCCGAACAAC   120

CTCAATGCTG AAGACGTCGA TATCCTGATG GAACGAAACC TTCGACTTCC AAACCTGGAG   180

AGCTTCGTAA GGGCTGTCAA GAACTTAGAA AATGCATCAG GTATTGAGGC AATTCTTCGT   240

AATCTCCAAC CATGTCTGCC CTCTGCCACG GCCGCACCCT CTCGACATCC AATCATCATC   300

AAGGCAGGTG ACTGGCAAGA ATTCCGGGAA AAACTGACGT TCTATCTGGT TACCCTTGAG   360

CAAGCGCAGG AACAACAG                                                 378
```

(2) INFORMATION FOR SEQ ID NO:405:

(i) SEQUENCE CHARACTERISTICS:
            (A) LENGTH: 378 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:405:

```
ATGGCATATC CAGAAACTGA TTACAAGGAC GACGATGACA AGGCTAACTG CTCTATAATG    60

ATCGATGAAA TTATACATCA CTTAAAGAGA CCACCTAACC CTTTGCTGGA CCCGAACAAC   120

CTCAATTCCG AAGACATGGA TATCCTGATG GAACGAAACC TTCGAACTCC AAACCTGCTC   180

GCATTCGTAA GGGCTGTCAA GCACTTAGAA AATGCATCAG GTATTGAGGC AATTCTTCGT   240

AATCTCCAAC CATGTCTGCC CTCTGCCACG GCCGCACCCT CTCGACATCC AATCATCATC   300

AAGGCAGGTG ACTGGCAAGA ATTCCGGGAA AAACTGACGT TCTATCTGGT TACCCTTGAG   360

CAAGCGCAGG AACAACAG                                                 378
```

(2) INFORMATION FOR SEQ ID NO:406:

(i) SEQUENCE CHARACTERISTICS:
            (A) LENGTH: 113 amino acids
            (B) TYPE: amino acid
            (D) TOPOLOGY: linear (ii) MOLECULE TYPE: peptide (xi) SEQUENCE DESCRIPTION: SEQ ID NO:406:

Met Ala Asn Cys Ser Asn Met Ile Asp Glu Ile Ile Thr His Leu Lys
1               5                  10                  15

Gln Pro Pro Leu Pro Leu Leu Asp Phe Asn Asn Leu Asn Asp Glu Asp
            20                  25                  30

```
Met Ser Ile Leu Met Glu Asn Asn Leu Arg Arg Pro Asn Leu Glu Ala
            35                  40                  45

Phe Asn Arg Ala Val Lys Ser Leu Gln Asn Ala Ser Ala Ile Glu Ser
         50                  55                  60

Ile Leu Lys Asn Leu Leu Pro Cys Leu Pro Leu Ala Thr Ala Ala Pro
65                  70                  75                  80

Thr Arg His Pro Ile Ile Ile Arg Asp Gly Asp Trp Asn Glu Phe Arg
                 85                  90                  95

Arg Lys Leu Thr Phe Tyr Leu Trp Thr Leu Glu Asn Ala Gln Ala Gln
            100                 105                 110

Gln (2) INFORMATION FOR SEQ ID NO:407:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:407:

Asn Cys Ser Asn Met Ile Asp Glu Ile Ile Thr His Leu Lys Gln Pro
1                5                  10                  15

Pro Leu Pro Leu Leu Asp Phe Asn Asn Leu Asn Gly Glu Asp Gln Asp
            20                  25                  30

Ile Leu Met Asp Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
         50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Arg Lys
                 85                  90                  95

Leu Thr Phe Tyr Leu Lys Thr Leu Glu Asn Ala Gln Ala Gln Gln
            100                 105                 110

(2) INFORMATION FOR SEQ ID NO:408:

(i) SEQUENCE CHARACTERISTICS:
        (A) LENGTH: 340 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:408:

ATGGCTAACT GCTCTAACAT GATCGATGAA ATCATCACCC ACCTGAAGCA GCCACCGCTG      60

CCGCTGCTGG ACTTCAACAA CCTCAATGGT GAAGACCAAG ATATCCTGAT GGAACAATAA    120

CCTTCGTCGT CCAAACCTCG AGGCATTCAA CCGTGCTGTC AACTCTCTGC AGAATGCATC    180

AGCAATTGAG AGCATTCTTA AAAATCTCCT GCCATGTCTG CCCCTGGCCA CGGCCGCACC    240

CACGCGACAT CCAATCCATA TCAAGGACGG TGACTGGAAT GAATTCCGTC GTAAACTGAC    300

CTTCTATCTG AAAACCTTGG AGAACGCGCA GGCTCAACAG                          340
```

(2) INFORMATION FOR SEQ ID NO:409:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:409:

CTTTAAGTGA TGTATAATTT CATCGATCAT TATAGAGCAG TTAGC                45

(2) INFORMATION FOR SEQ ID NO:410:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:410:

CACTTAAAGA GACCACCTGC ACCTTTGCTG GACCCG                          36

(2) INFORMATION FOR SEQ ID NO:411:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:411:

GAGGTTGTTC GGGTCCAGCA AAGGTGCAGG TGGTCT                          36

(2) INFORMATION FOR SEQ ID NO:412:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:412:

CACTTAAAGA GACCACCTAA CCCTTTGCTG GACCCG                          36

(2) INFORMATION FOR SEQ ID NO:413:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:413:

GAGGTTGTTC GGGTCCAGCA AAGGGTTAGG TGGTCT                          36

(2) INFORMATION FOR SEQ ID NO:414:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:414:

CACTTAAAGG TTCCACCTGC ACCTTTGCTG GACAGT                              36

(2) INFORMATION FOR SEQ ID NO:415:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:415:

GAGGTTGTTA CTGTCCAGCA AAGGTGCAGG TGGAAC                              36

What is claimed is:

1. A method of treating a patient having an immunodeficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:15)
wherein;
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;

Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;

Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

2. The method according to claim 1, wherein said mutant human interleukin-3 polypeptide has at least three times greater cell proliferative activity compared to native human interleukin-3.

3. The method according to claim 1, wherein said mutant human interleukin-3 polypeptide has at least ten times greater cell proliferative activity compared to native human interleukin-3.

4. A method of treating a patient having an immunodeficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:17) wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;

Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

5. The method according to claim 4, wherein said mutant human interleukin-3 polypeptide has at least three times greater cell proliferative activity compared to native human interleukin-3.

6. The method according to claim 4, wherein said mutant human interleukin-3 polypeptide has at least ten times greater cell proliferative activity compared to native human interleukin-3.

7. The method according to claim 4, wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

8. The method according to claim 7, wherein said mutant human interleukin-3 polypeptide has at least three times greater cell proliferative activity compared to native human interleukin-3.

9. The method according to claim 7, wherein said mutant human interleukin-3 polypeptide has at least ten times greater cell proliferative activity compared to native human interleukin-3.

10. A method of treating a patient having an immunodeficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:19)
wherein;
Xaa at position 3 is Ser, Lys, Gly, Asp, Met, Gln, or Arg;

Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;

Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, lie, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

11. The method according to claim 10, wherein said mutant human interleukin-3 polypeptide has at least three times greater cell proliferative activity compared to native human interleukin-3.

12. The method according to claim 10, wherein said mutant human interleukin-3 polypeptide has at least ten times greater cell proliferative activity compared to native human interleukin-3.

13. A method of treating a patient having an immunodeficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:21)
wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

14. The method according to claim 13, wherein said mutant human interleukin-3 polypeptide has at least three times greater cell proliferative activity compared to native human interleukin-3.

15. The method according to claim 13, wherein said mutant human interleukin-3 polypeptide has at least ten times greater cell proliferative activity compared to native human interleukin-3.

16. The method according to claim 13, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;
position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser, or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

17. The method according to claim 16, wherein said mutant human interleukin-3 polypeptide has at least three times greater cell proliferative activity compared to native human interleukin-3.

18. The method according to claim 16, wherein said mutant human interleukin-3 polypeptide has at least ten times greater cell proliferative activity compared to native human interleukin-3.

19. A method of treating a patient having an immunodeficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a polypeptide having an amino acid sequence of
(18I, 25H, 29R, 32A, 37P, 42A and 45V)-(15–125)human interleukin-3 (SEQ ID NO:66);
(18I, 25H, 29R, 32N, 37P, 42S and 45M)-(15–125)human interleukin-3 (SEQ ID NO:67);
(18I, 25H, 29V, 32A, 37S, 42S and 45M)-(15–125)human interleukin-3 (SEQ ID NO:68);
(51R, 55L, 59L, 62V, 67N and 69E)-(15–125)human interleukin-3 (SEQ ID NO:69);
(51R, 55L, 60S, 62V, 67N and 69E)-(15–125)human interleukin-3 (SEQ ID NO:70);
(51R, 55T, 59L, 62V, 67H and 69E)-(15–125)human interleukin-3 (SEQ ID NO:71);
(73G, 76A, 79R, 82Q, 87S, 93S, 98I, 101A and 105Q)-(15–125)human interleukin-3 (SEQ ID NO:72);
(73G, 76A, 79R, 82V, 87S, 93S, 98T, 101A and 105Q)-(15–125)human interleukin-3 (SEQ ID NO:73);
(73G, 76A, 79R, 82Q, 87S, 93S, 98I, 101A, 105Q, 109E, 116V, 120Q and 123E)-(15–125)human interleukin-3 (SEQ. ID. NO:76)
(73G, 76A, 79R, 82V, 87S, 93S, 98T, 101A, 105Q, 109E, 116V, 120Q and 123E)-(15–125)human interleukin-3 (SEQ ID NO:77);
(73G, 76A, 79R, 82V, 87S, 93S, 98T, 101A, 105Q, 109E, 116V, 117S, 120H and 123E)-(15–125)human interleukin-3 (SEQ ID NO:78);
(18I, 25H, 29R, 32A, 37P, 42A, 45V, 51R, 55L, 60S, 62V, 67N and 69E)-(15–125)human interleukin-3 (SEQ ID NO:79);
(18I, 25H, 29R, 32N, 37P, 42S, 45M, 51R, 55T, 59L, 62V, 67H and 69E)-(15–125)human interleukin-3 (SEQ ID NO:80);
(18I, 25H, 29V, 32A, 37S, 42S, 45M, 51R, 55L, 59L, 62V, 67N and 69E)-(15–125)human interleukin-3 (SEQ ID NO:81);
(42D, 45M, 46S, 50D, 95R, 98I, 100R, 116W)-(15–125) human interleukin-3 (residues 3–113 of SEQ ID NO:263);
(42D, 45M, 46S, 98I, 10R, 116W)-(15–125)human interleukin-3 (SEQ ID NO:406);
(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);
(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);
(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);
(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);
(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323); and said mutant human interleukin-3 polypeptide has increased cell proliferative activity compared to native human interleukin-3 in at least one assay selected from the group consisting of: AML cell proliferation, TF-1 cell proliferation and Methylcellulose assay;

(b) a polypeptide comprising an N-terminal methionine residue, alanine residue or methionine-alanine di-peptide immediately preceding said sequence according to (a).

20. The method according to claim 19, wherein said mutant human interleukin-3 polypeptide has at least three times greater cell proliferative activity compared to native human interleukin-3.

21. The method according to claim 19, wherein said mutant human interleukin-3 polypeptide has at least ten times greater cell proliferative activity compared to native human interleukin-3.

22. A method of treating a patient comprising the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a sequence of (SEQ ID NO:15)

wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;

Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and
  (b) a polypeptide comprising an N-terminal methionine residue, alanine residue or methionine-alanine di-peptide immediately preceding said sequence according to (a);
  (ii) removing hematopoietic cells from said patient;
  (iii) administering to said patient cancer radiation therapy or chemotherapy; and
  (iv) returning said hematopoietic cells to said patient.
23. The method according to claim 22, wherein said mutant human interleukin-3 polypeptide has at least three times greater cell proliferative activity compared to native human interleukin-3.
24. The method according to claim 22, wherein said mutant human interleukin-3 polypeptide has at least ten times greater cell proliferative activity compared to native human interleukin-3.
25. A method of treating a patient comprising the steps of:
  (i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:
  (a) a sequence of(SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;

Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);
(ii) removing hematopoietic cells from said patient;
(iii) administering to said patient cancer radiation therapy or chemotherapy; and
(iv) returning said hematopoietic cells to said patient.

26. The method according to claim 25, wherein said mutant human interleukin-3 polypeptide has at least three times greater cell proliferative activity compared to native human interleukin-3.

27. The method according to claim 25, wherein said mutant human interleukin-3 polypeptide has at least ten times greater cell proliferative activity compared to native human interleukin-3.

28. The method according to claim 25 wherein in said mutant human interleukin-3 (hIL-3) sequence the amino acids which differ from the corresponding residue in native human interleukin-3 are selected from the group consisting of:
position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

29. The method according to claim 28 wherein said mutant human interleukin-3 polypeptide has at least three times greater cell proliferative activity compared to native human interleukin-3.

30. The method according to claim 28, wherein said mutant human interleukin-3 polypeptide has at least ten times greater cell proliferative activity compared to native human interleukin-3.

31. A method of treating a patient comprising the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a sequence of(SEQ ID NO:19)
wherein;
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

32. The method according to claim 31, wherein said mutant human interleukin-3 polypeptide has at least three times greater cell proliferative activity compared to native human interleukin-3.

33. The method according to claim 31, wherein said mutant human interleukin-3 polypeptide has at least ten times greater cell proliferative activity compared to native human interleukin-3.

34. A method of treating a patient comprising the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a sequence of (SEQ ID NO:21)

wherein;

Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;

Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

35. The method according to claim 34, wherein said mutant human interleukin-3 polypeptide has at least three times greater cell proliferative activity compared to native human interleukin-3.

36. The method according to claim 34, wherein said mutant human interleukin-3 polypeptide has at least ten times greater cell proliferative activity compared to native human interleukin-3.

37. The method according to claim 34, wherein in said mutant human interleukin-3 (hIL-3) sequence the amino acids which differ from the corresponding residue in native human interleukin-3 are selected from the group consisting of:
position 28 wherein Xaa is Gly, Asp, Ser, Ile, Leu, Met, Tyr, or Ala;
position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser. or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

38. The method according to claim 37, wherein said mutant human interleukin-3 polypeptide has at least three times greater cell proliferative activity compared to native human interleukin-3.

39. The method according to claim 37, wherein said mutant human interleukin-3 polypeptide has at least ten times greater cell proliferative activity compared to native human interleukin-3.

40. A method of treating a patient comprising the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a polypeptide having an amino acid sequence of
(18I, 25H, 29R, 32A, 37P, 42A and 45V)-(15–125)human interleukin-3 (SEQ ID NO:66);
(18I, 25H, 29R, 32N, 37P, 42S and 45M)-(15–125)human interleukin-3 (SEQ ID NO:67);
(18I, 25H, 29V, 32A, 37S, 42S and 45M)-(15–125)human interleukin-3 (SEQ ID NO:68);
(51R, 55L, 59L, 62V, 67N and 69E)-(15–125)human interleukin-3 (SEQ ID NO:69);
(51R, 55L, 60S, 62V, 67N and 69E)-(15–125)human interleukin-3 (SEQ ID NO:70);
(51R, 55T, 59L, 62V, 67H and 69E)-(15–125)human interleukin-3 (SEQ ID NO:71);
(73G, 76A, 79R, 82Q, 87S, 93S, 98I, 101A and 105Q)-(15–125)human interleukin-3 (SEQ ID NO:72);
(73C, 76A, 79R, 82V, 87S, 93S, 98T, 101A and 105Q)-(15–125)human interleukin-3 (SEQ ID NO:73);
(73G, 76A, 79R, 82Q, 87S, 93S, 98I, 101A, 105Q, 109E, 116V, 120Q and 123E)-(15–125)human interleukin-3 (SEQ. ID. NO:76);
(73G, 76A, 79R, 82V, 87S, 93S, 98T, 101A, 105Q, 109E, 116V, 120Q and 123E)-(15–125)human interleukin-3 (SEQ ID NO:77);
(73G, 76A, 79R, 82V, 87S, 93S, 98T, 101A, 105Q, 109E, 116V, 117S, 120H and 123E)-(15–125)human interleukin-3 (SEQ ID NO:78);
(18I, 25H, 29R, 32A, 37P, 42A, 45V, 51R, 55L, 60S, 62V, 67N and 69E)-(15–125)human interleukin-3 (SEQ ID NO:79);
(18I, 25H, 29R, 32N, 37P, 42S, 45M, 51R, 55T, 59L, 62V, 67H and 69E)-(15–125)human interleukin-3 (SEQ ID NO:80);
(18I, 25H, 29V, 32A, 37S, 42S, 45M, 51R, 55L, 59L, 62V, 67N and 69E)-(15–125)human interleukin-3 (SEQ ID NO:81);
(42D, 45M, 46S, 50D, 95R, 98I, 100R, 116W)-(15–125) human interleukin-3 (residues 3–113 of SEQ ID NO:263);
(42D, 45M, 46S, 98I, 100R, 116W)-(15–125)human interleukin-3 (SEQ ID NO:406);
(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);
(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);

(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);

(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);

(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42S, 45M, 51R, 55T, 59L, 62V, 67H, 69E, 73G, 76A, 79R, 82Q, 87S, 93S, 98T, 101A, 105Q, 109L, 112Q, 116S)-(15–118)human interleukin-3 (residues 3–113 of SEQ ID NO:323); and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a);
(ii) removing hematopoietic cells from said patient;
(iii) administering to said patient cancer radiation therapy or chemotherapy; and
(iv) returning said hematopoietic cells to said patient.

41. The method according to claim 40, wherein said mutant human interleukin-3 polypeptide has at least three times greater cell proliferative activity compared to native human interleukin-3.

42. The method according to claim 40, wherein said mutant human interleukin-3 polypeptide has at least ten times greater cell proliferative activity compared to native human interleukin-3.

43. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:15)
wherein;
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is, Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;

Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;

Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

44. The method according to claim 43, wherein said mutant human interleukin-3 polypeptide has at least three times greater cell proliferative activity compared to native human interleukin-3.

45. The method according to claim 43, wherein said mutant human interleukin-3 polypeptide has at least ten times greater cell proliferative activity compared to native human interleukin-3.

46. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;

Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, GA u, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, le, or Asp;
Xaa at position 80 is Asn, Gly, Glu, or Arg;
Xaa a t position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is i Ile or Val;
Xaa at position 98 is His, Ile, Asn, Leu, Ala, Thr, Gln, Lys, Met, Ser, Tyr, Val or Pro;
Xaa at position 99 is Ile, Leu, or Val;
Xaa at position 100 is Lys, Arg, le, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is G Au or Gly;
Xaa at position 108 is Arg, Ala , or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

47. The method according to claim 46, wherein said mutant human interleukin-3 polypeptide has at least three times greater cell proliferative activity compared to native human interleukin-3.

48. The method according to claim 46, wherein said mutant human interleukin-3 polypeptide has at least ten times greater cell proliferative activity compared to native human interleukin-3.

49. The method according to claim 46 wherein in said mutant human interleukin-3 (hIL-3sequence the amino acids which differ from the corresponding residue in native human interleukin-3 are selected from the group consisting of:

position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

50. The method according to claim 49, wherein said mutant human interleukin-3 polypeptide has at least three times greater cell proliferative activity compared to native human interleukin-3.

51. The method according to claim 49, wherein said mutant human interleukin-3 polypeptide has at least ten times greater cell proliferative activity compared to native human interleukin-3.

52. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:
 (a) a sequence of (SEQ ID NO:19)
wherein;
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;

Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

53. The method according to claim 52, wherein said mutant human interleukin-3 polypeptide has at least three times greater cell proliferative activity compared to native human interleukin-3.

54. The method according to claim 52, wherein said mutant human interleukin-3 polypeptide has at least ten times greater cell proliferative activity compared to native human interleukin-3.

55. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:21) wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;

Xaa at position 109 is Ala, Met, Glu, His, Ser, Pro, Tyr, or Leu;

wherein from 4 to about 44 of the amino acids designated by Xaa are different from the corresponding amino acids of native (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in 123E)-(15–125)human interleukin-3 (residues 3–113 of SEQ ID NO:317);

(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323);

and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

62. The method according to claim 61, wherein said mutant human interleukin-3 polypeptide has at least three times greater cell proliferative activity compared to native human interleukin-3.

63. The method according to claim 61, wherein said mutant human interleukin-3 polypeptide has at least ten times greater cell proliferative activity compared to native human interleukin-3.

64. A method of treating a patient having an immunodeficiency or hematopoietic deficiency consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:15)

wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;

Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

65. The method according to claim 64, wherein said mutant human interleukin-3 polypeptide has at least three times greater cell proliferative activity compared to native human interleukin-3.

66. The method according to claim 64, wherein said mutant human interleukin-3 polypeptide has at least ten times greater cell proliferative activity compared to native human interleukin-3.

67. A method of treating a patient having an immunodeficiency or hematopoietic deficiency consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;

Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

68. The method according to claim 67, wherein said mutant human interleukin-3 polypeptide has at least three times greater cell proliferative activity compared to native human interleukin-3.

69. The method according to claim 67, wherein said mutant human interleukin-3 polypeptide has at least ten times greater cell proliferative activity compared to native human interleukin-3.

70. The method according to claim 67 wherein in said mutant human interleukin-3 (hIL-3) sequence the amino acids which differ from the corresponding residue in native human interleukin-3 are selected from the group consisting of:
position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

71. The method according to claim 70, wherein said mutant human interleukin-3 polypeptide has at least three times greater cell proliferative activity compared to native human interleukin-3.

72. The method according to claim 70, wherein said mutant human interleukin-3 polypeptide has at least ten times greater cell proliferative activity compared to native human interleukin-3.

73. A method of treating a patient having an immunodeficiency or hematopoietic deficiency consisting of administering to said patient, a therapeutically effective amount of a mutant human interleukin-3 (hIL-3) polypeptide consisting of a modified hIL-3 amino acid sequence selected from the group consisting of:
(a) a sequence of (SEQ ID NO:19)
wherein;
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;

Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, .Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gin, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;

Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

74. The method according to claim 73, wherein said mutant human interleukin-3 polypeptide has at least three times greater cell proliferative activity compared to native human interleukin-3.

75. The method according to claim 73, wherein said mutant human interleukin-3 polypeptide has at least ten times greater cell proliferative activity compared to native human interleukin-3.

76. A method of treating a patient having an immunodeficiency or hematopoietic deficiency consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:21) wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser. Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser. Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

77. The method according to claim 76, wherein said mutant human interleukin-3 polypeptide has at least three times greater cell proliferative activity compared to native human interleukin-3.

78. The method according to claim 76, wherein said mutant human interleukin-3 polypeptide has at least ten times greater cell proliferative activity compared to native human interleukin-3.

79. The method according to claim 76, wherein in said mutant human interleukin-3 (hIL-3) sequence the amino acids which differ from the corresponding residue in native human interleukin-3 are selected from the group consisting of:
position 28 wherein Xaa is Gly, Asp, Ser, Ile, Leu, Met, Tyr, or Ala;
position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser, or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

80. The method according to claim 79, wherein said mutant human interleukin-3 polypeptide has at least three times greater cell proliferative activity compared to native human interleukin-3.

81. The method according to claim 79, wherein said mutant human interleukin-3 polypeptide has at least ten times greater cell proliferative activity compared to native human interleukin-3.

82. A method of treating a patient having an immunodeficiency or hematopoietic deficiency consisting of administering to said patient, a therapeutically effective amount of a mutant human interleukin-3 (hIL-3) polypeptide consisting of a modified hIL-3 amino acid sequence selected from the group consisting of:
(a) a polypeptide having an amino acid sequence of
(18I, 25H, 29R, 32A, 37P, 42A and 45V)-(15–125)human interleukin-3 (SEQ ID NO:66);
(18I, 25H, 29R, 32N, 37P, 42S and 45M)-(15–125)human interleukin-3 (SEQ ID NO:67);
(18I, 25H, 29V, 32A, 37S, 42S and 45M)-(15–125)human interleukin-3 (SEQ ID NO:68);
(51R, 55L, 59L, 62V, 67N and 69E)-(15–125)human interleukin-3 (SEQ ID NO:69);
(51R, 55L, 60S, 62V, 67N and 69E)-(15–125)human interleukin-3 (SEQ ID NO:70);
(51R, 55T, 59L, 62V, 67H and 69E)-(15–125)human interleukin-3 (SEQ ID NO:71);
(73G, 76A, 79R, 82Q, 87S, 93S, 98I, 101A and 105Q)-(15–125)human interleukin-3 (SEQ ID NO:72);
(73G, 76A, 79R, 82V, 87S, 93S, 98T, 101A and 105Q)-(15–125)human interleukin-3 (SEQ ID NO:73);
(73G, 76A, 79R, 82Q, 87S, 93S, 98I, 101A, 105Q, 109E, 116V, 120Q and 123E)-(15–125)human interleukin-3 (SEQ. ID. NO:76);
(73G, 76A, 79R, 82V, 87S, 93S, 98T, 101A, 105Q, 109E, 116V, 120Q and 123E)-(15–125)human interleukin-3 (SEQ ID NO:77);
(73G, 76A, 79R, 82V, 87S, 93S, 98T, 101A, 105Q, 109E, 116V, 117S, 120H and 123E)-(15–125)human interleukin-3 (SEQ ID NO:78);
(18I, 25H, 29R, 32A, 37P, 42A, 45V, 51R, 55L, 60S, 62V, 67N and 69E)-(15–125)human interleukin-3 (SEQ ID NO:79);
(18I, 25H, 29R, 32N, 37P, 42S, 45M, 51R, 55T, 59L, 62V, 67H and 69E)-(15–125)human interleukin-3 (SEQ ID NO:80);
(18I, 25H, 29V, 32A, 37S, 42S, 45M, 51R, 55L, 59L, 62V, 67N and 69E)-(15–125)human interleukin-3 (SEQ ID NO:81);
(42D, 45M, 46S, 50D, 95R, 98I, 100R, 116W)-(15–125) human interleukin-3 (residues 3–113 of SEQ ID NO:263);
(42D, 45M, 46S, 98I, 100R, 116W)-(15–125)human interleukin-3 (SEQ ID NO:406);
(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);
(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);
(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);
(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);
(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);
(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);
(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323);

and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide comprising an N-terminal methionine residue, alanine residue or methionine-alanine di-peptide immediately preceding said sequence according to (a).

83. The method according to claim 82, wherein said mutant human interleukin-3 polypeptide has at least three times greater cell proliferative activity compared to native human interleukin-3.

84. The method according to claim 82, wherein said mutant human interleukin-3 polypeptide has at least ten times greater cell proliferative activity compared to native human interleukin-3.

85. A method of treating a patient consisting of the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:

(a) a sequence of (SEQ ID NO:15)

wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;

Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);
(ii) removing hematopoietic cells from said patient;
(iii) administering to said patient cancer radiation therapy or chemotherapy; and
(iv) returning said hematopoietic cells to said patient.

86. The method according to claim 85, wherein said mutant human interleukin-3 polypeptide has at least three times greater cell proliferative activity compared to native human interleukin-3.

87. The method according to claim 85, wherein said mutant human interleukin-3 polypeptide has at least ten times greater cell proliferative activity compared to native human interleukin-3.

88. A method of treating a patient consisting of the steps of:
(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:
(a) a sequence of (SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;
Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;

Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);

(ii) removing hematopoietic cells from said patient;

(iii)administering to said patient cancer radiation therapy or chemotherapy; and (iv) returning said hematoposetic cells to said patient.

89. The method according to claim 88, wherein said mutant human interleukin-3 polypeptide has at least three times greater cell proliferative activity compared to native human interleukin-3.

90. The method according to claim 88, wherein said mutant human interleukin-3 polypeptide has at least ten times greater cell proliferative activity compared to native human interleukin-3.

91. The method according to claim 88 wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

92. The method according to claim 91, wherein said mutant human interleukin-3 polypeptide has at least three times greater cell proliferative activity compared to native human interleukin-3.

93. The method according to claim 91, wherein said mutant human interleukin-3 polypeptide has at least ten times greater cell proliferative activity compared to native human interleukin-3.

94. A method of treating a patient consisting of the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:

(a) a sequence of(SEQ ID NO:19)

wherein;

Xaa at position 3 is Ser, Lys, Gly, Asp, Met, Gln, or Arg;
Xaa at position 4 is Asn, His, Leu, le, Phe, Arg, or Gln;
Xaa at position 5 is Met , Phe, Ile , Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;

Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;

Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and
  (b) a polypeptide consisting of an N-terminal methionine residue, alanine residue or methionine-alanine di-peptide immediately preceding said sequence according to (a);
  (ii) removing hematopoietic cells from said patient;
  (iii) administering to said patient cancer radiation therapy or chemotherapy; and
  (iv) returning said hematopoietic cells to said patient.

95. The method according to claim 94, wherein said mutant human interleukin-3 polypeptide has at least three times greater cell proliferative activity compared to native human interleukin-3.

96. The method according to claim 94, wherein said mutant human interleukin-3 polypeptide has at least ten times greater cell proliferative activity compared to native human interleukin-3.

97. A method of treating a patient consisting of the steps of:
  (i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:
  (a) a sequence of (SEQ ID NO:21)
wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

98. The method according to claim 97, wherein said mutant human interleukin-3 polypeptide has at least three times greater cell proliferative activity compared to native human interleukin-3.

99. The method according to claim 97, wherein said mutant human interleukin-3 polypeptide has at least ten times greater cell proliferative activity compared to native human interleukin-3.

100. The method according to claim 97, wherein in said mutant human interleukin-3 (hIL-3) sequence the amino acids which differ from the corresponding residue in native human interleukin-3 are selected from the group consisting of:

position 28 wherein Xaa is Gly, Asp, Ser, Ile, Leu, Met, Tyr, or Ala;
position 31 wherein Xaa is Gln, Val, Met or Asn;
position 32 wherein Xaa is Asp, Ser, Ala, Gln, His or Val;
position 36 wherein Xaa is Glu or Asp;
position 37 wherein Xaa is Asn, Pro or Thr;
position 48 wherein Xaa is Asn or Pro;
position 62 wherein Xaa is Ser, or Pro;
position 68 wherein Xaa is Leu, Trp, Asp, Asn, Glu, His, Phe, Ser or Tyr;
position 81 wherein Xaa is His, Arg, Thr, Asn or Ser;
position 84 wherein Xaa is His, Ile, Leu, Ala, Arg, Gln, Lys, Met, Ser, Tyr or Val;
position 86 wherein Xaa is Lys or Arg;
position 87 wherein Xaa is Asp;
position 91 wherein Xaa is Asn, or Pro;
position 94 wherein Xaa is Arg, Ala, or Ser;
position 102 wherein Xaa is Lys;
position 107 wherein Xaa is Ala, or Ile;
position 108 wherein Xaa is Gln, or Ile;
position 109 wherein Xaa is Ala, Met or Glu.

101. The method according to claim 100, wherein said mutant human interleukin-3 polypeptide has at least three times greater cell proliferative activity compared to native human interleukin-3.

102. The method according to claim 100, wherein said mutant human interleukin-3 polypeptide has at least ten times greater cell proliferative activity compared to native human interleukin-3.

103. A method of treating a patient consisting of the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide consists of a modified hIL-3 amino acid sequence selected from the group consisting of:

(a) a polypeptide having an amino acid sequence of
(18I, 25H, 29R, 32A, 37P, 42A and 45V)-(15–125)human interleukin-3 (SEQ ID NO:66);
(18I, 25H, 29R, 32N, 37P, 42S and 45M)-(15–125)human interleukin-3 (SEQ ID NO:67);
(18I, 25H, 29V, 32A, 37S, 42S and 45M)-(15–125)human interleukin-3 (SEQ ID NO:68);
(51R, 55L, 59L, 62V, 67N and 69E)-(15–125)human interleukin-3 (SEQ ID NO:69);
(51R, 55L, 60S, 62V, 67N and 69E)-(15–125)human interleukin-3 (SEQ ID NO:70);
(51R, 55T, 59L, 62V, 67H and 69E)-(15–125)human interleukin-3 (SEQ ID NO:71);
(73G, 76A, 79R, 82Q, 87S, 93S, 98I, 101A and 105Q)-(15–125)human interleukin-3 (SEQ ID NO:72);
(73G, 76A, 79R, 82V, 87S, 93S, 98T, 101A and 105Q)-(15–125)human interleukin-3 (SEQ ID NO:73);
(73G, 76A, 79R, 82Q, 87S, 93S, 98I, 101A, 105Q, 109E, 116V, 120Q and 123E)-(15–125)human interleukin-3 (SEQ. ID. NO:76);
(73G, 76A, 79R, 82V, 87S, 93S, 98T, 101A, 105Q, 109E, 116V, 120Q and 123E)-(15–125)human interleukin-3 (SEQ ID NO:77);
(73G, 76A, 79R, 82V, 87S, 93S, 98T, 101A, 105Q, 109E, 116V, 117S, 120H and 123E)-(15–125)human interleukin-3 (SEQ ID NO:78);
(18I, 25H, 29R, 32A, 37P, 42A, 45V, 51R, 55L, 60S, 62V, 67N and 69E)-(15–125)human interleukin-3 (SEQ ID NO:79);
(18I, 25H, 29R, 32N, 37P, 42S, 45M, 51R, 55T, 59L, 62V, 67H and 69E)-(15–125)human interleukin-3 (SEQ ID NO:80);
(18I, 25H, 29V, 32A, 37S, 42S, 45M, 51R, 55L, 59L, 62v, 67N and 69E)-(15–125)human interleukin-3 (SEQ ID NO:81);
(42D, 45M, 46S, 50D, 95R, 98I, 100R, 116W)-(15–125) human interleukin-3 (residues 3–113 of SEQ ID NO:263);
(42D, 45M, 46S, 98I, 100R, 116W)-(15–125)human interleukin-3 (SEQ ID NO:406);
(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);
(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);
(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);

(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);

(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323); and said mutant human interleukin-3 polypeptide has increased cell proliferative activity compared to native human interleukin-3 in at least one assay selected from the group consisting of: AML cell proliferation, TF-1 cell proliferation and Methylcellulose assay;

(b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

104. The method according to claim 103, wherein said mutant human interleukin-3 polypeptide has at least three times greater cell proliferative activity compared to native human interleukin-3.

105. The method according to claim 103, wherein said mutant human interleukin-3 polypeptide has at least ten times greater cell proliferative activity compared to native human interleukin-3.

106. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:15) wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;

Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position Ill is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

107. The method according to claim 106, wherein said mutant human interleukin-3 polypeptide has at least three times greater cell proliferative activity compared to native human interleukin-3.

108. The method according to claim 106, wherein said mutant human interleukin-3 polypeptide has at least ten times greater cell proliferative activity compared to native human interleukin-3.

109. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:17)
wherein;
Xaa at position 17 is Ser, Gly, Asp, Met, or Gln;
Xaa at position 18 is Asn, His, or Ile;
Xaa at position 19 is Met or Ile;
Xaa at position 21 is Asp or Glu;
Xaa at position 23 is Ile, Ala, Leu, or Gly;
Xaa at position 24 is Ile, Val, or Leu;
Xaa at position 25 is Thr, His, Gln, or Ala;
Xaa at position 26 is His or Ala;
Xaa at position 29 is Gln, Asn, or Val;
Xaa at position 30 is Pro, Gly, or Gln;
Xaa at position 31 is Pro, Asp, Gly, or Gln;
Xaa at position 32 is Leu, Arg, Gln, Asn, Gly, Ala, or Glu;
Xaa at position 33 is Pro or Glu;
Xaa at position 34 is Leu, Val, Gly, Ser, Lys, Ala, Arg, Gln, Glu, Ile, Phe, Thr or Met;
Xaa at position 35 is Leu, Ala, Asn, Pro, Gln, or Val;
Xaa at position 37 is Phe, Ser, Pro, or Trp;
Xaa at position 38 is Asn or Ala;

Xaa at position 42 is Gly, Asp, Ser, Cys, Ala, Asn, Ile, Leu, Met, Tyr or Arg;
Xaa at position 44 is Asp or Glu;
Xaa at position 45 is Gln, Val, Met, Leu, Thr, Ala, Asn, Glu, Ser or Lys;
Xaa at position 46 is Asp, Phe, Ser, Thr, Ala, Asn, Gln, Glu, His, Ile, Lys, Tyr, Val or Cys;
Xaa at position 50 is Glu, Ala, Asn, Ser or Asp;
Xaa at position 51 is Asn, Arg, Met, Pro, Ser, Thr, or His;
Xaa at position 54 is Arg or Ala;
Xaa at position 55 is Arg, Thr, Val, Leu, or Gly;
Xaa at position 56 is Pro, Gly, Ser, Gln, Ala, Arg, Asn, Glu, Leu, Thr, Val or Lys;
Xaa at position 60 is Ala or Ser;
Xaa at position 62 is Asn, Pro, Thr, or Ile;
Xaa at position 63 is Arg;
Xaa at position 64 is Ala or Asn;
Xaa at position 65 is Val or Thr;
Xaa at position 66 is Lys or Arg;
Xaa at position 67 is Ser, Phe, or His;
Xaa at position 68 is Leu, Ile, Phe, or His;
Xaa at position 69 is Gln, Ala, Pro, Thr, Glu, Arg, or Gly;
Xaa at position 71 is Ala, Pro, or Arg;
Xaa at position 72 is Ser, Glu, Arg, or Asp;
Xaa at position 73 is Ala or Leu;
Xaa at position 76 is Ser, Val, Ala, Asn, Glu, Pro, or Gly;
Xaa at position 77 is Ile or Leu;
Xaa at position 79 is Lys, Thr, Gly, Asn, Met, Arg, Ile, or Asp;
Xaa at position 80 is Asn, Gly, Glu, or Arg;
Xaa at position 82 is Leu, Gln, Trp, Arg, Asp, Ala, Asn, Glu, His, Ile, Met, Phe, Ser, Thr, Tyr or Val;
Xaa at position 83 is Pro or Thr;
Xaa at position 85 is Leu or Val;
Xaa at position 87 is Leu or Ser;
Xaa at position 88 is Ala or Trp;
Xaa at position 91 is Ala or Pro;
Xaa at position 93 is Thr, Asp, Ser, Pro, Ala, Leu, or Arg;
Xaa at position 95 is His, Pro, Arg, Val, Leu, Gly, Asn, Phe, Ser or Thr;
Xaa at position 96 is Pro or Tyr;
Xaa at position 97 is Ile or Val;
Xaa at position 98 is His, Ile, Asn, Leu, Ala, Thr, Gln, Lys, Met, Ser, Tyr, Val or Pro;
Xaa at position 99 is Ile, Leu, or Val;
Xaa at position 100 is Lys, Arg, Ile, Gln, Pro, or Ser;
Xaa at position 101 is Asp;
Xaa at position 104 is Trp or Leu;
Xaa at position 105 is Asn, Pro, Ala, Ser, Trp, Gln, Tyr, Leu, Lys, Ile, Asp, or His;
Xaa at position 106 is Glu or Gly;
Xaa at position 108 is Arg, Ala, or Ser;
Xaa at position 109 is Arg, Thr, Glu, Leu, or Ser;
Xaa at position 112 is Thr, Val, or Gln;
Xaa at position 114 is Tyr or Trp;
Xaa at position 115 is Leu or Ala;
Xaa at position 116 is Lys;
Xaa at position 117 is Thr or Ser;
Xaa at position 120 is Asn, Pro, Leu, His, Val, or Gln;
Xaa at position 121 is Ala, Ser, Ile, Asn, Pro, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 4 to about 44 of the amino acids designated by Xaa are different from the corresponding amino acids of native (1–133) human interleukin-3 with the proviso that no more than one of the amino acids at positions 63, 82, 87, 98, 112, and 121 are different from the corresponding amino acids in native human interleukin-3; and wherein from 1 to 14 amino acids are optionally deleted from the N-terminus and/or from 1 to 15 amino acids are optionally deleted from the C-terminus; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

110. The method according to claim 109, wherein said mutant human interleukin-3 polypeptide has at least three times greater cell proliferative activity compared to native human interleukin-3.

111. The method according to claim 109, wherein said mutant human interleukin-3 polypeptide has at least ten times greater cell proliferative activity compared to native human interleukin-3.

112. The method according to claim 109 wherein in said mutant human interleukin-3 (hIL-3) sequence the amino acids which differ from the corresponding residue in native human interleukin-3 are selected from the group consisting of:

position 42 wherein Xaa is Gly, Asp, Ser, Ile, Leu, Met, Tyr, or Ala;
position 45 wherein Xaa is Gln, Val, Met or Asn;
position 46 wherein Xaa is Asp, Ser, Gln, His or Val;
position 50 wherein Xaa is Glu or Asp;
position 51 wherein Xaa is Asn, Pro or Thr;
position 62 wherein Xaa is Asn or Pro;
position 76 wherein Xaa is Ser, or Pro;
position 82 wherein Xaa is Leu, Trp, Asp, Asn Glu, His, Phe, Ser or Tyr;
position 95 wherein Xaa is His, Arg, Thr, Asn or Ser;
position 98 wherein Xaa is His, Ile, Leu, Ala, Gln, Lys, Met, Ser, Tyr or Val;
position 100 wherein Xaa is Lys or Arg;
position 101 wherein Xaa is Asp;
position 105 wherein Xaa is Asn, or Pro;
position 108 wherein Xaa is Arg, Ala, or Ser;
position 116 wherein Xaa is Lys;
position 121 wherein Xaa is Ala, or Ile;
position 122 wherein Xaa is Gln, or Ile;
position 123 wherein Xaa is Ala, Met or Glu.

113. The method according to claim 112, wherein said mutant human interleukin-3 polypeptide has at least three times greater cell proliferative activity compared to native human interleukin-3.

114. The method according to claim 112, wherein said mutant human interleukin-3 polypeptide has at least ten times greater cell proliferative activity compared to native human interleukin-3.

115. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:19) wherein;
Xaa at position 3 is Ser, Lys, Gly, Asp, Met, Gln, or Arg;
Xaa at position 4 is Asn, His, Leu, Ile, Phe, Arg, or Gln;

Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, or Pro;
Xaa at position 87 is Asp;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;

Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding native amino acids of (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and (b) a polypeptide consisting of an N-terminal methionine residue, alanine residue or methionine-alanine di-peptide immediately preceding said sequence according to (a).

116. The method according to claim 115, wherein said mutant human interleukin-3 polypeptide has at least three times greater cell proliferative activity compared to native human interleukin-3.

117. The method according to claim 115, wherein said mutant human interleukin-3 polypeptide has at least ten times greater cell proliferative activity compared to native human interleukin-3.

118. A method of treating a side effect of cancer chemotherapy or radiation therapy in a patient consisting of administering to said patient, a therapeutically effective amount of a mutant human interleukin-3 (hIL-3) polypeptide consisting of a modified hIL-3 amino acid sequence selected from the group consisting of:

(a) a sequence of (SEQ ID NO:21)

wherein;
Xaa at position 3 is Ser, Gly, Asp, Met, or Gln;
Xaa at position 4 is Asn, His, or Ile;
Xaa at position 5 is Met or Ile;
Xaa at position 7 is Asp or Glu;
Xaa at position 9 is Ile, Ala, Leu, or Gly;
Xaa at position 10 is Ile, Val, or Leu;
Xaa at position 11 is Thr, His, Gln, or Ala;
Xaa at position 12 is His or Ala;
Xaa at position 15 is Gln, Asn, or Val;
Xaa at position 16 is Pro, Gly, or Gln;
Xaa at position 17 is Pro, Asp, Gly, or Gln;
Xaa at position 18 is Leu, Arg, Gln, Asn, Gly, Ala, or Glu;
Xaa at position 19 is Pro or Glu;
Xaa at position 20 is Leu, Val, Gly, Ser, Lys, Ala, Arg, Gln, Glu, Ile, Phe, Thr or Met;
Xaa at position 21 is Leu, Ala, Asn, Pro, Gln, or Val;
Xaa at position 23 is Phe, Ser, Pro, or Trp;
Xaa at position 24 is Asn or Ala;
Xaa at position 28 is Gly, Asp, Ser, Cys, Ala, Asn, Ile, Leu, Met Tyr or Arg;
Xaa at position 30 is Asp or Glu;
Xaa at position 31 is Gln, Val, Met, Leu, Thr, Ala, Asn, Glu, Ser or Lys;
Xaa at position 32 is Asp, Phe, Ser, Thr, Ala, Asn, Gln, Glu, His, Ile, Lys, Tyr, Val or Cys;
Xaa at position 36 is Glu, Ala, Asn, Ser or Asp;
Xaa at position 37 is Asn, Arg, Met, Pro, Ser, Thr, or His;
Xaa at position 40 is Arg or Ala;
Xaa at position 41 is Arg, Thr, Val, Leu, or Gly;
Xaa at position 42 is Pro, Gly, Ser, Gln, Ala, Arg, Asn, Glu, Leu, Thr, Val or Lys;
Xaa at position 46 is Ala or Ser;
Xaa at position 48 is Asn, Pro, Thr, or Ile;
Xaa at position 49 is Arg;
Xaa at position 50 is Ala or Asn;
Xaa at position 51 is Val or Thr;
Xaa at position 52 is Lys or Arg;
Xaa at position 53 is Ser, Phe, or His;
Xaa at position 54 is Leu, Ile, Phe, or His;
Xaa at position 55 is Gln, Ala, Pro, Thr, Glu, Arg, or Gly;
Xaa at position 57 is Ala, Pro, or Arg;
Xaa at position 58 is Ser, Glu, Arg, or Asp;
Xaa at position 59 is Ala or Leu;
Xaa at position 62 is Ser, Val, Ala, Asn, Glu, Pro, or Gly;
Xaa at position 63 is Ile or Leu;
Xaa at position 65 is Lys, Thr, Gly, Asn, Met, Arg, Ile, or Asp;
Xaa at position 66 is Asn, Gly, Glu, or Arg;
Xaa at position 68 is Leu, Gln, Trp, Arg, Asp, Ala, Asn, Glu, His, Ile, Met, Phe, Ser, Thr, Tyr or Val;
Xaa at position 69 is Pro or Thr;
Xaa at position 71 is Leu or Val;
Xaa at position 73 is Leu or Ser;
Xaa at position 74 is Ala or Trp;
Xaa at position 77 is Ala or Pro;
Xaa at position 79 is Thr, Asp, Ser, Pro, Ala, Leu, or Arg;
Xaa at position 81 is His, Pro, Arg, Val, Leu, Gly, Asn, Phe, Ser or Thr;
Xaa at position 82 is Pro or Tyr;
Xaa at position 83 is Ile or Val;
Xaa at position 84 is His, Ile, Asn, Leu, Ala, Thr, Gln, Lys, Met, Ser, Tyr, Val or Pro;
Xaa at position 85 is Ile, Leu, or Val;
Xaa at position 86 is Lys, Arg, Ile, Gln, Pro, or Ser;
Xaa at position 87 is Asp;
Xaa at position 90 is Trp or Leu;
Xaa at position 91 is Asn, Pro, Ala, Ser, Trp, Gln, Tyr, Leu, Lys, Ile, Asp, or His;
Xaa at position 92 is Glu, or Gly;
Xaa at position 94 is Arg, Ala, or Ser;
Xaa at position 95 is Arg, Thr, Glu, Leu, or Ser;
Xaa at position 98 is Thr, Val, or Gln;
Xaa at position 100 is Tyr or Trp;
Xaa at position 101 is Leu or Ala;
Xaa at position 102 is Lys;
Xaa at position 103 is Thr or Ser;
Xaa at position 106 is Asn, Pro, Leu, His, Val, or Gln;
Xaa at position 107 is Ala, Ser, Ile, Asn, Pro, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

wherein from 4 to about 44 of the amino acids designated by Xaa are different from the corresponding amino acids of native (1–133) human interleukin-3 with the proviso that no more than one of the amino acids at positions 49, 68, 73, 84, 98, and 107 are different from the corresponding amino acids in native human interleukin-3; and said mutant human interleukin-3 polypeptide has increased cell proliferative activity compared to native human interleukin-3 in at least one assay selected from the group consisting of: AML cell proliferation, TF-1 cell proliferation and Methylcellulose assay; and 93S, 98I, 101A, 105Q, 109E, 116V, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323); and said mutant human interleukin-3 polypeptide has increased cell proliferative activity compared to native human interleukin-3 in at least one assay selected from the group consisting of: AML cell proliferation, TF-1 cell proliferation and Methylcellulose assay;

(b) a polypeptide comprising an N-terminal methionine residue, alanine residue or methionine-alanine di-peptide immediately preceding said sequence according to (a).

125. The method according to claim 124, wherein said mutant human interleukin-3 polypeptide has at least three times greater cell proliferative activity compared to native human interleukin-3.

126. The method according to claim 124, wherein said mutant human interleukin-3 polypeptide has at least ten times greater cell proliferative activity compared to native human interleukin-3.

127. A method of treating a patient having an immuno-deficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:15)
wherein;
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;

Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and (b) a polypeptide comprising an N-terminal methionine residue, alanine residue or methionine-alanine di-peptide immediately preceding said sequence according to (a).

128. A method of treating a patient having an immuno-deficiency or hematopoietic deficiency comprising administering to said patient, a therapeutically effective amount of a mutant human interleukin-3 (hIL-3) polypeptide comprising a modified hIL-3 amino acid sequence selected from the group consisting of:

(a) a polypeptide having an amino acid sequence of
(18I, 25H, 29R, 32A, 37P, 42A and 45V)-(15–125)human interleukin-3 (SEQ ID NO:66);
(18I, 25H, 29R, 32N, 37P, 42S and 45M)-(15–125)human interleukin-3 (SEQ ID NO:67);
(18I, 25H, 29V, 32A, 37S, 42S and 45M)-(15–125)human interleukin-3 (SEQ ID NO:68);
(51R, 55L, 59L, 62V, 67N and 69E)-(15–125)human interleukin-3 (SEQ ID NO:69);
(51R, 55L, 60S, 62V, 67N and 69E)-(15–125)human interleukin-3 (SEQ ID NO:70)i
(51R, 55T, 59L, 62V, 67H and 69E)-(15–125)human interleukin-3 (SEQ ID NO:71);
(73G, 76A, 79R, 82Q, 87S, 93S, 98I, 101A and 105Q)-(15–125)human interleukin-3 (SEQ ID NO:72);
(73G, 76A, 79R, 82V, 87S, 93S, 98T, 101A and 105Q)-(15–125)human interleukin-3 (SEQ ID NO:73);
(73G, 76A, 79R, 82Q, 87S, 93S, 98I, 101A, 105Q, 109E, 116V, 120Q and 123E)-(15–125)human interleukin-3 (SEQ. ID. NO:76);
(73G, 76A, 79R, 82V, 87S, 93S, 98T, 101A, 105Q, 109E, 116V, 120Q and 123E)-(15–125)human interleukin-3 (SEQ ID NO:77);
(73G, 76A, 79R, 82V, 87S, 93S, 98T, 101A, 105Q, 109E, 116V, 117S, 120H and 123E)-(15–125)human interleukin-3 (SEQ ID NO:78);
(18I, 25H, 29R, 32A, 37P, 42A, 45V, 51R, 55L, 60S, 62V, 67N and 69E)-(15–125)human interleukin-3 (SEQ ID NO:79);
(18I, 25H, 29R, 32N, 37P, 42S, 45M, 51R, 55T, 59L, 62V, 67H and 69E)-(15–125)human interleukin-3 (SEQ ID NO:80);
(18I, 25H, 29V, 32A, 37S, 42S, 45M, 51R, 55L, 59L, 62V, 67N and 69E)-(15–125)human interleukin-3 (SEQ ID NO:81);
(42D, 45M, 46S, 50D, 95R, 98I, 100R, 116W)-(15–125) human interleukin-3 (residues 3–113 of SEQ ID NO:263);
(42D, 45M, 46S, 98I, 100R, 116W)-(15–125)human interleukin-3 (SEQ ID NO:406);
(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);
(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);

(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);

(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);

(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);

(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);

(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116v, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323);

(b) a polypeptide comprising an N-terminal methionine residue, alanine residue or methionine-alanine di-peptide immediately preceding said sequence according to (a).

129. A method of treating a patient comprising the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a sequence of (SEQ ID NO:15)

wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;

Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and (b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

130. A method of treating a patient comprising the steps of:

(i) administering to said patient, an amount of a mutant human interleukin-3 (IL-3) polypeptide, effective to promote the proliferation and/or differentiation of hematopoietic cells in said patient, wherein said mutant human interleukin-3 (hIL-3) polypeptide comprises a modified hIL-3 amino acid sequence selected from the group consisting of:

(a) a polypeptide having an amino acid sequence of (18I, 25H, 29R, 32A, 37P, 42A and 45V)-(15–125)human interleukin-3 (SEQ ID NO:66);

(18I, 25H, 29R, 32N, 37P, 42S and 45M)-(15–125)human interleukin-3 (SEQ ID NO:67);

(18I, 25H, 29V, 32A, 37S, 42S and 45M)-(15–125)human interleukin-3 (SEQ ID NO:68);

(51R, 55L, 59L, 62V, 67N and 69E)-(15–125)human interleukin-3 (SEQ ID NO:69)

(51R, 55L, 60S, 62V, 67N and 69E)-(15–125)human interleukin-3 (SEQ ID NO:70);

(51R, 55T, 59L, 62V, 67H and 69E)-(15–125)human interleukin-3 (SEQ ID NO:71);

(73G, 76A, 79R, 82Q, 87S, 93S, 98I, 101A and 105Q)-(15–125)human interleukin-3 (SEQ ID NO:72);

(73G, 76A, 79R, 82V, 87S, 93S, 98T, 101A and 105Q)-(15–125)human interleukin-3 (SEQ ID NO:73);

(73G, 76A, 79R, 82Q, 87S, 93S, 98I, 101A, 105Q, 109E, 116V, 120Q and 123E)-(15–125)human interleukin-3 (SEQ. ID. NO:76);

(73G, 76A, 79R, 82V, 87S, 93S, 98T, 101A, 105Q, 109E, 116V, 120Q and 123E)-(15–125)human interleukin-3 (SEQ ID NO:77);

(73G, 76A, 79R, 82V, 87S, 93S, 98T, 101A, 105Q, 109E, 116V, 117S, 120H and 123E)-(15–125)human interleukin-3 (SEQ ID NO:78);

(18I, 25H, 29R, 32A, 37P, 42A, 45V, 51R, 55L, 60S, 62V, 67N and 69E)-(15–125)human interleukin-3 (SEQ ID NO:79);

(18I, 25H, 29S, 32N, 37P, 42S, 45M, 51S, 55T, 59L, 62V, 67H and 69E)-(15–125)human interleukin-3 (SEQ ID NO:80);

(18I, 25H, 29V, 32A, 37S, 42S, 45M, 51R, 55L, 59L, 62V, 67N and 69E)-(15–125)human interleukin-3 (SEQ ID NO:81);

(42D, 45M, 46S, 50D, 95R, 98I, 100R, 116W)-(15–125) human interleukin-3 (residues 3–113 of SEQ ID NO:263);

(42D, 45M, 46S, 98I, 100R, 116W)-(15–125)human interleukin-3 (SEQ ID NO:406);

(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);

(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);

(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);

(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);

(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);

(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);

(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);

(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);

(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);

(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);

(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S)-(15–118)human interleukin-3 (residues 3–113 of SEQ ID NO:323); and (b) a polypeptide comprising an N-terminal methionine residue, alanine residue or methionine-alanine di-peptide immediately preceding said sequence according to (a);

(ii) removing hematopoietic cells from said patient;

(iii) administering to said patient cancer radiation therapy or chemotherapy; and (iv) returning said hematopoietic cells to said patient.

131. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a sequence of (SEQ ID NO:15)

wherein;

Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;

Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;

Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, Ala, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 6 to about 44 of the amino acids designated by Xaa are different from the corresponding amino acids of native (1–133) human interleukin-3; and wherein from 1 to 14 amino acids are optionally deleted from the N-terminus and/or from 1 to 15 amino acids are optionally deleted from the C-terminus; and (b) a polypeptide comprising an N-terminal methionine residue, alanine residue or methionine-alanine di-peptide immediately preceding said sequence according to (a).

132. A method of treating a side effect of cancer chemotherapy or radiation therapy in a patient comprising administering to said patient, a therapeutically effective amount of a mutant human interleukin-3 (hIL-3) polypeptide comprising a modified hIL-3 amino acid sequence selected from the group consisting of:

(a) a polypeptide having an amino acid sequence of
(18I, 25H, 29R, 32A, 37P, 42A and 45V)-(15–125)human interleukin-3 (SEQ ID NO:66);
(18I, 25H, 29R, 32N, 37P, 42S and 45M)-(15–125)human interleukin-3 (SEQ ID NO:67);

(18I, 25H, 29V, 32A, 37S, 42S and 45M)-(15–125)human interleukin-3 (SEQ ID NO:68);
(51R, 55L, 59L, 62V, 67N and 69E)-(15–125)human interleukin-3 (SEQ ID NO:69);
(51R, 55L, 60S, 62V, 67N and 69E)-(15–125)human interleukin-3 (SEQ ID NO:70);
(51R, 55T, 59L, 62V, 67H and 69E)-(15–125)human interleukin-3 (SEQ ID NO:71);
(73G, 76A, 79R, 82Q, 87S, 93S, 98I, 101A and 105Q)-(15–125)human interleukin-3 (SEQ ID NO:72);
(73G, 76A, 79R, 82V, 87S, 93S, 98T, 101A and 105Q)-(15–125)human interleukin-3 (SEQ ID NO:73);
(73G, 76A, 79R, 82Q, 87S, 93S, 98I, 101A, 105Q, 109E, 116V, 120Q and 123E)-(15–125)human interleukin-3 (SEQ. ID. NO:76);
(73G, 76A, 79R, 82V, 87S, 93S, 98T, 101A, 105Q, 109E, 116V, 120Q and 123E)-(15–125)human interleukin-3 (SEQ ID NO:77);
(73G, 76A, 79R, 82V, 87S, 93S, 98T, 101A, 105Q, 109E, 116V, 117S, 120H and 123E)-(15–125)human interleukin-3 (SEQ ID NO:78);
(18I, 25H, 29R, 32A, 37P, 42A, 45V, 51R, 55L, 60S, 62V, 67N and 69E)-(15–125)human interleukin-3 (SEQ ID NO:79);
(18I, 25H, 29R, 32N, 37P, 42S, 45M, 51R, 55T, 59L, 62V, 67H and 69E)-(15–125)human interleukin-3 (SEQ ID NO:80);
(18I, 25H, 29V, 32A, 37S, 42S, 45M, 51R, 55L, 59L, 62V, 67N and 69E)-(15–125)human interleukin-3 (SEQ ID NO:81);

(42D, 45M, 46S, 50D, 95R, 98I, 10R, 116W)-(15–125) human interleukin-3 (residues 3–113 of SEQ ID NO:263);

(42D, 45M, 46S, 98I, 100R, 116W)-(15–125)human interleukin-3 (SEQ ID NO:406);

(18I, 19A, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:276);

(18I, 19I, 25H, 29R, 32N, 37P, 42S, 45V, 49D, 51R, 55T, 59L, 62V, 67H, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:277);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:278);
(18I, 23A, 25H, 29V, 32A, 37S, 42S, 45M, 51R, 55L, 59L, 62V, 67N, 69E, 73G, 76A, 79R, 82Q, 87S, 93S, 98I, 101A, 105Q, 109E, 112Q, 116V, 120Q and 123E)-(15–125)human interleukin-3 (SEQ ID NO:279);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 116V,)-(15–119)human interleukin-3 (residues 3–113 of SEQ ID NO:287);
(18I, 23A, 25H, 29R, 32A, 37P, 42D, 45V, 46S, 50D, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:289);
(18I, 25H, 29R, 32A, 37P, 42A, 45V, 51R, 55L, 60S, 62V, 67N, 69E, 73G, 76A, 79R, 82Q, 87S, 93S, 98I, 101A, 105Q, 109E, 112Q, 116V)-(15–119)human interleukin-3 (residues 3–113 of SEQ ID NO:307);
(18I, 20P, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:317);
(18I, 23L, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:318);
(18I, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:319);
(18I, 19I, 20L, 23A, 25H, 29I, 32N, 34S, 37S, 38A, 42S, 45V, 46S, 51R, 55T, 59L, 62V, 67H, 69E, 73G, 76A, 79R, 82Q, 87S, 93S, 98I, 101A, 105Q, 109E, 116V, 120Q and 123E)-(15–125)human interleukin-3 (residues 3–113 of SEQ ID NO:320);
(18I, 25H, 29R, 32N, 37P, 42S, 45M, 50D, 51S, 55T, 59L, 62P, 63H, 67Q, 69E, 73G, 76A, 79R, 82Q, 87S, 93S, 98I, 101A, 105Q, 109E, 116V, 120Q and 123E)-(15–125) human interleukin-3 (residues 3–113 of SEQ ID NO:321);

(18I, 25H, 29R, 32N, 37P, 42S, 45M, 51R, 55T, 59L, 62V, 67H, 69E, 73G, 76A, 79R, 82Q, 87S, 93S, 98I, 101A, 105Q, 109L, 112Q, 116S, 120Q and 123E)-(15–125) human interleukin-3 (residues 3–113 of SEQ ID NO:322); and (18I, 25H, 29R, 32N, 37P, 42n, 45M, 51R, 55T, 59L, 62V, 67H, 69E, 73G, 76A, 79R, 82Q, 87S, 93S, 98I, 101A, 105Q, 109L, 112Q, 116S)-(15–118) human interleukin-3 (residues 3–113 of SEQ ID NO: 323); and said mutant human interleukin-3 polypeptide has increased cell proliferative activity compared to native human interleukin-3 in at least one assay selected from the group consisting of: AML cell proliferation, TF-1 cell proliferation and Methylcellulose assay;

a polypeptide comprising an N-terminal methionine residue, alanine residue or methionine-alanine di-peptide immediately preceding said sequence according to (a).

* * * * *